(12) United States Patent
Beatty et al.

(10) Patent No.: US 11,931,343 B2
(45) Date of Patent: Mar. 19, 2024

(54) CD73 INHIBITORS

(71) Applicant: ARCUS BIOSCIENCES, INC., Hayward, CA (US)

(72) Inventors: Joel Beatty, San Mateo, CA (US); Laurent Pierre Paul Debien, San Francisco, CA (US); Samuel Lawrie Drew, Millbrae, CA (US); Jeremy Fournier, Fremont, CA (US); Rebecca Louise Grange, Union City, CA (US); Steven Donald Jacob, Oakland, CA (US); Jenna Leigh Jeffrey, Oakland, CA (US); Kenneth V. Lawson, San Francisco, CA (US); Manmohan Reddy Leleti, Dublin, CA (US); Erick Allen Lindsey, San Diego, CA (US); Debashis Mandal, Fremont, CA (US); Jay Patrick Powers, Pacifica, CA (US); Anh Thu Tran, Union City, CA (US); Rhiannon Thomas-Tran, San Jose, CA (US); Xuelei Yan, Foster City, CA (US)

(73) Assignee: Arcus Biosciences, Inc., Hayward, CA (US)

( * ) Notice: Subject to any disclaimer, the term of this patent is extended or adjusted under 35 U.S.C. 154(b) by 434 days.

(21) Appl. No.: 17/271,795

(22) PCT Filed: Aug. 26, 2019

(86) PCT No.: PCT/US2019/048141
§ 371 (c)(1),
(2) Date: Feb. 26, 2021

(87) PCT Pub. No.: WO2020/146813
PCT Pub. Date: Mar. 5, 2020

(65) Prior Publication Data
US 2021/0346353 A1    Nov. 11, 2021

Related U.S. Application Data

(60) Provisional application No. 62/723,271, filed on Aug. 27, 2018.

(51) Int. Cl.
*A61K 31/4192* (2006.01)
*A61K 31/282* (2006.01)
(Continued)

(52) U.S. Cl.
CPC ........ *A61K 31/4192* (2013.01); *A61K 31/282* (2013.01); *A61K 31/422* (2013.01); *A61K 31/423* (2013.01); *A61K 31/437* (2013.01); *A61K 31/4439* (2013.01); *A61K 31/4985* (2013.01); *A61K 31/519* (2013.01); *A61K 31/704* (2013.01); *A61K 33/243* (2019.01); *A61K 39/3955* (2013.01); *C07D 401/14* (2013.01); *C07D 403/04* (2013.01); *C07D 403/14* (2013.01); *C07D 405/14* (2013.01); *C07D 413/14* (2013.01); *C07D 471/04* (2013.01); *C07D 487/04* (2013.01)

(58) Field of Classification Search
CPC .............. A61K 31/4192; A61K 31/282; A61K 31/422; A61K 31/423; A61K 31/437; A61K 31/4439; A61K 31/4985; A61K 31/519; A61K 31/704; A61K 33/243; A61K 39/3955; A61K 45/06; C07D 401/14; C07D 403/04; C07D 403/14; C07D 405/14; C07D 413/14; C07D 471/04; C07D 487/04; A61P 35/00; A61P 37/00
See application file for complete search history.

(56) References Cited

U.S. PATENT DOCUMENTS

2014/0296229 A1   10/2014   Engelhardt et al.

FOREIGN PATENT DOCUMENTS

| EP | WO 2019/043217 A1 | * | 3/2019 | ........... C07D 401/14 |
| WO | WO 2012/129338 A1 | * | 9/2012 | ........... C07D 413/14 |

(Continued)

OTHER PUBLICATIONS

CAS Registry No. 716321-26-5; entered STN on Jul. 26, 2004 (Year: 2004).*

(Continued)

*Primary Examiner* — Valerie Rodriguez-Garcia
*Assistant Examiner* — David M Shim
(74) *Attorney, Agent, or Firm* — Sheppard Mullin Richter & Hampton LLP

(57) ABSTRACT

Compounds, such as compounds having Formula (I):

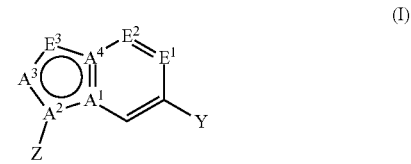

wherein each variable is as described herein, that modulate the conversion of AMP to adenosine by 5'-nucleotidase, ecto, and compositions containing the compounds and methods for synthesizing the compounds, are described herein. The use of such compounds and compositions for the treatment and/or prevention of a diverse array of diseases, disorders and conditions, including cancer- and immune-related disorders, that are mediated by 5'-nucleotidase, ecto is also provided.

11 Claims, 1 Drawing Sheet

(51) Int. Cl.
| | |
|---|---|
| *A61K 31/422* | (2006.01) |
| *A61K 31/423* | (2006.01) |
| *A61K 31/437* | (2006.01) |
| *A61K 31/4439* | (2006.01) |
| *A61K 31/4985* | (2006.01) |
| *A61K 31/519* | (2006.01) |
| *A61K 31/704* | (2006.01) |
| *A61K 33/243* | (2019.01) |
| *A61K 39/395* | (2006.01) |
| *C07D 401/14* | (2006.01) |
| *C07D 403/04* | (2006.01) |
| *C07D 403/14* | (2006.01) |
| *C07D 405/14* | (2006.01) |
| *C07D 413/14* | (2006.01) |
| *C07D 471/04* | (2006.01) |
| *C07D 487/04* | (2006.01) |

(56) References Cited

FOREIGN PATENT DOCUMENTS

| WO | WO-2014/173241 A1 | 10/2014 |
| WO | WO-2014173241 A1 | 10/2014 |
| WO | WO-2017098421 | 6/2017 |

OTHER PUBLICATIONS

International Search Report for PCT/US2019/048141, dated Jan. 6, 2020, 4 pages.
PUBCHEM Compound Summary for CID 22031856, created Dec. 5, 2007, 15 pages.
PUBCHEM Compound Summary for CID 101914570, created Dec. 18, 2015, 10 pages.
PUBCHEM Compound Summary for CID 126669413, created Apr. 22, 2017, 12 pages.
Written Opinion of the International Searching Authority for PCT/US2019/048141, 6 pages.
Pubmed Compound Summary for CID 101914570, '3-Chloro-7-cyclopropyl-5-methyl-5-phenylpyrrolo[2,3-c]pyridazin-6-one', U.S. National Library of Medicine, Dec. 18, 2015, 1-10.
Pubmed Compound Summary for CID 12669413, '1-Phenyl-6-(1H-pyrazol-4-yl)benzimidazole', U.S. National Library of Medicine, Apr. 22, 2017, 1-12.
Pubmed Compound Summary for CID 22031856, '3-(4-Fluorophenyl)-5-[5-(4-fluorophenyl)-1H-pyrazol-4-yl]-1H-benzimidazol-2-one', U.S. National Library of Medicine, Dec. 5, 2007, 1-15.
Extended European Search Report for European Patent Application No. 19854871.1 dated Mar. 21, 2022. 6 pages.

\* cited by examiner

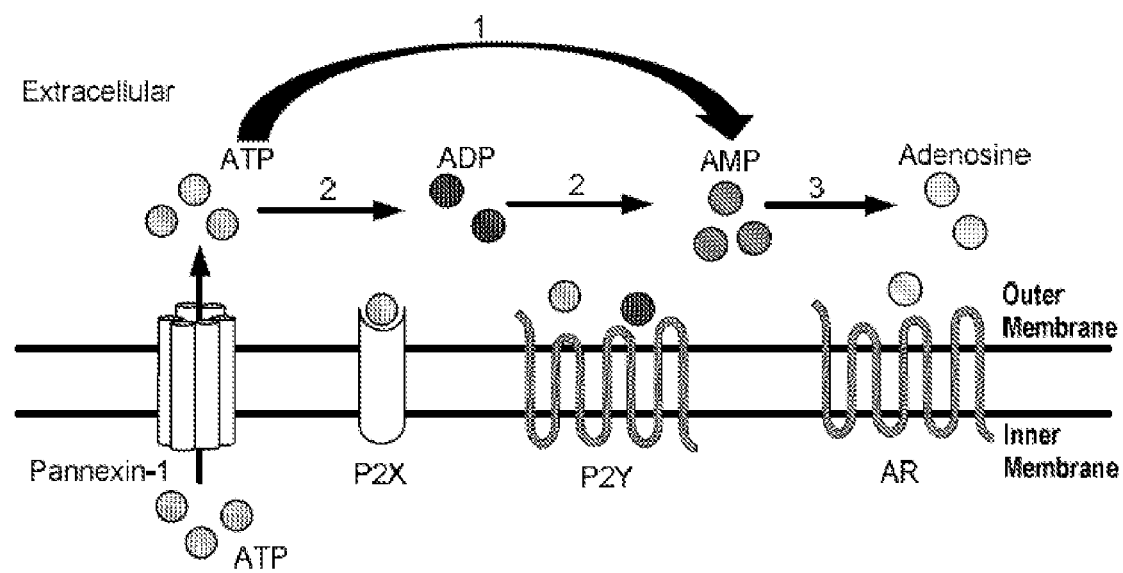

CD73 INHIBITORS

CROSS-REFERENCES TO RELATED APPLICATIONS

This application is the U.S. National Stage entry under § 371 of International Application No. PCT/US2019/048141, filed Aug. 26, 2019, which claims the benefit of priority to U.S. Provisional Application Ser. No. 62/723,271, filed Aug. 27, 2018, the contents of which are incorporated herein by reference in their entirety.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

FIELD

Provided herein are, for example, compounds and compositions for inhibition of adenosine by 5'-nucleotidase, ecto, also known as CD73, and pharmaceutical compositions comprising same. Also provided herein are, for example, methods of treating or preventing a disease, disorder or condition, or a symptom thereof, mediated by inhibition of adenosine by 5'-nucleotidase, ecto.

BACKGROUND OF THE INVENTION

Purinergic signaling, a type of extracellular signaling mediated by purine nucleotides and nucleosides such as ATP and adenosine, involves the activation of purinergic receptors in the cell and/or in nearby cells, resulting in the regulation of cellular functions. Most cells have the ability to release nucleotides, which generally occurs via regulated exocytosis (see Praetorius, H. A.; Leipziger, J. (1 Mar. 2010) *Ann Rev Physiology* 72(1): 377-393). The released nucleotides can then be hydrolyzed extracellularly by a variety of cellular membrane-bound enzymes referred to as ectonucleotidases.

Ectonucleotides catalyze the conversion of ATP to adenosine, an endogenous modulator that impacts multiple systems, including the immune system, the cardiovascular system, the central nervous system, and the respiratory system. Adenosine also promotes fibrosis in a variety of tissues. In the first step of the production of adenosine, ectonucleoside triphosphate diphosphohydrolase 1 (EN-TPD1), also known as CD39 (Cluster of Differentiation 39), hydrolyzes ATP to ADP, and then ADP to AMP. In the next step, AMP is converted to adenosine by 5'-nucleotidase, ecto (NT5E or 5NT), also known as CD73 (Cluster of Differentiation 73).

The enzymatic activities of CD39 and CD73 play strategic roles in calibrating the duration, magnitude, and chemical nature of purinergic signals delivered to various cells (e.g., immune cells). Alteration of these enzymatic activities can change the course or dictate the outcome of several pathophysiological events, including cancer, autoimmune diseases, infections, atherosclerosis, and ischemia-reperfusion injury, suggesting that these ecto-enzymes represent novel therapeutic targets for managing a variety of disorders.

CD73 inhibition with monoclonal antibodies, siRNA, or small molecules delays tumor growth and metastasis (Stagg, J. (2010) PNAS U.S.A. 107:1547-52). For example, anti-CD73 antibody therapy was shown to inhibit breast tumor growth and metastasis in animal models (Stagg, J. (26 Jan. 2010) PNAS U.S.A, 107(4):1547-52). In addition, the use of antibodies that specifically bind CD73 has been evaluated for the treatment of bleeding disorders (e.g., hemophilia) (U.S. Pat. No. 9,090,697). Recently, there have been several efforts to develop therapeutically useful CD73 small molecule inhibitors. For example, Bhattarai et al. ((2015) J Med Chem 58:6248-63) have studied derivatives and analogs of α,β-Methylene-ADP (AOPCP), one of the most metabolically stable, potent and selective CD73 inhibitors known, and purine CD73 derivatives have been reported in the patent literature (WO 2015/164573). However, the development of small molecules has been hampered due to, for example, less than ideal metabolic stability.

In view of the role played by CD73 in cancer, as well as a diverse array of other diseases, disorders and conditions, and the current lack of CD73 inhibitors available to medical practitioners, new CD73 inhibitors, and compositions and methods associated therewith, are needed.

BRIEF SUMMARY OF THE INVENTION

The present invention relates to compounds that modulate the conversion of AMP to adenosine by 5'-nucleotidase, ecto (NT5E or 5NT; also known as CD73), and compositions (e.g., pharmaceutical compositions) comprising the compounds. Such compounds, including methods of their synthesis, and compositions are described in detail below.

The present invention also relates to the use of such compounds and compositions for the treatment and/or prevention of a diverse array of diseases, disorders and conditions mediated, in whole or in part, by CD73. CD73 inhibitors have been linked to the treatment of a diverse array of disorders, including cancer, fibrosis, neurological and neurodegenerative disorders (e.g., depression and Parkinson's disease), cerebral and cardiac ischemic diseases, immune-related disorders, and disorders with an inflammatory component. [See, e.g., Sorrentino et al (2013) OncoImmunol, 2:e22448, doi: 10.4161/onci.22448; and Regateiro et al. (2012) Clin. Exp. Immunol, 171:1-7]. In particular embodiments, the compounds described herein act to inhibit the immunosuppressive activity and/or the anti-inflammatory activity of CD73, and are useful as therapeutic or prophylactic therapy when such inhibition is desired. Unless otherwise indicated, when uses of the compounds of the present invention are described herein, it is to be understood that such compounds may be in the form of a composition (e.g., a pharmaceutical composition).

As used herein, the terms "CD73 inhibitor", "CD73 blocker", "adenosine by 5'-nucleotidase, ecto inhibitor", "NT5E inhibitor", "5NT inhibitor" and all other related art-accepted terms refer to a compound capable of modulating, either directly or indirectly, the CD73 receptor in an in vitro assay, an in vivo model, and/or other means indicative of therapeutic efficacy. The terms also refer to compounds that exhibit at least some therapeutic benefit in a human subject.

Although the compounds of the present invention are believed to effect their activity by inhibition of CD73, a precise understanding of the compounds' underlying mechanism of action is not required to practice the invention. For example, the compounds can also effect their activity, at least in part, through modulation (e.g., inhibition) of other components of the purinergic signaling pathway (e.g., CD39). The purinergic signaling system consists of transporters, enzymes and receptors responsible for the synthesis, release, action, and extracellular inactivation of (primarily) ATP and its extracellular breakdown product adenosine (Sperlagh, B. et al. (December 2012) Neuropsychopharmacologia Hungarica 14(4):231-38). Because inhibition of CD73 results in decreased adenosine, CD73 inhibitors can be used for the treatment of diseases or disorders mediated by adenosine and its actions on adenosine receptors, including A1, $A_{2A}$, $A_{2B}$ and A3. [see Yegutkin, G G (May 2008) Biochimica Biophysica Acta 1783(5):673-94].

For purposes of the present disclosure, the purinergic signaling process can be described as comprising the following components. The purinergic receptors (P1, P2X and P2Y), a first component, are membrane receptors that mediate various physiological functions (e.g., relaxation of gut smooth muscle) as a response to the release of ATP or adenosine; in general, all cells have the ability to release nucleotides into the extracellular environment, frequently through regulated exocytosis. The nucleoside transporters (NTs), a second component, are membrane transport proteins which transport nucleoside substrates (e.g., adenosine) across cell membranes; the extracellular concentration of adenosine can be regulated by NTs, possibly in the form of a feedback loop connecting receptor signaling with transporter function. As previously described, the ectonucleotidases (CD73 and CD39) hydrolyze nucleotides released into the extracellular environment and comprise a further component. Another component of the purinergic signaling process comprises the pannexins; in particular, the pannexin-1 channel (PANX1) is an integral component of the P2X/P2Y purinergic signaling pathway and the key contributor to pathophysiological ATP release.

In one particular aspect, the present invention provides compounds having Formula (I):

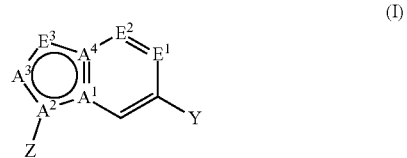

(I)

or a pharmaceutically acceptable salt, hydrate, N-oxide, or solvate thereof, wherein the letters $A^1$, $A^2$, $A^3$, $A^4$, $E^1$, $E^2$, $E^3$, Y and Z have the meanings provided in the Detailed Description below, and wherein additional embodiments of this disclosure are provided as Formulae (Ia), (Ib), (Ia1), (Ib1), (Ia2), (Ib2), (Ia3), (Ib3), (Ia4), (Ib4), (Ia5), (Ib5), (Ia6), (Ib6), (Ia7), (Ib7), (Ia8) and (Ib8).

In some embodiments, the present invention contemplates methods for treating or preventing cancer in a subject (e.g., a human) comprising administering to the subject a therapeutically effective amount of at least one CD73 inhibitor described herein. The present invention includes methods of treating or preventing a cancer in a subject by administering to the subject a CD73 inhibitor in an amount effective to reverse or stop the progression of CD73-mediated immunosuppression. In some embodiments, the CD73-mediated immunosuppression is mediated by an antigen-presenting cell (APC).

Examples of the cancers that can be treated using the compounds and compositions described herein include, but are not limited to: cancers of the prostate, colorectum, pancreas, cervix, stomach, endometrium, brain, liver, bladder, ovary, testis, head, neck, skin (including melanoma and basal carcinoma), mesothelial lining, white blood cell (including lymphoma and leukemia), esophagus, breast, muscle, connective tissue, lung (including small-cell lung carcinoma and non-small-cell lung carcinoma), adrenal gland, thyroid, kidney, or bone; glioblastoma, mesothelioma, renal cell carcinoma, gastric carcinoma, sarcoma, choriocarcinoma, cutaneous basocellular carcinoma, and testicular seminoma. In some embodiments of the present invention, the cancer is melanoma, colon cancer, pancreatic cancer, breast cancer, prostate cancer, lung cancer, leukemia, a brain tumor, lymphoma, sarcoma, ovarian cancer, or Kaposi's sarcoma. Cancers that are candidates for treatment with the compounds and compositions of the present invention are discussed further hereafter.

The present invention contemplates methods of treating a subject receiving a bone marrow transplant or peripheral blood stem cell transplant by administering a therapeutically effective amount of an CD73 inhibitor sufficient to increase the delayed-type hypersensitivity reaction to tumor antigen, delay the time-to-relapse of post-transplant malignancy, increase relapse-free survival time post-transplant, and/or increase long-term post-transplant survival.

In certain embodiments, the present invention contemplates methods for treating or preventing an infective disorder (e.g., a viral infection) in a subject (e.g., a human) comprising administering to the subject a therapeutically effective amount of at least one CD73 inhibitor (e.g., a novel inhibitor of the instant invention). In some embodiments, the infective disorder is a viral infection (e.g., a chronic viral infection), a bacterial infection, a fungal infection, or a parasitic infection. In certain embodiments, the viral infection is human immunodeficiency virus or cytomegalovirus.

In still other embodiments, the present invention contemplates methods for treating and/or preventing immune-related diseases, disorders and conditions; diseases having an inflammatory component; as well as disorders associated with the foregoing; with at least one CD73 inhibitor of the instant invention. Examples of immune-related diseases, disorders and conditions are described hereafter.

Other diseases, disorders and conditions that can be treated or prevented, in whole or in part, by modulation of CD73 activity are candidate indications for the CD73 inhibitor compounds of the present invention.

The present invention further contemplates the use of the CD73 inhibitors described herein in combination with one or more additional agents. The one or more additional agents may have some CD73-modulating activity and/or they may function through distinct mechanisms of action. In some embodiments, such agents comprise radiation (e.g., localized radiation therapy or total body radiation therapy) and/or other treatment modalities of a non-pharmacological nature. When combination therapy is utilized, the CD73 inhibitor(s) and the one additional agent(s) may be in the form of a single composition or multiple compositions, and the treatment modalities can be administered concurrently, sequentially, or through some other regimen. By way of example, the present invention contemplates a treatment regimen wherein a radiation phase is followed by a chemotherapeutic phase. The combination therapy can have an additive or synergistic effect. Other benefits of combination therapy are described hereafter.

In some embodiments, the present invention further comprises the use of the CD73 inhibitors described herein in combination with bone marrow transplantation, peripheral blood stem cell transplantation, or other types of transplantation therapy.

In particular embodiments, the present invention contemplates the use of the inhibitors of CD73 function described herein in combination with immune checkpoint inhibitors. The blockade of immune checkpoints, which results in the amplification of antigen-specific T cell responses, has been shown to be a promising approach in human cancer therapeutics. Examples of immune checkpoints (ligands and receptors), some of which are selectively upregulated in various types of tumor cells, that are candidates for blockade include PD1 (programmed cell death protein 1); PDL1 (PD1 ligand); BTLA (B and T lymphocyte attenuator); CTLA4 (cytotoxic T-lymphocyte associated antigen 4); TIM3 (T-cell membrane protein 3); LAG3 (lymphocyte activation gene 3); A2aR (adenosine A2a receptor A2aR); and Killer Inhibitory Receptors. Immune checkpoint inhibitors, and combination therapy therewith, are discussed in detail elsewhere herein.

In other embodiments, the present invention provides methods for treating cancer in a subject, comprising administering to the subject a therapeutically effective amount of at least one CD73 inhibitor and at least one chemotherapeutic agent, such agents including, but not limited to alkylating agents (e.g., nitrogen mustards such as chlorambucil, cyclophosphamide, isofamide, mechlorethamine, melphalan, and uracil mustard; aziridines such as thiotepa; methanesulphonate esters such as busulfan; nucleoside analogs (e.g., gemcitabine); nitroso ureas such as carmustine, lomustine, and streptozocin; topoisomerase 1 inhibitors (e.g., irinotecan); platinum complexes such as cisplatin, carboplatin and oxaliplatin; bioreductive alkylators such as mitomycin, procarbazine, dacarbazine and altretamine); DNA strand-breakage agents (e.g., bleomycin); topoisomerase II inhibitors (e.g., amsacrine, dactinomycin, daunorubicin, idarubicin, mitoxantrone, doxorubicin, etoposide, teniposide and epirubicin); DNA minor groove binding agents (e.g., plicamydin); antimetabolites (e.g., folate antagonists such as methotrexate, trimetrexate and pemetrexed; pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); tubulin interactive agents (e.g., vincristine, estramustine, vinblastine, docetaxol, epothilone derivatives, and paclitaxel); hormonal agents (e.g., estrogens; conjugated estrogens; ethinyl estradiol; diethylstilbesterol; chlortrianisen; idenestrol; progestins such as hydroxyprogesterone caproate, medroxyprogesterone, and megestrol; and androgens such as testosterone, testosterone propionate, fluoxymesterone, and methyltestosterone); adrenal corticosteroids (e.g., prednisone, dexamethasone, methylprednisolone, and prednisolone); leutinizing hormone releasing agents or gonadotropin-releasing hormone antagonists (e.g., leuprolide acetate and goserelin acetate); and antihormonal antigens (e.g., tamoxifen, antiandrogen agents such as flutamide; and antiadrenal agents such as mitotane and aminoglutethimide). The present invention also contemplates the use of the CD73 inhibitors in combination with other agents known in the art (e.g., arsenic trioxide) and other chemotherapeutic agents that may be developed in the future.

In some embodiments drawn to methods of treating cancer, the administration of a therapeutically effective amount of an CD73 inhibitor in combination with at least one chemotherapeutic agent results in a cancer survival rate greater than the cancer survival rate observed by administering either agent alone. In further embodiments drawn to methods of treating cancer, the administration of a therapeutically effective amount of an CD73 inhibitor in combination with at least one chemotherapeutic agent results in a reduction of tumor size or a slowing of tumor growth greater than reduction of the tumor size or tumor growth observed by administration of either agent alone.

In further embodiments, the present invention contemplates methods for treating or preventing cancer in a subject, comprising administering to the subject a therapeutically effective amount of at least one CD73 inhibitor and at least one signal transduction inhibitor (STI). In a particular embodiment, the at least one STI is selected from the group consisting of bcr/abl kinase inhibitors, epidermal growth factor (EGF) receptor inhibitors, her-2/neu receptor inhibitors, and farnesyl transferase inhibitors (FTIs). Other candidate STI agents are set forth elsewhere herein.

The present invention also contemplates methods of augmenting the rejection of tumor cells in a subject comprising administering an CD73 inhibitor in conjunction with at least one chemotherapeutic agent and/or radiation therapy, wherein the resulting rejection of tumor cells is greater than that obtained by administering either the CD73 inhibitor, the chemotherapeutic agent or the radiation therapy alone.

In further embodiments, the present invention provides methods for treating cancer in a subject, comprising administering to the subject a therapeutically effective amount of at least one CD73 inhibitor and at least one immunomodulator other than an CD73 inhibitor.

The present invention contemplates embodiments comprising methods for treating or preventing an infective disorder (e.g., a viral infection) in a subject (e.g., a human) comprising administering to the subject a therapeutically effective amount of at least one CD73 inhibitor and a therapeutically effective amount of an anti-infective agent(s), such as one or more antimicrobial agents.

In additional embodiments, treatment of an infective disorder is effected through the co-administration of a vaccine in combination with administration of a therapeutically effective amount of an CD73 inhibitor of the present invention. In some embodiments, the vaccine is an anti-viral vaccine, including, for example, an anti-HIV vaccine. In other embodiments, the vaccine is effective against tuberculosis or malaria. In still other embodiments, the vaccine is a tumor vaccine (e.g., a vaccine effective against melanoma); the tumor vaccine can comprise genetically modified tumor cells or a genetically modified cell line, including genetically modified tumor cells or a genetically modified cell line that has been transfected to express granulocyte-macrophage stimulating factor (GM-CSF). In particular embodiments, the vaccine includes one or more immunogenic peptides and/or dendritic cells.

In certain embodiments drawn to treatment of an infection by administering an CD73 inhibitor and at least one additional therapeutic agent, a symptom of infection observed after administering both the CD73 inhibitor and the additional therapeutic agent is improved over the same symptom of infection observed after administering either alone. In some embodiments, the symptom of infection observed can be reduction in viral load, increase in $CD4^+$ T cell count, decrease in opportunistic infections, increased survival time, eradication of chronic infection, or a combination thereof.

BRIEF DESCRIPTION OF THE DRAWINGS

FIG. 1 depicts a simplified representation of extracellular purinergic signaling.

DETAILED DESCRIPTION OF THE INVENTION

Before the present invention is further described, it is to be understood that the invention is not limited to the particular embodiments set forth herein, and it is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology such as "solely," "only" and the like in connection with the recitation of claim elements, or use of a "negative" limitation.

The publications discussed herein are provided solely for their disclosure prior to the filing date of the present application. Further, the dates of publication provided may be different from the actual publication dates, which may need to be independently confirmed.

General

The number of subjects diagnosed with cancer and the number of deaths attributable to cancer continue to rise. Traditional treatment approaches comprising chemotherapy and radiotherapy are generally difficult for the patient to tolerate and become less effective as cancers (e.g., tumors) evolve to circumvent such treatments. Recent experimental evidence indicates that CD73 inhibitors may represent an important new treatment modality for cancer (e.g., breast cancer) treatment.

Promising data also support the role of inhibitors of CD73 function to inhibit the anti-inflammatory activity of CD73 and/or the immunosuppressive activity of CD73, and thus CD73 inhibitors may be useful to treat, for example, immunosuppressive diseases (e.g., HIV and AIDs). Inhibition of CD73 may also be an important treatment strategy for patients with neurological or neuropsychiatric diseases or disorders such as depression.

The present invention is drawn to, inter alia, small molecule compounds having CD73 inhibitory activity, as well as compositions thereof, and methods of using the compounds and compositions for the treatment and prevention of the diseases, disorders and conditions described herein.

Definitions

Unless otherwise indicated, the following terms are intended to have the meaning set forth below. Other terms are defined elsewhere throughout the specification.

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like.

The term "cycloalkyl" refers to hydrocarbon rings having the indicated number of ring atoms (e.g., $C_{3-6}$ cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc.

The term "cycloheteroalkyl" refers to a cycloalkyl ring having the indicated number of ring vertices (or members) and having from one to five heteroatoms selected from N, O, and S, which replace one to five of the carbon vertices, and wherein the nitrogen and sulfur atoms are optionally oxidized, and the nitrogen atom(s) are optionally quaternized. The cycloheteroalkyl may be a monocyclic, a bicyclic or a polycyclic ring system. Non limiting examples of cycloheteroalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrahydrothiophene, quinuclidine, and the like. A cycloheteroalkyl group can be attached to the remainder of the molecule through a ring carbon or a heteroatom. When 'optionally substituted' is used to describe either of the terms "cycloheteroalkyl" or "cycloheteroalkyl-alkyl", it is meant to refer to those groups wherein the cycloheteroalkyl or alkyl portion is optionally substituted as in the definitions below that refer to the alkyl portion. For example, an optionally substituted cycloheteroalkyl-alkyl group can be optionally substituted on either or both of the cycloheteroalkyl and alkyl portions as in the definitions for alkyl substituents below.

As used herein, a wavy line, "〜", that intersects a single, double or triple bond in any chemical structure depicted herein, represent the point attachment of the single, double, or triple bond to the remainder of the molecule. Additionally, a bond extending to the center of a ring (e.g., a phenyl ring) is meant to indicate attachment at any of the available ring vertices. One of skill in the art will understand that multiple substituents shown as being attached to a ring will occupy ring vertices that provide stable compounds and are otherwise sterically compatible. For a divalent component, a representation is meant to include either orientation (forward or reverse). For example, the group "—C(O) NH—" is meant to include a linkage in either orientation: —C(O)NH— or —NHC(O)—, and similarly, "—O—CH$_2$CH$_2$—" is meant to include both —O—CH$_2$CH$_2$— and —CH$_2$CH$_2$—O—.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as dialkylamino or —NR$^a$R$^b$ is meant to include piperidinyl, pyrrolidinyl, morpholinyl, azetidinyl and the like.

The terms "arylalkyl" and "heteroarylalkyl" are used in their conventional sense, and refer to those groups wherein an aryl group or a heteroaryl group is attached remainder of the molecule via $C_1$-$C_4$ alkylene linker. An exemplary embodiment of "arylalkyl" is phenylmethyl (or benzyl). Similarly, an exemplary embodiment of "heteroarylalkyl" is, for example, 3-pyridylpropyl. When 'optionally substituted' is used to describe either of the terms "arylalkyl" or "heteroarylalkyl", it is meant to refer to those groups wherein the aryl or heteroaryl portion is optionally substituted as in the definitions below, and the alkyl portion is optionally substituted as in the definitions below.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. Non-limiting examples of aryl groups include phenyl, naphthyl and biphenyl.

The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of heteroaryl groups include pyridyl, pyridazinyl, pyrazinyl, pyrimindinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for a heteroaryl ring can be selected from the group of acceptable substituents described below.

The above terms (e.g., "alkyl," "aryl" and "heteroaryl"), in some embodiments, will be optionally substituted. Selected substituents for each type of radical are provided below.

Optional substituents for the alkyl radicals (including those groups often referred to as alkylene, alkenyl, alkynyl and cycloalkyl) can be a variety of groups selected from: halogen, —OR', —NR'R", —SR', —SiR'R"R''', —OC(O)R', —C(O)R', —CONR'R", —OC(O)NR'R", —NR"C(O)R', —NR'—C(O)NR"R''', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", S(O)$_2$R", —CN and —NO$_2$ in a number ranging from zero to (2 m'+1), where m' is the total number of carbon atoms in such radical. R', R" and R''' each independently refer to hydrogen, unsubstituted $C_{1-8}$ alkyl, unsubstituted aryl, aryl substituted with 1-3 halogens, unsubstituted $C_{1-8}$ alkyl, $C_{1-8}$ alkoxy or $C_{1-8}$ thioalkoxy groups, or unsubstituted aryl-$C_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl.

Similarly, optional substituents for the aryl and heteroaryl groups are varied and are generally selected from: -halogen, —OR', —OC(O)R', —NR'R", —SR', —R', —CN, —NO$_2$, CO$_2$R', —CONR'R", —C(O)R', —OC(O)NR'R", —NR"C(O)R', —NR"C(O)$_2$R', —NR'—C(O)NR"R''', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —N$_3$, perfluoro($C_1$-$C_4$)alkoxy, and perfluoro($C_1$-$C_4$)alkyl, in a number ranging from zero to the total number of open valences on the aromatic ring system; and where R', R" and R''' are independently selected from hydrogen, $C_{1-8}$ alkyl, $C_{1-8}$ haloalkyl, $C_{3-6}$ cycloalkyl, $C_{2-8}$ alkenyl and $C_{2-8}$ alkynyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted $C_{1-6}$ alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. When a stereochemical depiction is shown, it is meant to refer the compound in which one of the isomers is present and substantially free of the other isomer. 'Substantially free of' another isomer indicates at least an 80/20 ratio of the two isomers, more preferably 90/10, or 95/5 or more. In some embodiments, one of the isomers will be present in an amount of at least 99%.

The compounds of the present invention may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3H$), iodine-125 ($^{125}I$) or carbon-14 ($^{14}C$), or non-radioactive isotopes, such as deuterium ($^2H$) or carbon-13 ($^{13}C$). Such isotopic variations can provide additional utilities to those described elsewhere within this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present invention.

The terms "patient" or "subject" are used interchangeably to refer to a human or a non-human animal (e.g., a mammal).

The terms "administration", "administer" and the like, as they apply to, for example, a subject, cell, tissue, organ, or biological fluid, refer to contact of, for example, an inhibitor of CD73, a pharmaceutical composition comprising same, or a diagnostic agent to the subject, cell, tissue, organ, or biological fluid. In the context of a cell, administration includes contact (e.g., in vitro or ex vivo) of a reagent to the cell, as well as contact of a reagent to a fluid, where the fluid is in contact with the cell.

The terms "treat", "treating", treatment" and the like refer to a course of action (such as administering an inhibitor of CD73 or a pharmaceutical composition comprising same) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (e.g., arresting the development or further development of the disease, disorder or condition or clinical symptoms association therewith) an active disease.

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering an CD73 inhibitor or a pharmaceutical composition comprising same) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based on a variety of factors that are in the realm of a physician's or caregiver's expertise.

The phrase "therapeutically effective amount" refers to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like. By way of example, measurement of the serum level of an CD73 inhibitor (or, e.g., a metabolite thereof) at a particular time post-administration may be indicative of whether a therapeutically effective amount has been used.

The phrase "in a sufficient amount to effect a change" means that there is a detectable difference between a level of an indicator measured before (e.g., a baseline level) and after administration of a particular therapy. Indicators include any objective parameter (e.g., serum concentration) or subjective parameter (e.g., a subject's feeling of well-being).

The term "small molecules" refers to chemical compounds having a molecular weight that is less than about 10 kDa, less than about 2 kDa, or less than about 1 kDa. Small molecules include, but are not limited to, inorganic molecules, organic molecules, organic molecules containing an inorganic component, molecules comprising a radioactive atom, and synthetic molecules. Therapeutically, a small molecule may be more permeable to cells, less susceptible to degradation, and less likely to elicit an immune response than large molecules.

The term "ligand" refers to, for example, a peptide, a polypeptide, a membrane-associated or membrane-bound molecule, or a complex thereof, that can act as an agonist or antagonist of a receptor. A ligand encompasses natural and synthetic ligands, e.g., cytokines, cytokine variants, analogs, muteins, and binding compositions derived from antibodies, as well as small molecules. The term also encompasses an agent that is neither an agonist nor antagonist, but that can bind to a receptor without significantly influencing its biological properties, e.g., signaling or adhesion. Moreover, the term includes a membrane-bound ligand that has been changed by, e.g., chemical or recombinant methods, to a soluble version of the membrane-bound ligand. A ligand or receptor may be entirely intracellular, that is, it may reside in the cytosol, nucleus, or some other intracellular compartment. The complex of a ligand and receptor is termed a "ligand-receptor complex."

The terms "inhibitors" and "antagonists", or "activators" and "agonists" refer to inhibitory or activating molecules, respectively, for example, for the activation of, e.g., a ligand, receptor, cofactor, gene, cell, tissue, or organ. Inhibitors are molecules that decrease, block, prevent, delay activation, inactivate, desensitize, or down-regulate, e.g., a gene, protein, ligand, receptor, or cell. Activators are molecules that increase, activate, facilitate, enhance activation, sensitize, or up-regulate, e.g., a gene, protein, ligand, receptor, or cell. An inhibitor may also be defined as a molecule that reduces, blocks, or inactivates a constitutive activity. An "agonist" is a molecule that interacts with a target to cause or promote an increase in the activation of the target. An "antagonist" is a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist.

The terms "modulate", "modulation" and the like refer to the ability of a molecule (e.g., an activator or an inhibitor) to increase or decrease the function or activity of CD73, either directly or indirectly. A modulator may act alone, or it may use a cofactor, e.g., a protein, metal ion, or small molecule. Examples of modulators include small molecule compounds and other bioorganic molecules. Numerous libraries of small molecule compounds (e.g., combinatorial libraries) are commercially available and can serve as a starting point for identifying a modulator. The skilled artisan is able to develop one or more assays (e.g., biochemical or cell-based assays) in which such compound libraries can be screened in order to identify one or more compounds having the desired properties; thereafter, the skilled medicinal chemist is able to optimize such one or more compounds by, for example, synthesizing and evaluating analogs and derivatives thereof. Synthetic and/or molecular modeling studies can also be utilized in the identification of an Activator.

The "activity" of a molecule may describe or refer to the binding of the molecule to a ligand or to a receptor; to catalytic activity; to the ability to stimulate gene expression or cell signaling, differentiation, or maturation; to antigenic activity; to the modulation of activities of other molecules; and the like. The term "proliferative activity" encompasses an activity that promotes, that is necessary for, or that is specifically associated with, for example, normal cell division, as well as cancer, tumors, dysplasia, cell transformation, metastasis, and angiogenesis.

As used herein, "comparable", "comparable activity", "activity comparable to", "comparable effect", "effect comparable to", and the like are relative terms that can be viewed quantitatively and/or qualitatively. The meaning of the terms is frequently dependent on the context in which they are used. By way of example, two agents that both activate a receptor can be viewed as having a comparable effect from a qualitative perspective, but the two agents can be viewed as lacking a comparable effect from a quantitative perspective if one agent is only able to achieve 20% of the activity of the other agent as determined in an art-accepted assay (e.g., a dose-response assay) or in an art-accepted animal model. When comparing one result to another result (e.g., one result to a reference standard), "comparable" frequently (though not always) means that one result deviates from a reference standard by less than 35%, by less than 30%, by less than 25%, by less than 20%, by less than 15%, by less than 10%, by less than 7%, by less than 5%, by less than 4%, by less than 3%, by less than 2%, or by less than 1%. In particular embodiments, one result is comparable to a reference standard if it deviates by less than 15%, by less than 10%, or by less than 5% from the reference standard. By way of example, but not limitation, the activity or effect may refer to efficacy, stability, solubility, or immunogenicity.

"Substantially pure" indicates that a component makes up greater than about 50% of the total content of the composition, and typically greater than about 60% of the total content. More typically, "substantially pure" refers to compositions in which at least 75%, at least 85%, at least 90% or more of the total composition is the component of interest. In some cases, the component of interest will make up greater than about 90%, or greater than about 95% of the total content of the composition.

The terms "specifically binds" or "selectively binds", when referring to a ligand/receptor, antibody/antigen, or other binding pair, indicates a binding reaction which is determinative of the presence of the protein in a heterogeneous population of proteins and other biologics. Thus, under designated conditions, a specified ligand binds to a particular receptor and does not bind in a significant amount to other proteins present in the sample. The antibody, or binding composition derived from the antigen-binding site of an antibody, of the contemplated method binds to its antigen, or a variant or mutein thereof, with an affinity that is at least two-fold greater, at least ten times greater, at least 20-times greater, or at least 100-times greater than the affinity with any other antibody, or binding composition derived therefrom. In a particular embodiment, the antibody will have an affinity that is greater than about $10^9$ liters/mol, as determined by, e.g., Scatchard analysis (Munsen, et al. 1980 Analyt. Biochem. 107:220-239).

The term "response," for example, of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming. In certain contexts, the terms "activation", "stimulation", and the like refer to cell activation as regulated by internal mechanisms, as well as by external or environmental factors; whereas the terms "inhibition", "down-regulation" and the like refer to the opposite effects.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence, fusion proteins with heterologous and homologous leader sequences, with or without N-terminus methionine residues; immunologically tagged proteins; and the like.

As used herein, the terms "variants" and "homologs" are used interchangeably to refer to amino acid or DNA sequences that are similar to reference amino acid or nucleic acid sequences, respectively. The term encompasses naturally-occurring variants and non-naturally-occurring variants. Naturally-occurring variants include homologs (polypeptides and nucleic acids that differ in amino acid or nucleotide sequence, respectively, from one species to another), and allelic variants (polypeptides and nucleic acids that differ in amino acid or nucleotide sequence, respectively, from one individual to another within a species). Thus, variants and homologs encompass naturally occurring DNA sequences and proteins encoded thereby and their isoforms, as well as splice variants of a protein or gene. The terms also encompass nucleic acid sequences that vary in one or more bases from a naturally-occurring DNA sequence but still translate into an amino acid sequence that corresponds to the naturally-occurring protein due to degeneracy of the genetic code. Non-naturally-occurring variants and homologs include polypeptides and nucleic acids that comprise a change in amino acid or nucleotide sequence, respectively, where the change in sequence is artificially introduced (e.g., muteins); for example, the change is generated in the laboratory by human intervention ("hand of man"). Therefore, non-naturally occurring variants and homologs may also refer to those that differ from the naturally-occurring sequences by one or more conservative substitutions and/or tags and/or conjugates.

The term "muteins" as used herein refers broadly to mutated recombinant proteins. These proteins usually carry single or multiple amino acid substitutions and are frequently derived from cloned genes that have been subjected to site-directed or random mutagenesis, or from completely synthetic genes.

The terms "DNA", "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

5'-Nucleotidase, Ecto and Inhibition Thereof

Human CD73 (also referred to as 5'-nucleotidase, ecto; NT5E; or 5NT) is a 574 amino acid residue protein (Accession No. AAH6593). Eukaryotic CD73 functions as a non-covalent homodimer with two structural domains, wherein the N- and C-terminal domains are connected by a hinge region that enables the enzyme to undergo large domain movements and switch between open and closed conformations (Knapp, K. et al. (2012) Structure 20:2161-73).

As used herein, the terms "CD73 inhibitor", "CD73 blocker", "adenosine by 5'-nucleotidase, ecto inhibitor", "NT5E inhibitor", "5NT inhibitor" and all other related art-accepted terms refer to a compound capable of modulating, either directly or indirectly, the CD73 receptor in an in vitro assay, an in vivo model, and/or other means indicative of therapeutic efficacy. The terms also refer to compounds that exhibit at least some therapeutic benefit in a human subject. An CD73 inhibitor may be a competitive, noncompetitive, or irreversible CD73 inhibitor. "A competitive CD73 inhibitor" is a compound that reversibly inhibits CD73 enzyme activity at the catalytic site; "a noncompetitive CD73 inhibitor" is a compound that reversibly inhibits CD73 enzyme activity at a non-catalytic site; and "an irreversible CD73 inhibitor" is a compound that irreversibly eliminates CD73 enzyme activity by forming a covalent bond (or other stable means of inhibiting enzyme function) with the enzyme.

CD73 inhibitors can modulate purinergic signaling, a type of extracellular signaling mediated by purine nucleotides and nucleosides such as ATP and adenosine. Purinergic signaling involves the activation of purinergic receptors in the cell and/or in nearby cells, resulting in the regulation of cellular functions. The enzymatic activity of CD73 plays a strategic role in calibrating the duration, magnitude, and chemical nature of purinergic signals delivered to various cells (e.g., immune cells). Alteration of these enzymatic activities can change the course or dictate the outcome of several pathophysiological events, including cancer, autoimmune and inflammatory diseases, infections, atherosclerosis, and ischemia-reperfusion injury, suggesting that these ecto-enzymes represent novel therapeutic targets for managing a variety of disorders.

Studies using tissues that overexpress CD73 and using CD73 knock-out mice have provided evidence that CD73 inhibitors have potential utility for melanomas, lung cancer, prostate cancer, and breast cancer (see, e.g., Sadej R. (2006) Melanoma Res 16:213-22). Because higher expression levels of CD73 are associated with tumor neovascularization, invasiveness, resistance to chemotherapy, and metastasis, CD73 inhibitors can be used to control tumor progression and metastasis. Other potential utilities are discussed elsewhere herein.

As set forth above, although the compounds of the present invention are believed to exert their activity by inhibition of CD73, a precise understanding of the compounds' underlying mechanism of action is not required to practice the invention. For example, the compounds can also exert their activity, at least in part, through modulation (e.g., inhibition) of other components of the purinergic signaling pathway (e.g., CD39). The purinergic signaling system consists of transporters, enzymes and receptors responsible for the synthesis, release, action, and extracellular inactivation of (primarily) ATP and its extracellular breakdown product adenosine (Sperlagh, B. et al. (December 2012) Neuropsychopharmacologia Hungarica 14(4):231-38). FIG. 1 depicts a simplified representation of extracellular purinergic signaling (see, e.g., North R A (October 2002) *Physiological Reviews* 82(4):1013-67). As indicated therein, there are several potential opportunities for modulation of the signaling process. However, as will be apparent to the skilled artisan, some of these opportunities are more tractable than others.

Identification of CD73 Inhibitors Possessing Desirable Characteristics

The present invention is drawn, in part, to the identification of inhibitors of CD73 with at least one property or characteristic that is of therapeutic relevance. Candidate inhibitors may be identified by using, for example, an art-accepted assay or model, examples of which are will be apparent to the skilled artisan. The assay used to determine the CD73 inhibitory activity of the compounds described herein is set forth in the Experimental section.

After identification, candidate inhibitors can be further evaluated by using techniques that provide data regarding characteristics of the inhibitors (e.g., pharmacokinetic parameters). Comparisons of the candidate inhibitors to a reference standard (which may the "best-of-class" of current inhibitors) are indicative of the potential viability of such candidates.

CD73 inhibitors that can serve as reference or benchmark compounds include α,β-Methylene-ADP (AOPCP) and its derivatives and analogs described by Bhattarai et al. ((2015) J Med Chem 58:6248-63) and the purine CD73 derivatives reported in PCT Publn. 2015/164573. Other reference compounds subsequently identified by the skilled artisan can also be used to assess the viability of candidate CD73 inhibitors.

Compounds of the Invention

Provided herein are compounds having Formula (I):

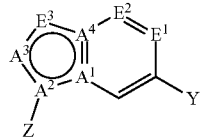

(I)

or a pharmaceutically acceptable salt, hydrate, N-oxide, or solvate thereof, wherein, each of $A^1$, $A^2$ and $A^4$ is independently selected from the group consisting of C, CH and N;

$A^3$ is selected from the group consisting of C(O), CH and N;

each $E^1$ and $E^2$ is independently selected from the group consisting of N, $NR^1$, C(O) and $CR^1$;

$E^3$ is selected from the group consisting of N, $NR^1$ and $CR^1$;

at least two of $A^1$, $A^2$, $A^3$, $A^4$, $E^1$, $E^2$ and $E^3$ are N or $NR^1$;

each $R^1$ is independently selected from the group consisting of hydrogen, halogen, CN, $NH_2$, NH—$C_1$-$C_6$ alkyl, $C_1$-$C_6$ alkyl, $C_1$-$C_6$ haloalkyl, $C_1$-$C_6$ alkoxy, and $C_1$-$C_6$ haloalkoxy, each of which is substituted with from 0 to 3 R;

Y is an optionally substituted 5-6 membered heteroaryl or an optionally substituted 4-7 membered heterocycle, wherein from 1 to 3 ring vertices are selected from N, O, S, SO and $SO_2$;

Z is selected from the group consisting of
i) optionally substituted phenyl;
ii) optionally substituted 5- or 6-membered heteroaryl;
iii) optionally substituted naphthyl; and
iv) optionally substituted 9- or 10-membered heteroaryl;

each R is independently selected from the group consisting of H, halogen, CN, $NH_2$, $NHR^a$, $NR^aR^b$, $R^c$, OH, $OR^a$, $SR^a$, $SO_2R^a$, —$X^a$—$NH_2$, —$X^a$—$NHR^a$, —$X^a$—$NR^aR^b$, —$X^a$—OH, —$X^a$—$OR^a$, —$X^a$—$R^a$, —$X^a$—$SR^a$ and —$X^a$—$SO_2R^a$;

each $R^a$, $R^b$ and $R^c$ is independently selected from the group consisting of $C_1$-$C_6$ alkyl, $C_1$-$C_6$ haloalkyl, $C_1$-$C_6$ hydroxyalkyl, $C_{3-7}$ cycloalkyl, $C_2$-$C_6$ alkenyl and $C_2$-$C_6$ alkynyl, or $R^a$ and $R^b$ attached to N form a 4- to 7-membered ring; and each $X^a$ is independently selected from the group consisting of C(O), $C_1$-$C_4$ alkylene, —O—$C_1$-$C_4$ alkylene and $C_1$-$C_4$ alkylene-O—.

In one group of embodiments, compounds are provided or a pharmaceutically acceptable salt, hydrate, N-oxide, or solvate thereof, having a formula selected from the group consisting of (Ia) and (Ib):

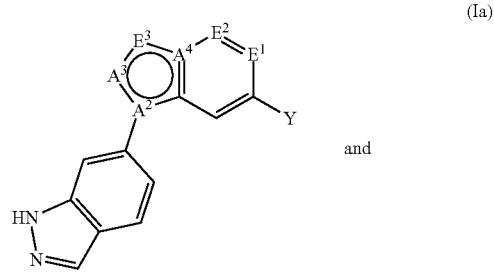

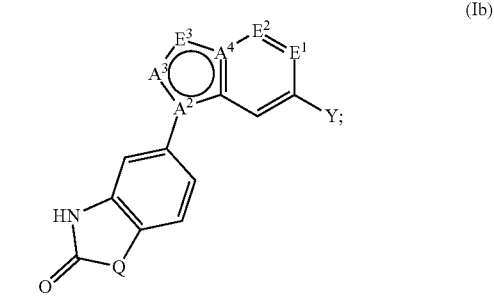

wherein Q is selected from the group consisting of NH, $CH_2$ and O, and the remaining groups are as provided with reference to formula (I).

In one group of embodiments, compounds are provided having a formula selected from (Ia1) and (Ib1), or a pharmaceutically acceptable salt, hydrate, N-oxide, or solvate thereof:

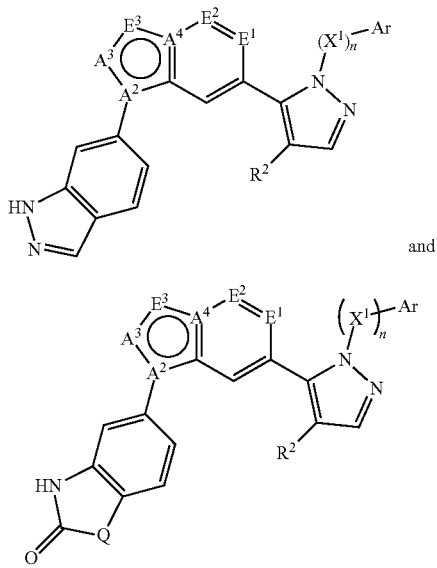

(Ia1)

and (Ib1)

wherein Ar is an unsubstituted or substituted aryl or heteroaryl;
n is 0, 1, or 2;
each $X^1$ is independently —$CHR^3$—;
$R^2$ is selected from the group consisting of H, halogen, CN, $C_1$-$C_4$ alkyl and $C_1$-$C_4$ haloalkyl;
each $R^3$ is independently selected from the group consisting of H and unsubstituted or substituted $C_1$-$C_4$ alkyl;
and the remaining groups are as provided with reference to formula (I).

In one group of embodiments, compounds are provided having a formula selected from (Ia2) and (Ib2), or a pharmaceutically acceptable salt, hydrate, N-oxide, or solvate thereof:

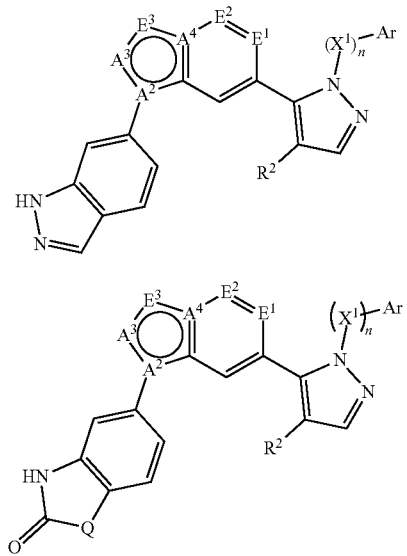

(Ia2)

(Ib2)

wherein the groups are as provided with reference to formula (I) and other embodiments above.

In one group of embodiments, compounds are provided having a formula selected from (Ia3) and (Ib3), or a pharmaceutically acceptable salt, hydrate, N-oxide, or solvate thereof:

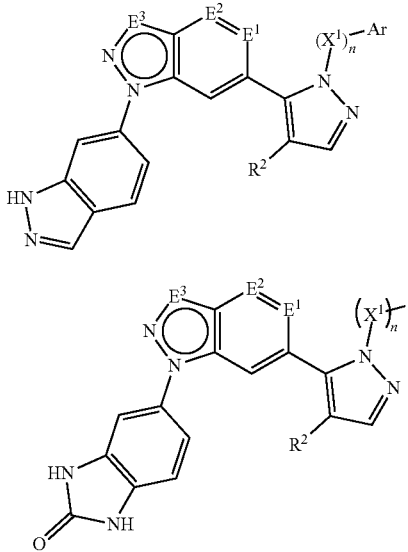

(Ia3)

and (Ib3)

wherein the groups are as provided with reference to formula (I) and other embodiments above.

In one group of embodiments, compounds are provided having a formula selected from (Ia4) and (Ib4), or a pharmaceutically acceptable salt, hydrate, N-oxide, or solvate thereof:

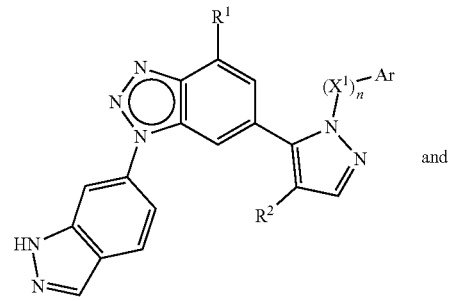

(Ia4)

and

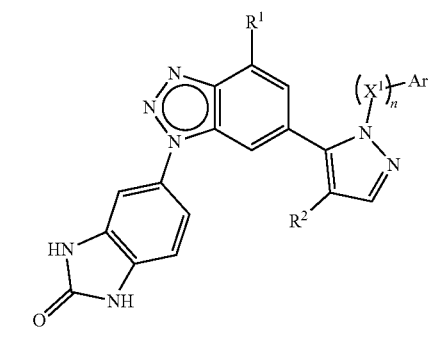

(Ib4)

wherein the groups are as provided with reference to formula (I) and other embodiments above.

In one group of embodiments, compounds are provided having a formula selected from (Ia5) and (Ib5), or a pharmaceutically acceptable salt, hydrate, N-oxide, or solvate thereof:

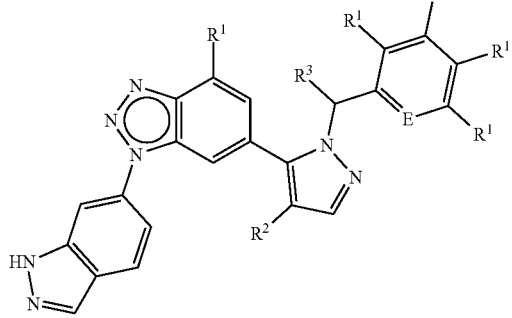

(Ia5)

and

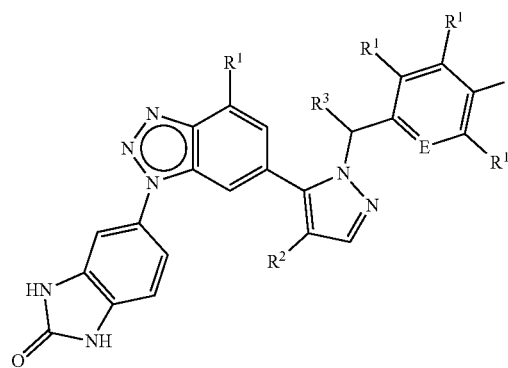

(Ib5)

wherein the groups are as provided with reference to formula (I) and other embodiments above.

In one group of embodiments, compounds are provided having a formula selected from (Ia6) and (Ib6), or a pharmaceutically acceptable salt, hydrate, N-oxide, or solvate thereof:

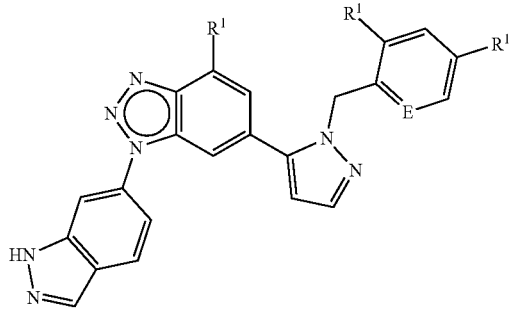

(Ia6)

and

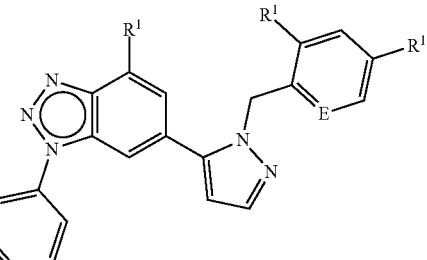

(Ib6)

wherein the groups are as provided with reference to formula (I) and other embodiments above.

In one group of embodiments, compounds are provided having a formula selected from (Ia7) and (Ib7), or a pharmaceutically acceptable salt, hydrate, N-oxide, or solvate thereof:

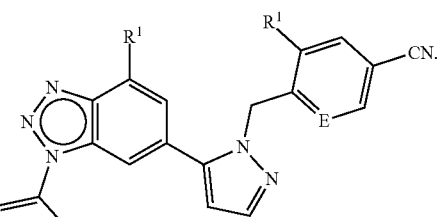

(Ia7) and

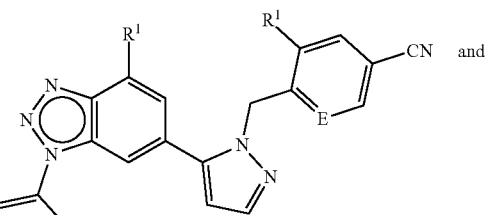

(Ib7)

wherein the groups are as provided with reference to formula (I) and other embodiments above.

In one group of embodiments, compounds are provided having a formula selected from (Ia8) and (Ib8), or a pharmaceutically acceptable salt, hydrate, N-oxide, or solvate thereof:

(Ia8)

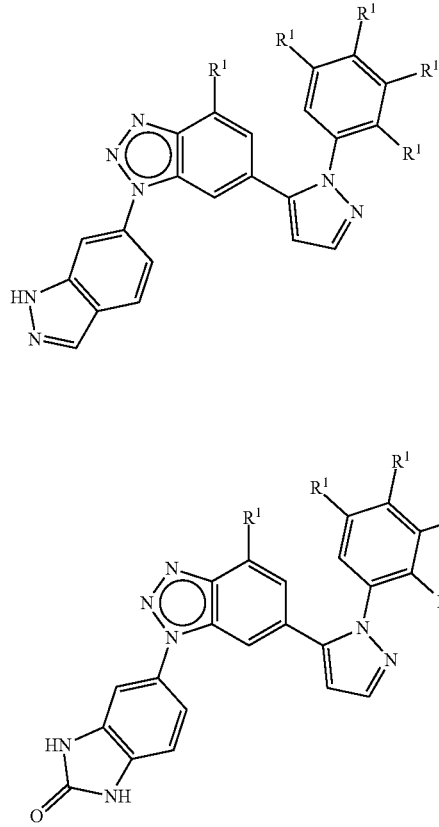

and (Ib8)

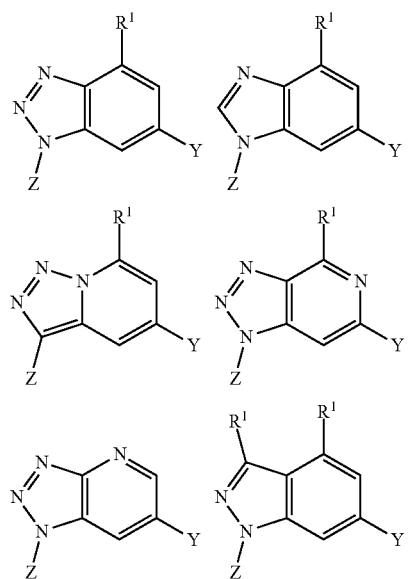

wherein the groups are as provided with reference to formula (I) and other embodiments above.

In one group of embodiments, compounds are provided having formula (I) above, or a pharmaceutically acceptable salt, hydrate, N-oxide, or solvate thereof, wherein having a formula selected from the group consisting of:

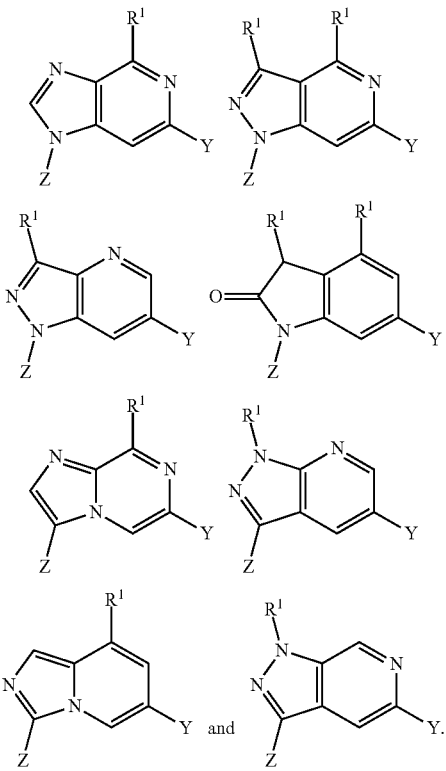

In one group of embodiments, compounds are provided having formula (I) above, or a pharmaceutically acceptable salt, hydrate, N-oxide, or solvate thereof, wherein having a formula selected from the group consisting of:

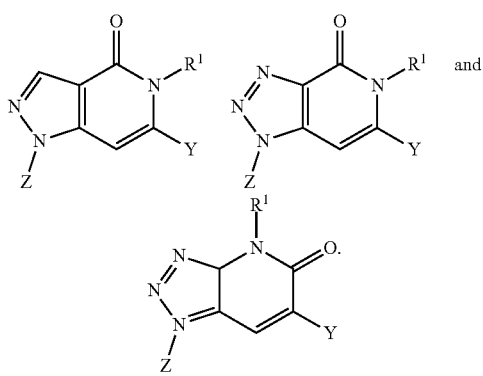

In one group of embodiments, compounds are provided having formula (I) above, or a pharmaceutically acceptable salt, hydrate, N-oxide, or solvate thereof, wherein Y is a pyrazole, substituted with a member selected from the group consisting of:

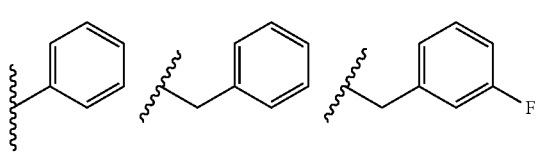

-continued

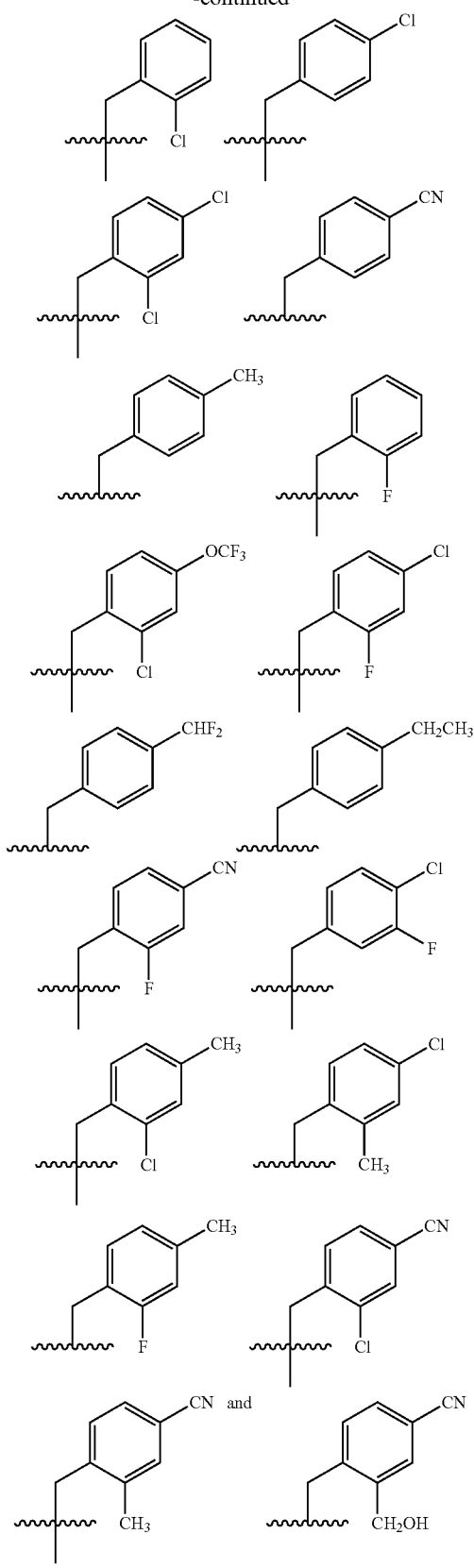

In another group of embodiments, compounds are provided having formula (I) above, or a pharmaceutically acceptable salt, hydrate, N-oxide, or solvate thereof, wherein Y is a pyrazole, substituted with a member selected from the group consisting of:

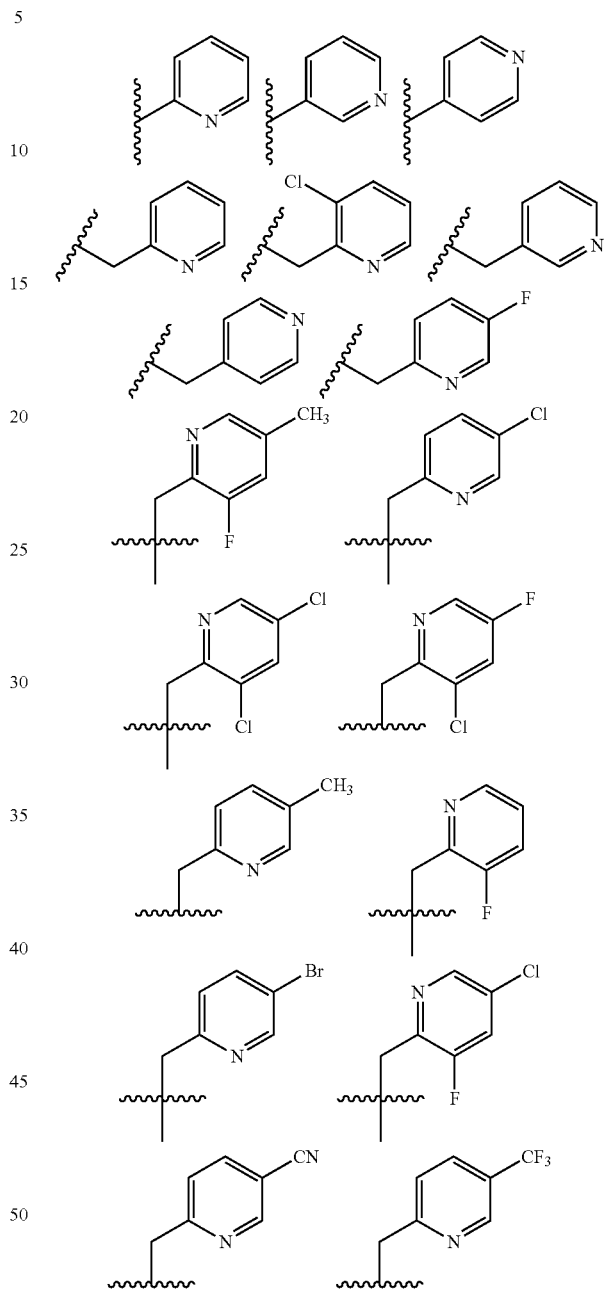

In still another group of embodiments, compounds are provided having formula (I) above, or a pharmaceutically acceptable salt, hydrate, N-oxide, or solvate thereof, wherein Y is a pyrazole, substituted with a member selected from the group consisting of:

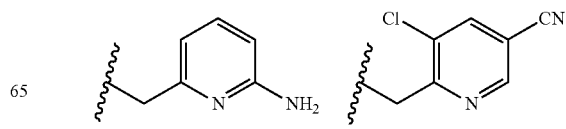

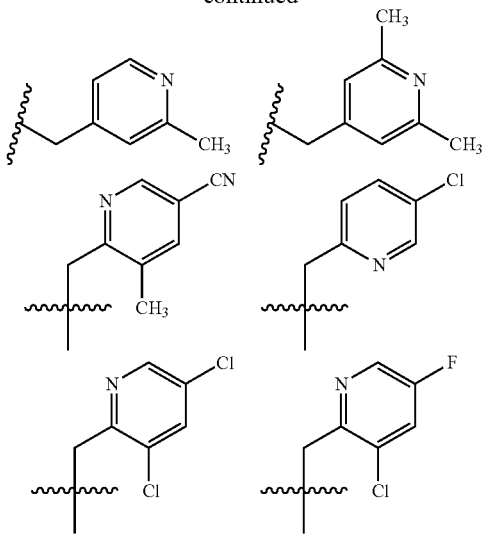

Methods of Synthesis

In general, the compounds provided herein can be prepare by conventional methods as described in the Examples below.

Modifications to Enhance Inhibitor Characteristics

It is frequently beneficial, and sometimes imperative, to improve one of more physical properties of the treatment modalities disclosed herein and/or the manner in which they are administered. Improvements of physical properties include, for example, methods of increasing water solubility, bioavailability, serum half-life, and/or therapeutic half-life; and/or modulating biological activity.

Modifications known in the art include pegylation, Fc-fusion and albumin fusion. Although generally associated with large molecule agents (e.g., polypeptides), such modifications have recently been evaluated with particular small molecules. By way of example, Chiang, M. et al. (J. Am. Chem. Soc., 2014, 136(9):3370-73) describe a small molecule agonist of the adenosine 2a receptor conjugated to the immunoglobulin Fc domain. The small molecule-Fc conjugate retained potent Fc receptor and adenosine 2a receptor interactions and showed superior properties compared to the unconjugated small molecule. Covalent attachment of PEG molecules to small molecule therapeutics has also been described (Li, W. et al., Progress in Polymer Science, 2013 38:421-44).

Therapeutic and Prophylactic Uses

The present invention contemplates the use of the CD73 inhibitors described herein in the treatment or prevention of a broad range of diseases, disorders and/or conditions, and/or the symptoms thereof. While particular uses are described in detail hereafter, it is to be understood that the present invention is not so limited. Furthermore, although general categories of particular diseases, disorders and conditions are set forth hereafter, some of the diseases, disorders and conditions may be a member of more than one category, and others may not be a member of any of the disclosed categories.

Oncology-related Disorders. In accordance with the present invention, an CD73 inhibitor can be used to treat or prevent a proliferative condition or disorder, including a cancer, for example, cancer of the uterus, cervix, breast, prostate, testes, gastrointestinal tract (e.g., esophagus, oropharynx, stomach, small or large intestines, colon, or rectum), kidney, renal cell, bladder, bone, bone marrow, skin, head or neck, liver, gall bladder, heart, lung, pancreas, salivary gland, adrenal gland, thyroid, brain (e.g., gliomas), ganglia, central nervous system (CNS) and peripheral nervous system (PNS), and cancers of the hematopoietic system and the immune system (e.g., spleen or thymus). The present invention also provides methods of treating or preventing other cancer-related diseases, disorders or conditions, including, for example, immunogenic tumors, non-immunogenic tumors, dormant tumors, virus-induced cancers (e.g., epithelial cell cancers, endothelial cell cancers, squamous cell carcinomas and papillomavirus), adenocarcinomas, lymphomas, carcinomas, melanomas, leukemias, myelomas, sarcomas, teratocarcinomas, chemically-induced cancers, metastasis, and angiogenesis. The invention contemplates reducing tolerance to a tumor cell or cancer cell antigen, e.g., by modulating activity of a regulatory T-cell and/or a CD8+ T-cell (see, e.g., Ramirez-Montagut, et al. (2003) Oncogene 22:3180-87; and Sawaya, et al. (2003) New Engl. J. Med. 349:1501-09). In particular embodiments, the tumor or cancer is colon cancer, ovarian cancer, breast cancer, melanoma, lung cancer, glioblastoma, or leukemia. The use of the term(s) cancer-related diseases, disorders and conditions is meant to refer broadly to conditions that are associated, directly or indirectly, with cancer, and includes, e.g., angiogenesis and precancerous conditions such as dysplasia.

In certain embodiments, a cancer be metastatic or at risk of becoming metastatic, or may occur in a diffuse tissue, including cancers of the blood or bone marrow (e.g., leukemia). In some further embodiments, the compounds of the invention can be used to overcome T-cell tolerance.

In some embodiments, the present invention provides methods for treating a proliferative condition, cancer, tumor, or precancerous condition with an CD73 inhibitor and at least one additional therapeutic or diagnostic agent, examples of which are set forth elsewhere herein.

Immune-related Disorders and Disorders with an Inflammatory Component. As used herein, terms such as "immune disease", "immune condition", "immune disorder", "inflammatory disease", "inflammatory condition", "inflammatory disorder" and the like are meant to broadly encompass any immune-related condition (e.g., an autoimmune disease) or a disorder with an inflammatory component that can be treated by the CD73 inhibitors described herein such that some therapeutic benefit is obtained. Such conditions frequently are inextricably intertwined with other diseases, disorders and conditions. By way of example, an "immune condition" may refer to proliferative conditions, such as cancer, tumors, and angiogenesis; including infections (acute and chronic), tumors, and cancers that resist eradication by the immune system.

The CD73 inhibitors of the present invention can be used to increase or enhance an immune response; to improve immunization, including increasing vaccine efficacy; and to increase inflammation. Immune deficiencies associated with immune deficiency diseases, immunosuppressive medical treatment, acute and/or chronic infection, and aging can be treated using the compounds disclosed herein. The CD73 inhibitors can also be used to stimulate the immune system of patients suffering from iatrogenically-induced immune suppression, including those who have undergone bone marrow transplants, chemotherapy, or radiotherapy.

In particular embodiments of the present disclosure, the CD73 inhibitors are used to increase or enhance an immune response to an antigen by providing adjuvant activity. In a particular embodiment, at least one antigen or vaccine is administered to a subject in combination with at least one CD73 inhibitor of the present invention to prolong an immune response to the antigen or vaccine. Therapeutic compositions are also provided which include at least one antigenic agent or vaccine component, including, but not limited to, viruses, bacteria, and fungi, or portions thereof, proteins, peptides, tumor-specific antigens, and nucleic acid vaccines, in combination with at least one CD73 inhibitor of the present invention.

Microbial-related Disorders. By inhibiting the immunosuppressive and anti-inflammatory activity of CD73, the present invention contemplates the use of the CD73 inhibitors described herein in the treatment and/or prevention of any viral, bacterial, fungal, parasitic or other infective disease, disorder or condition for which treatment with an CD73 inhibitor may be beneficial. Examples of such diseases and disorders include HIV and AIDS, staphylococcal and streptococcal infections (e.g., *Staphylococcus aureus* and *Streptococcus sanguinis*, respectively), leishmania, toxoplasma, trichomonas, *Giardia, Candida albicans, Bacillus anthracis*, and *Pseudomonas aeruginosa*. Compounds of the invention can be used to treat sepsis, decrease or inhibit bacterial growth, and reduce or inhibit inflammatory cytokines.

CNS-related and Neurological Disorders. Inhibition of CD73 may also be an important treatment strategy for patients with neurological, neuropsychiatric, neurodegenerative or other diseases, disorders and conditions having some association with the central nervous system, including disorders associated with impairment of cognitive function and motor function. Examples include Parkinson's disease, extra pyramidal syndrome (EPS), dystonia, akathisia, tardive dyskinesia, restless leg syndrome (RLS), epilepsy, periodic limb movement in sleep (PLMS), attention deficit disorders, depression, anxiety, dementia, Alzheimer's disease, Huntington's disease, multiple sclerosis, cerebral ischemia, hemorrhagic stroke, subarachnoid hemorrhage, and traumatic brain injury.

Other Disorders. Embodiments of the present invention contemplate the administration of the CD73 inhibitors described herein to a subject for the treatment or prevention of any other disorder that may benefit from at least some level of CD73 inhibition. Such diseases, disorders and conditions include, for example, cardiovascular (e.g., cardiac ischemia), gastrointestinal (e.g., Crohn's disease), metabolic (e.g., diabetes), hepatic (e.g., hepatic fibrosis, NASH, and NAFLD), pulmonary (e.g., COPD and asthma), ophthalmologic (e.g., diabetic retinopathy), and renal (e.g., renal failure) disorders.

In some embodiments, the CD73 inhibitors of the present invention may be used to inhibit statin-induced adenosine production, or reduce or decrease increases in blood glucose caused by a statin in a subject taking a statin (e.g., lovastatin and pravastatin)

Pharmaceutical Compositions

The CD73 inhibitors of the present invention may be in the form of compositions suitable for administration to a subject. In general, such compositions are "pharmaceutical compositions" comprising an CD73 inhibitor(s) and one or more pharmaceutically acceptable or physiologically acceptable diluents, carriers or excipients. In certain embodiments, the CD73 inhibitors are present in a therapeutically acceptable amount. The pharmaceutical compositions may be used in the methods of the present invention; thus, for example, the pharmaceutical compositions can be administered ex vivo or in vivo to a subject in order to practice the therapeutic and prophylactic methods and uses described herein.

The pharmaceutical compositions of the present invention can be formulated to be compatible with the intended method or route of administration; exemplary routes of administration are set forth herein. Furthermore, the pharmaceutical compositions may be used in combination with other therapeutically active agents or compounds as described herein in order to treat or prevent the diseases, disorders and conditions as contemplated by the present invention.

The pharmaceutical compositions containing the active ingredient (e.g., an inhibitor of CD73 function) may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylenevinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly (methylmethacrylate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions of the present invention may also be in the form of oil-in-water emulsions. The oily phase may be a vegetable oil, for example olive oil or arachis oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

The pharmaceutical compositions typically comprise a therapeutically effective amount of an CD73 inhibitor contemplated by the present invention and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (IVIES), 2-(N-Morpholino)ethanesulfonic acid sodium salt (IVIES), 3-(N-Morpholino)propanesulfonic acid (MOPS), and N-tris[Hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampoule, syringe, or autoinjector (similar to, e.g., an EpiPen®)), whereas a multi-use container (e.g., a multi-use vial) is provided in other embodiments.

Formulations can also include carriers to protect the composition against rapid degradation or elimination from the body, such as a controlled release formulation, including liposomes, hydrogels, prodrugs and microencapsulated delivery systems. For example, a time delay material such as glyceryl monostearate or glyceryl stearate alone, or in combination with a wax, may be employed. Any drug delivery apparatus may be used to deliver an CD73 inhibitor, including implants (e.g., implantable pumps) and catheter systems, slow injection pumps and devices, all of which are well known to the skilled artisan.

Depot injections, which are generally administered subcutaneously or intramuscularly, may also be utilized to release the CD73 inhibitors disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor EL™ (BASF, Parsippany, NJ) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose any bland fixed oil may be employed, including synthetic mono- or diglycerides. Moreover, fatty acids such as oleic acid, find use in the preparation of injectables. Prolonged absorption of particular injectable formulations can be achieved by including an agent that delays absorption (e.g., aluminum monostearate or gelatin).

The present invention contemplates the administration of the CD73 inhibitors in the form of suppositories for rectal administration. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The CD73 inhibitors contemplated by the present invention may be in the form of any other suitable pharmaceutical composition (e.g., sprays for nasal or inhalation use) currently known or developed in the future.

Routes of Administration

The present invention contemplates the use of CD73 inhibitors alone or in combination with one or more active therapeutic agents. The additional active therapeutic agents can be small chemical molecules; macromolecules such as proteins, antibodies, peptibodies, peptides, DNA, RNA or fragments or such macromolecules; or cellular or gene therapies. The combination therapy may target different, but complementary mechanisms of action and thereby have a synergistic therapeutic or prophylactic effect on the underlying disease, disorder, or condition. In addition or alternatively, the combination therapy may allow for a dose reduction of one or more of the agents, thereby ameliorating, reducing or eliminating adverse effects associated with one or more of the agents.

The active therapeutic agents in such combination therapy can be formulated as a single composition or as separate compositions. If administered separately, each therapeutic agent in the combination can be given at or around the same time, or at different times. Furthermore, the therapeutic agents are administered "in combination" even if they have different forms of administration (e.g., oral capsule and intravenous), they are given at different dosing intervals, one therapeutic agent is given at a constant dosing regimen while another is titrated up, titrated down or discontinued, or each therapeutic agent in the combination is independently titrated up, titrated down, increased or decreased in dosage, or discontinued and/or resumed during a patient's course of therapy. If the combination is formulated as separate compositions, in some embodiments, the separate compositions are provided together in a kit.

In one embodiment, the present invention is used in combination with a chemotherapeutic agent, which agents are well known to those skilled in the art, to treat and/or prevent a proliferative condition, cancer, tumor or precancerous disease, disorder or condition. Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chiorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate and pemetrexed; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel and doxetaxel; chlorambucil; gemcitabine; 6-thioguanine; mercaptopurine; methotrexate; platinum and platinum coordination complexes such as cisplatin, carboplatin and oxaliplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylornithine (DMFO); retinoic acid; esperamicins; capecitabine; and pharmaceutically acceptable salts, acids or derivatives of any of the above.

In certain embodiments, the chemotherapeutic agent may additionally include antihormonal agents that act to regulate or inhibit hormonal action on tumors such as anti-estrogens, including tamoxifen, raloxifene, aromatase inhibiting 4(5)-imidazoles, 4-hydroxytamoxifen, trioxifene, keoxifene, onapristone, and toremifene; and anti-androgens such as flutamide, nilutamide, bicalutamide, leuprolide, and goserelin. In other embodiments, the chemotherapeutic agent may additionally include a hormone or related hormonal agent.

In another embodiment, the present invention is used in combination with a signal transduction inhibitor, which is an agent that selectively inhibits one or more steps in a signaling pathway, to achieve additive or synergistic suppression of tumor growth. Signal transduction inhibitors include bcr/abl kinase inhibitors (e.g., GLEEVEC®), epidermal growth factor receptor inhibitors including kinase inhibitors and antibodies, her-2/neu receptor inhibitors (e.g., HERCEPTIN®), inhibitors of Akt family kinases or the Akt pathway (e.g., rapamycin), cell cycle kinase inhibitors (e.g., flavopiridol), and phosphatidyl inositol kinase inhibitors.

In another embodiment, the present invention is used in combination with a monoclonal antibody, or an antigen binding portion thereof. Antibodies which can be used in such combination therapy may be murine, chimeric, humanized or fully human. In certain embodiments, the monoclonal antibody may target immune system checkpoints (ligands and receptors), such as PD1 (programmed cell death protein 1), PDL1 (PD1 ligand), BTLA (B and T lymphocyte attenuator), CTLA4 (cytotoxic T-lymphocyte associated antigen 4), TIM3 (T-cell membrane protein 3), LAG3 (lymphocyte activation gene 3), TIGIT (T cell immunoreceptor with Ig and ITIM domains), and killer inhibitory receptors, which can be divided into two classes based on their structural features: killer cell immunoglobulin-like receptors and C-type lectin receptors (members of the type II transmembrane receptor family). Other less well-defined immune checkpoints have been described in the literature, including both receptors (e.g., the 2B4 (also known as CD244) receptor) and ligands (e.g., certain B7 family inhibitory ligands such B7-H3 (also known as CD276) and B7-H4 (also known as B7-S1, B7x and VCTN1)). [See Pardoll, (April 2012) Nature Rev. Cancer 12:252-64]. In other embodiments, the antibody is conjugated to a chemical compound that is cytotoxic to a cancer cell or to a liposome. In other embodiments, the antibody is a bispecific antibody in which a first antibody is derivatized or linked to one or more other functional molecules to generate a multi-specific molecule capable of binding to two or more binding sites and/or target molecules.

In another embodiment, the present invention is used in combination with therapeutic agents that modulate the tumor microenvironment. Adenosine mediates its immunosuppressive actions through four G protein-coupled receptors. In particular, the A2A (ADORA2A) and A2B (ADORA2B) adenosine receptors expressed by immune cells are emerging as key regulators of antitumor immunity. [*Oncoimmunology*. 2016 May; 5(5): e1127496]. Moreover, adenosine receptor 2A blockade has been shown to increase the efficacy of anti-PD-1 through enhanced anti-tumor T cell responses (P. Beavis, et al., Cancer Immunol Res DOI: 10.1158/2326-6066.CIR-14-0211 Published 11 Feb. 2015). Such therapeutic agents may target both A2A and A2B receptors, or may be selective for either A2A or A2B. Arginase I (ARG-1) depletes arginine from the tumor microenvironment, leading to impaired T cell function such as stopped proliferation and secretion of cytokines. [Rodriguez et al (2002). Regulation of T cell receptor CD3zeta chain expression by L-arginine. J Biol Chem 277: 21123-21129; Munder, Arginase in the Immune System, British Journal of Pharmacology (2009) 158 638-651].

In another embodiment, the present invention is used in combination with an antigen presenting cell, which mediates cellular immune response by processing and presenting antigens for recognition by certain lymphocytes such as T cells. Antigen presenting cells include dendritic cells, which can be used to prime antigen-specific responses, and macrophages. In another embodiment, the present invention is used in combination with TLR agonists to stimulate such antigen presenting cells.

In another embodiment, the present invention is used in combination with adoptive cell therapy, a new and promising form of personalized immunotherapy in which immune cells with anti-tumor activity are administered to cancer patients. Adoptive cell therapy is being explored using tumor-infiltrating lymphocytes (TIL) and T cells engineered to express, for example, chimeric antigen receptors (CAR) or T cell receptors (TCR). Adoptive cell therapy generally involves collecting T cells from an individual, genetically modifying them to target a specific antigen or to enhance their anti-tumor effects, amplifying them to a sufficient number, and infusion of the genetically modified T cells into a cancer patient. T cells can be collected from the patient to whom the expanded cells are later reinfused (e.g., autologous) or can be collected from donor patients (e.g., allogeneic).

In another embodiment, the present invention is used in combination with RNA interference-based therapies to silence gene expression. RNAi begins with the cleavage of longer double-stranded RNAs into small interfering RNAs (siRNAs). One strand of the siRNA is incorporated into a ribonucleoprotein complex known as the RNA-induced silencing complex (RISC), which is then used to identify mRNA molecules that are at least partially complementary to the incorporated siRNA strand. RISC can bind to or cleave the mRNA, both of which inhibits translation.

In another embodiment, the present invention is used in combination with an anti-viral agent targeting various viral life-cycle stages and having different mechanisms of action, including inhibitors of viral uncoating (e.g., amantadine and rimantidine), reverse transcriptase inhibitors (e.g., acyclovir, zidovudine, and lamivudine), agents that target integrase, agents that block attachment of transcription factors to viral DNA, agents (e.g., antisense molecules) that impact translation (e.g., fomivirsen), agents that modulate translation/ribozyme function, protease inhibitors, viral assembly modulators (e.g., rifampicin), antiretrovirals such as, for example, nucleoside analogue reverse transcriptase inhibitors (e.g., azidothymidine (AZT), ddI, ddC, 3TC, d4T), non-nucleoside reverse transcriptase inhibitors (e.g., efavirenz, nevirapine), nucleotide analogue reverse transcriptase inhibitors, and agents that prevent release of viral particles (e.g., zanamivir and oseltamivir). Other examples of antiviral agents include abacavir, adefovir, amprenavir, ampligen, arbidol, atazanavir, atripla, boceprevirertet, cidofovir, combivir, darunavir, delavirdine, didanosine, docosanol, edoxudine, emtricitabine, enfuvirtide, entecavir, famciclovir, fosamprenavir, foscarnet, fosfonet, ganciclovir, ibacitabine, imunovir, idoxuridine, imiquimod, indinavir, inosine, various interferons (e.g., peginterferon alfa-2a), lopinavir, loviride, maraviroc, moroxydine, methisazone, nelfinavir, nexavir, penciclovir, peramivir, pleconaril, podophyllotoxin, raltegravir, ribavirin, ritonavir, pyramidine, saquinavir, stavudine, telaprevir, tenofovir, tipranavir, trifluridine, trizivir, tromantadine, truvada, valaciclovir, valganciclovir, vicriviroc, vidarabine, viramidine, and zalcitabine.

In another embodiment, the present invention is used in combination with an antibacterial agent. Examples of antibacterial agents include those that target the bacterial cell wall (e.g., cephalosporins and penicillins) or the cell membrane (e.g., polymyxins), or interfere with essential bacterial enzymes (e.g., sulfonamides, rifamycins, and quinolines). Most antibacterial agents that target protein synthesis (e.g., tetracyclines and macrolides) are bacteriostatic, whereas agents such as the aminoglycoside are bactericidal. Another means of categorizing antibacterial agents is based on their target specificity; "narrow-spectrum" agents target specific types of bacteria (e.g., Gram-positive bacteria such as *Streptococcus*), while "broad-spectrum" agents have activity against a broader range of bacteria. The skilled artisan is aware of types of antibacterial agents that are appropriate for use in specific bacterial infections.

In another embodiment, the present invention is used in combination with an antifungal agent. Examples of antifungal agents include polyenes (e.g., amphotericin, nystatin, and pimaricin), azoles (e.g., fluconazole, itraconazole, and ketoconazole), allylamines (e.g., naftifine, and terbinafine), morpholines (e.g., amorolfine), and antimetabolites (e.g., 5-fluorocytosine).

In another embodiment, the present invention is used in combination to treat and/or prevent certain cardiovascular- and/or metabolic-related diseases, disorders and conditions. Examples of therapeutic agents useful in combination with a CD73 inhibitor include statins (e.g., CRESTOR, LESCOL, LIPITOR, MEVACOR, PRAVACOL, and ZOCOR), which inhibit the enzymatic synthesis of cholesterol; bile acid resins (e.g., COLESTID, LO-CHOLEST, PREVALITE, QUESTRAN, and WELCHOL), which sequester cholesterol and prevent its absorption; ezetimibe (ZETIA), which blocks cholesterol absorption; fabric acid (e.g., TRICOR), which reduces triglycerides and may modestly increase HDL; niacin (e.g., NIACOR), which modestly lowers LDL cholesterol and triglycerides; and/or a combination of the aforementioned (e.g., VYTORIN (ezetimibe with simvastatin). Alternative cholesterol treatments that may be candidates for use in combination with the CD73 inhibitors described herein include various supplements and herbs (e.g., garlic, policosanol, and guggul).

Examples of other therapeutic treatments that can be used in combination with one or more compounds of the present invention include radiotherapy, transplantation and surgery, which are well known to those skilled in the art.

The present invention encompasses pharmaceutically acceptable salts, acids or derivatives of the agents (and members of the classes of agents) set forth above.

Dosing

The CD73 inhibitors of the present invention may be administered to a subject in an amount that is dependent upon, for example, the goal of administration (e.g., the degree of resolution desired); the age, weight, sex, and health and physical condition of the subject to which the formulation is being administered; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (the maximum tolerated dose (MTD)) and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount is more than the calculated ED50, in other situations the effective amount is less than the calculated ED50, and in still other situations the effective amount is the same as the calculated ED50.

In addition, an effective dose of the CD73 inhibitors of the present invention may be an amount that, when administered in one or more doses to a subject, produces a desired result relative to a healthy subject. For example, for a subject experiencing a particular disorder, an effective dose may be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

In certain embodiments, the CD73 inhibitors contemplated by the present invention may be administered (e.g., orally) at dosage levels of about 0.01 mg/kg to about 50 mg/kg, or about 1 mg/kg to about 25 mg/kg, of subject body weight per day, one or more times a day, to obtain the desired therapeutic effect.

For administration of an oral agent, the compositions can be provided in the form of tablets, capsules and the like containing from 1.0 to 1000 milligrams of the active ingredient, particularly 1.0, 3.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient.

In certain embodiments, the dosage of the desired CD73 inhibitor is contained in a "unit dosage form". The phrase "unit dosage form" refers to physically discrete units, each unit containing a predetermined amount of the CD73 inhibitor, either alone or in combination with one or more additional agents, sufficient to produce the desired effect. It will be appreciated that the parameters of a unit dosage form will depend on the particular agent and the effect to be achieved.

Kits

The present invention also contemplates kits comprising an CD73 inhibitor, and pharmaceutical compositions thereof. The kits are generally in the form of a physical structure housing various components, as described below, and may be utilized, for example, in practicing the methods described above.

A kit can include one or more of the CD73 inhibitors disclosed herein (provided in, e.g., a sterile container), which may be in the form of a pharmaceutical composition suitable for administration to a subject. The CD73 inhibitors can be provided in a form that is ready for use (e.g., a tablet or capsule) or in a form requiring, for example, reconstitution or dilution (e.g., a powder) prior to administration. When the CD73 inhibitors are in a form that needs to be reconstituted or diluted by a user, the kit may also include diluents (e.g., sterile water), buffers, pharmaceutically acceptable excipients, and the like, packaged with or separately from the CD73 inhibitors. When combination therapy is contemplated, the kit may contain the several agents separately or they may already be combined in the kit. Each component of the kit may be enclosed within an individual container, and all of the various containers may be within a single package. A kit of the present invention may be designed for conditions necessary to properly maintain the components housed therein (e.g., refrigeration or freezing).

A kit may contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampule, tube or vial).

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via the internet, are provided.

EXAMPLES

The following examples are put forth so as to provide those of ordinary skill in the art with a complete disclosure and description of how to make and use the present invention, and are not intended to limit the scope of what the inventors regard as their invention, nor are they intended to represent that the experiments below were performed or that they are all of the experiments that may be performed. It is to be understood that exemplary descriptions written in the present tense were not necessarily performed, but rather that the descriptions can be performed to generate data and the like of a nature described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: wt=wildtype; bp=base pair(s); kb=kilobase(s); nt=nucleotides(s); aa=amino acid(s); s or sec=second(s); min=minute(s); h or hr=hour(s); ng=nanogram; µg=microgram; mg=milligram; g=gram; kg=kilogram; dl or dL=deciliter; µl or µL=microliter; ml or mL=milliliter; l or L=liter; µM=micromolar; mM=millimolar; M=molar; kDa=kilodalton; i.m.=intramuscular(ly); i.p.=intraperitoneal(ly); SC or SQ=subcutaneous(ly); QD=daily; BID=twice daily; QW=weekly; QM=monthly; HPLC=high performance liquid chromatography; BW=body weight; U=unit; ns=not statistically significant; PBS=phosphate-buffered saline; IHC=immunohistochemistry; DMEM=Dulbeco's Modification of Eagle's Medium; EDTA=ethylenediaminetetraacetic acid.

LC: Agilent 1100 series; Mass spectrometer: Agilent G6120BA, single quad
LC-MS method: Agilent Zorbax Eclipse Plus C18, 4.6×100 mm, 3.5 µM, 35° C., 1.5 mL/min flow rate, a 2.5 min gradient of 0% to 100% B with 0.5 min wash at 100% B; A=0.1% of formic acid/5% acetonitrile/94.9% water; B=0.1% of formic acid/5% water/94.9% acetonitrile
Flash column: ISCO Rf+
Reverse phase HPLC: ISCO-EZ; Column: Kinetex 5 µm EVO C18 100 A; 250×21.2 mm (Phenomenex)

Example 1

Synthesis of 5-(6-{1-[(2,4-dichlorophenyl)methyl]-1H-pyrazol-5-yl}-1H-[1,2,3]triazolo[4,5-c]pyridin-1-yl)-2,3-dihydro-1H-1,3-benzodiazol-2-one

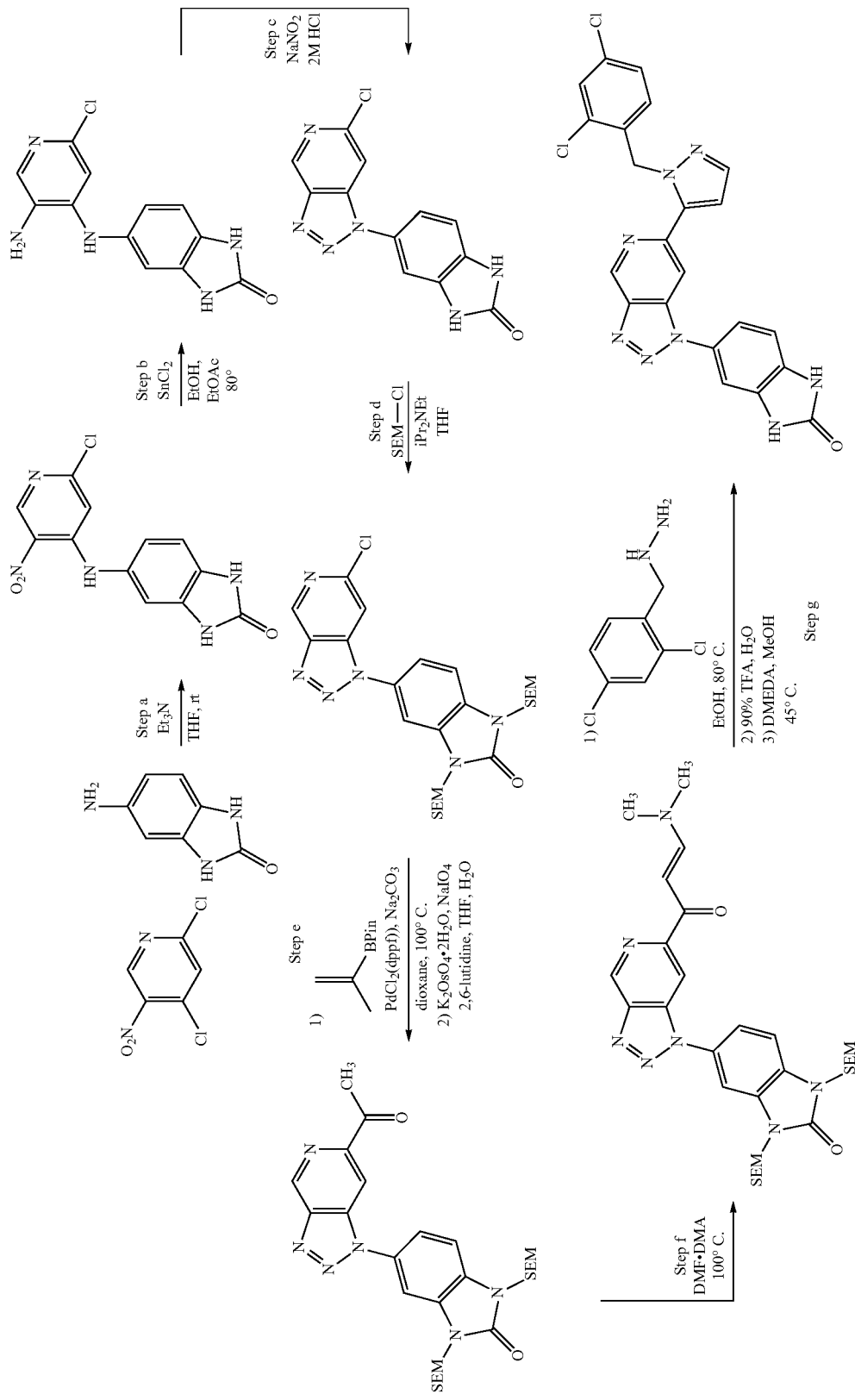

Step a: To a solution of 2,4-dichloro-5-nitro-pyridine (10.1 g, 52.3 mmol) and 5-aminobenzimidazolone (7.8 g, 52.3 mmol) in THF (261 mL) was added Et$_3$N (8.0 mL, 57.5 mmol). The mixture was stirred at room temperature overnight. Upon completion, the reaction was filtered and the cake washed with THF. The solid was slurried in water and filtered. The cake was washed with water and Et$_2$O. The solid was dried under high vacuum overnight and used without further purification. ESI MS [M+H]$^+$ for C$_{12}$H$_8$ClN$_5$O$_3$, calcd 306.0. found 306.1.

Step b: The product from step a (52.3 mmol) was suspended in EtOAc (325 mL) and EtOH (235 mL) and heated to 80° C. SnCl$_2$ (49.6 g, 262 mmol) was added in portions over one hour and heating continued overnight. Upon completion, the reaction was cooled to 0° C. in an ice-bath and 1.0 M Na$_2$CO$_3$ was added until pH>7. The resulting precipitate was filtered through Celite®. The filter cake was washed with methanol and THF. The filtrate was evaporated under reduced pressure and the resulting solids triturated with water and Et$_2$O to provide the desired 1,2-diamine (13.31 g, 92% yield) in high purity. ESI MS [M+H]$^+$ for C$_{12}$H$_{10}$ClN$_5$O, calcd 276.1. found 276.1.

Step c: To a solution of the product from step b (13.31 g, 48.3 mmol) in 2 M aq. HCl (193 mL) at room temperature was added NaNO$_2$ (4.0 g, 58.0 mmol) in portions over 30 minutes. The reaction was stirred for one hour following final addition. The reaction was filtered and washed with water. The wet precipitate was dried under high vacuum overnight to afford the desired triazolopyridine (11.57 g, 84% yield).

Step d: To a solution of the product from step c (11.57 g, 40.4 mmol) and iPr$_2$NEt (28.1 mL, 161.6 mmol) in THF (202 mL) was added SEM-Cl (28.6 mL, 161.6 mmol). After stirring for one hour at room temperature an addition 1 equivalent of iPr$_2$NEt and SEM-Cl were added and the reaction stirred for 4 hours. The reaction was subsequently diluted with EtOAc and filtered through Celite®. The filtrate was washed with water, brine, dried over MgSO$_4$ and concentrated in vacuo. The crude product was purified by column chromatography (SiO$_2$, 10-50% EtOAc/hexane) which provided the desired product (3.8 g, 17% yield).

Step e: A flask charged with the product from step d (3.8 g, 6.94 mmol) and PdCl$_2$(dppf) (507 mg, 0.69 mmol) was evacuated and backfilled with N$_2$ (3×). Degassed dioxane (69 mL), 1.0M aq. Na$_2$CO$_3$ (28 mL) and isopropenylboronic acid pinacol ester (1.95 mL, 10.4 mmol) was subsequently added. The mixture was heated to 100° C. for two hours. After cooling to room temperature, the reaction was partitioned between EtOAc and water. The organic layer was washed with brine, dried over MgSO$_4$, and concentrated under reduced pressure. The crude product was purified by column chromatography (SiO$_2$, 5-50% EtOAc/hexane) which afforded the desired product (2.84 g, 74% yield).

To a solution of the olefin from previous reaction (2.84 g, 5.14 mmol) in THF (69 mL) and water (34 mL) were added NaIO$_4$ (6.6 g, 30.8 mmol), 2,6-lutidine (1.2 mL, 10.3 mmol) and K$_2$OsO$_4$.2H$_2$O (96 mg, 0.26 mmol). The resulting heavy suspension was stirred overnight at room temperature. The reaction was partitioned between EtOAc and water. The organic layer was washed with water, brine, dried over MgSO$_4$, and concentrated under reduced pressure. The crude product was used without further purification.

Step f: A solution of the product from step e in N,N-Dimethylformamide dimethyl acetal (34 mL) was stirred in a sealed vial at 100° C. overnight. Upon completion, the reaction mixture was cooled to 25° C., concentrated under reduced pressure, and purified by column chromatography (SiO$_2$, 0-10% MeOH/CH$_2$Cl$_2$), which provided the product (2.29 g, 73% yield).

Step g: A solution of the product from step f (150 mg, 0.25 mmol) and (2,4-dichlorobenzyl)hydrazine HCl salt (67 mg, 0.30 mmol) in EtOH (2.5 mL) was stirred at 80° C. in a sealed vial for two hours. The reaction mixture was then cooled to 25° C. and concentrated under reduced pressure. To the resulting residue was added 90% v/v TFA/H$_2$O. The mixture was stirred at room temperature for 30 minutes then diluted with toluene and evaporated to dryness. The residue was reconstituted in methanol and DMEDA (10 eq.) was added. The mixture was heated to 45° C. for 30 minutes. Upon completion, the reaction was cooled to room temperature and concentrated to dryness. The crude product was purified by preparative HPLC (C18, MeCN/H$_2$O/0.1% TFA) to yield 5-(6-{1-[(2,4-dichlorophenyl)methyl]-1H-pyrazol-5-yl}-1H-[1,2,3]triazolo[4,5-c]pyridin-1-yl)-2,3-dihydro-1H-1,3-benzodiazol-2-one. $^1$H NMR (400 MHz, DMSO-d$_6$) δ 11.11-10.87 (m, 2H), 9.53 (s, 1H), 8.47 (s, 1H), 8.19 (s, 1H), 7.80 (dd, J=8.5, 2.7 Hz, 1H), 7.66-7.55 (m, 1H), 7.45-7.29 (m, 2H), 7.16 (d, J=8.2 Hz, 1H), 7.06 (s, 1H), 6.90 (d, J=8.3 Hz, 1H), 6.01 (s, 2H). ESI MS [M+H]$^+$ for C$_{22}$H$_{14}$Cl$_2$N$_8$O, calcd 477.1. found 477.2.

Example 2

Synthesis of 3-Chloro-4-({5-[1-(2-oxo-1,3-benzimidazol-5-yl)-1,2,3,5-tetraaza-1H-inden-6-yl]-1H-pyrazol-1-yl}methyl)benzonitrile

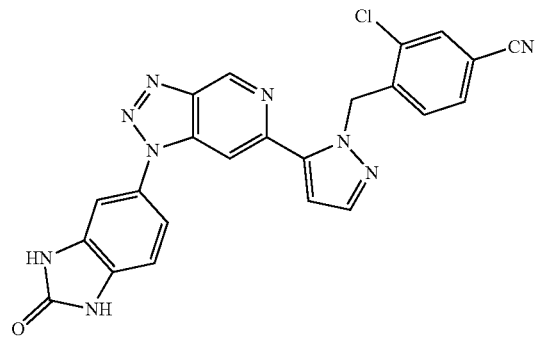 [SMILES: N#Cc1ccc(Cn2nccc2-c2cc3c(cn2)nnn3-c2ccc3[nH]c(=O)[nH]c3c2)c(Cl)c1]

The title compound was synthesized in a similar fashion to Example 1: $^1$H NMR (400 MHz, DMSO-d$_6$) δ 11.01 (m, 2H), 9.50 (dd, J=1.2, 2.5 Hz, 1H), 8.19 (dd, J=1.2, 2.4 Hz, 1H), 8.06 (m, 1H), 7.72-7.64 (m, 2H), 7.44-7.33 (m, 2H), 7.21-7.13 (m, 2H), 6.73 (d, J=8.2 Hz, 1H), 6.10 (s, 2H). ESI MS [M+H]$^+$ for C$_{23}$H$_{14}$ClN$_9$O, calcd 468.1. found 468.3.

Example 3

Synthesis of p-({5-[1-(1H-Indazol-6-yl)-1,2,3,4-tetraaza-1H-inden-6-yl]-1H-pyrazol-1-yl}methyl)benzonitrile

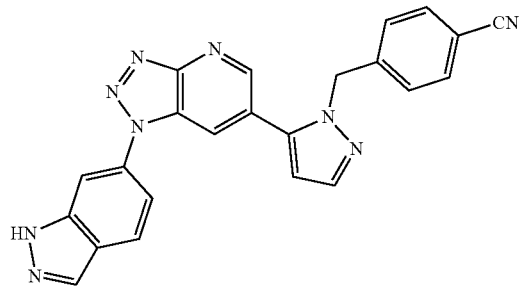 [SMILES: N#Cc1ccc(Cn2nccc2-c2cnc3nnn(-c4ccc5cn[nH]c5c4)c3c2)cc1]

The title compound was synthesized in a similar fashion to Example 1: $^1$H NMR (400 MHz, CDCl$_3$) δ 8.73 (d, J=2.0 Hz, 1H), 8.58 (s, 1H), 8.36 (d, J=2.0 Hz, 1H), 8.22-8.19 (m, 2H), 8.17 (d, J=1.7 Hz, 1H), 8.01 (d, J=8.7 Hz, 1H), 7.76 (s, 1H), 7.37 (s, 1H), 7.22 (d, J=8.4 Hz, 1H), 6.79 (d, J=8.4 Hz, 1H), 6.59 (s, 1H), 5.45 (s, 2H). ESI MS [M+H]$^+$ for C$_{23}$H$_{15}$N$_9$, calcd 418.15. found 418.3.

Example 4

Synthesis of 6-{2-[(2,4-Dichlorophenyl)methyl]-2H-pyrazol-3-yl}1-(1H-indazol-6-yl)-1,2,3,4-tetraaza-1H-indene

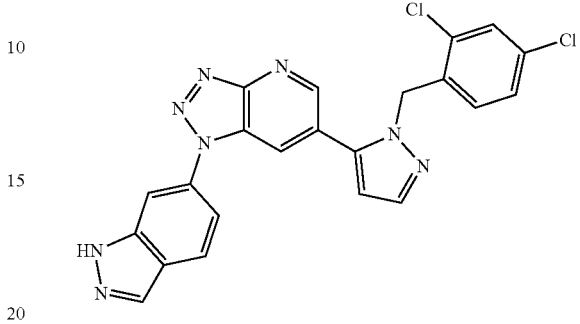

The title compound was synthesized in a similar fashion to Example 1. $^1$H NMR (400 MHz, CDCl$_3$) δ 8.83 (s, 1H), 8.26 (s, 1H), 7.96 (d, J=8.5 Hz, 1H), 7.84 (dd, J=3.7, 1.2 Hz, 2H), 7.75 (s, 1H), 7.35 (dd, J=8.5, 1.8 Hz, 1H), 7.22-7.17 (m, 2H), 6.87 (d, J=8.2 Hz, 1H), 6.61 (s, 1H), 5.42 (s, 2H). ESI MS [M+H]$^+$ for C$_{22}$H$_{14}$Cl$_2$N$_8$, calcd 461.07. found 461.2.

Example 5

Synthesis of 4-Chloro-1-(2H-indazol-6-yl)-6-[1-(3-methylphenyl)-1H-pyrazol-5-yl]-1H-1,2,3-benzotriazole

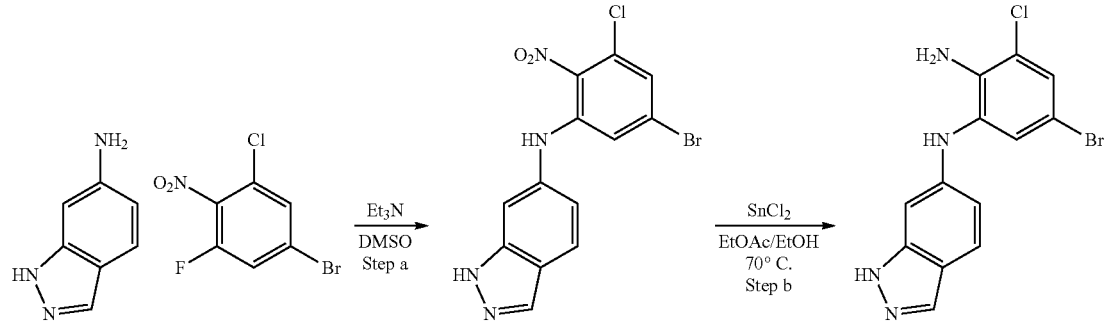

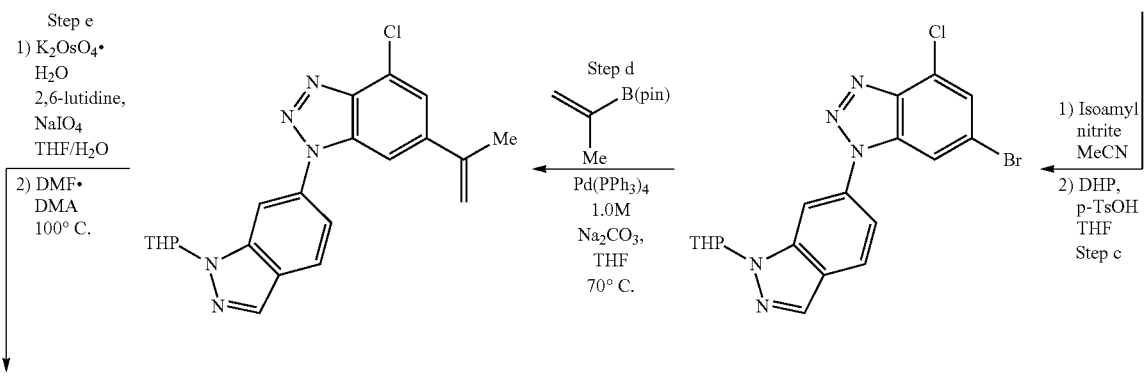

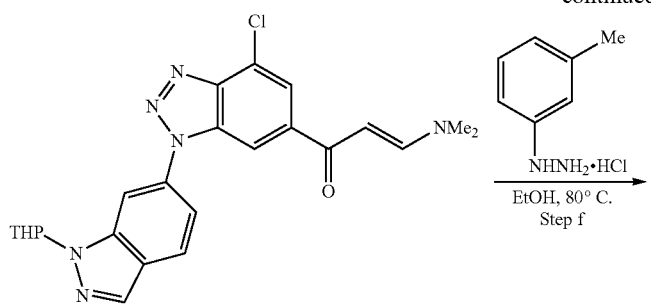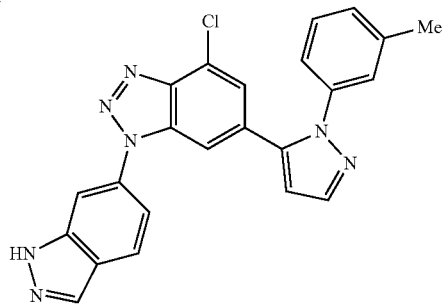

Step a: To a suspension of 2-chloro-4-bromo-6-fluoronitrobenzene (31.6 g, 133 mmol) in DMSO (133 mL) and Et$_3$N (133 mL) was added 6-aminoindazole (21.3 g, 160 mmol). The mixture was heated overnight at 90° C. with vigorous stirring. After cooling to room temperature, the reaction was partitioned between H$_2$O and EtOAc. The organics were washed with H$_2$O (3×) and brine, dried over MgSO$_4$, then concentrated in vacuo. The crude product was purified by column chromatography (SiO$_2$, CH$_2$Cl$_2$/hexane) to afford the desired product (15.4 g, 32% yield). ESI MS [M+H]$^+$ for C$_{13}$H$_8$BrClN$_4$O$_2$, calcd 365.0. found 365.1.

Step b: A solution of the product from step a (15.8 g, 43 mmol) in EtOAc (172 mL) and EtOH (123 mL) was heated to 75° C. then SnCl$_2$ (24.5 g, 129 mmol) was added in portions over 45 minutes. The mixture was heated overnight. Upon completion, the reaction was cooled to 0° C. in an ice-bath and 1.0 M Na$_2$CO$_3$ was added until pH>7. The resulting precipitate was filtered through Celite®. The filter cake was washed with EtOAc and H$_2$O. The filtrate was transferred to a separatory funnel and the organics were separated, washed with brine, then dried over MgSO$_4$. Concentration under reduced pressure afforded the desired 1,2-diamine (13.6 g, 98% yield) which was used without further purification. ESI MS [M+H]$^+$ for C$_{13}$H$_{10}$BrClN$_4$, calcd 337.0. found 337.0.

Step c: To a suspension of the product from step b (13.61 g, 42.4 mmol) in acetonitrile (424 mL) was added isoamylnitrite (8.6 mL, 63.6 mmol). The mixture was heated to 60° C. for three hours. Upon completion, the reaction was cooled to room temperature and concentrated to dryness. The crude material was reconstituted in THF (215 mL) treated with DHP (19.3 mL, 212 mmol) followed by p-TsOH (806 mg, 4.2 mmol). After stirring overnight, the reaction was concentrated to dryness. Column chromatography (SiO$_2$, 0-30% EtOAc/hexane) afforded the desired product (12.0 g, 65% yield).

Step d: A solution of 6-bromo-4-chloro-1-[1-(tetrahydro-2H-pyran-2-yl)-1H-indazol-6-yl]-1,2,3-benzotriazole (2.2 g, 5.0 mmol, 1.0 equiv), isopropenylboronic acid pinacol ester (2.5 g, 14.9 mmol, 3.0 equiv), and 1.0 M aqueous Na$_2$CO$_3$ (14.9 mL, 14.9 mmol, 3.0 equiv) in 25 mL THF (0.2 M) was sparged with N$_2$ for 10 minutes. Pd(PPh$_3$)$_4$ (574 mg, 0.5 mmol, 0.1 equiv) was then added and the reaction heated to 70° C. under N$_2$ atmosphere for 2.5 h. Upon completion, the organic phase of the biphasic reaction mixture was separated, filtered through Celite® (washed with 3×10 mL EtOAc), and concentrated in vacuo. The resulting residue was purified by column chromatography (hexanes→7:3 hexanes:EtOAc) to give 4-chloro-6-isopropenyl-1-[1-(tetrahydro-2H-pyran-2-yl)-1H-indazol-6-yl]-1,2,3-benzotriazole (1.5 g, 78% yield) as a yellow oil. ESI MS [M+H]$^+$ for C$_{21}$H$_{20}$ClN$_5$O, calcd 394.1. found 394.0.

Step e: To a solution of 4-chloro-6-isopropenyl-1-[1-(tetrahydro-2H-pyran-2-yl)-1H-indazol-6-yl]-1,2,3-benzotriazole (1.5 g, 3.9 mmol, 1.0 equiv) in 78 mL THF/H$_2$O (2:1, 0.05 M) was added sodium periodate (5.0 g, 23.3 mmol, 6.0 equiv) followed by 2,6-lutidine (0.9 mL, 7.8 mmol, 2.0 equiv) and K$_2$OsO$_4$.2H$_2$O (72 mg, 0.19 mmol, 0.05 equiv). The reaction was stirred at room temperature for 14 h. Following this time, the reaction mixture was diluted with EtOAc (100 mL) and quenched with saturated aqueous Na$_2$S$_2$O$_3$ (100 mL). The biphasic mixture was stirred vigorously for 15 minutes then transferred to a separatory funnel and the organic phase collected. The aqueous phase was extracted with EtOAc (2×50 mL) and then the combined organic extracts were dried over Na$_2$SO$_4$ and concentrated in vacuo. 1-{7-chloro-3-[1-(tetrahydro-2H-pyran-2-yl)-1H-indazol-6-yl]-1,2,3-benzotriazol-5-yl}-1-ethanone was used in the subsequent reaction without further purification. ESI MS [M+H]$^+$ for C$_{20}$H$_{18}$ClN$_5$O$_2$, calcd 396.1. found 396.1.

1-{7-Chloro-3-[1-(tetrahydro-2H-pyran-2-yl)-1H-indazol-6-yl]-1,2,3-benzotriazol-5-yl}-1-ethanone was taken up in 75 mL N,N-Dimethylformamide dimethyl acetal (0.05 M) and the reaction heated to 100° C. for 2.5 h. Upon completion, the reaction mixture was cooled to room temperature and concentrated in vacuo. The resulting residue was purified by column chromatography (hexanes→1:1 EtOAc:hexanes) to give 1-{7-chloro-3-[1-(tetrahydro-2H-pyran-2-yl)-1H-indazol-6-yl]-1,2,3-benzotriazol-5-yl}-3-(dimethylamino)-2-propen-1-one as a pale yellow foam (1.2 g, 69% yield over two steps). ESI MS [M+H]$^+$ for C$_{23}$H$_{23}$ClN$_6$O$_2$, calcd 451.2. found 451.2.

Step f: To a solution of 1-{7-chloro-3-[1-(tetrahydro-2H-pyran-2-yl)-1H-indazol-6-yl]-1,2,3-benzotriazol-5-yl}-3-(dimethylamino)-2-propen-1-one (50 mg, 0.11 mmol, 1 equiv) in ethanol (0.7 mL, 0.18 M) was added 3-methylphenylhydrazine HCl (44 mg, 0.28 mmol, 2.5 equiv). The reaction was heated to 80 C for 3 h. Following this time, the reaction was cooled to room temperature and concentrated vacuo. The resulting residue was purified by reversed-phase column chromatography (C18 column, 95:5 H$_2$O/acetonitrile→5:95 H$_2$O/acetonitrile with 0.1% CF$_3$CO$_2$H over 35 min) to give 4-chloro-1-(1H-indazol-6-yl)-6-[2-(m-tolyl)-2H-pyrazol-3-yl]-1,2,3-benzotriazole as a white solid (15 mg, 32%). $^1$H NMR (400 MHz, DMSO-d$_6$) δ 8.29 (t, J=1.2 Hz, 1H), 7.99 (dt, J=8.5, 1.1 Hz, 1H), 7.93 (s, 1H), 7.81 (t, J=1.6 Hz, 1H), 7.54 (d, J=1.4 Hz, 2H), 7.36-7.25 (m, 3H), 7.21 (dt, J=8.6, 1.6 Hz, 1H), 7.05 (d, J=7.1 Hz, 1H), 6.98 (t, J=1.6 Hz, 1H), 2.54 (d, J=1.3 Hz, 0H), 2.29 (s, 3H). ESI MS [M−H]$^−$ for C$_{23}$H$_{16}$ClN$_7$, calcd 424.1. found 424.3.

Example 6

Synthesis of 6-{1-[(4-Chloro-2-fluorophenyl)methyl]-1H-pyrazol-5-yl}-4-fluoro-1-(2H-indazol-6-yl)-1H-1,2,3-benzotriazole

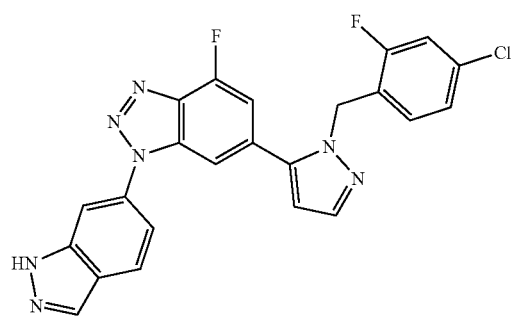 [SMILES: Fc1cc(Cl)ccc1Cn1nccc1-c1cc(F)c2nnn(-c3ccc4cn[nH]c4c3)c2c1]

The title compound was synthesized in a similar fashion to Example 5. $^1$H NMR (400 MHz, DMSO-$d_6$) δ 13.44 (s, 1H), 8.27 (s, 1H), 8.10-7.93 (m, 2H), 7.71-7.56 (m, 2H), 7.58-7.44 (m, 2H), 7.25-7.08 (m, 2H), 6.95 (t, J=8.1 Hz, 1H), 6.64 (s, 1H), 5.44 (s, 2H). ESI MS [M+H]$^+$ for $C_{23}H_{14}ClF_2N_7$, calcd 462.1. found 462.2.

Example 7

Synthesis of 4-Fluoro-1-(2H-indazol-6-yl)-6-[1-(oxan-3-yl)-1H-pyrazol-5-yl]-1H-1,2,3-benzotriazole

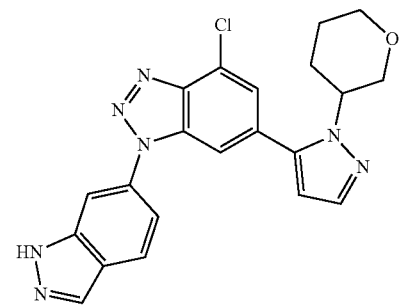 [SMILES: Clc1cc(-c2ccnn2C2CCCOC2)cc2c1nnn2-c1ccc2cn[nH]c2c1]

The title compound was synthesized in a similar fashion to Example 5. $^1$H NMR (400 MHz, DMSO-$d_6$) δ 8.26 (d, J=1.0 Hz, 1H), 8.10-8.03 (m, 2H), 7.78 (s, 1H), 7.64 (d, J=9.1 Hz, 2H), 7.60-7.50 (m, 2H), 6.51 (d, J=1.8 Hz, 1H), 4.27 (dq, J=10.8, 5.1 Hz, 1H), 3.98-3.85 (m, 1H), 3.85-3.71 (m, 1H), 3.58 (t, J=10.6 Hz, 1H), 3.29 (d, J=10.9 Hz, 1H), 2.18-1.96 (m, 2H), 1.76-1.46 (m, 2H). ESI MS [M+H]$^+$ for $C_{21}H_{18}ClN_7O$, calcd 420.1. found 420.3.

Example 8

Synthesis of 6-{1-[(4-Chloro-2-fluorophenyl)methyl]-1H-pyrazol-5-yl}-1-(2H-indazol-6-yl)-1H-1,2,3-benzotriazole

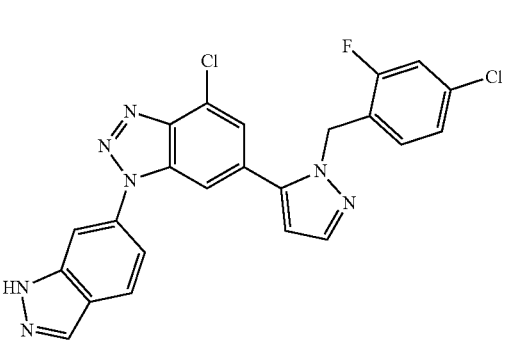

The title compound was synthesized in a similar fashion to Example 5. $^1$H NMR (400 MHz, DMSO-$d_6$) δ 13.40 (s, 1H), 8.35-8.18 (m, 2H), 8.09-7.94 (m, 2H), 7.86 (s, 1H), 7.62 (s, 1H), 7.57 (d, J=8.6 Hz, 1H), 7.52 (d, J=8.6 Hz, 1H), 7.31-7.13 (m, 2H), 6.94 (t, J=8.2 Hz, 1H), 6.61 (s, 1H), 5.42 (s, 2H). ESI MS [M+H]$^+$ for $C_{23}H_{14}Cl_2FN_7$, calcd 478.1. found 478.2.

Example 9

Synthesis of 3-[6-(1-Benzyl-1H-pyrazol-5-yl)-4-chloro-1H-1,2,3-benzotriazol-1-yl]phenol

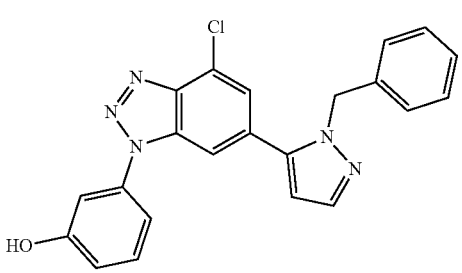 [SMILES: Oc1cccc(-n2nnc3c(Cl)cc(-c4ccnn4Cc4ccccc4)cc32)c1]

The title compound was synthesized in a similar fashion to Example 5. $^1$H NMR (400 MHz, DMSO-$d_6$) δ 10.11 (s, 1H), 7.68-7.58 (m, 3H), 7.38 (t, J=8.1 Hz, 1H), 7.27-7.14 (m, 4H), 7.09 (d, J=7.9 Hz, 1H), 7.02-6.89 (m, 3H), 6.69 (s, 1H), 5.44 (s, 2H). ESI MS [M+H]$^+$ for $C_{22}H_{16}ClN_5O$, calcd 402.1. found 402.3.

Example 10

Synthesis of 4-Fluoro-1-(1H-indazol-6-yl)-6-[2-(m-tolyl)-2H-pyrazol-3-yl]-1,2,3-benzotriazole

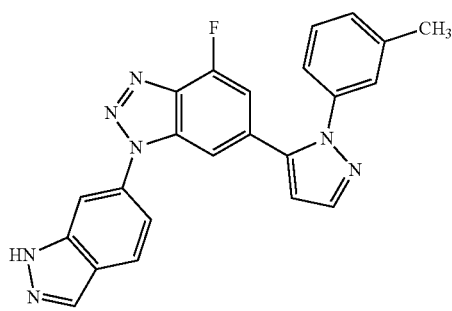 [SMILES: Cc1cccc(-n2nccc2-c2cc(F)c3nnn(-c4ccc5cn[nH]c5c4)c3c2)c1]

The title compound was synthesized in a similar fashion to Example 5. $^1$H NMR (400 MHz, DMSO-d$_6$) δ 8.29 (s, 1H), 8.03-7.91 (m, 2H), 7.80 (dd, J=1.9, 0.6 Hz, 1H), 7.44 (d, J=1.3 Hz, 1H), 7.36-7.25 (m, 4H), 7.23 (dd, J=8.7, 1.8 Hz, 1H), 7.05 (d, J=7.5 Hz, 1H), 6.95 (dd, J=1.9, 0.6 Hz, 1H), 2.28 (s, 3H). ESI MS [M+H]$^+$ for C$_{23}$H$_{16}$FN$_7$, calcd 410.2. found 410.2.

Example 11

Synthesis of 4-({5-[4-Chloro-1-(2H-indazol-6-yl)-1H-1,2,3-benzotriazol-6-yl]-1H-pyrazol-1-yl}methyl)benzonitrile

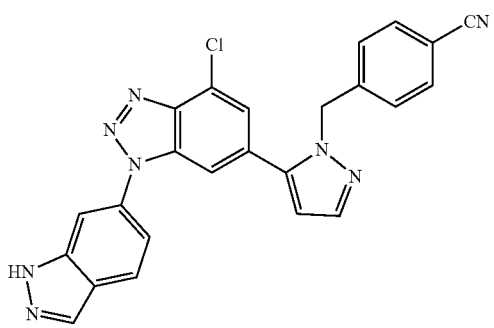 [SMILES: N#Cc1ccc(Cn2nccc2-c2cc(Cl)c3nnn(-c4ccc5cn[nH]c5c4)c3c2)cc1]

The title compound was synthesized in a similar fashion to Example 5. $^1$H NMR (400 MHz, DMSO-d$_6$) δ 13.49-13.42 (m, 1H), 8.28 (q, J=1.2 Hz, 1H), 8.05-7.95 (m, 2H), 7.70 (dt, J=3.3, 1.7 Hz, 2H), 7.67-7.61 (m, 2H), 7.49-7.42 (m, 1H), 7.15 (d, J=8.0 Hz, 2H), 6.74 (dd, J=1.9, 1.0 Hz, 1H), 5.76 (d, J=1.0 Hz, 1H), 5.57 (d, J=1.7 Hz, 2H). ESI MS [M+H]$^+$ C24H15ClN8, calcd 451.1. found 451.1.

Example 12

Synthesis of 4-({5-[4-Fluoro-1-(2H-indazol-6-yl)-1H-1,2,3-benzotriazol-6-yl]-1H-pyrazol-1-yl}methyl)benzonitrile

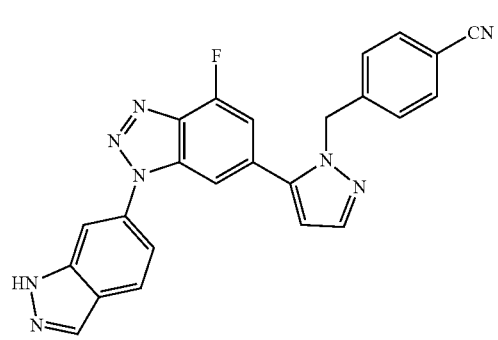 [SMILES: N#Cc1ccc(Cn2nccc2-c2cc(F)c3nnn(-c4ccc5cn[nH]c5c4)c3c2)cc1]

The title compound was synthesized in similar fashion to Example 5. $^1$H NMR (400 MHz, DMSO-d$_6$) δ 13.46 (s, 1H), 8.28 (s, 1H), 8.01 (dd, J=8.6, 0.7 Hz, 1H), 7.98 (s, 1H), 7.70 (d, J=1.9 Hz, 1H), 7.65-7.58 (m, 2H), 7.54 (d, J=1.2 Hz, 1H), 7.51 (dd, J=11.1, 1.1 Hz, 1H), 7.46 (dd, J=8.6, 1.8 Hz, 1H), 7.19-7.08 (m, 2H), 6.72 (d, J=1.9 Hz, 1H), 5.58 (s, 2H). ESI MS [M+H]$^+$ C24H15FN8, calcd 435.1. found 435.2.

Example 13

Synthesis of 6-({5-[4-Chloro-1-(2H-indazol-6-yl)-1H-1,2,3-benzotriazol-6-yl]-1H-pyrazol-1-yl}methyl)pyridine-3-carbonitrile

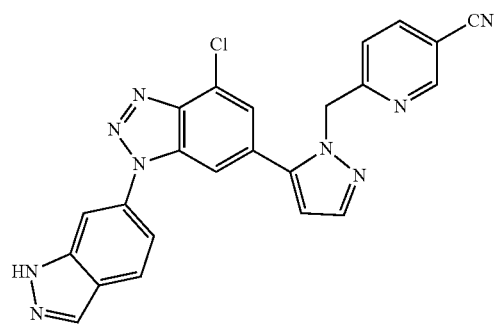 [SMILES: N#Cc1ccc(Cn2nccc2-c2cc(Cl)c3nnn(-c4ccc5cn[nH]c5c4)c3c2)nc1]

The title compound was synthesized in similar fashion to Example 5. $^1$H NMR (400 MHz, DMSO-d$_6$) δ 13.44 (s, 1H), 8.31-8.20 (m, 2H), 8.12 (d, J=2.3 Hz, 1H), 8.01 (d, J=8.1 Hz, 2H), 7.87-7.77 (m, 1H), 7.69-7.61 (m, 1H), 7.51 (d, J=9.7 Hz, 1H), 7.42-7.31 (m, 1H), 6.71 (d, J=2.8 Hz, 1H), 5.76 (d, J=3.7 Hz, 1H), 5.61 (d, J=3.8 Hz, 2H). ESI MS [M+H]$^+$ C23H14ClN9, calcd 452.1. found 452.2.

Example 14

Synthesis of 4-Chloro-6-{2-[(2,4-dichlorophenyl)methyl]-2H-pyrazol-3-yl}-1-(1H-indazol-6-yl)-1,2,3-benzotriazole

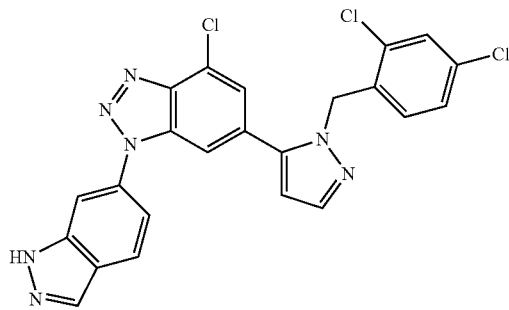 [SMILES: Clc1ccc(Cn2nccc2-c2cc(Cl)c3nnn(-c4ccc5cn[nH]c5c4)c3c2)c(Cl)c1]

The title compound was synthesized in a similar fashion to Example 5. $^1$H NMR (400 MHz, DMSO-d$_6$) δ 13.49 (s, 1H), 8.33 (s, 1H), 8.09-7.97 (m, 2H), 7.82-7.66 (m, 2H), 7.48 (d, J=8.6 Hz, 1H), 7.45-7.27 (m, 1H), 6.89 (dd, J=8.2, 1.5 Hz, 1H), 6.77 (d, J=1.9 Hz, 1H), 5.51 (s, 2H). ESI MS [M+H]$^+$ for C$_{23}$H$_{15}$Cl$_3$N$_7$, calcd 494.0. found 494.2.

Example 15

Synthesis of 6-({5-[7-Chloro-3-(2-oxo-1,3-benzimidazol-5-yl)-1,2,3-benzotriazol-5-yl]-1H-pyrazol-1-yl}methyl)nicotinonitrile

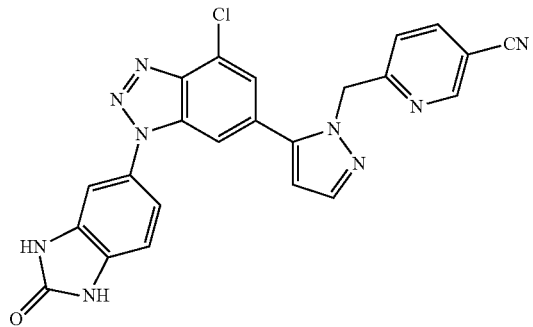 [SMILES: N#Cc1ccc(Cn2nccc2-c2cc(Cl)c3nnn(-c4ccc5[nH]c(=O)[nH]c5c4)c3c2)nc1]

The title compound was synthesized in a similar fashion to Example 5. $^1$H NMR (400 MHz, Acetone-d$_6$) δ 10.04 (s, 1H), 10.03 (s, 1H), 8.78 (s, 1H), 8.17 (d, J=8.1 Hz, 1H), 8.07-8.04 (m, 1H), 7.69-7.65 (m, 1H), 7.61-7.56 (m, 1H), 7.49-7.45 (m, 1H), 7.41-7.33 (m, 2H), 7.24 (d, J=8.2 Hz, 1H), 6.64-6.59 (m, 1H), 5.60 (s, 2H). ESI MS [M+H]$^+$ for C$_{23}$H$_{15}$ClN$_9$O, calcd 468.1. found 468.1.

Example 16

Synthesis of 4-({5-[7-Fluoro-3-(2-oxo-1,3-benzimidazol-5-yl)-1,2,3-benzotriazol-5-yl]-1H-pyrazol-1-yl}methyl)-3-(trifluoromethyl)benzonitrile

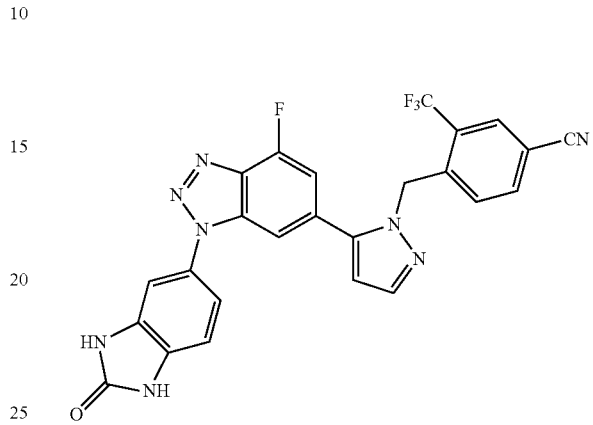

The title compound was synthesized in a similar fashion to Example 5. $^1$H NMR (400 MHz, DMSO-d$_6$) δ 7.18-7.10 (m, 2H), 6.99 (dd, J=2.0, 1.0 Hz, 1H), 6.62-6.50 (m, 2H), 6.46-6.35 (m, 3H), 6.18 (d, J=8.3 Hz, 1H), 5.96 (dd, J=2.0, 1.0 Hz, 1H), 4.90 (s, 2H). ESI MS [M+H]$^+$ for C$_{25}$H$_{15}$F$_4$N$_8$O, calcd 519.1. found 519.0.

Example 17

Synthesis of 4-({5-[4-Fluoro-1-(5-fluoro-2H-indazol-6-yl)-1H-1,2,3-benzotriazol-6-yl]-1H-pyrazol-1-yl}methyl)benzonitrile

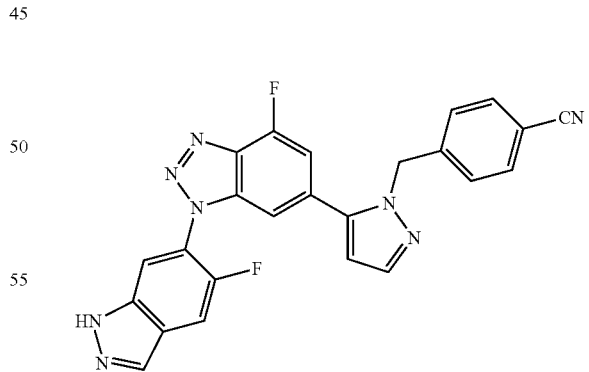

The title compound was synthesized in a similar fashion to Example 5. $^1$H NMR (400 MHz, DMSO-d$_6$) δ 13.66 (s, 1H), 8.31 (br t, J=1.6 Hz, 1H), 8.08 (d, J=7.5 Hz, 1H), 7.97 (d, J=10.1 Hz, 1H), 7.69 (d, J=2.1 Hz, 1H), 7.58 (d, J=7.4 Hz, 2H), 7.52 (d, J=10.1 Hz, 1H), 7.32 (br t, J=1.6 Hz, 1H), 7.09 (d, =8.4 Hz, 2H), 6.70 (d, 2.1 Hz, 1H), 5.55 (s, 2H). ESI MS [M+H]$^+$ for C$_{24}$H$_{14}$F$_2$N$_8$ calcd 453.1. found 453.0.

Example 18

Synthesis of 6-{2-[(5-Chloro-2-pyridyl)methyl]-2H-pyrazol-3-yl}-4-fluoro-1-(1H-indazol-6-yl)-1,2,3-benzotriazole

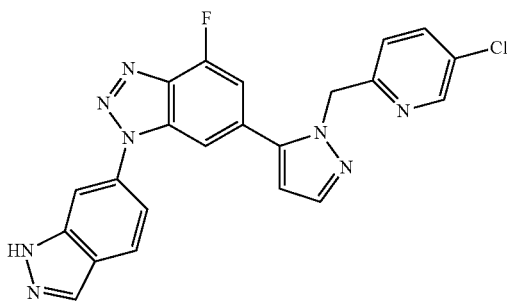 [SMILES: Fc1cc(-c2ccnn2Cc2ccc(Cl)cn2)cc2c1nnn2-c1ccc2cn[nH]c2c1]

The title compound was synthesized in a similar fashion to Example 5. $^1$H NMR (400 MHz, CDCl$_3$) δ 10.57 (s, 1H), 8.28 (s, 1H), 8.26 (s, 1H), 7.96 (d, J=8.5 Hz, 1H), 7.93 (s, 1H), 7.76 (t, J=1.4 Hz, 1H), 7.66 (t, J=1.8 Hz, 1H), 7.65-7.61 (m, 1H), 7.48 (d, J=8.5 Hz, 1H), 7.29 (d, J=10.2 Hz, 1H), 7.16 (d, J=8.3 Hz, 1H), 6.49 (t, J=1.8 Hz, 1H), 5.45 (s, 2H). ESI MS [M+H]$^+$ for C$_{22}$H$_{14}$ClFN$_8$, calcd 445.10. found 445.3.

Example 19

Synthesis of 5-(6-{1-[(4-Chloro-2-methanesulfonylphenyl)methyl]-1H-pyrazol-5-yl}-4-fluoro-1H-1,2,3-benzotriazol-1-yl)-2,3-dihydro-1H-1,3-benzodiazol-2-one

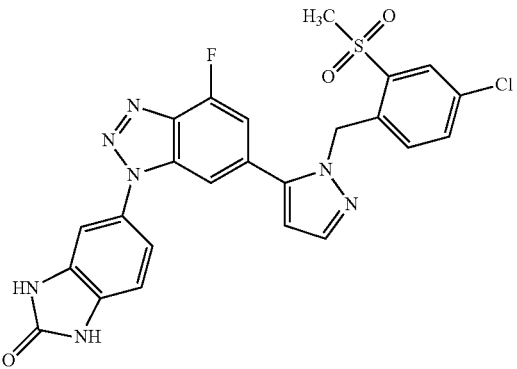 [SMILES: CS(=O)(=O)c1cc(Cl)ccc1Cn1nccc1-c1cc(F)c2nnn(-c3ccc4[nH]c(=O)[nH]c4c3)c2c1]

The title compound was synthesized in a similar fashion to Example 5. $^1$H NMR (400 MHz, DMSO-d$_6$) δ 11.04 (s, 1H), 10.96 (s, 1H), 7.80 (d, J=2.3 Hz, 1H), 7.76-7.70 (m, 2H), 7.49 (d, J=11.1 Hz, 1H), 7.36 (s, 1H), 7.23 (s, 1H), 7.16 (d, J=8.2 Hz, 1H), 7.06 (d, J=9.1 Hz, 1H), 6.80 (d, J=8.4 Hz, 1H), 6.76 (d, J=1.9 Hz, 1H), 5.89 (s, 2H), 3.17 (s, 3H). ESI MS [M+H]$^+$ for C$_{24}$H$_{17}$ClFN$_7$O$_3$S, calcd 538.08. found 538.2.

Example 20

Synthesis of 4-({5-[4-Chloro-1-(2-oxo-2,3-dihydro-1H-1,3-benzodiazol-5-yl)-1H-1,2,3-benzotriazol-6-yl]-1H-pyrazol-1-yl}methyl)-3-fluorobenzonitrile

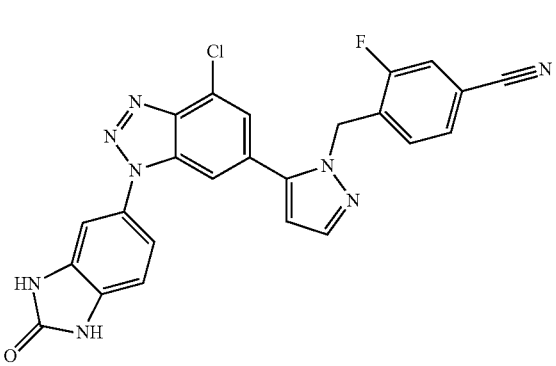 [SMILES: N#Cc1ccc(Cn2nccc2-c2cc(Cl)c3nnn(-c4ccc5[nH]c(=O)[nH]c5c4)c3c2)c(F)c1]

The title compound was synthesized in a similar fashion to Example 5. $^1$H NMR (400 MHz, Methanol-d$_4$) δ 7.68 (d, J=2.2 Hz, 1H), 7.64-7.57 (m, 1H), 7.55 (t, J=1.6 Hz, 1H), 7.51-7.43 (m, 1H), 7.39 (td, J=4.7, 2.0 Hz, 2H), 7.36-7.28 (m, 1H), 7.24 (dd, J=8.3, 2.3 Hz, 1H), 7.09 (t, J=7.8 Hz, 1H), 6.63 (d, J=2.2 Hz, 1H), 5.52 (s, 2H). ESI MS [M+H]$^+$ for C$_{24}$H$_{14}$ClFN$_8$O, calcd 485.1. found 485.2.

Example 21

Synthesis of 4-({5-[5-Chloro-1-(2H-indazol-6-yl)-1H-1,2,3-benzotriazol-6-yl]-1H-pyrazol-1-yl}methyl)-3-fluorobenzonitrile

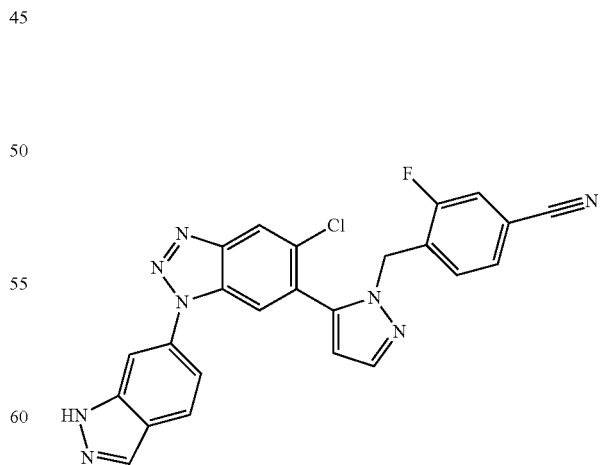

The title compound was synthesized in a similar fashion to Example 5. $^1$H NMR (400 MHz, DMSO-d$_6$) δ 13.41 (s, 1H), 8.55 (s, 1H), 8.28-8.22 (m, 1H), 8.07-8.00 (m, 3H), 7.97 (s, 1H), 7.72-7.61 (m, 1H), 7.61-7.49 (m, 2H), 7.15 (t, J=7.7 Hz, 1H), 6.50 (d, J=2.0 Hz, 1H), 5.31 (s, 2H). ESI MS [M+H]⁺ for $C_{24}H_{14}ClN_8$, calcd 469.1. found 469.0.

Example 22

Synthesis of 5-Chloro-1-(2H-indazol-6-yl)-6-[1-(3-methylphenyl)-1H-pyrazol-5-yl]-1H-1,2,3-benzotriazole

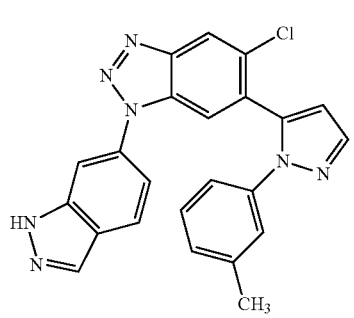 [SMILES: Cc1cccc(-n2nccc2-c2cc3c(cc2Cl)nnn3-c2ccc3cn[nH]c3c2)c1]

The title compound was synthesized in a similar fashion to Example 5. ¹H NMR (400 MHz, DMSO-d₆) δ 13.39 (s, 1H), 8.41 (d, J=1.3 Hz, 1H), 8.28-8.22 (m, 1H), 8.18 (q, J=0.9 Hz, 1H), 8.04 (d, J=8.6 Hz, 2H), 7.84-7.77 (m, 1H), 7.57 (dd, J=8.6, 1.8 Hz, 1H), 7.24 (s, 1H), 7.10 (dd, J=17.2, 7.6 Hz, 2H), 6.93 (d, J=7.7 Hz, 1H), 6.71-6.64 (m, 1H), 2.22 (s, 3H). ESI MS [M+H]⁺ for $C_{23}H_{16}ClN_7$, calcd 426.1. found 426.2.

Example 23

Synthesis of 4-({5-[4-Chloro-1-(2H-indazol-6-yl)-1H-1,2,3-benzotriazol-6-yl]-1H-pyrazol-1-yl}methyl)-3-fluorobenzonitrile

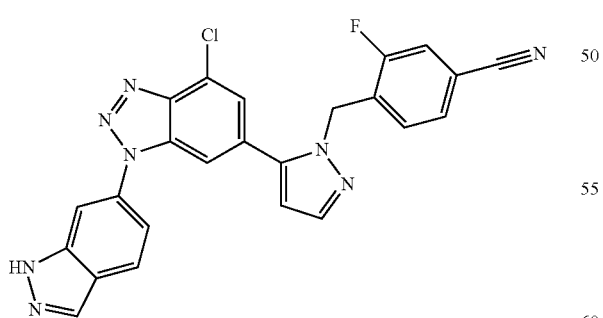

The title compound was synthesized in a similar fashion to Example 5. ¹H NMR (400 MHz, Chloroform-d) δ 8.30 (s, 1H), 8.01-7.88 (m, 2H), 7.68 (dd, J=1.9, 1.0 Hz, 1H), 7.50 (t, J=1.1 Hz, 1H), 7.46-7.37 (m, 3H), 7.14 (t, J=8.5 Hz, 2H), 6.50 (dd, J=1.9, 1.0 Hz, 1H), 5.42 (s, 2H). ESI MS [M+H]⁺ for $C_{24}H_{14}ClFN_8$, calcd 469.1. found 469.1.

Example 24

Synthesis of 5-Chloro-6-[1-(3-chlorophenyl)-1H-pyrazol-5-yl]-1-(2H-indazol-6-yl)-1H-1,2,3-benzotriazole

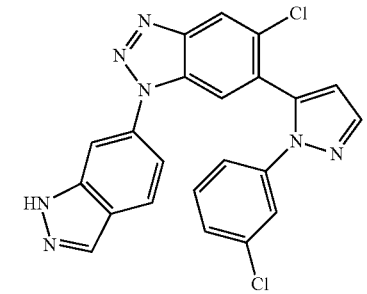 [SMILES: Clc1cccc(-n2nccc2-c2cc3c(cc2Cl)nnn3-c2ccc3cn[nH]c3c2)c1]

The title compound was synthesized in a similar fashion to Example 5. ¹H NMR (400 MHz, DMSO-d₆) δ 13.41 (s, 1H), 8.46-8.40 (m, 1H), 8.31-8.21 (m, 2H), 8.13-8.03 (m, 3H), 7.87 (qd, J=1.3, 0.6 Hz, 1H), 7.70-7.59 (m, 1H), 7.47 (dd, J=2.4, 1.4 Hz, 1H), 7.40-7.26 (m, 2H), 7.14 (ddt, J=6.5, 2.1, 1.1 Hz, 1H), 6.72 (dq, J=1.6, 0.8 Hz, 1H). ESI MS [M+H]⁺ for $C_{22}H_{13}Cl_2N_7$, calcd 446.1. found 446.0.

Example 25

Synthesis of 4-Chloro-6-{1-[(5-fluoropyridin-2-yl)methyl]-1H-pyrazol-5-yl}-1-(2H-indazol-6-yl)-1H-1,2,3-benzotriazole

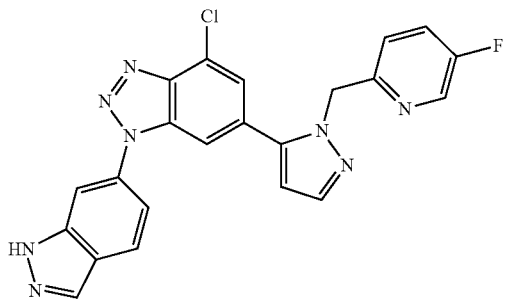 [SMILES: Fc1ccc(Cn2nccc2-c2cc(Cl)c3nnn(-c4ccc5cn[nH]c5c4)c3c2)nc1]

The title compound was synthesized in a similar fashion to Example 5. ¹H NMR (400 MHz, Chloroform-d) δ 10.51 (s, 1H), 8.25 (s, 1H), 8.17 (d, J=2.8 Hz, 1H), 8.01-7.90 (m, 4H), 7.66 (d, J=1.9 Hz, 1H), 7.61 (d, J=1.3 Hz, 1H), 7.51 (dd, J=8.4, 1.9 Hz, 1H), 7.41-7.33 (m, 1H), 6.49 (d, J=1.9 Hz, 1H), 5.45 (s, 2H); ¹⁹F NMR (376 MHz, CDCl₃) δ −85.0, −127.4 (m) ppm. ESI MS [M+H]⁺ for $C_{22}H_{15}ClFN_8$, calcd 445.1. found 445.2.

Example 26

Synthesis of 5-(4-Chloro-6-{1-[(2-fluoro-4-methylphenyl)methyl]-1H-pyrazol-5-yl}-1H-1,2,3-benzotriazol-1-yl)-2,3-dihydro-1H-1,3-benzimidazol-2-one

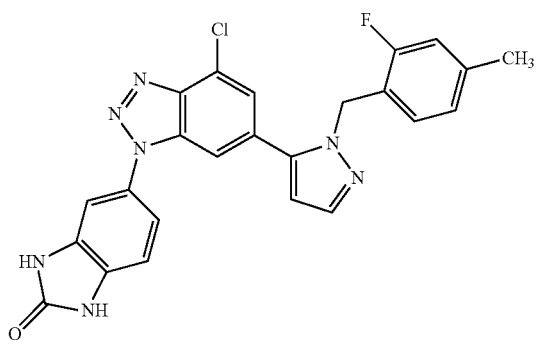 [SMILES: Cc1ccc(Cn2nccc2-c2cc(Cl)c3nnn(-c4ccc5[nH]c(=O)[nH]c5c4)c3c2)c(F)c1]

The title compound was synthesized in a similar fashion to Example 5. $^1$H NMR (400 MHz, DMSO-d$_6$) δ 11.04 (s, 2H), 7.70-7.60 (m, 2H), 7.57 (d, J=1.7 Hz, 1H), 7.32-7.21 (m, 2H), 7.14-7.04 (m, 1H), 6.89 (d, J=7.8 Hz, 1H), 6.80 (dd, J=15.4, 9.3 Hz, 2H), 6.65 (t, J=1.8 Hz, 1H), 5.37 (s, 2H), 2.21 (s, 3H); $^{19}$F NMR (376 MHz, DMSO-d$_6$) δ −119.40 (dd, J=11.2, 8.0 Hz). ESI MS [M+H]$^+$ for C$_{24}$H$_{18}$ClFN$_7$O, calcd 474.1. found 474.2.

Example 27

Synthesis of m-[4-Methyl-6-(2-methyl-2H-pyrazol-3-yl)-1,2,3-benzotriazol-1-yl]phenol

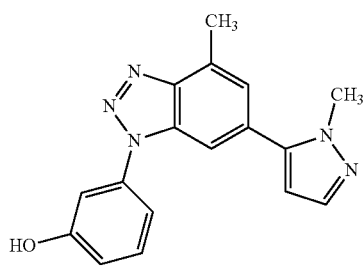 [SMILES: Cc1cc(-c2ccnn2C)cc2c1nnn2-c1cccc(O)c1]

The title compound was synthesized in a similar fashion to Example 5. $^1$H NMR (400 MHz, DMSO-d$_6$) δ 10.06 (s, 1H), 7.74 (s, 1H), 7.49 (d, J=1.9 Hz, 1H), 7.47-7.43 (m, overlap, 2H), 7.32 (d, J=8.1 Hz, 1H), 7.26-7.25 (m, 1H), 6.94 (d, J=8.1 Hz, 1H), 6.52 (d, J=1.9 Hz, 1H), 3.87 (s, 3H), 2.79 (s, 3H). ESI MS [M+H]$^+$ for C$_{17}$H$_{15}$N$_5$O, calcd 306.3. found 306.2.

Example 28

Synthesis of m-[6-(2-Benzyl-2H-pyrazol-3-yl)-4-methyl-1,2,3-benzotriazol-1-yl]phenol

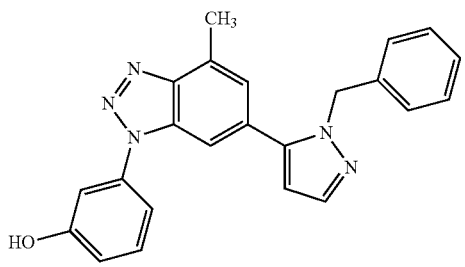

The title compound was synthesized in a similar fashion to Example 5. $^1$H NMR (400 MHz, DMSO-d$_6$) δ 10.06 (s, 1H), 7.63 (s, 1H), 7.49 (s, 1H), 7.38-7.33 (m, 2H), 7.26-7.15 (m, 4H), 7.07 (d, J=8.0 Hz, 1H), 6.99 (d, J=7.7 Hz, 2H), 6.93 (d, J=8.0 Hz, 1H), 6.60 (s, 1H), 5.42 (s, 2H), 2.73 (s, 3H). ESI MS [M+H]$^+$ for C$_{23}$H$_{19}$N$_5$O, calcd 382.4. found 382.2.

Example 29

Synthesis of p-({5-[1-Methyl-3-(2-oxo-1,3-benzimidazol-5-yl)-1,2,6-triaza-1H-inden-5-yl]-1H-pyrazol-1-yl}methyl)benzonitrile

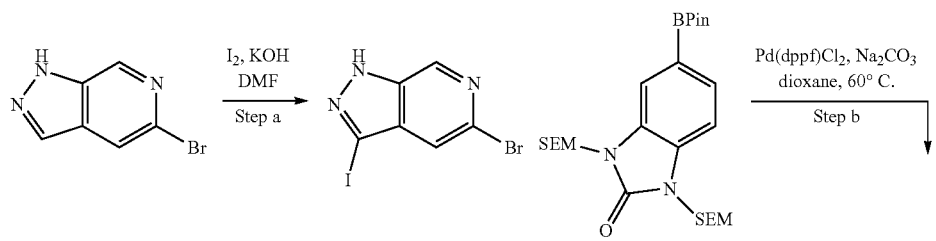

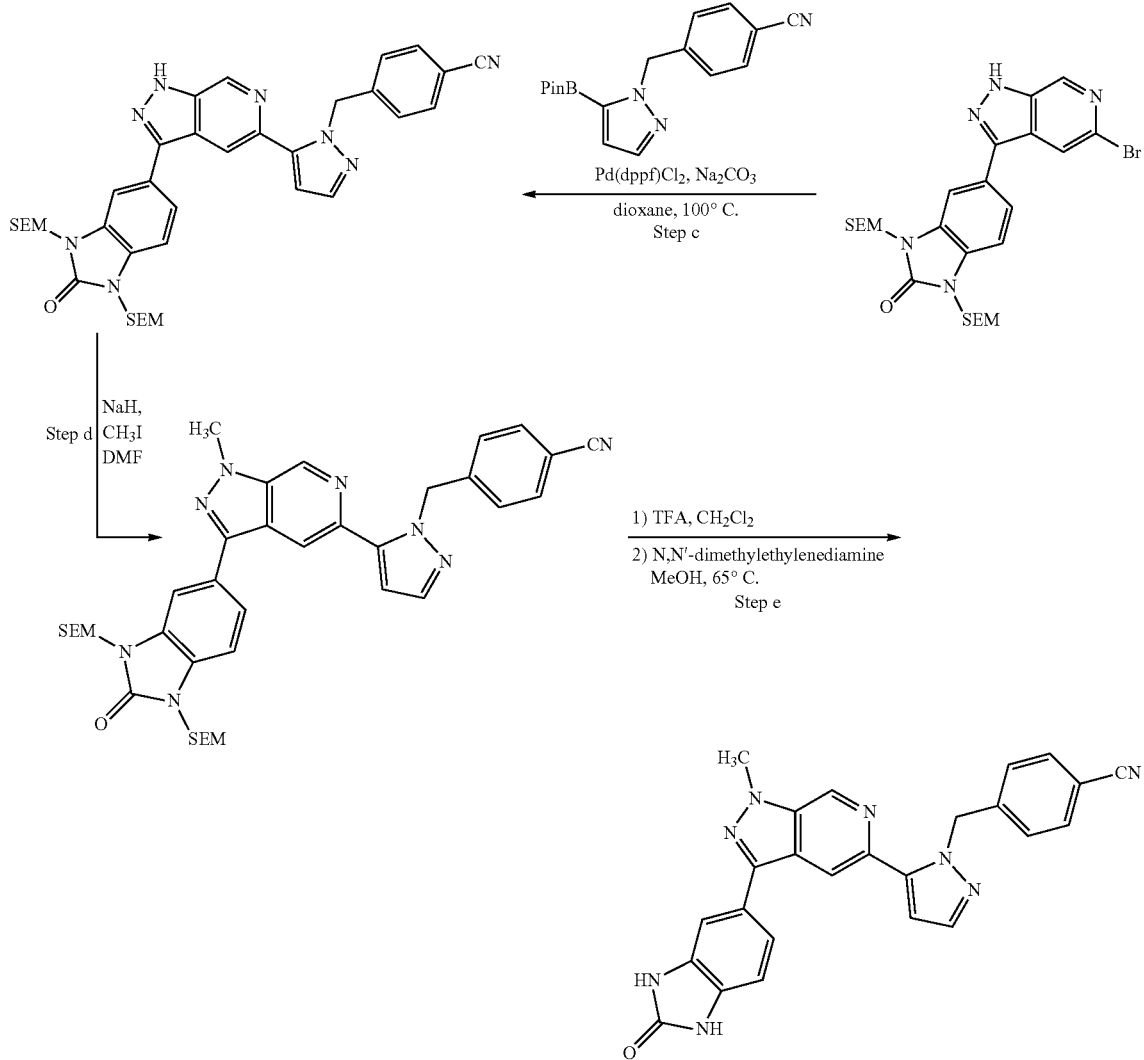

Step a: To a solution of 5-bromo-1H-pyrazolo[3,4-c]pyridine (3.0 g, 15.2 mmol) in DMF (30 ml) was added iodine (7.7 g, 30.3 mmol) followed by powdered potassium hydroxide (3.2 g, 57.6 mmol). After 40 minutes, the reaction was quenched with a 1:1 solution of saturated aqueous sodium thiosulfate and water. The resulting solution was extracted with ethyl acetate and the organics were concentrated to yield an analytically pure tan solid. Yield: 2.21 g, (45%).

Step b: The product from Step a (1.18 g, 3.65 mmol) was combined with doubly SEM-protected 1,3-dihydro-5-(4,4,5,5-tetramethyl-1,3,2-dioxaborolan-2-yl)-2H-benzimidazol-2-one (1.9 g, 3.65 mmol), and Pd(dppf)Cl$_2$ (267 mg, 0.365 mmol) in dioxane (36.5 ml). A solution of 1 M aqueous Na$_2$CO$_3$ (11.0 ml) was added, and the solution was sparged with nitrogen for one minute. The reaction was sealed and heated to 110° C. for 15 hours, at which point the reaction was concentrated onto Celite® and purified by flash chromatography over silica gel (ethyl acetate/hexanes 0% to 40%). Yield: 247 mg, (12%).

Step c: The product from Step b (247 mg, 0.42 mmol) was combined with p-{[5-(4,4,5,5-tetramethyl-1,3,2-dioxaborolan-2-yl)-1H-pyrazol-1-yl]methyl}benzonitrile (155 mg, 0.5 mmol), and Pd(dppf)Cl$_2$ (30 mg, 0.04 mmol) in dioxane (4.2 ml). A solution of 1 M aqueous Na$_2$CO$_3$ was added (1.26 ml) and the reaction was sparged with nitrogen for one minute. The reaction vessel was sealed and the reaction was heated to 100° C. for 15 hours. Upon completion, the reaction mixture was concentrated onto Celite® and purified by flash chromatography over silica gel (ethyl acetate/hexanes 20% to 50%). Yield: 199.2 mg (68%).

Step d: The product from Step c (100 mg, 0.144 mmol) was dissolved in DMF (0.5 ml). Sodium hydride (60% dispersion in mineral oil, 7 mg, 0.17 mmol) was added to the solution, followed by iodomethane (11 µl, 0.17 mmol). The reaction was complete within 30 minutes, at which time the reaction was quenched with water and extracted with ethyl acetate. The organic layer was washed with brine, dried over sodium sulfate, and concentrated onto Celite®. The crude mass was purified by column chromatography over silica gel (ethyl acetate/hexanes 20% to 60%). Yield: 30.7 mg, (30%).

Step e: The product from Step d was dissolved in CH$_2$Cl$_2$ (0.5 ml) and TFA (0.5 ml) was added to the solution. The reaction was stirred at room temperature for 30 minutes, at which time the starting material had been fully consumed. The reaction was concentrated to a crude oil and re-dissolved in methanol (1.0 ml). N,N'-dimethylethylenediamine (0.5 ml) was added to the reaction mixture and the solution was heated to 65° C. for 16 hours. Upon completion, the reaction was concentrated, taken up in a minimal volume of DMSO and purified by preparative HPLC to afford the title compound. $^1$H NMR (400 MHz, DMSO-d$_6$) δ 10.77 (s, 1H), 10.71 (s, 1H), 9.21 (s, 1H), 8.26 (s, 1H), 7.72 (d, J=7.7 Hz, 2H), 7.63-7.60 (m, overlap, 2H), 7.50 (s, 1H), 7.24 (d, J=7.7 Hz, 2H), 7.05 (d, J=8.0 Hz, 1H), 6.95 (s, 1H), 5.96 (s, 2H), 4.20 (s, 3H). ESI MS [M+H]$^+$ for C$_{25}$H$_{18}$N$_8$O, calcd 447.2. found 447.2.

Example 30

Synthesis of 4-({5-[1-(2H-Indazol-6-yl)-3-methyl-1H-pyrazolo[4,3-c]pyridin-6-yl]-1H-pyrazol-1-yl}methyl)benzonitrile Step a: A mixture of 1-(4,6-dichloropyridin-3-yl)ethan-1-one (0.180 g, 0.95 mmol, 1.0 mol. equiv.), hydrazine monohydrate (0.10 mL, 1.30 mmol, 1.4 mol. equiv.) and triethylamine (0.14 mL, 0.95 mmol, 1.0 mol. equiv.) in iPrOH (1.0 mL) was stirred at 80° C. overnight. The reaction mixture was cooled and diluted with saturated aqueous NaHCO$_3$ solution (15 mL) and EtOAc (15 mL). The aqueous layer was separated and back extracted with additional EtOAc (15 mL). The organic layers were combined, dried over MgSO$_4$, filtered and evaporated to give crude product that was used in the next step without purification (0.14 g, 0.84 mmol, 87%). ESI MS [M+H]$^+$ for C$_7$H$_6$ClN$_3$, calcd 168.0. found 168.0.

Step b: A mixture of the product from strep a (0.200 g, 1.19 mmol, 1.0 mol. equiv.), 6-iodo-1-(tetrahydro-2H-pyran-2-yl)-1H-indazole (0.580 g, 1.79 mmol, 1.5 mol. equiv.), N,N-dimethylethylenediamine (0.040 mL, 0.36 mmol, 0.3 mol. equiv.) and K$_3$PO$_4$ (0.500 g, 2.38 mmol, 2.0

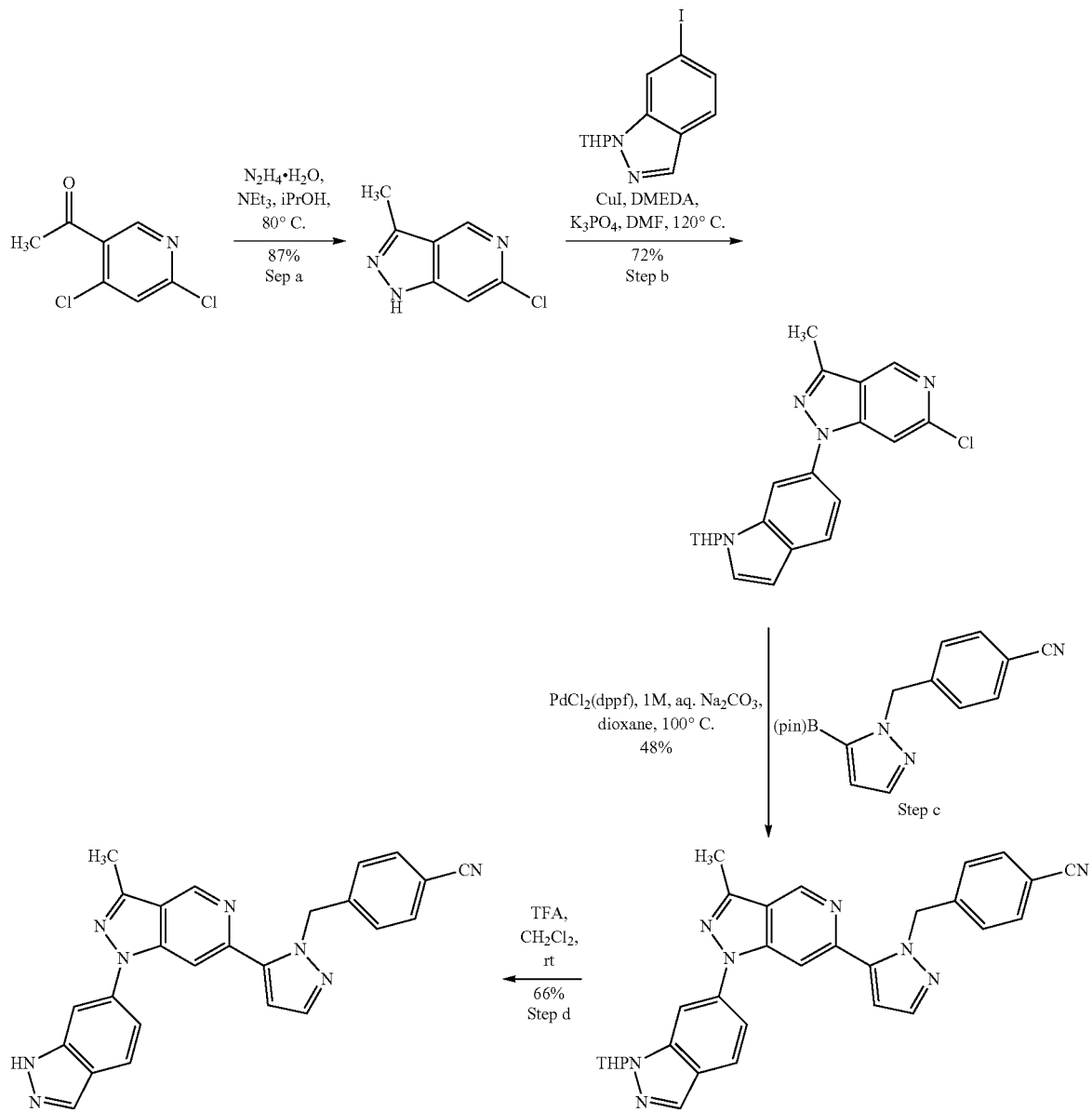

mol. equiv.) in dry DMF (4 mL) was purged with $N_2$ for 5 minutes. CuI (0.034 g, 0.18 mmol, 2.0 mol. equiv.) was added and the reaction vial was further purged with $N_2$ for 2 minutes, and then sealed. The reaction mixture was stirred overnight at 120° C. The reaction mixture was cooled and diluted with saturated aqueous $NaHCO_3$ solution (15 mL) and EtOAc (15 mL). The aqueous layer was separated and back extracted with additional EtOAc (15 mL). The organic layers were combined, washed with water (2×20 mL), brine (20 mL), and dried over $MgSO_4$. Concentration under reduced pressure and purification by column chromatography ($SiO_2$, 0 to 80% gradient of $CH_2Cl_2$/EtOAc) furnished the title compound as a yellow solid (0.320 g, 0.870 mmol, 73%). ESI MS [M+H]$^+$ for $C_{19}H_8ClN_5O$, calcd 368.1. found 368.0.

Step c: A reaction vial containing the product from step b (0.300 g, 0.820 mmol, 1.0 mol. equiv.), pyrazole boronic ester (0.300 g, 0.970 mmol, 1.2 mol. equiv.) and $PdCl_2(dppf)$ (0.060 g, 0.082 mmol, 0.10 mol. equiv.) in 1.0 M aqueous $Na_2CO_3$ solution (2.5 mL) and 1,4-dioxane (3 mL) was purged with $N_2$ for 5 minutes, sealed, and stirred at 100° C. for 3 hours. The reaction mixture was cooled and diluted with water (15 mL) and EtOAc (15 mL). The aqueous layer was separated and back extracted with additional EtOAc (15 mL). The organic layers were combined, washed with brine (20 mL), and dried over $MgSO_4$. Concentration under reduced pressure and purification by column chromatography ($SiO_2$, 0 to 100% gradient of $CH_2Cl_2$/EtOAc) furnished the title compound as a yellow solid (0.20 g, 0.39 mmol, 48%). ESI MS [M+H]$^+$ for $C_{30}H_{26}N_8O$, calcd 515.2. found 515.2.

Step d: A mixture of the product from step c (0.200 g, 0.390 mmol) in TFA (0.3 mL) and $CH_2Cl_2$ (3 mL) was stirred at room temperature overnight. The reaction mixture was diluted with saturated aqueous $NaHCO_3$ solution (15 mL) and $CH_2Cl_2$ (15 mL). The aqueous layer was separated and back extracted with additional $CH_2Cl_2$ (15 mL). The organic layers were combined, washed with brine (20 mL), and dried over $MgSO_4$. Concentration under reduced pressure and purification by column chromatography ($SiO_2$, 0 to 90% gradient of $CH_2Cl_2$/EtOAc) furnished the title compound as a white solid (0.110 g, 0.260 mmol, 66%). $^1$H NMR (400 MHz, DMSO-$d_6$) δ 13.2 (s, 1H) 9.24 (s, 1H), 8.19 (s, 1H), 8.08 (s, 1H), 7.96 (d, J=8.7 Hz, 1H), 7.87 (s, 1H), 7.74 (d, J=8.1 Hz, 2H), 7.63 (s, 1H), 7.56 (d, J=8.1 Hz, 1H), 7.27 (d, J=8.1 Hz, 2H), 7.04 (s, 1H), 6.05 (s, 2H), 2.69 (s, 3H); ESI MS [M+H]$^+$ for $C_{25}H_{18}N_8$, calcd 431.2. found 431.1.

Example 31

Synthesis of p-({5-[1-(1H-Indazol-6-yl)-3-methyl-1,2,4-triaza-1H-inden-6-yl]-1H-pyrazol-1-yl}methyl)benzonitrile

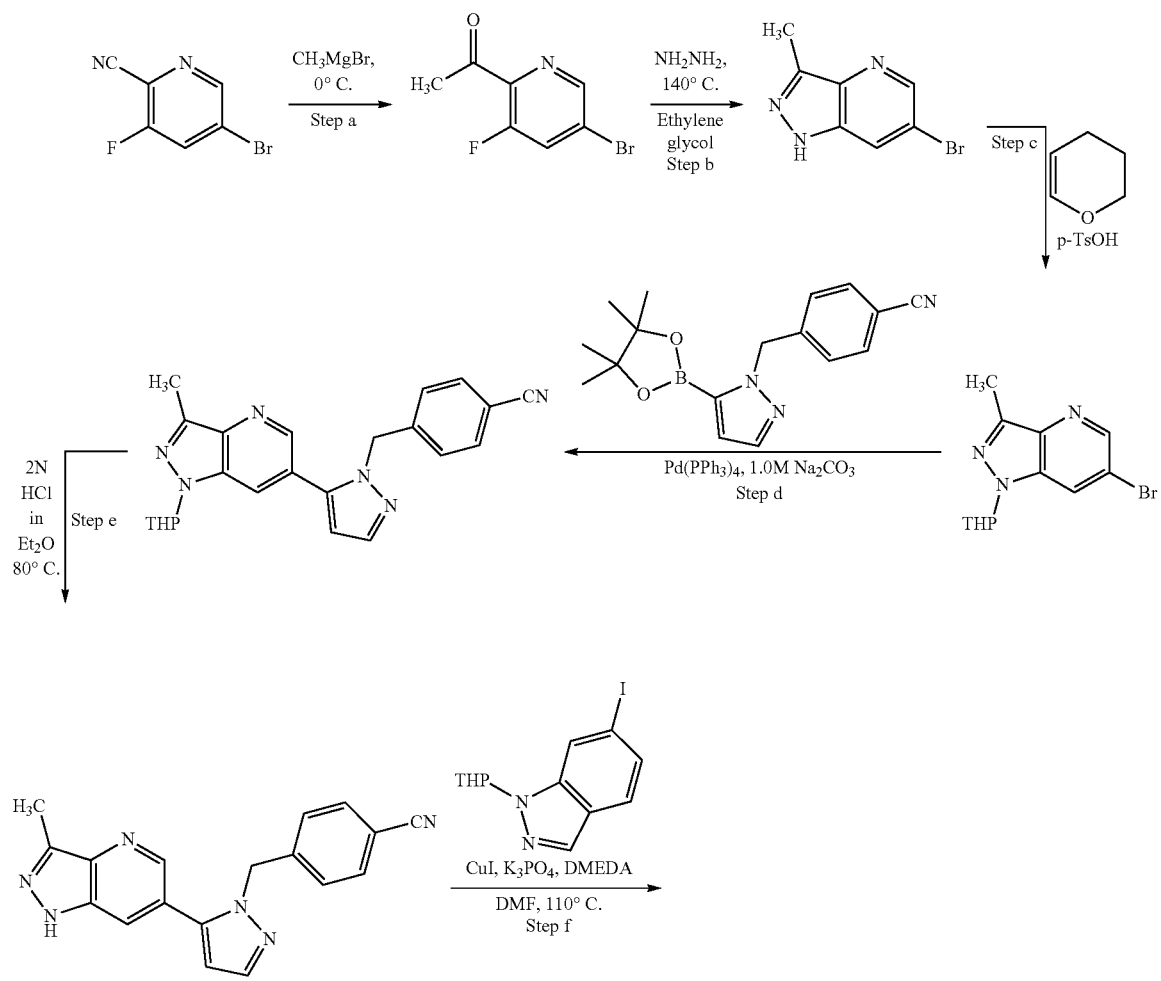

-continued

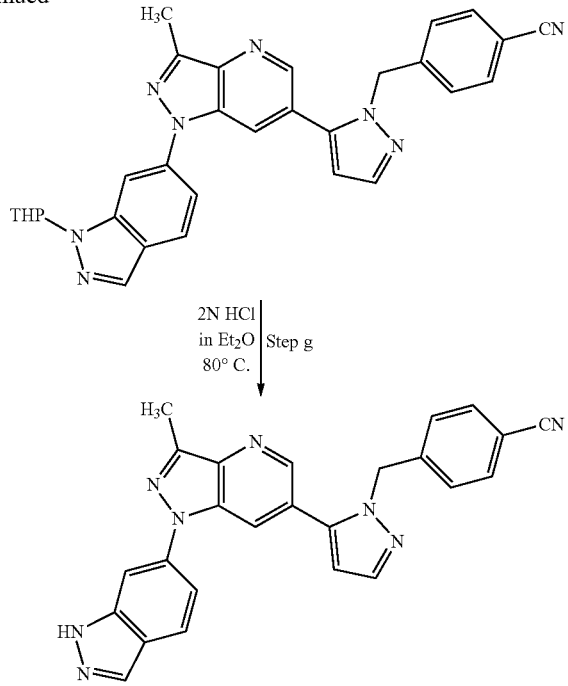

Step a: To a solution of 5-bromo-3-fluoro-2-pyridinecarbonitrile (15 g, 75 mmol) in THF (150 mL) at 0° C. under nitrogen atmosphere was added MeMgBr (1.4 M in THF/toluene 1:3, 107 mL, 150 mmol) slowly. The reaction mixture was stirred at 0° C. for 2 h after addition. Ice cold 2 N aqueous HCl solution was added to the reaction mixture carefully. The resulting mixture was stirred at room temperature for 12 h, then extracted with EtOAc (200 mL×2). The combined organic layers were dried over $Na_2SO_4$, filtered and concentrated. The residue was purified with a chromatographic column of silica gel eluted with dichloromethane to give the desired product (6.8 g, 42%).

Step b: To a solution of the product from step a (6.8 g, 31.2 mmol) in ethylene glycol (60 mL) were added hydrazine hydrate (2.34 g, 46.8 mmol). The reaction mixture was stirred at 140° C. for 14 h, then cooled down to room temperature, diluted with saturated $NaHCO_3$ solution (100 mL). The resulting mixture was extracted with EtOAc (200 mL×2). The combined organic layers were washed with brine (100 mL 2), dried over $Na_2SO_4$, filtered and concentrated.

Step c: To a solution of the product from step b (2.12 g, 10 mmol) and p-TsOH (172 mg, 1.0 mmol) in THF (50 mL) were added 3,4-dihydro-2H-pyran (2.52 g, 30 mmol). The mixture was stirred at 45° C. for 1 h, then cooled to room temperature, diluted with saturated aqueous $NaHCO_3$ solution (50 mL). The resulting mixture was extracted with EtOAc (100 mL×2). The combined organic layers were washed with brine (100 mL), dried over $Na_2SO_4$, filtered and concentrated. The residue was purified with a chromatographic column of silica gel eluted with 20-50% EtOAc in Hexanes to give the desired product (quantitative yield).

Step d: To a mixture of the product from step c (400 mg, 1.36 mmol), p-{[5-(4,4,5,5-Tetramethyl-1,3,2-dioxaborolan-2-yl)-1H-pyrazol-1-yl]methyl}benzonitrile (921 mg, 2.98 mmol) and 1.0 M $Na_2CO_3$ aqueous solution (4.08 mL) in THF (7 mL) was added $Pd(PPh_3)_4$ (157 mg, 0.136 mmol). Air was removed from the system by cycles of vacuum followed by backfilling with nitrogen. The vial was sealed, heated at 70° C. for 4 h, then cooled down to room temperature. The mixture reaction was diluted with water (10 mL) and extracted with EtOAc (30 mL×2). The combined organic layers were washed with brine (30 mL), dried over $Na_2SO_4$, filtered and concentrated. The residue was purified with a chromatographic column of silica gel eluted with 20-60% EtOAc in Hexanes to give the desired product (quantitative yield).

Step e: To a solution of the product from step d (400 mg, 1.0 mmol) in EtOH (5 mL) was added 2 N aqueous HCl in $Et_2O$ (1 mL). The vial was sealed, heated at 80° C. for 1.5 h, then cooled down to room temperature. The mixture reaction was quenched with saturated aqueous $NaHCO_3$ solution (50 mL) and extracted with EtOAc (30 mL×2). The combined organic layers were washed with brine (30 mL), dried over $Na_2SO_4$, filtered and concentrated. The residue was purified with a chromatographic column of silica gel eluted with 40-90% EtOAc in hexanes to give the desired product (140 mg, 45%).

Step f: A mixture of the product from step e (140 mg, 0.48 mmol), 6-iodo-1-(tetrahydro-2H-pyran-2-yl)-1H-indazole (175 mg, 0.54 mmol), N,N'-Dimethylethylenediamine (26 mg, 0.29 mmol) and $K_3PO_4$ (204 mg, 0.96 mmol) in DMF (2 mL) was treated with CuI (28 mg, 0.144 mmol). Air was removed from the system by cycles of vacuum followed by backfilling with nitrogen. The vial was sealed, heated at 110° C. for 14 h, then cooled down to room temperature. The mixture reaction was diluted with water (10 mL) and extracted with EtOAc (30 mL×2). The combined organic layers were washed with brine (30 mL), dried over $Na_2SO_4$, filtered and concentrated. The residue was purified with a chromatographic column of silica gel eluted with 20-100% EtOAc in hexanes to give the desired product (60 mg, 24%).

Step g: To a solution of the product from step f (60 mg, 0.12 mmol) in EtOH (5 mL) was added 2 N aqueous HCl in Et$_2$O (1 mL). The vial was sealed, heated at 80° C. for 1.5 h, then cooled down to room temperature. The mixture reaction was quenched with saturated aqueous NaHCO$_3$ solution (50 mL) and extracted with EtOAc (30 mL×2). The combined organic layers were washed with brine (30 mL), dried over Na$_2$SO$_4$, filtered and concentrated. The residue was purified by preparative HPLC to afford the desired product (40 mg, 78%). $^1$H NMR (400 MHz, Chloroform-d) δ 11.10 (broad, 1H), 8.55 (s, 1H), 8.17 (s, 1H), 7.89-7.76 (m, 2H), 7.72 (dt, J=2.3, 5.4 Hz, 2H), 7.49 (dd, J=3.1, 8.6 Hz, 2H), 7.36-7.24 (m, 1H), 7.11 (dd, J=3.1, 8.4 Hz, 2H), 6.53 (d, J=1.9 Hz, 1H), 5.41 (s, 2H), 2.78 (s, 3H). ESI MS [M+H]$^+$ for C$_{25}$H$_{18}$N$_8$, calcd 431.1. found 431.3.

Example 32

Synthesis of 6-(6-{1-[(4-Chlorophenyl)methyl]-1H-pyrazol-5-yl}-3-methyl-1H-pyrazolo[4,3-b]pyridin-1-yl)-2H-indazole

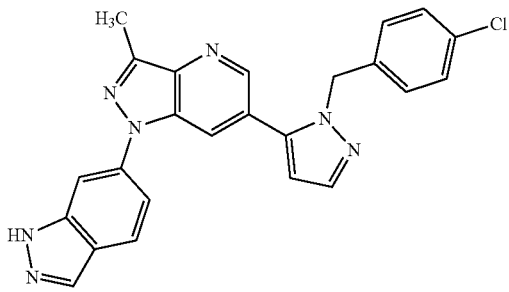 [SMILES: Cc1nn(-c2ccc3cn[nH]c3c2)c2cc(-c3ccnn3Cc3ccc(Cl)cc3)cnc12]

The title compound was synthesized in a similar fashion to Example 31: $^1$H NMR (400 MHz, Chloroform-d) δ 10.16 (s, 1H), 8.61 (dd, J=1.8, 0.9 Hz, 1H), 8.20-8.07 (m, 1H), 7.88-7.77 (m, 2H), 7.70 (dq, J=2.0, 1.0 Hz, 1H), 7.64-7.53 (m, 1H), 7.37-7.29 (m, 1H), 7.24-7.14 (m, 2H), 6.97 (d, J=8.1 Hz, 2H), 6.54-6.36 (m, 1H), 5.33 (s, 2H), 2.80 (s, 3H). ESI MS [M+H]$^+$ for C$_{24}$H$_{18}$ClN$_7$, calcd 440.1. found 440.2.

Example 33

Synthesis of 5-(6-{2-[(2,4-Dichlorophenyl)methyl]-2H-pyrazol-3-yl}-1,2,4-triaza-1H-inden-1-yl)-1,3-benzimidazol-2-one

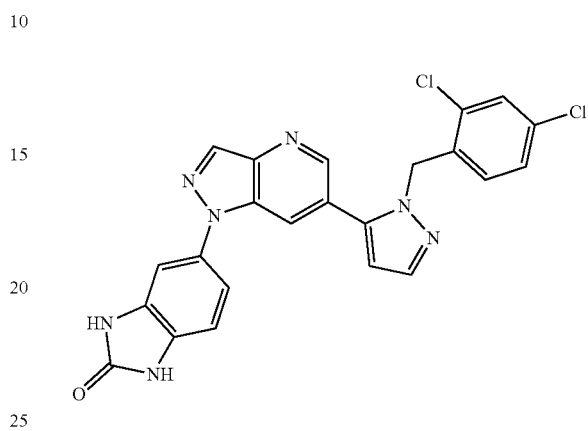

The title compound was synthesized in a similar fashion to Example 31: $^1$H NMR (400 MHz, DMSO-d$_6$) δ 10.87 (s, 1H), 10.84 (s, 1H), 8.64 (s, 1H), 8.60 (s, 1H), 7.95 (s, 1H), 7.69 (s, 1H), 7.44 (s, 1H), 7.36 (d, J=8.2 Hz, 1H), 7.17-7.14 (m, 2H), 7.00 (d, J=8.2 Hz, 1H), 6.84 (d, J=8.2 Hz, 1H), 6.72 (s, 1H), 5.45 (s, 2H). ESI MS [M+H]$^+$ for C$_{23}$H$_{15}$Cl$_2$N$_7$O, calcd 476.1. found 476.0.

Example 34

Synthesis of 4-({5-[1-(2H-Indazol-6-yl)-1H-1,2,3-benzotriazol-6-yl]-1H-pyrazol-1-yl}methyl)benzonitrile

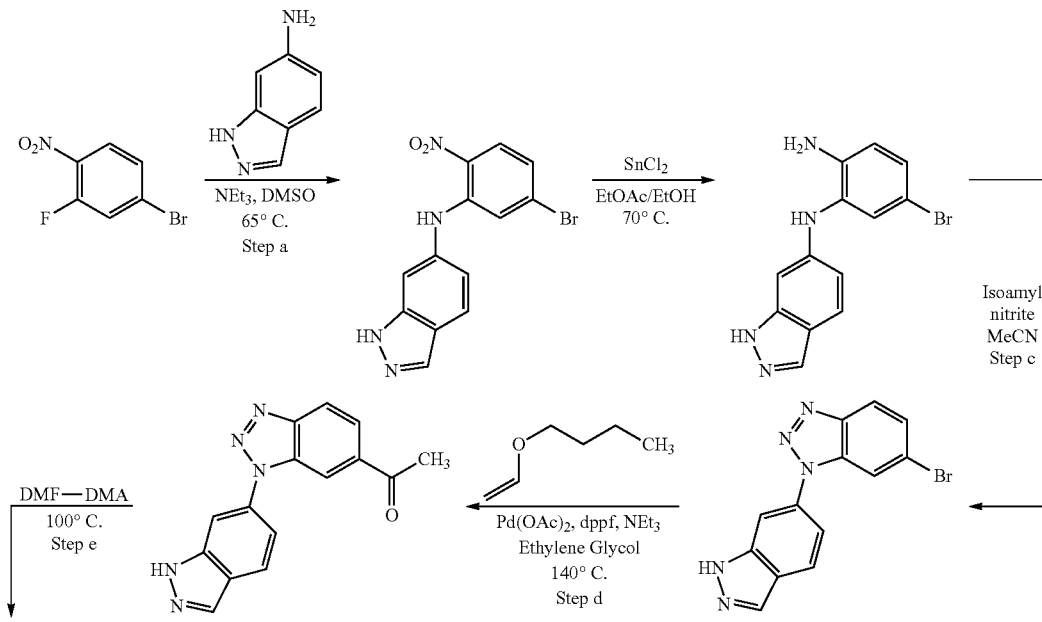

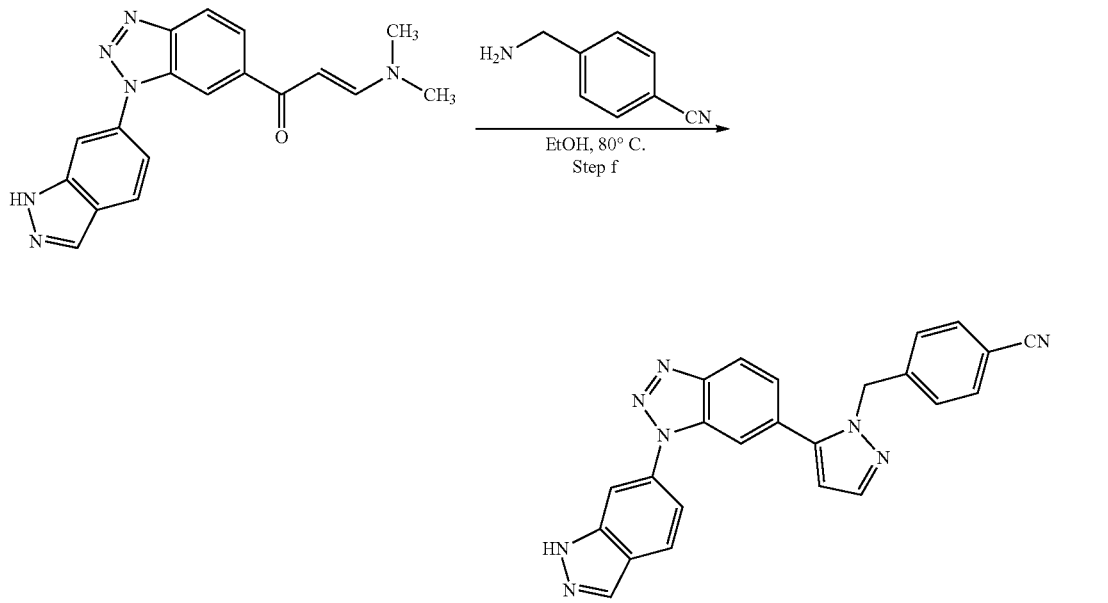

Step a: 2-Fluoro-4-bromonitrobenzene (7 g, 32 mmol) was dissolved in 8 mL of DMSO. 6-Aminoindazole (4.7 g, 35 mmol) was then added, followed by 8 mL of triethylamine. The mixture was warmed to 65° C. and allowed to stir overnight. The mixture was then cooled to room temperature, diluted with ethyl acetate, and washed with water. The organic layer was dried using anhydrous $Na_2SO_4$, filtered, and concentrated. The solid was washed with MTBE and used without further purification (8 g, 75%). ESI MS [M−H]$^+$ for $C_{13}H_8BrN_4O_2$, calcd 330.98. found 331.0.

Step b: The product from Step a was dissolved in 100 mL of ethyl acetate and 70 mL of ethanol. The slurry was then warmed to 70° C. and $SnCl_2$ (16.2 g, 73 mmol) was added in portions. The mixture was then stirred at 70° C. overnight. The mixture was cooled to room temperature and 200 mL of saturated $Na_2CO_3$ was added. The slurry was then filtered over Celite® and washed with ethyl acetate; the filtrate was dried using anhydrous $Na_2SO_4$ and concentrated. The crude material was purified using column chromatography (7.5 g, 100%) ESI MS [M+H]$^+$ for $C_{13}H_{12}BrN_4$, calcd 303.0. found 303.2.

Step c: The product from step b (5.3 g, 17.5 mmol) was dissolved in 180 mL of acetonitrile and isoamyl nitrite (3.5 mL, 26.3 mmol) was added dropwise. The mixture was then warmed to 65° C. and stirred for 4 hours. The mixture was cooled to room temperature, concentrated and purified using column chromatography (3.31 g, 60%) ESI MS [M+H]$^+$ for $C_{13}H_9BrN_5$, calcd 314.0. found 314.0.

Step d: The product from Step c (5.0 g, 15.9 mmol, 1.0 equiv) and triethylamine (4.4 mL, 31.8 mmol, 2.0 equiv) in 32 mL of ethylene glycol (0.5 M) was sparged with $N_2$ for 10 minutes. Pd(OAc)$_2$ (107 mg, 0.5 mmol, 0.1 equiv), 1,1'-bis(diphenylphosphino)ferrocene (554 mg, 1.0 mmol, 0.2 equiv), and n-butyl vinyl ether (4.1 mL 31.8 mmol, 2.0 equiv) were then added and the reaction heated to 140° C. under $N_2$ atmosphere for 14 h. Additional triethylamine (4.4 mL, 31.8 mmol, 2.0 equiv), Pd(OAc)$_2$ (107 mg, 0.5 mmol, 0.1 equiv), 1,1'-bis(diphenylphosphino)ferrocene (554 mg, 1.0 mmol, 0.2 equiv), and n-butyl vinyl ether (4.1 mL 31.8 mmol, 2.0 equiv) were added at this time, and the reaction continued at 140° C. for an additional 6 h. The reaction was then cooled to room temperature, diluted with 64 mL dioxane, and 1 N aqueous HCl (32 mL) was added. The biphasic mixture was stirred until the reaction was complete by TLC analysis and then diluted with water (200 mL) and EtOAc (200 mL). The organic phase was collected and the aqueous phase was extracted with EtOAc (2×50 mL). The combined organic extracts were dried over $Na_2SO_4$ and concentrated in vacuo. The resulting residue was purified by column chromatography ($CH_2Cl_2 \rightarrow$ 9:1 $CH_2Cl_2$:MeOH) to give the 1-[3-(1H-Indazol-6-yl)-1,2,3-benzotriazol-5-yl]-1-ethanone (3.6 g, 82% yield). ESI MS [M+H]$^+$ for $C_{15}H_{11}N_5O$, calcd 278.3. found 278.3.

Step e: The product from Step d (3.6 g, 12.9 mmol) was taken up in 26 mL DMF-DMA (0.5 M) and the reaction heated to 100° C. for 2.5 h. Upon completion, the reaction mixture was cooled to room temperature and concentrated in vacuo. The resulting residue was purified by column chromatography ($CH_2Cl_2 \rightarrow$ 9:1 $CH_2Cl_2$:MeOH) to give 3-(dimethylamino)-1-[3-(1H-indazol-6-yl)-1,2,3-benzotriazol-5-yl]-2-propen-1-one as a pale yellow solid (1.9 g, 45% yield). ESI MS [M+H]$^+$ for $C_{18}H_{16}N_6O$, calcd 333.4. found 333.3.

Step f: The product from Step e (50 mg, 0.115 mmol) was dissolved in ethanol. The hydrazine was then added and the mixture was warmed to 80° C. for 30 min. The mixture was then cooled to room temperature, concentrated, and purified using column chromatography to give the desire product as a pale yellow solid in 42% yield (40 mg): $^1$H NMR (400 MHz, DMSO-d$_6$) δ 13.39 (s, 1H), 8.30-8.20 (m, 2H), 8.02-7.90 (m, 2H), 7.72 (s, 1H), 7.67 (d, J=2.0 Hz, 1H), 7.63 (d, J=7.9 Hz, 2H), 7.54 (d, J=8.6 Hz, 1H), 7.46 (dd, J=8.5, 1.9 Hz, 1H), 7.12 (d, J=8.0 Hz, 2H), 6.66 (d, J=2.0 Hz, 1H), 5.54 (s, 2H). ESI MS [M+H]$^+$ for $C_{24}H_{17}N_8$, calcd 417.2. found 417.2.

Example 35

Synthesis of 1-(1H-Indazol-6-yl)-6-[2-(m-tolyl)-2H-pyrazol-3-yl]-1,2,3-benzotriazole

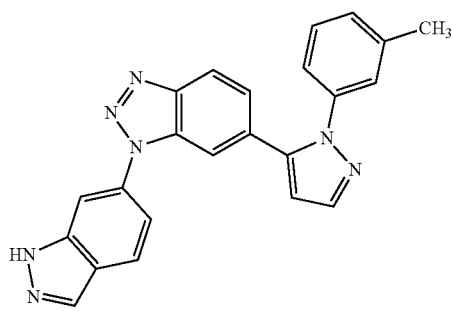 [SMILES: Cc1cccc(-n2nccc2-c2ccc3nnn(-c4ccc5cn[nH]c5c4)c3c2)c1]

The title compound was synthesized in a similar fashion to Example 34. ¹H NMR (400 MHz, DMSO-d₆) δ 13.41 (s, 1H), 8.27 (q, J=1.2 Hz, 1H), 8.15 (dt, J=8.6, 0.9 Hz, 1H), 8.04-7.93 (m, 2H), 7.80 (dd, J=1.9, 1.1 Hz, 1H), 7.73 (q, J=1.2 Hz, 1H), 7.39-7.24 (m, 5H), 7.02 (d, J=7.5 Hz, 1H), 6.89 (dd, J=2.0, 1.1 Hz, 1H), 2.28 (s, 3H). ESI MS [M–H]⁻ for $C_{23}H_{17}N_7$, calcd 390.2. found 390.3.

Example 36

Synthesis of p-({5-[3-(2-Oxo-1,3-benzimidazol-5-yl)-1,2,3-benzotriazol-5-yl]-1H-pyrazol-1-yl}methyl)benzonitrile

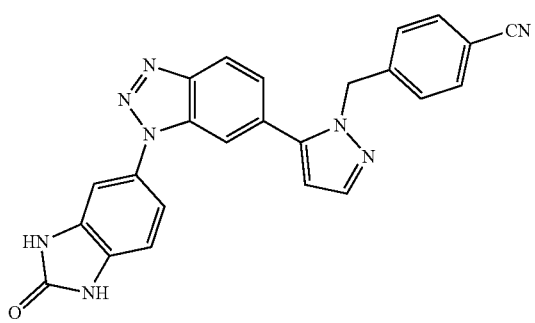 [SMILES: N#Cc1ccc(Cn2nccc2-c2ccc3nnn(-c4ccc5[nH]c(=O)[nH]c5c4)c3c2)cc1]

The title compound was synthesized in a similar fashion to Example 34. ¹H NMR (400 MHz, DMSO-d₆) δ 10.99 (s, 1H), 10.95 (s, 1H), 8.22 (d, J=8.6 Hz, 1H), 7.69-7.67 (m, 3H), 7.60 (s, 1H), 7.50 (d, J=8.6 Hz, 1H), 7.27-7.24 (m, 2H), 7.13 (d, J=8.0 Hz, 2H), 7.09 (d, J=8.0 Hz, 1H), 6.64 (s, 1H), 5.52 (s, 2H). ESI MS [M+H]⁺ for $C_{24}H_{16}N_8O$, calcd 433.4. found 433.1.

Example 37

Synthesis of p-({4-Chloro-5-[3-(2-oxo-1,3-benzimidazol-5-yl)-1,2,3-benzotriazol-5-yl]-1H-pyrazol-1-yl}methyl)benzonitrile

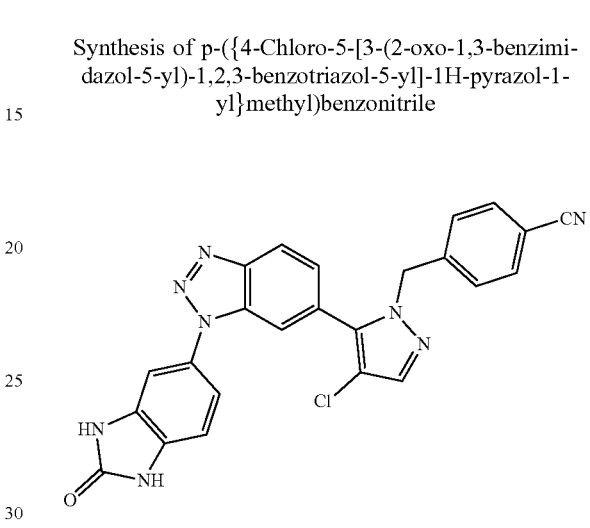

The title compound was synthesized in a similar fashion to Example 34. ¹H NMR (400 MHz, DMSO-d₆) δ 11.01 (s, 1H), 10.97 (s, 1H), 8.29 (d, J=8.7 Hz, 1H), 7.87 (d, J=1.7 Hz, 1H), 7.75-7.65 (m, 2H), 7.49-7.42 (m, 1H), 7.33-7.24 (m, 2H), 7.13-7.11 (m, 4H), 5.44 (s, 2H). ESI MS [M+H]⁺ for $C_{24}H_{15}ClN_8O$, calcd 467.1. found 467.2.

Example 38

Synthesis of 6-(1-(2,4-Dichlorobenzyl)-1H-pyrazol-5-yl)-1-(1H-indazol-6-yl)-1H-pyrazolo[4,3-b]pyridin-3-amine

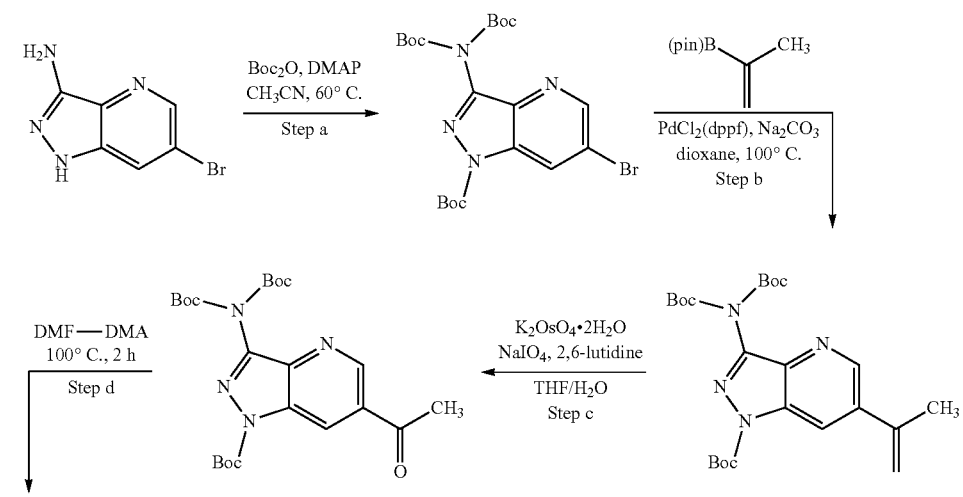

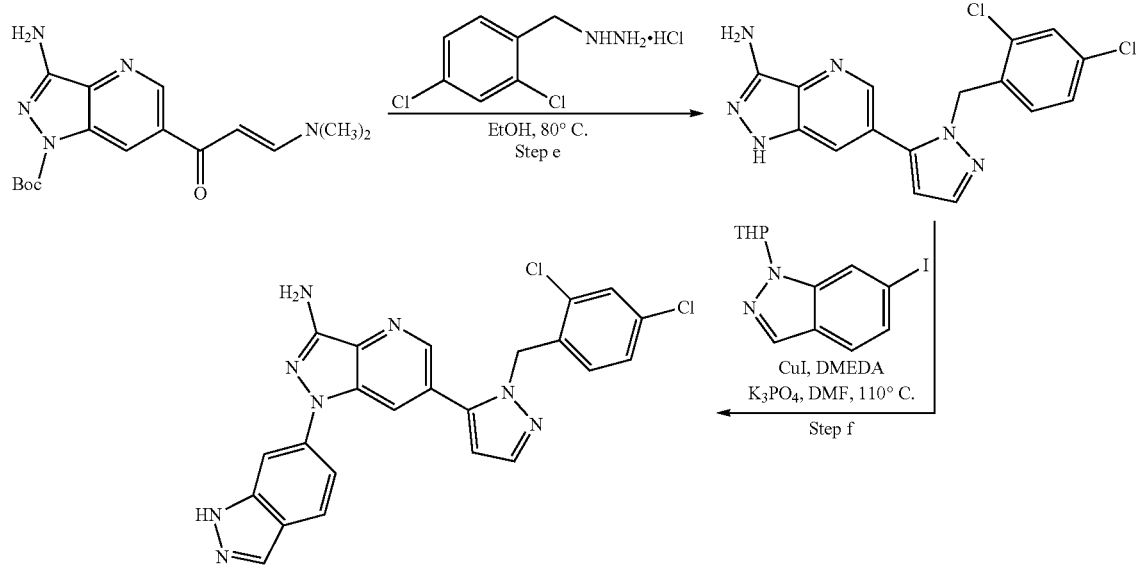

Step a: To a solution of 6-bromo-1H-pyrazolo[4,3-b]pyridin-3-amine (5.04 g, 23.6 mmol, 1.0 equiv) in CH₃CN (118 mL) was added Boc₂O (25.8 g, 118 mmol, 5.0 equiv), followed by DMAP (144 mg, 1.18 mmol, 5 mol %). The resulting mixture was stirred at reflux for 12 h. Upon completion, the reaction mixture was cooled to 25° C., concentrated under reduced pressure, and purified by column chromatography (SiO₂, CH₂Cl₂/EtOAc) to afford tert-butyl 3-(bis(tert-butoxycarbonyl)amino)-6-bromo-1H-pyrazolo[4,3-b]pyridine-1-carboxylate (12.0 g) as a white solid.

Step b: To a solution of the product from step a (12.0 g, 23.4 mmol, 1.0 equiv) in dioxane (116 mL) was added isopropenylboronate (4.39 mL, 23.4 mmol, 1.0 equiv), followed by 2 M aqueous Na₂CO₃ (35 mL, 70.1 mmol, 3.0 equiv). The mixture was degassed by bubbling nitrogen through the solution for 5 minutes. To the resulting mixture was added PdCl₂(dppf) (1.71 g, 2.34 mmol, 10 mol %). The reaction mixture was then stirred under a nitrogen atmosphere at 100° C. for 3 h. Upon completion, the reaction mixture was cooled to 25° C., diluted with EtOAc (200 mL), filtered over Celite® and concentrated under reduced pressure. Purification by column chromatography (SiO₂, CH₂Cl₂/EtOAc) provided the desired product (3.85 g, 35% yield), as well as a mixture of mono- and bis-Boc-protected products.

Step c: To a solution of the product from step b (3.85 g, 8.12 mmol, 1.0 equiv) in 2:1 THF/H₂O (40 mL) was added NaIO₄ (10.4 g, 48.7 mmol, 6.0 equiv), followed by 2,6-lutidine (1.89 mL, 16.2 mmol, 2.0 equiv) and K₂OsO₄·2H₂O (149 mg, 0.406 mmol, 5 mol %). The resulting suspension was stirred vigorously at 25° C. for 1 h. Upon completion, the reaction was quenched by addition of saturated aqueous Na₂S₂O₃ (15 mL) and the reaction mixture was extracted with EtOAc (3×50 mL). The combined organic extracts were dried (Na₂SO₄), filtered and concentrated under reduced pressure to afford the product, which was used in step d without further purification.

Step d: A solution of the product from step c (3.65 g, 9.76 mmol, 1.0 equiv) in DMF-DMA (19.5 mL) was stirred in a sealed vial at 100° C. for 2 h. Upon completion, the reaction mixture was cooled to 25° C., concentrated under reduced pressure, and purified by column chromatography (SiO₂, CH₂Cl₂/MeOH), which provided the mono-Boc-protected product (178 mg, 3% yield).

Step e: A solution of the product from step d (178 mg, 0.536 mmol, 1.0 equiv) and (2,4-dichlorobenzyl)hydrazine HCl salt (146 mg, 0.643 mmol, 1.2 equiv) in EtOH (5.4 mL) was stirred at 80° C. in a sealed vial for 1.5 h. The reaction mixture was then cooled to 25° C. and a solution of HCl in dioxane (1N, 0.54 mL, 1.0 equiv) was added. The resulting mixture was stirred an additional 1 h at 80° C. Upon completion, the reaction mixture was cooled to 25° C., concentrated under reduced pressure, and purified by column chromatography (SiO₂, CH₂Cl₂/MeOH), which provided 6-(1-(2,4-dichlorobenzyl)-1H-pyrazol-5-yl)-1H-pyrazolo[4,3-b]pyridin-3-amine (103 mg, 54% yield).

Step f: A suspension of the product from step e (103 mg, 0.288 mmol, 1.0 equiv), 6-iodo-1-(tetrahydro-2H-pyran-2-yl)-1H-indazole (104 mg, 0.317 mmol, 1.1 equiv), K₃PO₄ (122 mg, 0.576 mmol, 2.0 equiv), CuI (55.0 mg, 0.288 mmol, 1.0 equiv), and N,N'-dimethylethylenediamine (6.0 uL, 0.576 mmol, 2.0 equiv) in DMF (0.58 mL, 0.5 M) was degassed by bubbling nitrogen through the solution for 5 minutes. The resulting mixture was then stirred in a sealed vial at 135° C. for 20 h. Upon completion, the reaction mixture was cooled to 25° C. and diluted with water (5 mL). The resulting precipitate was collected by vacuum filtration and rinsed several times with water. The solid was then re-dissolved in a mixture of MeOH (2 mL) and 1 N HCl/dioxane (3 mL) and stirred at 45° C. for 1 h. Upon completion, the reaction mixture was cooled to 25° C. and concentrated under reduced pressure. The crude product was purified by column chromatography (SiO₂, CH₂Cl₂→50% MeOH/CH₂Cl₂) followed by reverse phase preparative HPLC (H₂O/MeCN gradient with 0.1% TFA), which provided 6-(1-(2,4-dichlorobenzyl)-1H-pyrazol-5-yl)-1-(1H-indazol-6-yl)-1H-pyrazolo[4,3-b]pyridin-3-amine, TFA salt (5 mg, 4% yield), as a pale yellow solid. ¹H NMR (400 MHz, DMSO-d₆) δ 13.04 (s, 1H), 8.43 (s, 1H), 8.10 (s, 2H), 7.79 (d, J=8.4 Hz, 1H), 7.71 (s, 1H), 7.53 (s, 1H), 7.39 (m, 2H), 6.86 (d, J=8.3 Hz, 1H), 6.74 (s, 1H), 6.13 (brs, 2H), 5.49 (s, 2H). ESI MS [M+H]⁺ for C₂₃H₁₇Cl₂N₈, calcd 475.1. found 475.0.

Example 39

Synthesis of p-({5-[3-Amino-1-(2-oxo-1,3-benzimidazol-5-yl)-1,2,5-triaza-1H-inden-6-yl]-1H-pyrazol-1-yl}methyl)benzonitrile

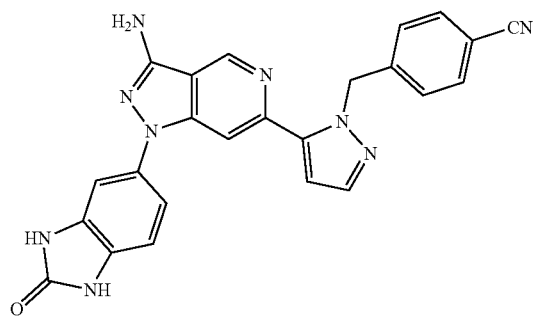 [SMILES: N#Cc1ccc(Cn2nccc2-c2cc3c(cn2)c(N)nn3-c2ccc3[nH]c(=O)[nH]c3c2)cc1]

The title compound was synthesized in a similar fashion to Example 38. $^1$H NMR (400 MHz, DMSO-$d_6$) δ 10.75 (s, 2H), 9.08 (s, 1H), 7.75-7.70 (m, overlap, 3H), 7.62 (s, 1H), 7.24-7.21 (m, overlap, 3H), 7.16 (s, 1H), 7.00 (d, J=8.3 Hz, 1H), 6.92 (s, 1H), 5.94 (s, 2H). ESI MS [M+H]$^+$ for $C_{24}H_{17}N_9O$, calcd 448.2. found 448.1.

Example 40

Synthesis of 6-((5-(3-Amino-1-(1H-indazol-6-yl)-1H-pyrazolo[4,3-b]pyridin-6-yl)-1H-pyrazol-1-yl)methyl)nicotinonitrile

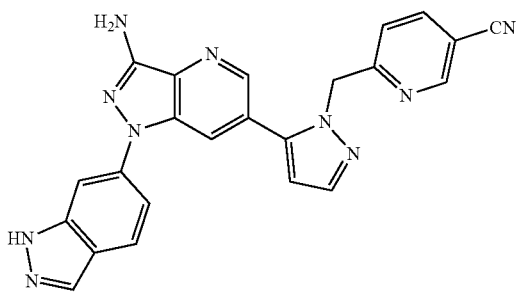 [SMILES: N#Cc1ccc(Cn2nccc2-c2cnc3c(N)nn(-c4ccc5cn[nH]c5c4)c3c2)nc1]

The title compound was synthesized in a similar fashion to Example 38. $^1$H NMR (400 MHz, DMSO-$d_6$) δ 8.92 (s, 1H), 8.55 (s, 1H), 8.43 (s, 1H), 8.30 (dt, J=8.1, 2.0 Hz, 1H), 8.10 (s, 1H), 7.81 (dd, J=8.7, 1.8 Hz, 1H), 7.73 (s, 1H), 7.67 (s, 1H), 7.46 (d, J=8.9 Hz, 1H), 7.39 (d, J=8.2 Hz, 1H), 6.72 (s, 1H), 6.20-5.50 (brs, 3H), 5.62 (s, 2H). ESI MS [M+H]$^+$ for $C_{23}H_{17}N_{10}$, calcd 433.2. found 433.3.

Example 41

Synthesis of 6-(1-((5-Chloropyridin-2-yl)methyl)-1H-pyrazol-5-yl)-1-(1H-indazol-6-yl)-1H-pyrazolo[4,3-b]pyridin-3-amine

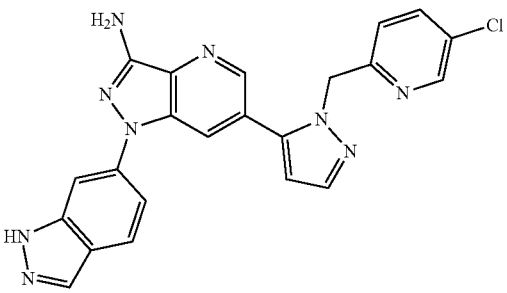 [SMILES: Nc1nn(-c2ccc3cn[nH]c3c2)c2cc(-c3ccnn3Cc3ccc(Cl)cn3)cnc12]

The title compound was synthesized in a similar fashion to Example 38. $^1$H NMR (400 MHz, Methanol-$d_4$) δ 8.54 (d, J=1.7 Hz, 1H), 8.40 (d, J=1.7 Hz, 1H), 8.31 (dd, J=2.5, 0.8 Hz, 1H), 8.09 (d, J=1.1 Hz, 1H), 7.82 (dd, J=8.7, 0.8 Hz, 1H), 7.77 (dd, J=8.4, 2.5 Hz, 1H), 7.72-7.70 (m, 1H), 7.67 (d, J=2.0 Hz, 1H), 7.39 (dd, J=8.7, 1.8 Hz, 1H), 7.20 (dd, J=8.4, 0.7 Hz, 1H), 6.65 (d, J=2.0 Hz, 1H), 5.46 (s, 2H). ESI MS [M+H]$^+$ for $C_{22}H_{17}ClN_9$, calcd 442.1. found 442.2.

Example 42

Synthesis of 6-(5-{1-[(2,4-Dichlorophenyl)methyl]-1H-pyrazol-5-yl}-[1,2,3]triazolo[1,5-a]pyridin-3-yl)-2H-indazole

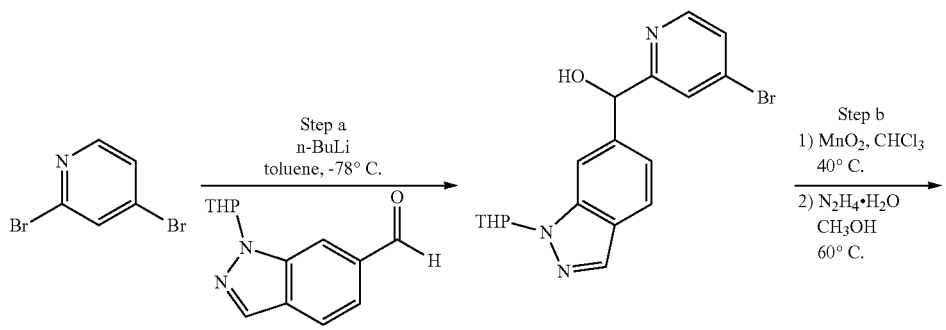

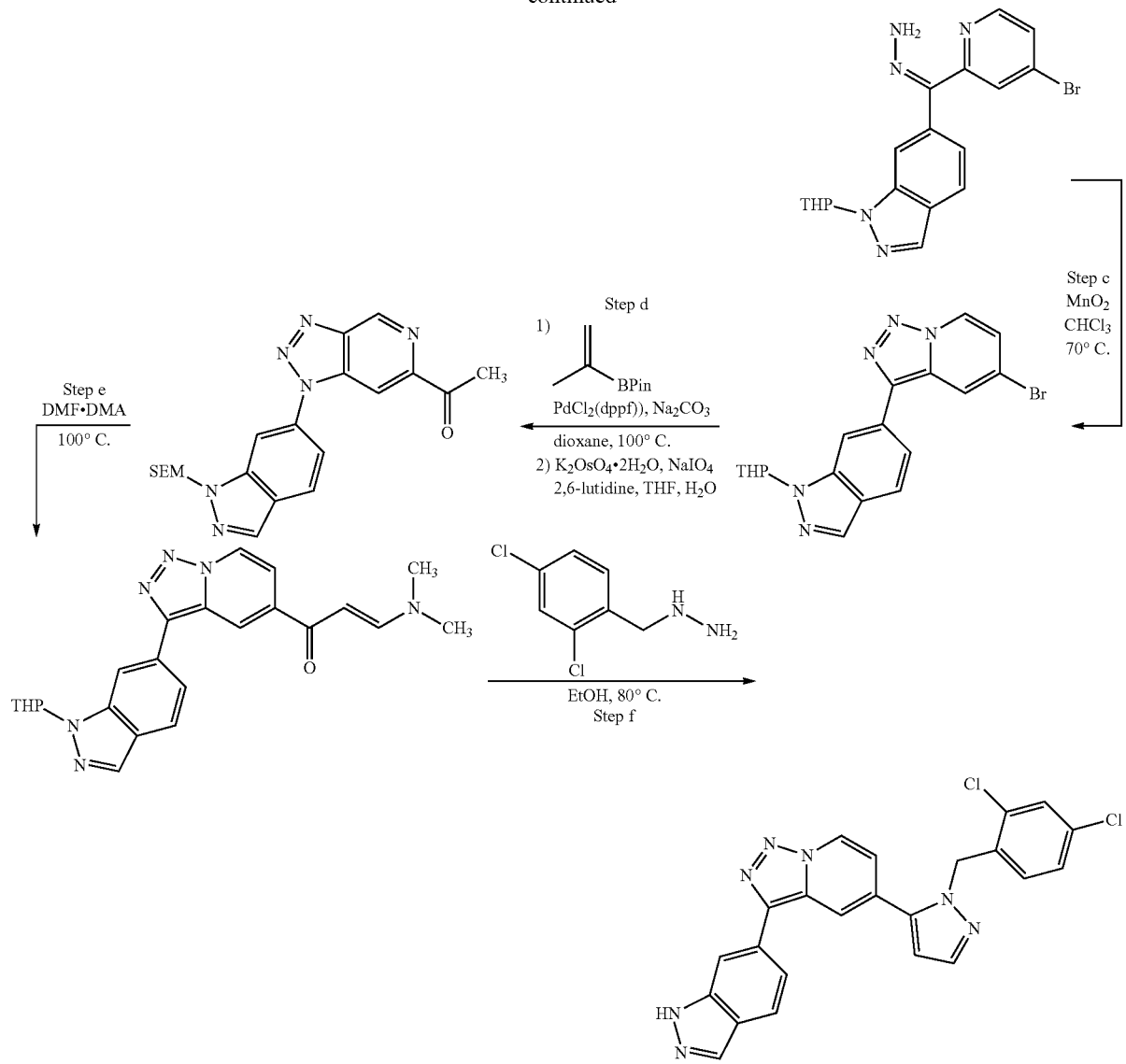

Step a: To a solution of 2,4-dibromopyridine (3.90 g, 16.5 mmol) in toluene (110 mL) at −78° C. was added dropwise n-BuLi (2.5M in hexane, 7.92 mL, 19.8 mmol). After stirring at −78° C. for one hour, a solution of aldehyde (4.17 g, 18.1 mmol) in toluene (10 mL) was added dropwise. The reaction was held at this temperature for one hour then allowed to warm to −20° C. overnight. The reaction was quenched with NH$_4$Cl (saturated aqueous) then partitioned between EtOAc and water. The organic layer was washed with brine, dried over MgSO$_4$ and concentrated under reduced pressure. The desired product (4.23 g, 66% yield) was isolated following column chromatograph (SiO$_2$, 0-50% EtOAc/CH$_2$Cl$_2$). ESI MS [M+H]$^+$ for C$_{18}$H$_{18}$BrN$_3$O$_2$, calcd 388.1. found 388.2.

Step b: To a solution of diaryl-carbinol from step a (4.23 g, 10.9 mmol) in chloroform (55 mL) was added MnO$_2$ (activated, 20 g). The suspension was heated to 40° C. for 2.5 hours then cooled to room temperature and filtered through a pad of Celite®. The filter cake was rinsed with CH$_2$Cl$_2$ and concentrated under reduced pressure. The desired product was used in the subsequent step without further purification To a solution of crude di-aryl ketone from the previous reaction in MeOH (36 mL) was added hydrazine hydrate (5.3 mL, 109 mmol). The reaction mixture was heated to 60° C. overnight. After cooling to room temperature, the reaction was concentrated to ¼ volume with a stream of nitrogen then partitioned between CH$_2$Cl$_2$ and water. The organic layer was dried (MgSO$_4$) and concentrated in vacuo. Column chromatography (SiO$_2$, 0-10% MeOH/CH$_2$Cl$_2$) provided the desired hydrazone (2.02 g, 56% yield). ESI MS [M+H]$^+$ for C$_{18}$H$_{18}$BrN$_5$, calcd 400.1. found 400.1.

Step c: A suspension of the product from step b (2.02 g, 5.05 mmol) and MnO$_2$ (8.8 g, 100.9 mmol) in chloroform was heated to 70° C. for two hours. The reaction was cooled to room temperature and filtered through a pad of Celite®. The filter cake was rinsed with CH$_2$Cl$_2$ and concentrated under reduced pressure. The desired product was used in the subsequent step without further purification. ESI MS [M+H]$^+$ for C$_{18}$H$_{16}$BrN$_5$O, calcd 398.1. found 398.2.

Step d: A flask charged with the product from step c (1.6 g, 4.02 mmol) and PdCl$_2$(dppf) (294 mg, 0.40 mmol) was evacuated and backfilled with N$_2$ (3×). Degassed dioxane (40 mL), 1.0 M aqueous Na$_2$CO$_3$ (16.1 mL) and isopropenylboronic acid pinacol ester (2.27 mL, 12.1 mmol) were subsequently added. The mixture was heated to 100° C. overnight. After cooling to room temperature, the reaction was partitioned between EtOAc and water. The organic layer was washed with brine, dried over MgSO$_4$, and concentrated under reduced pressure. The crude product was used without further purification. ESI MS [M+H]$^+$ for C$_{21}$H$_{21}$N$_5$O, calcd 360.2. found 360.3.

To a solution of the crude olefin (4.02 mmol) in THF (50 mL) and water (25 mL) were added NaIO$_4$ (5.2 g, 24.1 mmol), 2,6-lutidine (937 μL, 8.04 mmol) and K$_2$OsO$_4$.2H$_2$O (75 mg, 0.20 mmol). The resulting heavy suspension was stirred overnight at room temperature. The reaction was partitioned between EtOAc and water. The organic layer was washed with water, brine, dried over MgSO$_4$, and concentrated under reduced pressure. The crude product was used without further purification. ESI MS [M+H]$^+$ for C$_{20}$H$_{19}$N$_5$O$_2$, calcd 362.2. found 362.3.

Step e: A solution of the product from step c in N,N-dimethylformamide dimethyl acetal (40 mL) was stirred in a sealed vial at 100° C. overnight. Upon completion, the reaction mixture was cooled to 25° C., concentrated under reduced pressure, and purified by column chromatography (SiO$_2$, 0-10% MeOH/CH$_2$Cl$_2$), which provided the product (536 mg, 32% yield). ESI MS [M+H]$^+$ for C$_{23}$H$_{24}$N$_6$O$_2$, calcd 417.2. found 417.3.

Step f: A solution of the product from step e (145 mg, 0.35 mmol) and (2,4-dichlorobenzyl)hydrazine HCl salt (198 mg, 0.87 mmol) in EtOH (3.5 mL) was stirred at 80° C. in a sealed vial for two hours which resulted in complete THP deprotection. The reaction mixture was then cooled to 25° C., concentrated under reduced pressure, and purified by column chromatography (SiO$_2$, CH$_2$Cl$_2$/MeOH), which provided 6-(5-{1-[(2,4-dichlorophenyl)methyl]-1H-pyrazol-5-yl}-[1,2,3]triazolo[1,5-a]pyridin-3-yl)-2H-indazole (73 mg, 45% yield). $^1$H NMR (400 MHz, DMSO-d$_6$) δ 13.13 (s, 1H), 9.21 (d, J=7.2 Hz, 1H), 8.22-8.04 (m, 3H), 7.83 (d, J=8.4 Hz, 1H), 7.71 (s, 1H), 7.59 (s, 1H), 7.54 (d, J=8.4 Hz, 1H), 7.38 (d, J=8.4 Hz, 1H), 7.29 (d, J=7.2 Hz, 1H), 6.89-6.74 (m, 2H), 5.57 (s, 2H). ESI MS [M+H]$^+$ for C$_{23}$H$_{15}$Cl$_2$N$_7$, calcd 460.1. found 460.1.

TABLE 1

Specific Examples (Potency: CD73 IC$_{50}$: + means > 1 μM, ++ means 100 nM to 1 μM, +++ means < 100 nM).

| Example | Structure | Potency |
| --- | --- | --- |
| 1 | 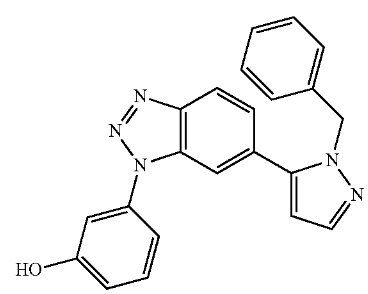 [SMILES: Oc1cccc(-n2nnc3ccc(-c4ccnn4Cc4ccccc4)cc32)c1] | ++ |
| 2 | 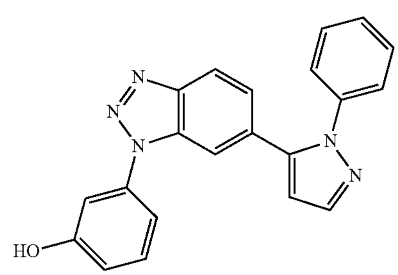 [SMILES: Oc1cccc(-n2nnc3ccc(-c4ccnn4-c4ccccc4)cc32)c1] | + |
| 3 | 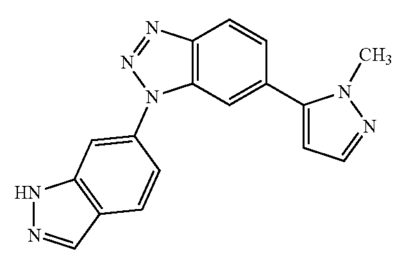 [SMILES: Cn1nccc1-c1ccc2nnn(-c3ccc4cn[nH]c4c3)c2c1] | + |

TABLE 1-continued

Specific Examples (Potency: CD73 IC$_{50}$: + means > 1 μM, ++ means 100 nM to 1 μM,
+++ means < 100 nM).

| Example | Structure | Potency |
|---|---|---|
| 4 | 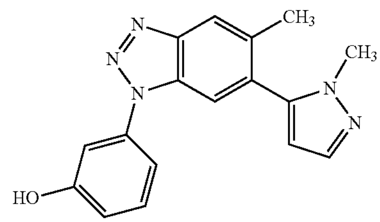 [SMILES: Cc1cc2nnn(-c3cccc(O)c3)c2cc1-c1ccnn1C] | + |
| 5 | 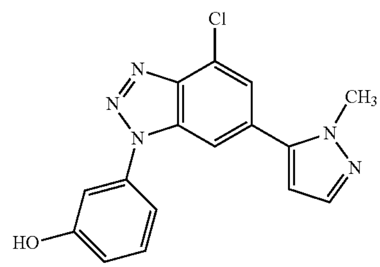 [SMILES: Cn1nccc1-c1cc(Cl)c2nnn(-c3cccc(O)c3)c2c1] | + |
| 6 | 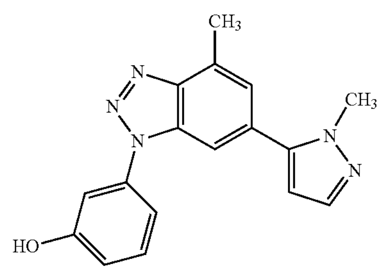 [SMILES: Cc1cc(-c2ccnn2C)cc2c1nnn2-c1cccc(O)c1] | + |
| 7 | 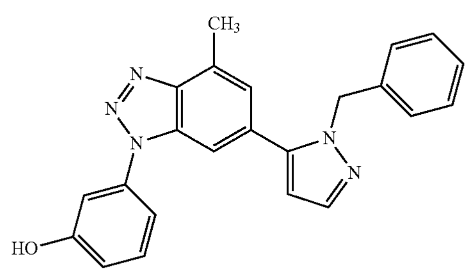 [SMILES: Cc1cc(-c2ccnn2Cc2ccccc2)cc2c1nnn2-c1cccc(O)c1] | ++ |
| 8 | 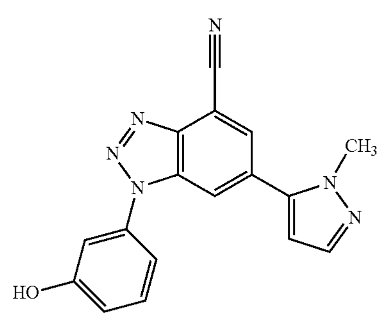 [SMILES: Cn1nccc1-c1cc(C#N)c2nnn(-c3cccc(O)c3)c2c1] | + |

TABLE 1-continued

Specific Examples (Potency: CD73 IC$_{50}$: + means > 1 μM, ++ means 100 nM to 1 μM, +++ means < 100 nM).

| Example | Structure | Potency |
|---------|-----------|---------|
| 9 | 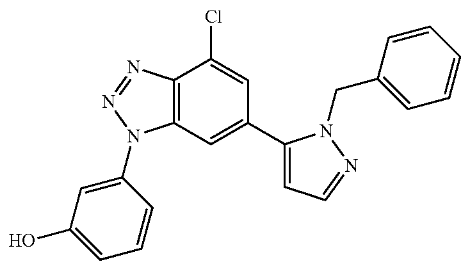 [SMILES: Oc1cccc(-n2nnc3c(Cl)cc(-c4ccnn4Cc4ccccc4)cc32)c1] | +++ |
| 10 | 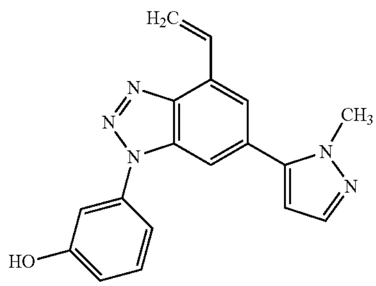 [SMILES: C=Cc1cc(-c2ccnn2C)cc2c1nnn2-c1cccc(O)c1] | + |
| 11 | 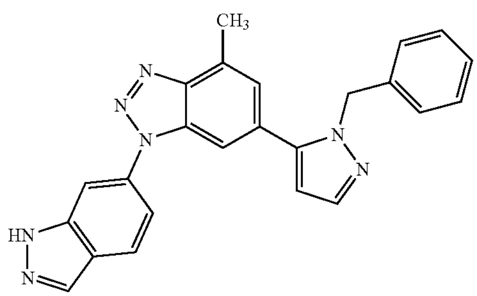 [SMILES: Cc1cc(-c2ccnn2Cc2ccccc2)cc2c1nnn2-c1ccc2cn[nH]c2c1] | ++ |
| 12 | 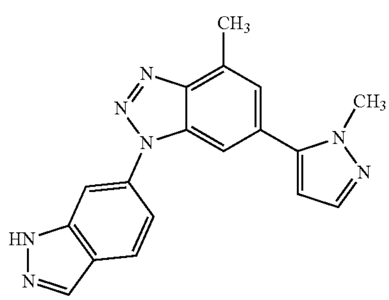 [SMILES: Cc1cc(-c2ccnn2C)cc2c1nnn2-c1ccc2cn[nH]c2c1] | ++ |
| 13 | 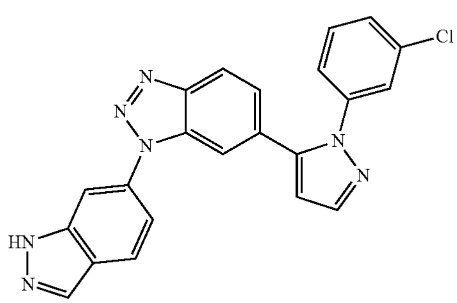 [SMILES: Clc1cccc(-n2nccc2-c2ccc3nnn(-c4ccc5cn[nH]c5c4)c3c2)c1] | ++ |

TABLE 1-continued
Specific Examples (Potency: CD73 IC$_{50}$: + means > 1 µM, ++ means 100 nM to 1 µM, +++ means < 100 nM).
| Example | Structure | Potency |
|---|---|---|
| 14 | 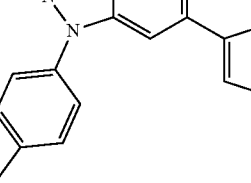 | + |
| 15 | 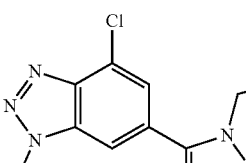 | ++ |
| 16 | 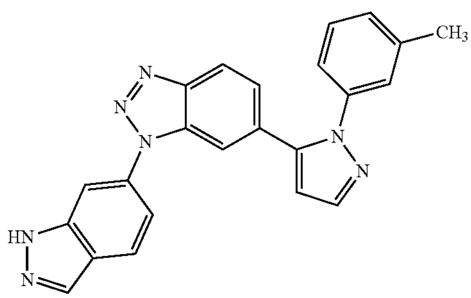 [SMILES: Cc1cccc(-n2nccc2-c2ccc3nnn(-c4ccc5cn[nH]c5c4)c3c2)c1] | ++ |
| 17 | 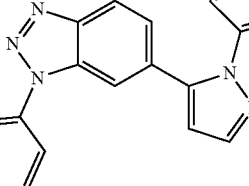 | + |
| 18 | 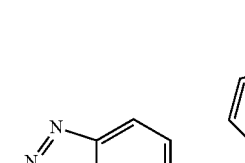 | + |

TABLE 1-continued

Specific Examples (Potency: CD73 IC$_{50}$: + means > 1 µM, ++ means 100 nM to 1 µM, +++ means < 100 nM).

| Example | Structure | Potency |
|---------|-----------|---------|
| 19 | 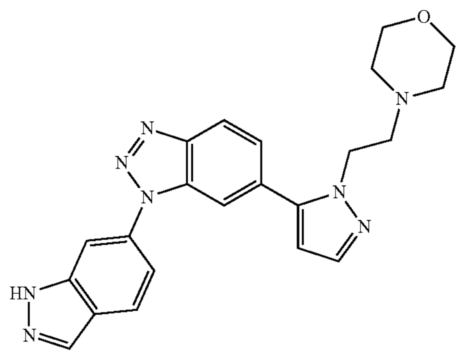 [SMILES: c1cc(-c2ccc3nnn(-c4ccc5cn[nH]c5c4)c3c2)n(CCN2CCOCC2)n1] | + |
| 20 | 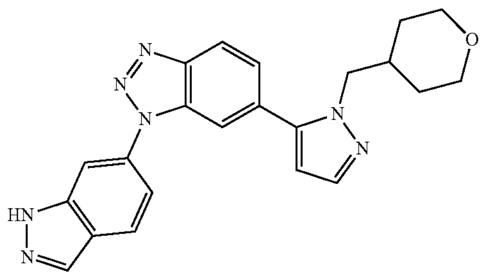 [SMILES: c1cc(-c2ccc3nnn(-c4ccc5cn[nH]c5c4)c3c2)n(CC2CCOCC2)n1] | + |
| 21 | 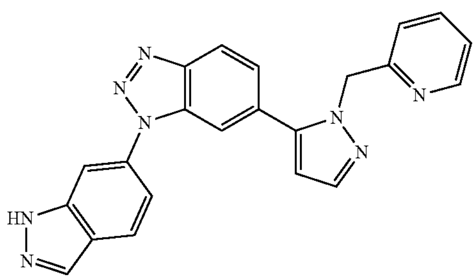 [SMILES: c1ccc(Cn2nccc2-c2ccc3nnn(-c4ccc5cn[nH]c5c4)c3c2)nc1] | ++ |
| 22 | 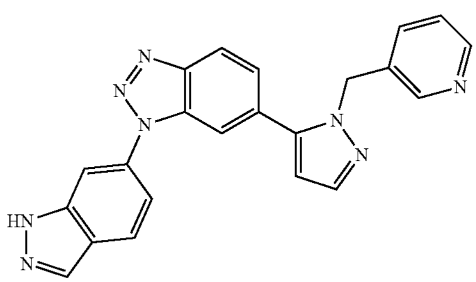 [SMILES: c1cncc(Cn2nccc2-c2ccc3nnn(-c4ccc5cn[nH]c5c4)c3c2)c1] | + |
| 23 | 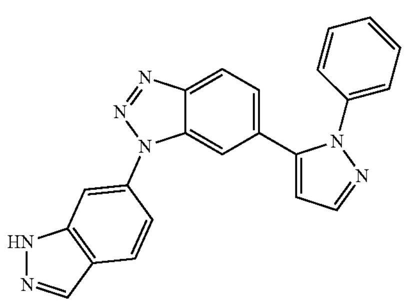 [SMILES: c1ccc(-n2nccc2-c2ccc3nnn(-c4ccc5cn[nH]c5c4)c3c2)cc1] | + |

TABLE 1-continued

Specific Examples (Potency: CD73 IC$_{50}$: + means > 1 µM, ++ means 100 nM to 1 µM, +++ means < 100 nM).

| Example | Structure | Potency |
|---------|-----------|---------|
| 24 | 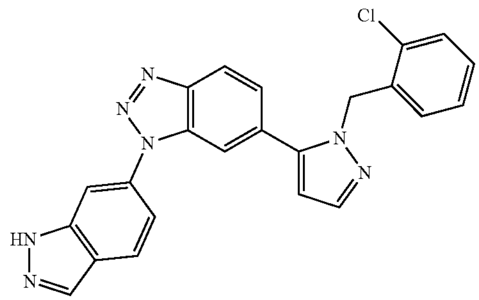 | ++ |
| 25 | 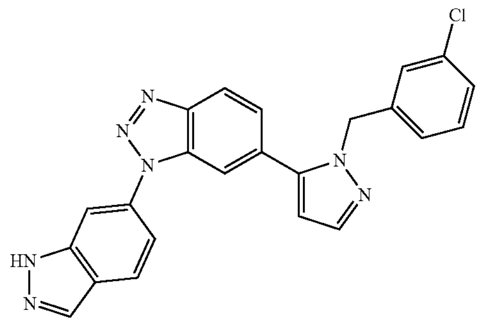 [SMILES: Clc1cccc(Cn2nccc2-c2ccc3nnn(-c4ccc5cn[nH]c5c4)c3c2)c1] | + |
| 26 | 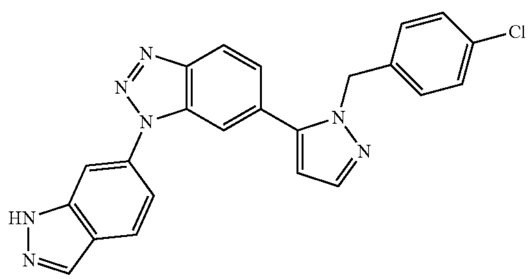 [SMILES: Clc1ccc(Cn2nccc2-c2ccc3nnn(-c4ccc5cn[nH]c5c4)c3c2)cc1] | +++ |
| 27 | 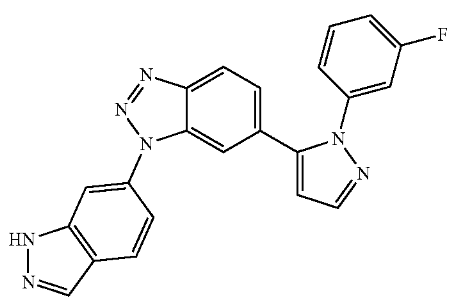 [SMILES: Fc1cccc(-n2nccc2-c2ccc3nnn(-c4ccc5cn[nH]c5c4)c3c2)c1] | + |
| 28 | 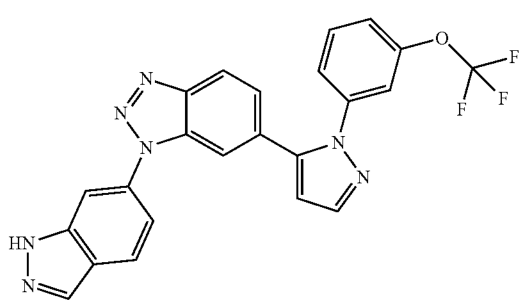 [SMILES: FC(F)(F)Oc1cccc(-n2nccc2-c2ccc3nnn(-c4ccc5cn[nH]c5c4)c3c2)c1] | ++ |

TABLE 1-continued

Specific Examples (Potency: CD73 IC$_{50}$: + means > 1 μM, ++ means 100 nM to 1 μM, +++ means < 100 nM).

| Example | Structure | Potency |
|---|---|---|
| 29 | 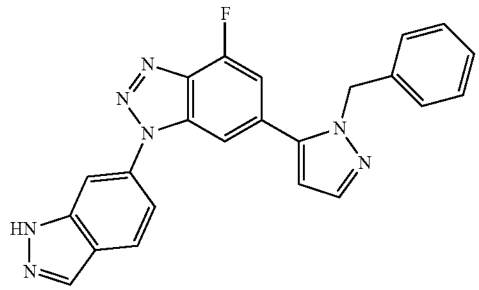 [SMILES: Fc1cc(-c2ccnn2Cc2ccccc2)cc2c1nnn2-c1ccc2cn[nH]c2c1] | ++ |
| 30 | 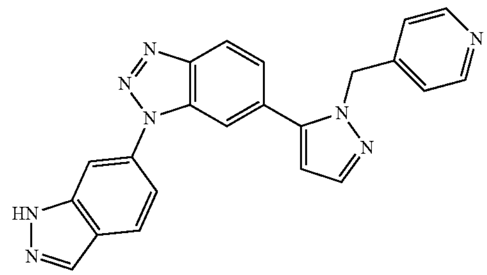 [SMILES: c1cc(Cn2nccc2-c2ccc3nnn(-c4ccc5cn[nH]c5c4)c3c2)ccn1] | ++ |
| 31 | 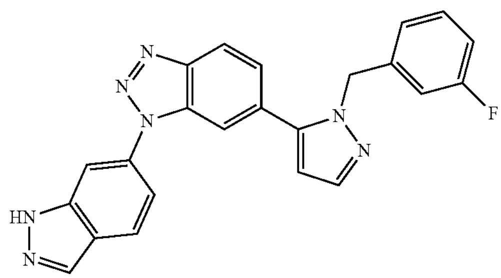 [SMILES: Fc1cccc(Cn2nccc2-c2ccc3nnn(-c4ccc5cn[nH]c5c4)c3c2)c1] | ++ |
| 32 | 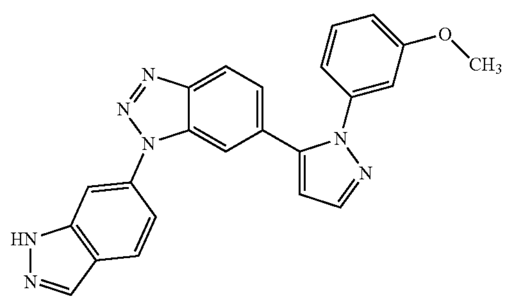 [SMILES: COc1cccc(-n2nccc2-c2ccc3nnn(-c4ccc5cn[nH]c5c4)c3c2)c1] | ++ |
| 33 | 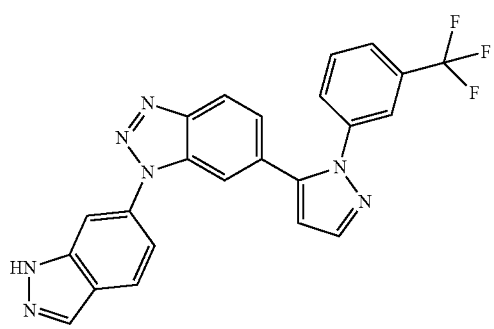 [SMILES: FC(F)(F)c1cccc(-n2nccc2-c2ccc3nnn(-c4ccc5cn[nH]c5c4)c3c2)c1] | ++ |

TABLE 1-continued

Specific Examples (Potency: CD73 IC$_{50}$: + means > 1 μM, ++ means 100 nM to 1 μM, +++ means < 100 nM).

| Example | Structure | Potency |
|---|---|---|
| 34 | 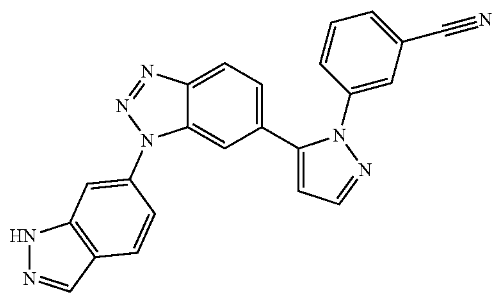 [SMILES: N#Cc1cccc(-n2nccc2-c2ccc3nnn(-c4ccc5cn[nH]c5c4)c3c2)c1] | + |
| 35 | 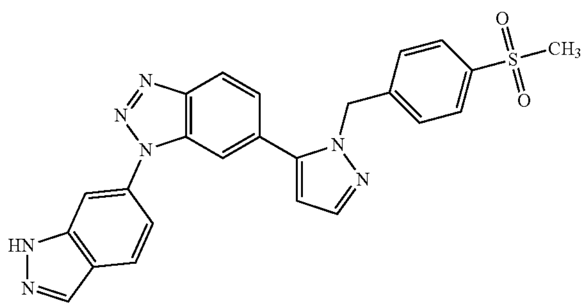 [SMILES: CS(=O)(=O)c1ccc(Cn2nccc2-c2ccc3nnn(-c4ccc5cn[nH]c5c4)c3c2)cc1] | + |
| 36 | 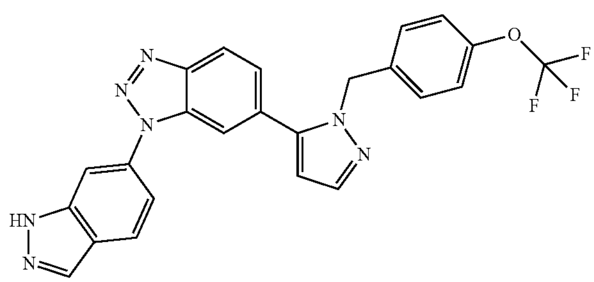 [SMILES: FC(F)(F)Oc1ccc(Cn2nccc2-c2ccc3nnn(-c4ccc5cn[nH]c5c4)c3c2)cc1] | ++ |
| 37 | 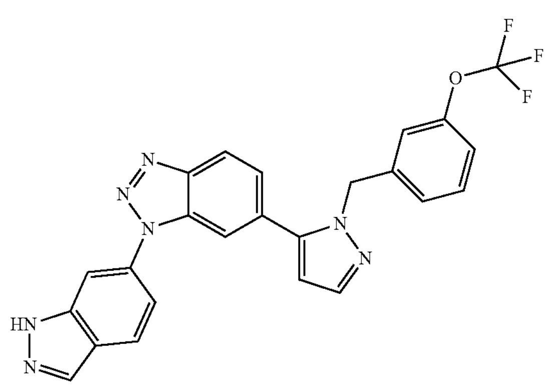 [SMILES: FC(F)(F)Oc1cccc(Cn2nccc2-c2ccc3nnn(-c4ccc5cn[nH]c5c4)c3c2)c1] | + |

TABLE 1-continued

Specific Examples (Potency: CD73 IC$_{50}$: + means > 1 µM, ++ means 100 nM to 1 µM, +++ means < 100 nM).

| Example | Structure | Potency |
|---------|-----------|---------|
| 38 | 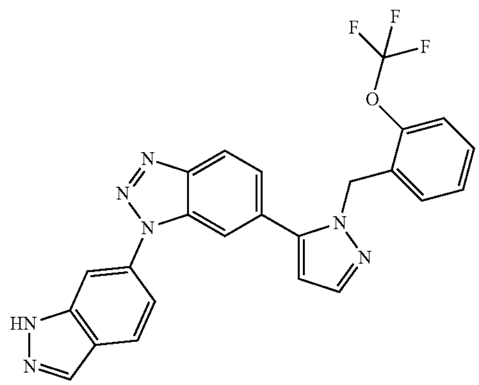 [SMILES: FC(F)(F)Oc1ccccc1Cn1nccc1-c1ccc2nnn(-c3ccc4cn[nH]c4c3)c2c1] | ++ |
| 39 | 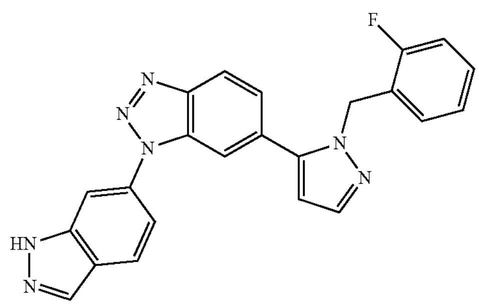 [SMILES: Fc1ccccc1Cn1nccc1-c1ccc2nnn(-c3ccc4cn[nH]c4c3)c2c1] | ++ |
| 40 | 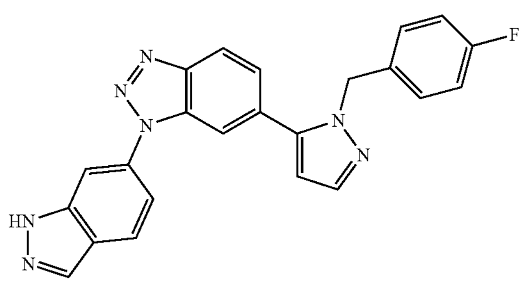 [SMILES: Fc1ccc(Cn2nccc2-c2ccc3nnn(-c4ccc5cn[nH]c5c4)c3c2)cc1] | ++ |
| 41 | 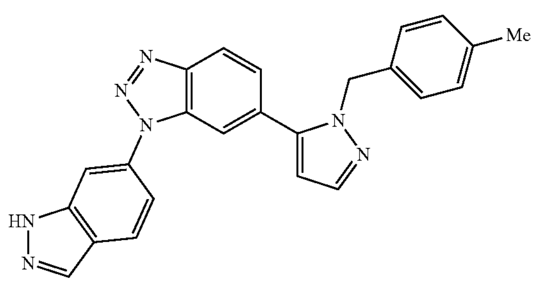 [SMILES: Cc1ccc(Cn2nccc2-c2ccc3nnn(-c4ccc5cn[nH]c5c4)c3c2)cc1] | +++ |
| 42 | 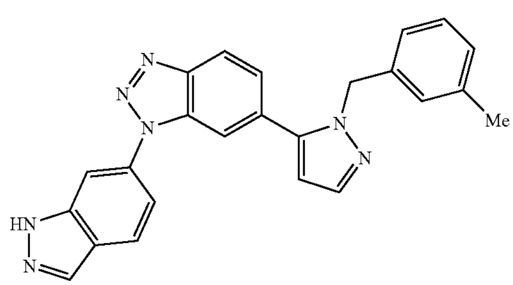 [SMILES: Cc1cccc(Cn2nccc2-c2ccc3nnn(-c4ccc5cn[nH]c5c4)c3c2)c1] | ++ |

TABLE 1-continued

Specific Examples (Potency: CD73 IC$_{50}$: + means > 1 μM, ++ means 100 nM to 1 μM, +++ means < 100 nM).

| Example | Structure | Potency |
|---|---|---|
| 43 | 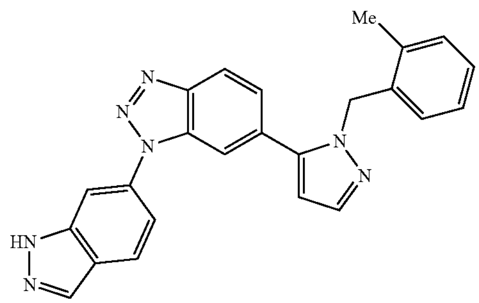 [SMILES: Cc1ccccc1Cn1nccc1-c1ccc2nnn(-c3ccc4cn[nH]c4c3)c2c1] | ++ |
| 44 | 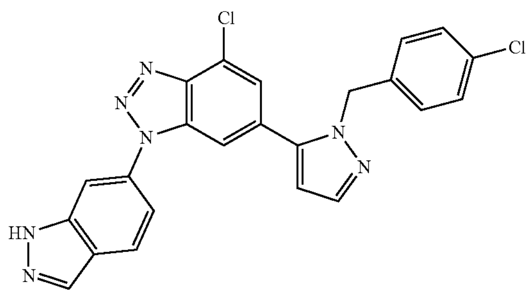 [SMILES: Clc1ccc(Cn2nccc2-c2cc(Cl)c3nnn(-c4ccc5cn[nH]c5c4)c3c2)cc1] | +++ |
| 45 | 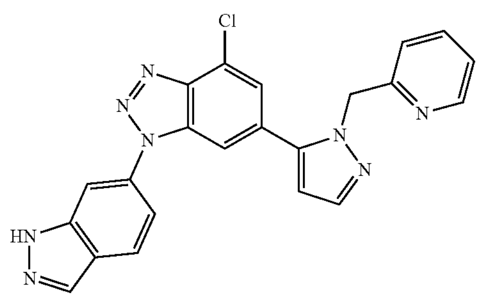 [SMILES: Clc1cc(-c2ccnn2Cc2ccccn2)cc2c1nnn2-c1ccc2cn[nH]c2c1] | ++ |
| 46 | 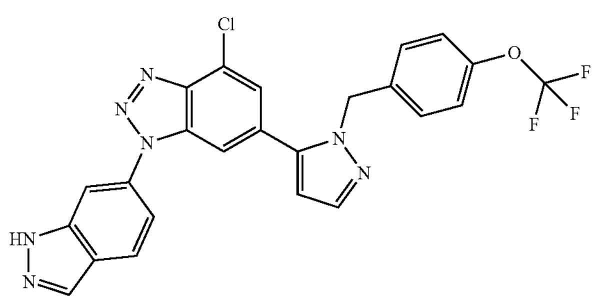 [SMILES: FC(F)(F)Oc1ccc(Cn2nccc2-c2cc(Cl)c3nnn(-c4ccc5cn[nH]c5c4)c3c2)cc1] | +++ |
| 47 | 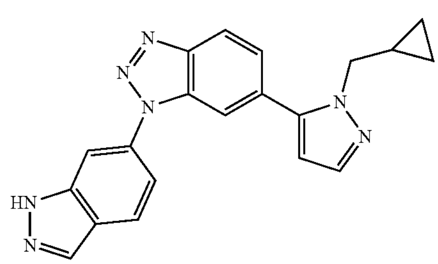 [SMILES: c1cc(-c2ccc3nnn(-c4ccc5cn[nH]c5c4)c3c2)n(CC2CC2)n1] | + |

TABLE 1-continued

Specific Examples (Potency: CD73 IC$_{50}$: + means > 1 μM, ++ means 100 nM to 1 μM, +++ means < 100 nM).

| Example | Structure | Potency |
|---|---|---|
| 48 | 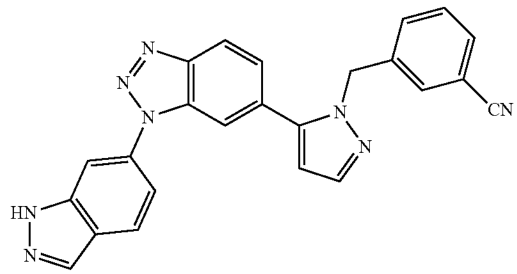 [SMILES: N#Cc1cccc(Cn2nccc2-c2ccc3nnn(-c4ccc5cn[nH]c5c4)c3c2)c1] | + |
| 49 | 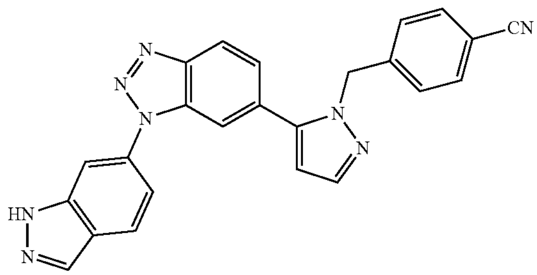 [SMILES: N#Cc1ccc(Cn2nccc2-c2ccc3nnn(-c4ccc5cn[nH]c5c4)c3c2)cc1] | +++ |
| 50 | 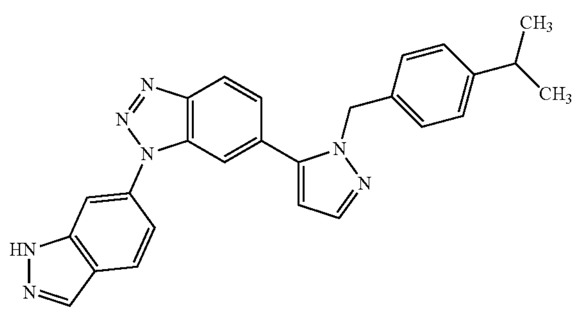 [SMILES: CC(C)c1ccc(Cn2nccc2-c2ccc3nnn(-c4ccc5cn[nH]c5c4)c3c2)cc1] | ++ |
| 51 | 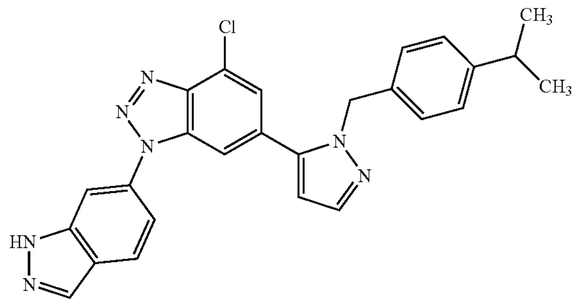 [SMILES: CC(C)c1ccc(Cn2nccc2-c2cc(Cl)c3nnn(-c4ccc5cn[nH]c5c4)c3c2)cc1] | ++ |
| 52 | 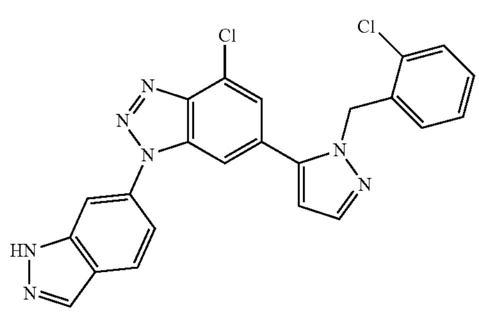 | +++ |

TABLE 1-continued
Specific Examples (Potency: CD73 $IC_{50}$: + means > 1 μM, ++ means 100 nM to 1 μM, +++ means < 100 nM).
| Example | Structure | Potency |
|---|---|---|
| 53 | 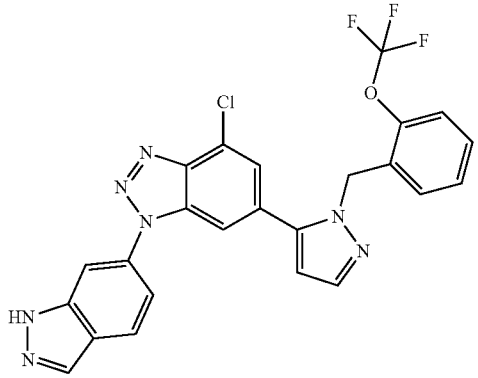 [SMILES: FC(F)(F)Oc1ccccc1Cn1nccc1-c1cc(Cl)c2nnn(-c3ccc4cn[nH]c4c3)c2c1] | ++ |
| 54 | 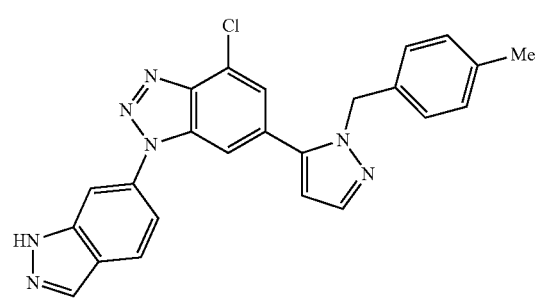 | +++ |
| 55 | 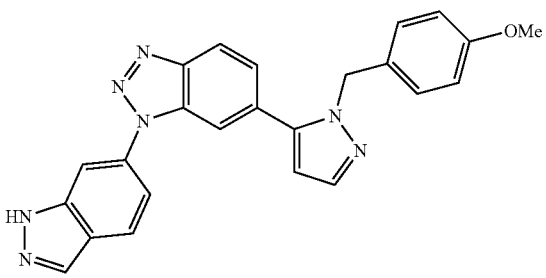 [SMILES: COc1ccc(Cn2nccc2-c2ccc3nnn(-c4ccc5cn[nH]c5c4)c3c2)cc1] | ++ |
| 56 | 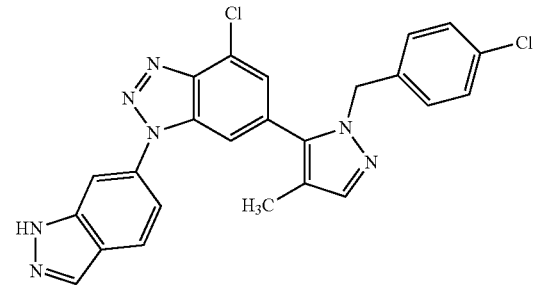 [SMILES: Cc1cnn(Cc2ccc(Cl)cc2)c1-c1cc(Cl)c2nnn(-c3ccc4cn[nH]c4c3)c2c1] | ++ |
| 57 | 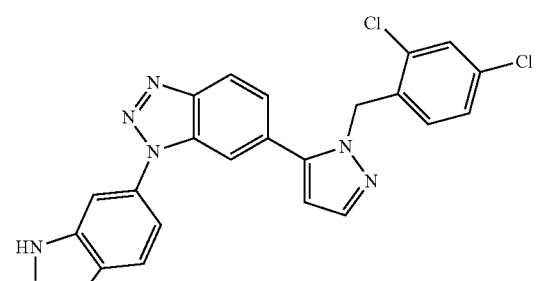 | +++ |

TABLE 1-continued
Specific Examples (Potency: CD73 IC$_{50}$: + means > 1 μM, ++ means 100 nM to 1 μM, +++ means < 100 nM).
| Example | Structure | Potency |
|---|---|---|
| 58 | 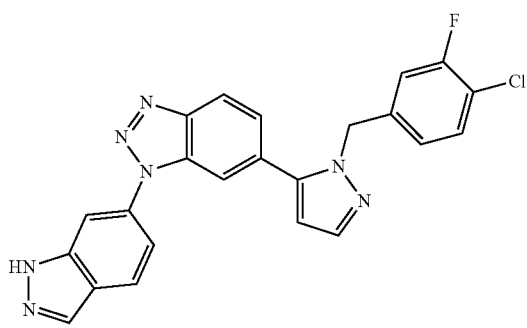 | +++ |
| 59 | 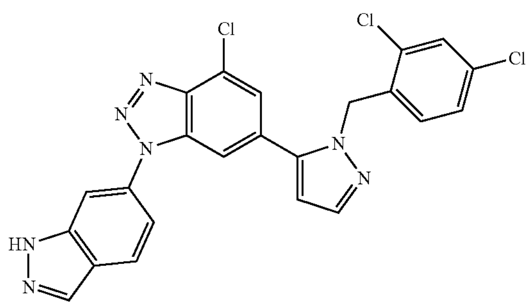 | +++ |
| 60 | 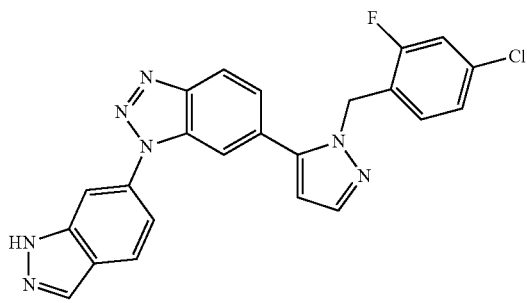 [SMILES: Clc1ccc(Cn2nccc2-c2ccc3nnn(-c4ccc5cn[nH]c5c4)c3c2)c(Cl)c1] | +++ |
| 61 | 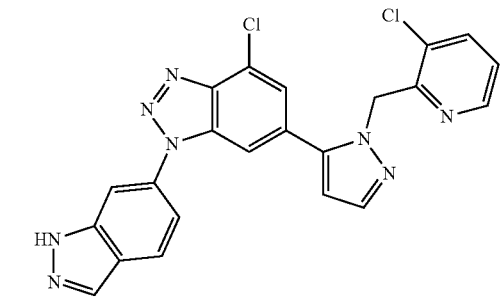 [SMILES: Clc1cccnc1Cn1nccc1-c1cc(Cl)c2nnn(-c3ccc4cn[nH]c4c3)c2c1] | + |

TABLE 1-continued

Specific Examples (Potency: CD73 IC$_{50}$: + means > 1 μM, ++ means 100 nM to 1 μM, +++ means < 100 nM).

| Example | Structure | Potency |
|---------|-----------|---------|
| 62 | 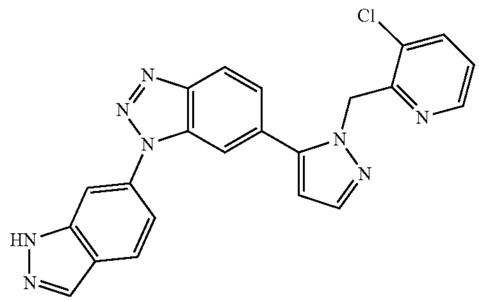 | + |
| 63 | 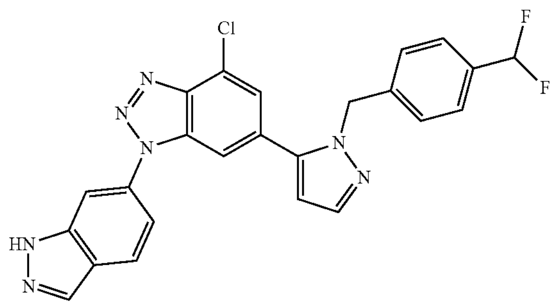 | +++ |
| 64 | 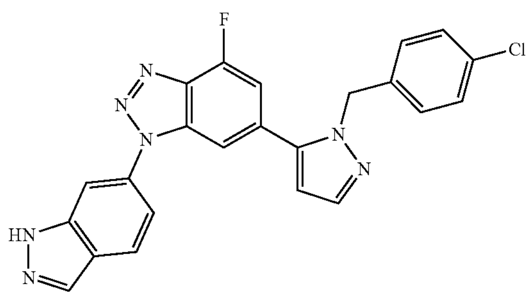 | +++ |
| 65 | 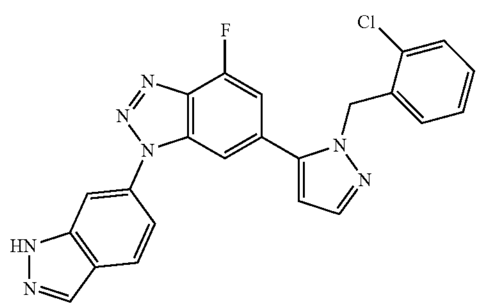 [SMILES: Fc1cc(-c2ccnn2Cc2ccccc2Cl)cc2c1nnn2-c1ccc2cn[nH]c2c1] | ++ |
| 66 | 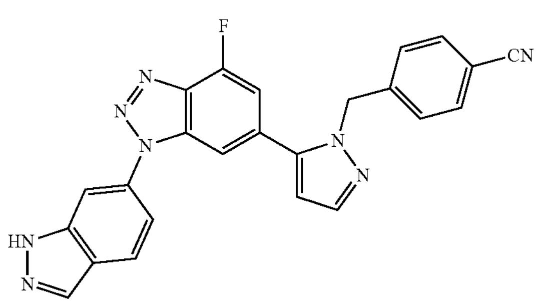 [SMILES: N#Cc1ccc(Cn2nccc2-c2cc(F)c3nnn(-c4ccc5cn[nH]c5c4)c3c2)cc1] | +++ |

TABLE 1-continued
Specific Examples (Potency: CD73 IC$_{50}$: + means > 1 μM, ++ means 100 nM to 1 μM, +++ means < 100 nM).
| Example | Structure | Potency |
|---------|-----------|---------|
| 67 | 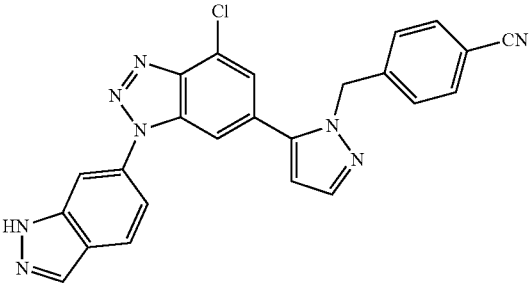 | +++ |
| 68 | 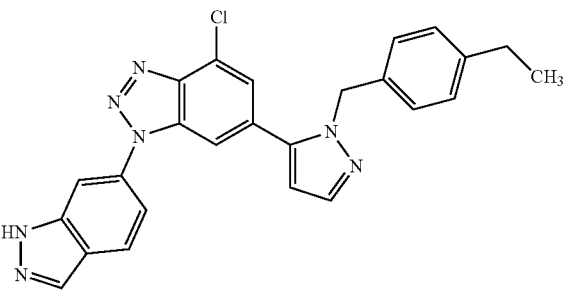 [SMILES: CCc1ccc(Cn2nccc2-c2cc(Cl)c3nnn(-c4ccc5cn[nH]c5c4)c3c2)cc1] | +++ |
| 69 | 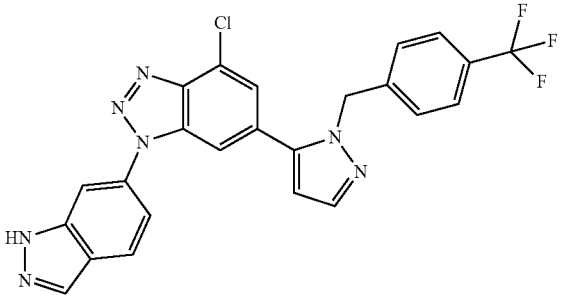 [SMILES: FC(F)(F)c1ccc(Cn2nccc2-c2cc(Cl)c3nnn(-c4ccc5cn[nH]c5c4)c3c2)cc1] | ++ |
| 70 | 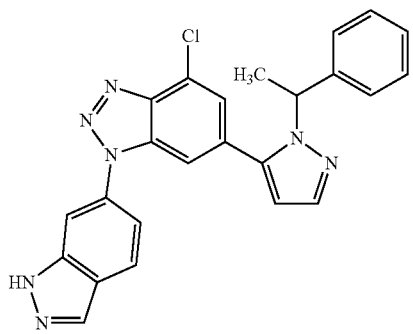 [SMILES: CC(c1ccccc1)n1nccc1-c1cc(Cl)c2nnn(-c3ccc4cn[nH]c4c3)c2c1] | ++ |
| 71 | 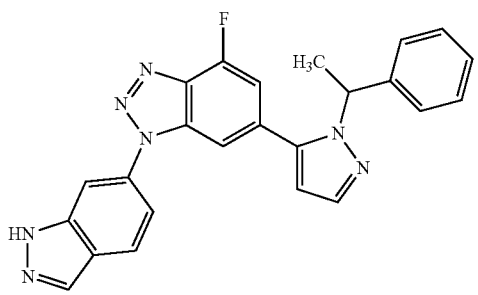 [SMILES: CC(c1ccccc1)n1nccc1-c1cc(F)c2nnn(-c3ccc4cn[nH]c4c3)c2c1] | + |

TABLE 1-continued

Specific Examples (Potency: CD73 IC$_{50}$: + means > 1 μM, ++ means 100 nM to 1 μM, +++ means < 100 nM).

| Example | Structure | Potency |
|---------|-----------|---------|
| 72 | 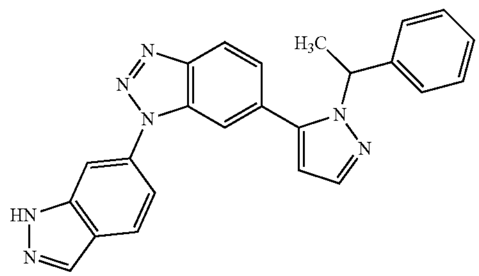 [SMILES: CC(c1ccccc1)n1nccc1-c1ccc2nnn(-c3ccc4cn[nH]c4c3)c2c1] | + |
| 73 | 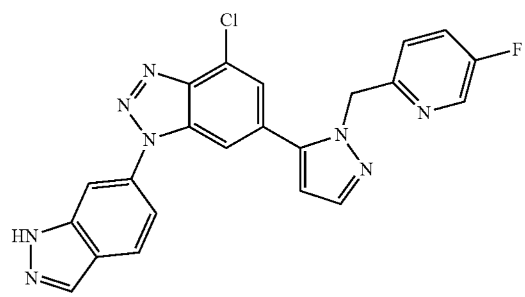 [SMILES: Fc1ccc(Cn2nccc2-c2cc(Cl)c3nnn(-c4ccc5cn[nH]c5c4)c3c2)nc1] | +++ |
| 74 | 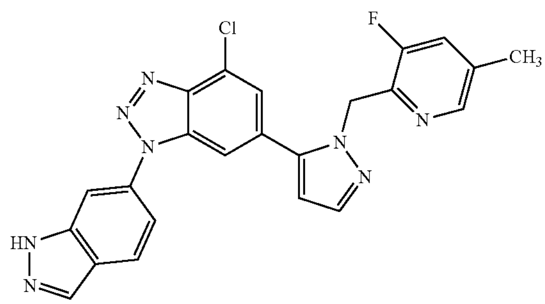 [SMILES: Cc1cnc(Cn2nccc2-c2cc(Cl)c3nnn(-c4ccc5cn[nH]c5c4)c3c2)c(F)c1] | ++ |
| 75 | 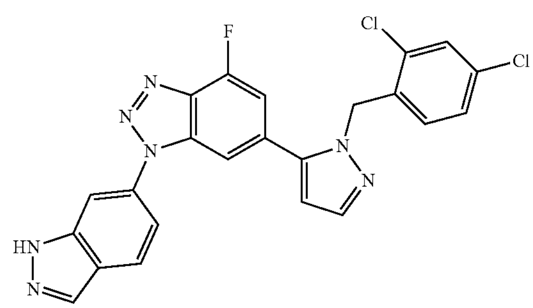 | +++ |
| 76 | 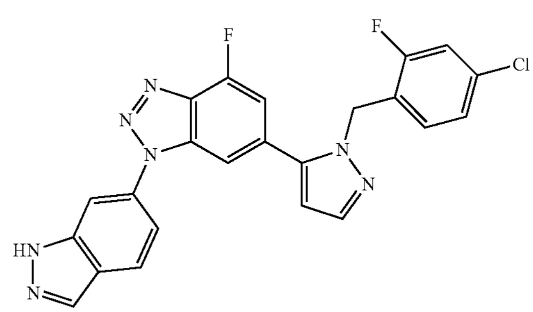 [SMILES: Fc1cc(-c2ccnn2Cc2ccc(Cl)cc2Cl)cc2c1nnn2-c1ccc2cn[nH]c2c1] | +++ |

TABLE 1-continued

Specific Examples (Potency: CD73 IC$_{50}$: + means > 1 µM, ++ means 100 nM to 1 µM, +++ means < 100 nM).

| Example | Structure | Potency |
|---------|-----------|---------|
| 77 | 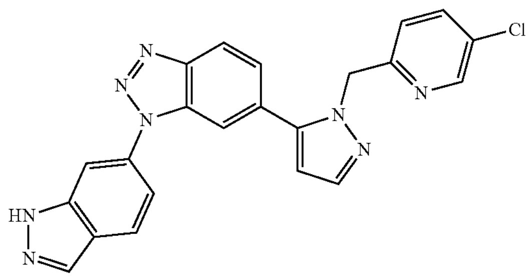 [SMILES: Clc1ccc(Cn2nccc2-c2ccc3nnn(-c4ccc5cn[nH]c5c4)c3c2)nc1] | ++ |
| 78 | 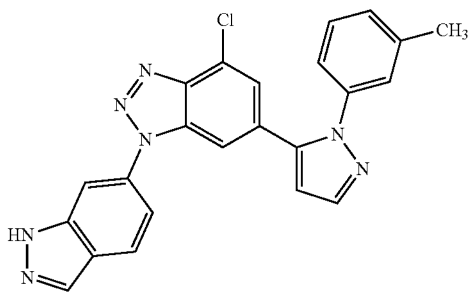 [SMILES: Cc1cccc(-n2nccc2-c2cc(Cl)c3nnn(-c4ccc5cn[nH]c5c4)c3c2)c1] | ++ |
| 79 | 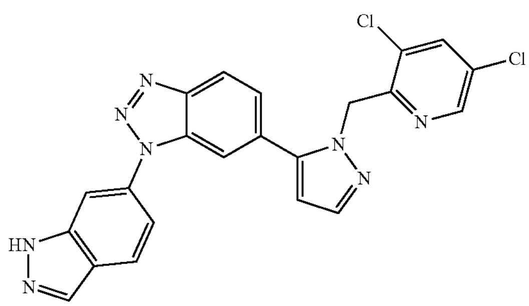 [SMILES: Clc1cnc(Cn2nccc2-c2ccc3nnn(-c4ccc5cn[nH]c5c4)c3c2)c(Cl)c1] | ++ |
| 80 | 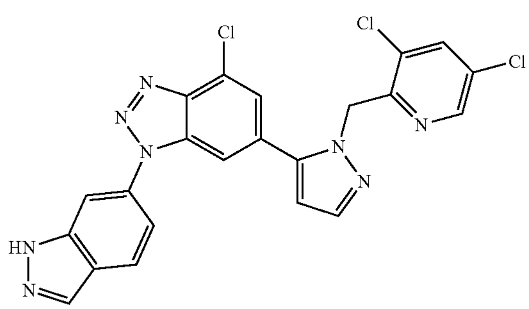 | ++ |
| 81 | 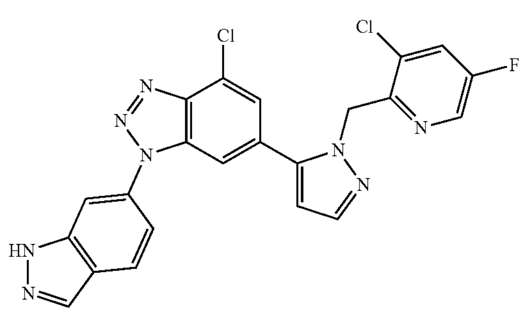 [SMILES: Fc1cnc(Cn2nccc2-c2cc(Cl)c3nnn(-c4ccc5cn[nH]c5c4)c3c2)c(Cl)c1] | ++ |

TABLE 1-continued

Specific Examples (Potency: CD73 $IC_{50}$: + means > 1 μM, ++ means 100 nM to 1 μM, +++ means < 100 nM).

| Example | Structure | Potency |
|---------|-----------|---------|
| 82 | 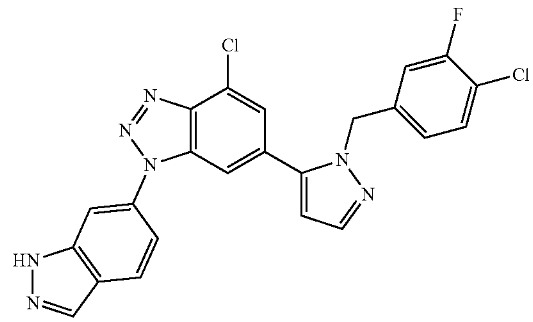 [SMILES: Fc1cc(Cn2nccc2-c2cc(Cl)c3nnn(-c4ccc5cn[nH]c5c4)c3c2)ccc1Cl] | +++ |
| 83 | 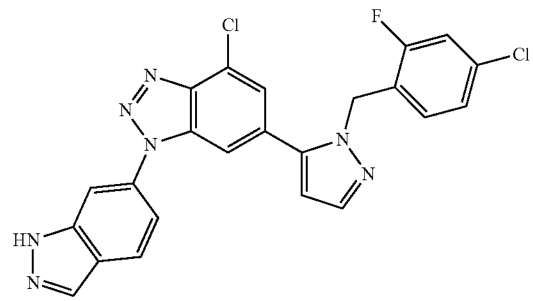 | +++ |
| 84 | 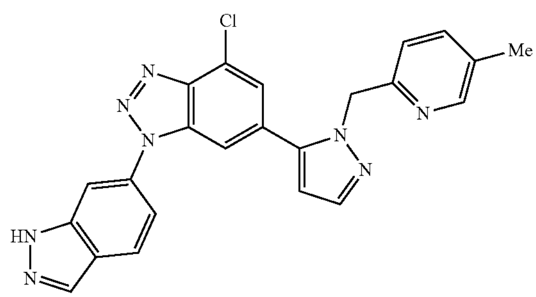 [SMILES: Cc1ccc(Cn2nccc2-c2cc(Cl)c3nnn(-c4ccc5cn[nH]c5c4)c3c2)nc1] | ++ |
| 85 | 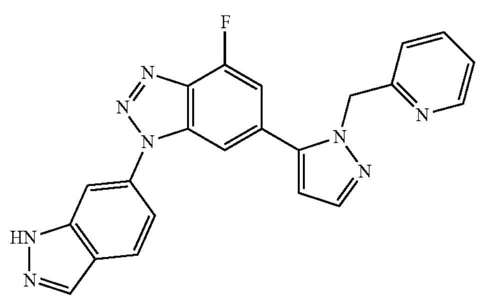 | ++ |
| 86 | 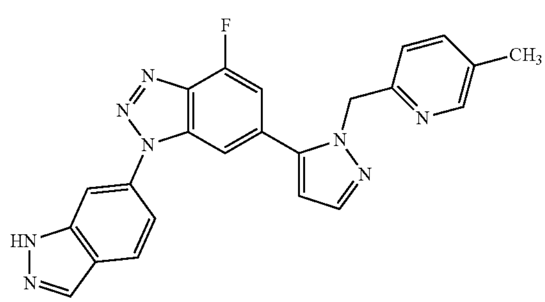 [SMILES: Cc1ccc(Cn2nccc2-c2cc(F)c3nnn(-c4ccc5cn[nH]c5c4)c3c2)nc1] | ++ |

TABLE 1-continued

Specific Examples (Potency: CD73 IC$_{50}$: + means > 1 µM, ++ means 100 nM to 1 µM, +++ means < 100 nM).

| Example | Structure | Potency |
|---------|-----------|---------|
| 87 | 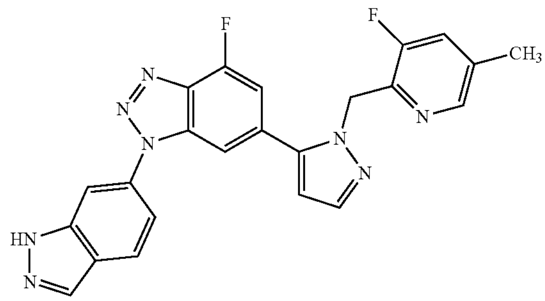 [SMILES: Cc1cnc(Cn2nccc2-c2cc(F)c3nnn(-c4ccc5cn[nH]c5c4)c3c2)c(F)c1] | + |
| 88 | 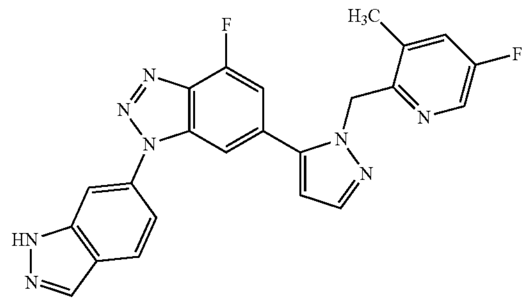 [SMILES: Cc1cc(F)cnc1Cn1nccc1-c1cc(F)c2nnn(-c3ccc4cn[nH]c4c3)c2c1] | + |
| 89 | 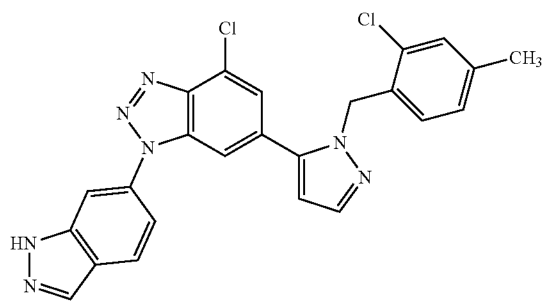 | +++ |
| 90 | 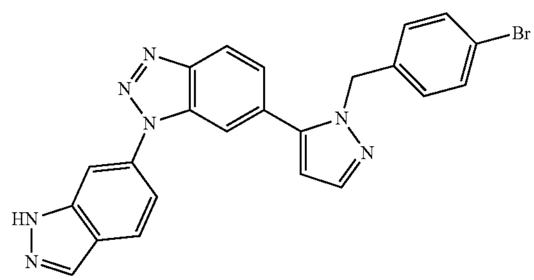 [SMILES: Brc1ccc(Cn2nccc2-c2ccc3nnn(-c4ccc5cn[nH]c5c4)c3c2)cc1] | ++ |
| 91 | 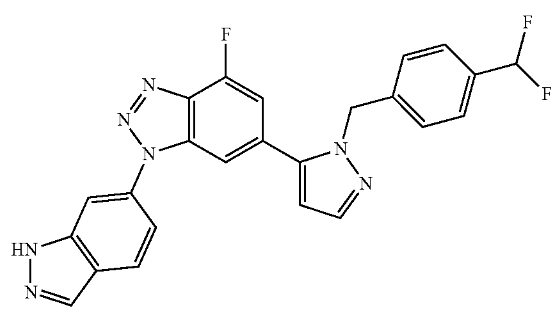 [SMILES: Fc1cc(-c2ccnn2Cc2ccc(C(F)F)cc2)cc2c1nnn2-c1ccc2cn[nH]c2c1] | ++ |

TABLE 1-continued

Specific Examples (Potency: CD73 IC$_{50}$: + means > 1 μM, ++ means 100 nM to 1 μM, +++ means < 100 nM).

| Example | Structure | Potency |
|---------|-----------|---------|
| 92 | 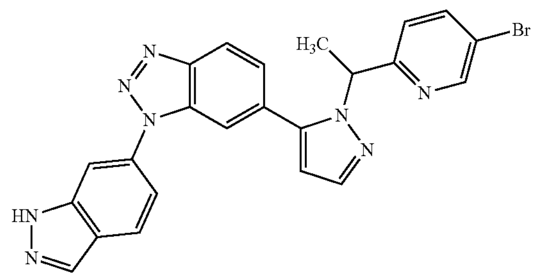 [SMILES: CC(c1ccc(Br)cn1)n1nccc1-c1ccc2nnn(-c3ccc4cn[nH]c4c3)c2c1] | ++ |
| 93 | 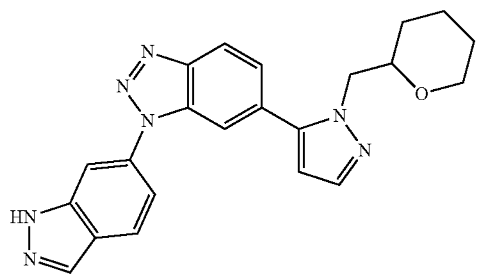 [SMILES: c1cc(-c2ccc3nnn(-c4ccc5cn[nH]c5c4)c3c2)n(CC2CCCCO2)n1] | + |
| 94 | 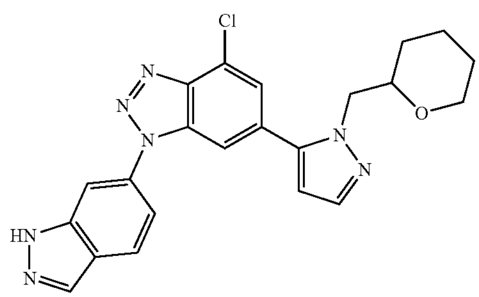 [SMILES: Clc1cc(-c2ccnn2CC2CCCCO2)cc2c1nnn2-c1ccc2cn[nH]c2c1] | ++ |
| 95 | 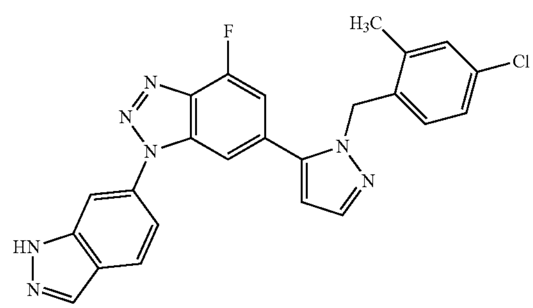 [SMILES: Cc1cc(Cl)ccc1Cn1nccc1-c1cc(F)c2nnn(-c3ccc4cn[nH]c4c3)c2c1] | +++ |
| 96 | 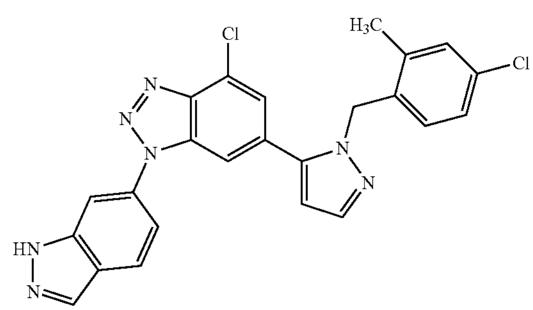 [SMILES: Cc1cc(Cl)ccc1Cn1nccc1-c1cc(Cl)c2nnn(-c3ccc4cn[nH]c4c3)c2c1] | +++ |

TABLE 1-continued

Specific Examples (Potency: CD73 IC$_{50}$: + means > 1 μM, ++ means 100 nM to 1 μM, +++ means < 100 nM).

| Example | Structure | Potency |
|---------|-----------|---------|
| 97 | 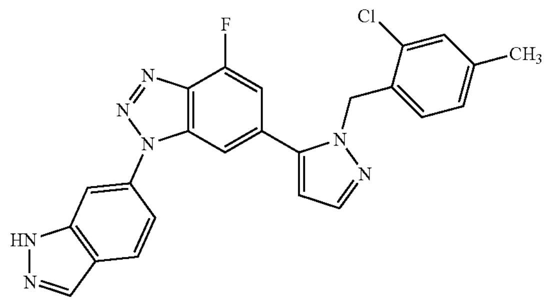 | +++ |
| 98 | 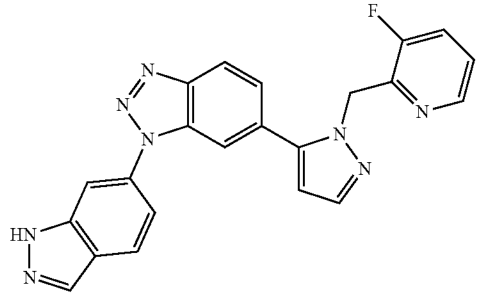 [SMILES: Fc1cccnc1Cn1nccc1-c1ccc2nnn(-c3ccc4cn[nH]c4c3)c2c1] | + |
| 99 | 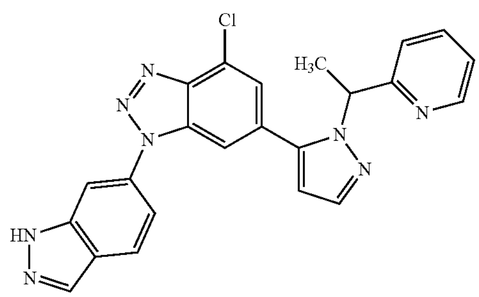 [SMILES: CC(c1ccccn1)n1nccc1-c1cc(Cl)c2nnn(-c3ccc4cn[nH]c4c3)c2c1] | + |
| 100 | 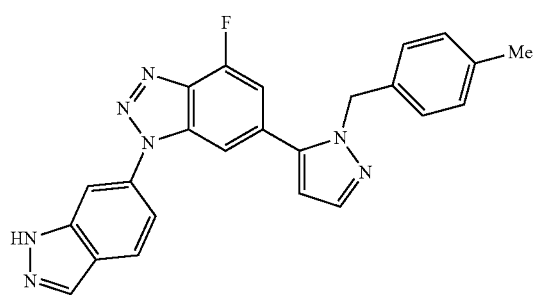 [SMILES: Cc1ccc(Cn2nccc2-c2cc(F)c3nnn(-c4ccc5cn[nH]c5c4)c3c2)cc1] | ++ |
| 101 | 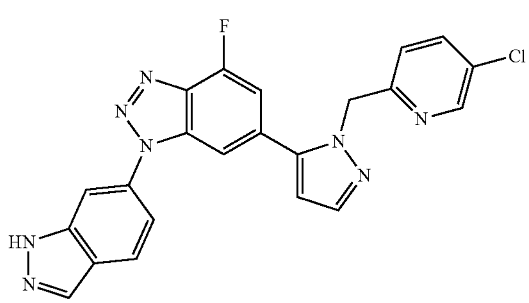 | +++ |

TABLE 1-continued

Specific Examples (Potency: CD73 $IC_{50}$: + means > 1 μM, ++ means 100 nM to 1 μM, +++ means < 100 nM).

| Example | Structure | Potency |
|---------|-----------|---------|
| 102 | 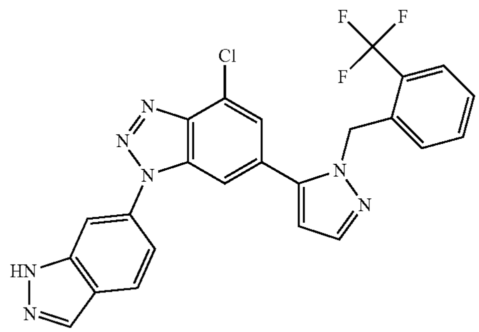 [SMILES: FC(F)(F)c1ccccc1Cn1nccc1-c1cc(Cl)c2nnn(-c3ccc4cn[nH]c4c3)c2c1] | ++ |
| 103 | 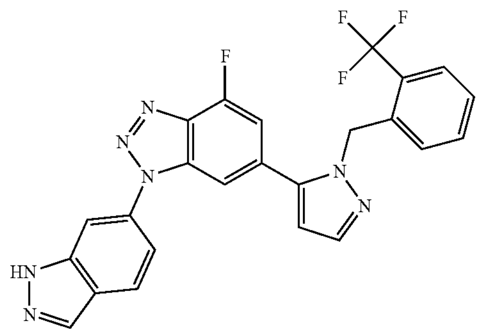 [SMILES: Fc1cc(-c2ccnn2Cc2ccccc2C(F)(F)F)cc2c1nnn2-c1ccc2cn[nH]c2c1] | ++ |
| 104 | 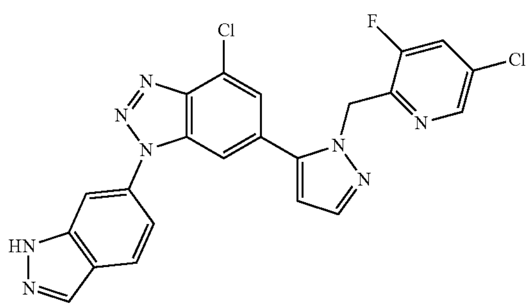 [SMILES: Fc1cc(Cl)cnc1Cn1nccc1-c1cc(Cl)c2nnn(-c3ccc4cn[nH]c4c3)c2c1] | ++ |
| 105 | 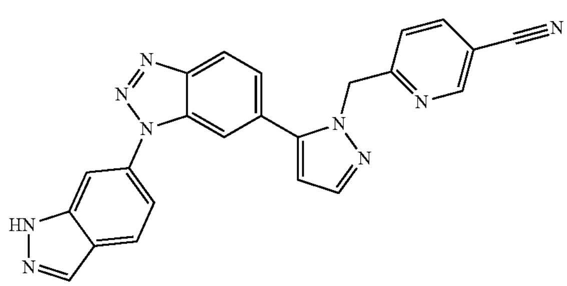 [SMILES: N#Cc1ccc(Cn2nccc2-c2ccc3nnn(-c4ccc5cn[nH]c5c4)c3c2)nc1] | +++ |
| 106 | 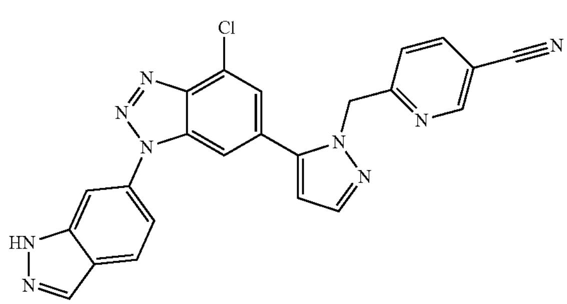 | ++ |

TABLE 1-continued

Specific Examples (Potency: CD73 IC$_{50}$: + means > 1 μM, ++ means 100 nM to 1 μM, +++ means < 100 nM).

| Example | Structure | Potency |
|---------|-----------|---------|
| 107 | 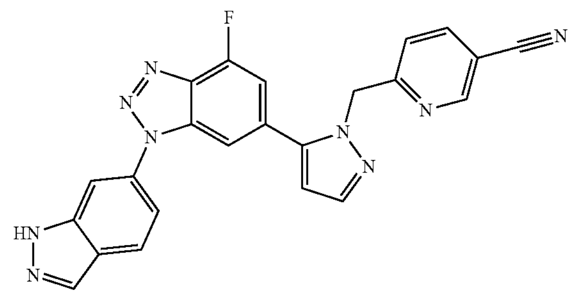 [SMILES: N#Cc1ccc(Cn2nccc2-c2cc(F)c3nnn(-c4ccc5cn[nH]c5c4)c3c2)nc1] | ++ |
| 108 | 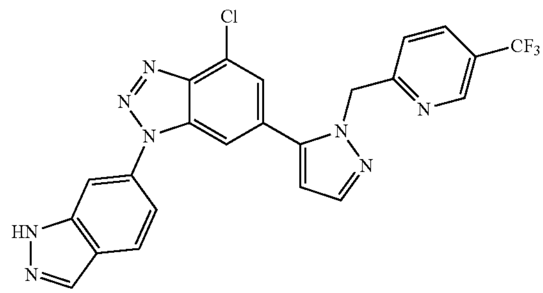 [SMILES: FC(F)(F)c1ccc(Cn2nccc2-c2cc(Cl)c3nnn(-c4ccc5cn[nH]c5c4)c3c2)nc1] | ++ |
| 109 | 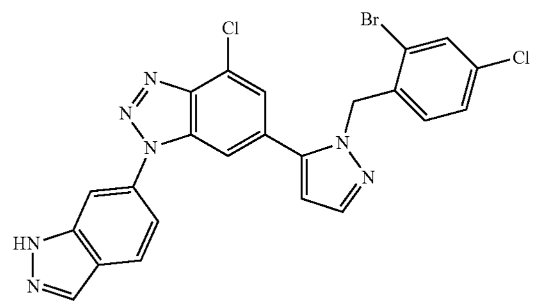 [SMILES: Clc1ccc(Cn2nccc2-c2cc(Cl)c3nnn(-c4ccc5cn[nH]c5c4)c3c2)c(Br)c1] | ++ |
| 110 | 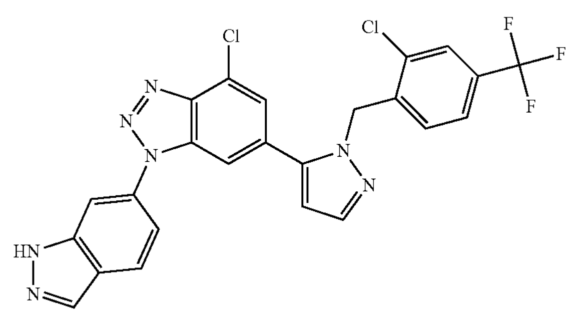 [SMILES: FC(F)(F)c1ccc(Cn2nccc2-c2cc(Cl)c3nnn(-c4ccc5cn[nH]c5c4)c3c2)c(Cl)c1] | ++ |
| 111 | 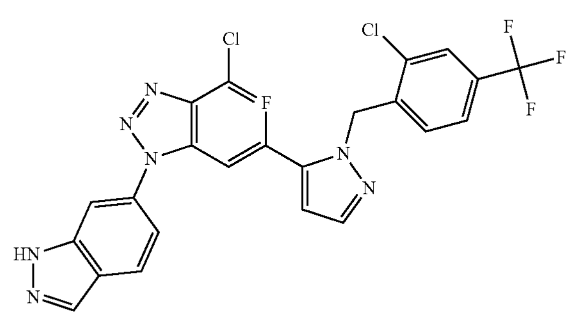 | ++ |

TABLE 1-continued

Specific Examples (Potency: CD73 IC$_{50}$: + means > 1 μM, ++ means 100 nM to 1 μM, +++ means < 100 nM).

| Example | Structure | Potency |
|---|---|---|
| 112 | 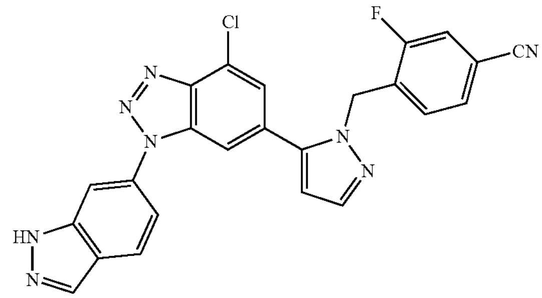 [SMILES: N#Cc1ccc(Cn2nccc2-c2cc(Cl)c3nnn(-c4ccc5cn[nH]c5c4)c3c2)c(F)c1] | +++ |
| 113 | 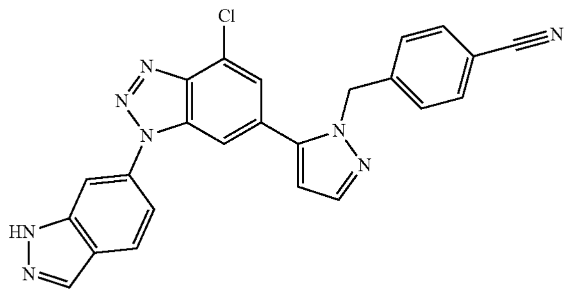 [SMILES: N#Cc1ccc(Cn2nccc2-c2cc(Cl)c3nnn(-c4ccc5cn[nH]c5c4)c3c2)cc1] | + |
| 114 | 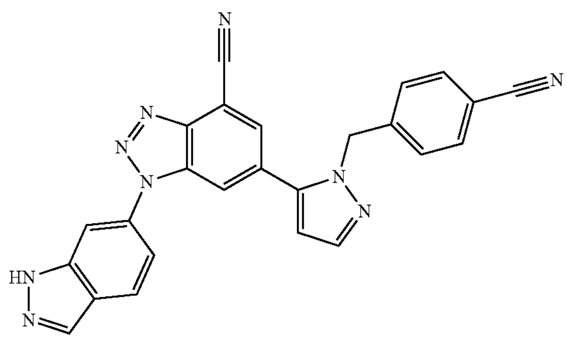 [SMILES: N#Cc1ccc(Cn2nccc2-c2cc(C#N)c3nnn(-c4ccc5cn[nH]c5c4)c3c2)cc1] | ++ |
| 115 | 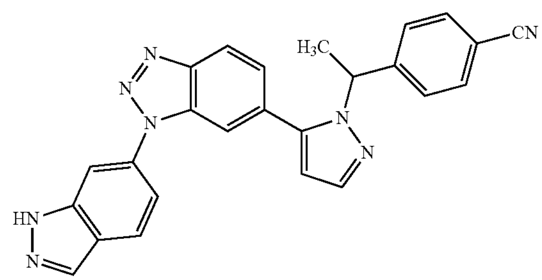 [SMILES: CC(c1ccc(C#N)cc1)n1nccc1-c1ccc2nnn(-c3ccc4cn[nH]c4c3)c2c1] | ++ |
| 116 | 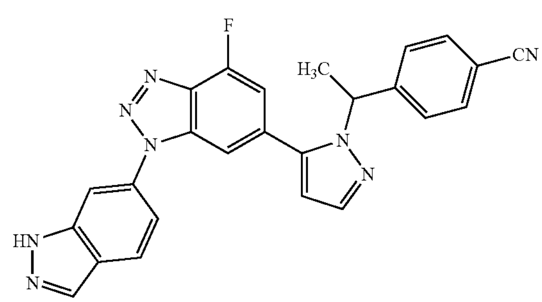 [SMILES: CC(c1ccc(C#N)cc1)n1nccc1-c1cc(Cl)c2nnn(-c3ccc4cn[nH]c4c3)c2c1] | ++ |

TABLE 1-continued
Specific Examples (Potency: CD73 IC$_{50}$: + means > 1 µM, ++ means 100 nM to 1 µM, +++ means < 100 nM).
| Example | Structure | Potency |
|---|---|---|
| 117 | 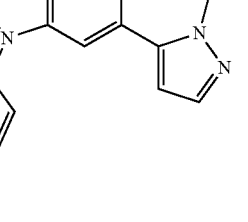 | ++ |
| 118 | 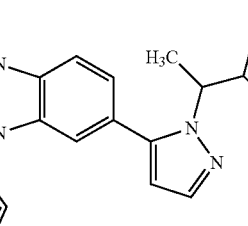 | + |
| 119 | 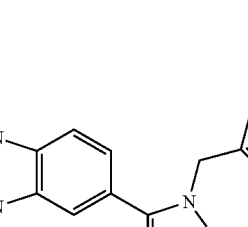 | ++ |
| 120 | 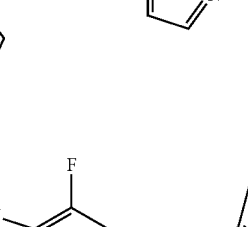 | + |
| 121 | 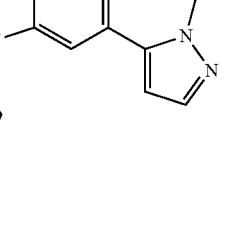 | + |

TABLE 1-continued

Specific Examples (Potency: CD73 IC$_{50}$: + means > 1 µM, ++ means 100 nM to 1 µM, +++ means < 100 nM).

| Example | Structure | Potency |
|---|---|---|
| 122 | 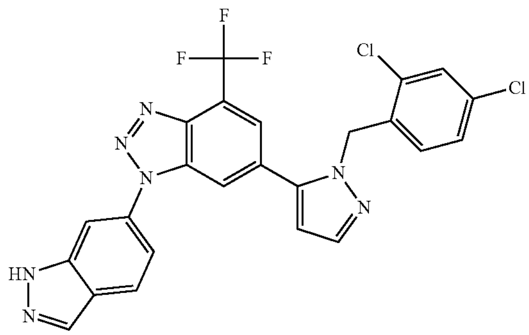 [SMILES: FC(F)(F)c1cc(-c2ccnn2Cc2ccc(Cl)cc2Cl)cc2c1nnn2-c1ccc2cn[nH]c2c1] | ++ |
| 123 | 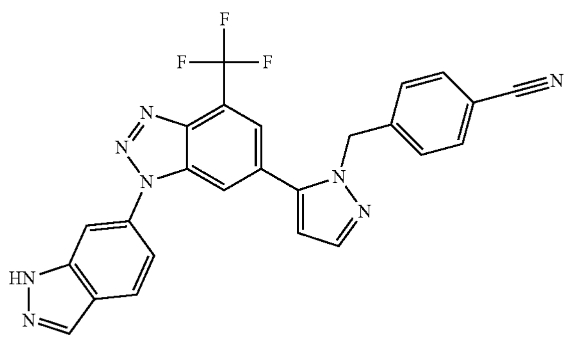 [SMILES: N#Cc1ccc(Cn2nccc2-c2cc(C(F)(F)F)c3nnn(-c4ccc5cn[nH]c5c4)c3c2)cc1] | ++ |
| 124 | 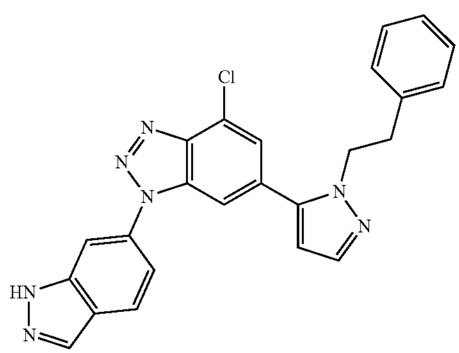 [SMILES: Clc1cc(-c2ccnn2CCc2ccccc2)cc2c1nnn2-c1ccc2cn[nH]c2c1] | ++ |
| 125 | 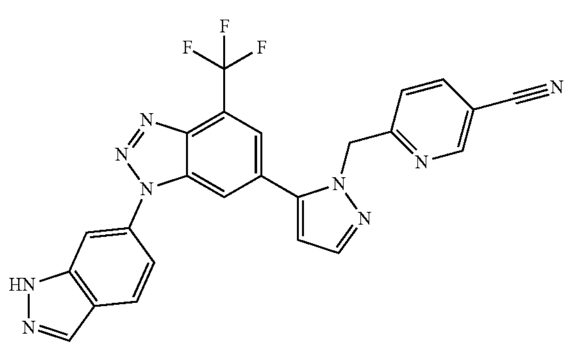 [SMILES: N#Cc1ccc(Cn2nccc2-c2cc(C(F)(F)F)c3nnn(-c4ccc5cn[nH]c5c4)c3c2)nc1] | ++ |

TABLE 1-continued

Specific Examples (Potency: CD73 IC$_{50}$: + means > 1 μM, ++ means 100 nM to 1 μM, +++ means < 100 nM).

| Example | Structure | Potency |
|---|---|---|
| 126 | 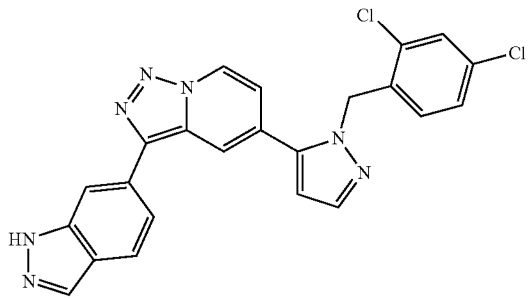 [SMILES: Clc1ccc(Cn2nccc2-c2ccn3nnc(-c4ccc5cn[nH]c5c4)c3c2)c(Cl)c1] | +++ |
| 127 | 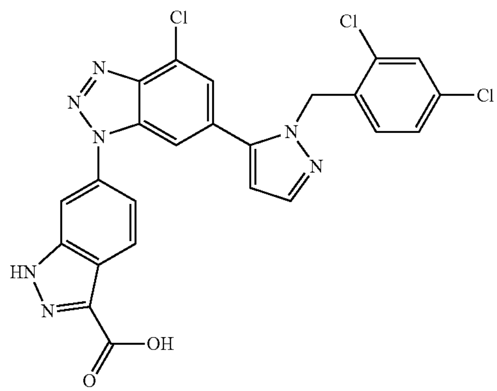 [SMILES: O=C(O)c1n[nH]c2cc(-n3nnc4c(Cl)cc(-c5ccnn5Cc5ccc(Cl)cc5Cl)cc43)ccc12] | + |
| 128 | 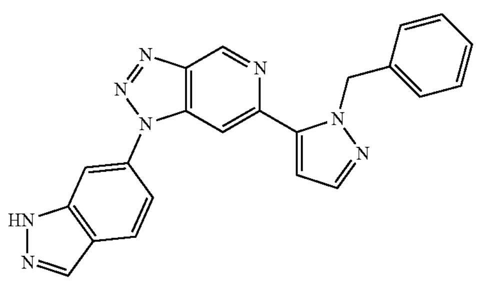 [SMILES: c1ccc(Cn2nccc2-c2cc3c(cn2)nnn3-c2ccc3cn[nH]c3c2)cc1] | ++ |
| 129 | 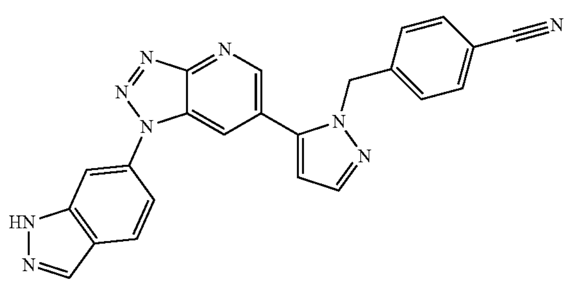 [SMILES: N#Cc1ccc(Cn2nccc2-c2cnc3nnn(-c4ccc5cn[nH]c5c4)c3c2)cc1] | ++ |
| 130 | 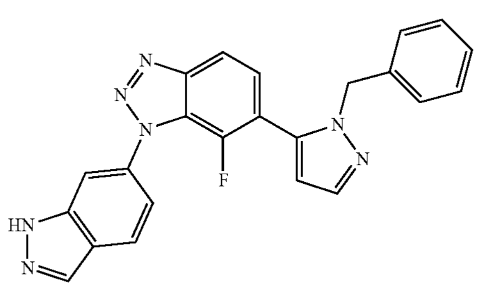 [SMILES: Fc1c(-c2ccnn2Cc2ccccc2)ccc2nnn(-c3ccc4cn[nH]c4c3)c12] | + |

TABLE 1-continued

Specific Examples (Potency: CD73 IC$_{50}$: + means > 1 μM, ++ means 100 nM to 1 μM, +++ means < 100 nM).

| Example | Structure | Potency |
|---------|-----------|---------|
| 131 | 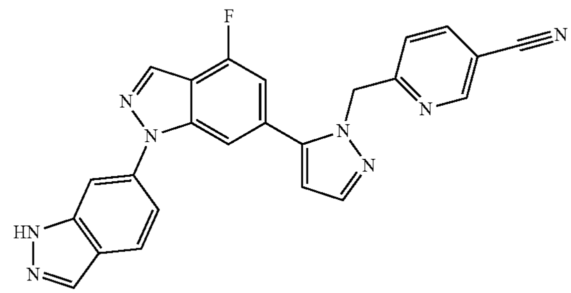 [SMILES: N#Cc1ccc(Cn2nccc2-c2cc(F)c3cnn(-c4ccc5cn[nH]c5c4)c3c2)nc1] | + |
| 132 | 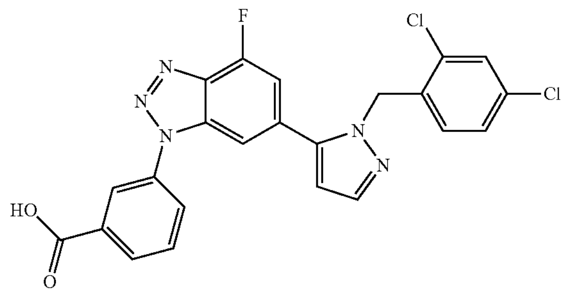 [SMILES: O=C(O)c1cccc(-n2nnc3c(F)cc(-c4ccnn4Cc4ccc(Cl)cc4Cl)cc32)c1] | + |
| 133 | 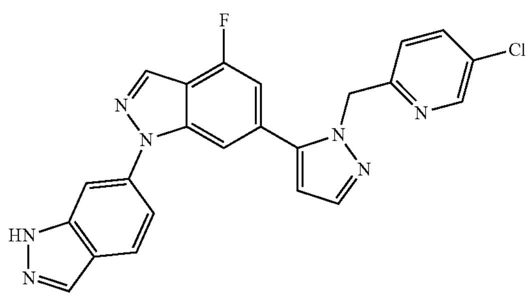 [SMILES: Fc1cc(-c2ccnn2Cc2ccc(Cl)cn2)cc2c1cnn2-c1ccc2cn[nH]c2c1] | + |
| 134 | 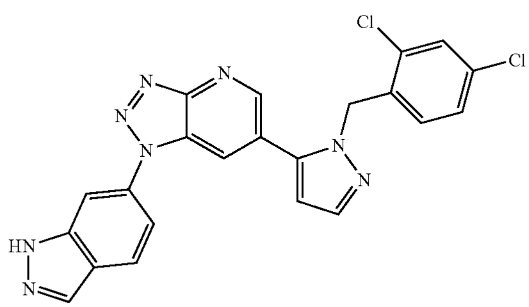 [SMILES: Clc1ccc(Cn2nccc2-c2cnc3nnn(-c4ccc5cn[nH]c5c4)c3c2)c(Cl)c1] | ++ |
| 135 | 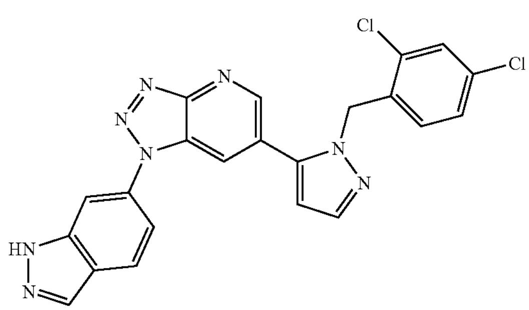 [SMILES: Clc1ccc(Cn2nccc2-c2cnc3nnn(-c4ccc5cn[nH]c5c4)c3c2)c(Cl)c1] | ++ |

TABLE 1-continued

Specific Examples (Potency: CD73 IC$_{50}$: + means > 1 μM, ++ means 100 nM to 1 μM, +++ means < 100 nM).

| Example | Structure | Potency |
|---|---|---|
| 136 | 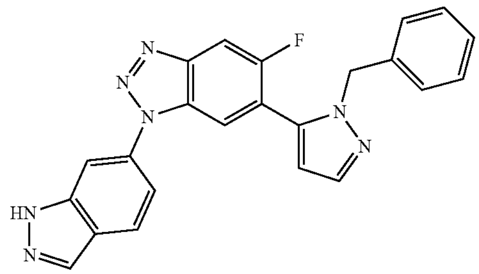 [SMILES: Fc1cc2nnn(-c3ccc4cn[nH]c4c3)c2cc1-c1ccnn1Cc1ccccc1] | + |
| 137 | 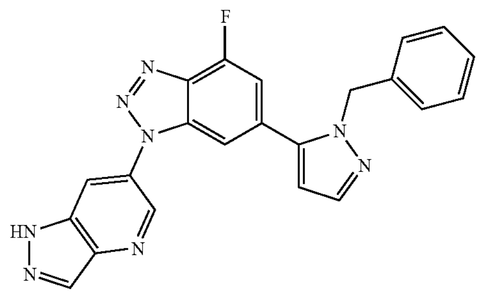 [SMILES: Fc1cc(-c2ccnn2Cc2ccccc2)cc2c1nnn2-c1cnc2cn[nH]c2c1] | + |
| 138 | 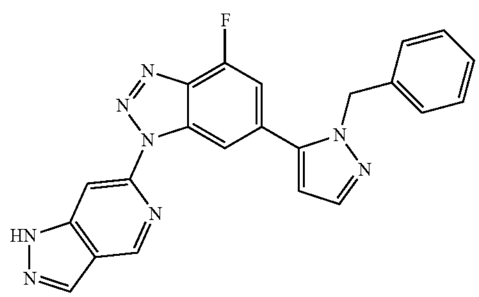 [SMILES: Fc1cc(-c2ccnn2Cc2ccccc2)cc2c1nnn2-c1cc2[nH]ncc2cn1] | + |
| 139 | 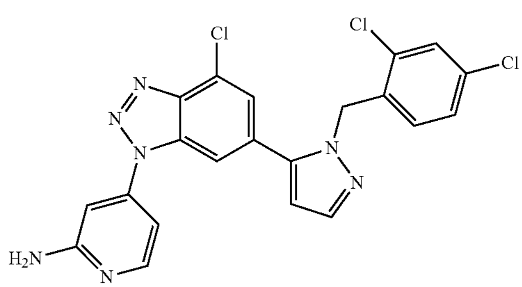 [SMILES: Nc1cc(-n2nnc3c(Cl)cc(-c4ccnn4Cc4ccc(Cl)cc4Cl)cc32)ccn1] | ++ |
| 140 | 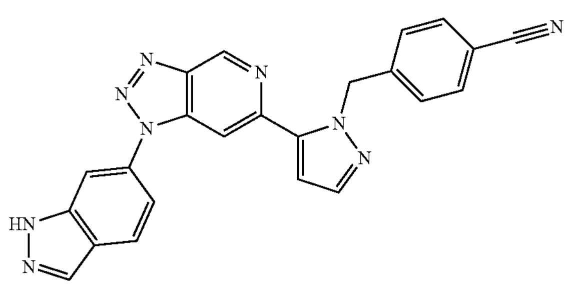 [SMILES: N#Cc1ccc(Cn2nccc2-c2cc3c(cn2)nnn3-c2ccc3cn[nH]c3c2)cc1] | ++ |

TABLE 1-continued

Specific Examples (Potency: CD73 IC$_{50}$: + means > 1 μM, ++ means 100 nM to 1 μM, +++ means < 100 nM).

| Example | Structure | Potency |
|---|---|---|
| 141 | 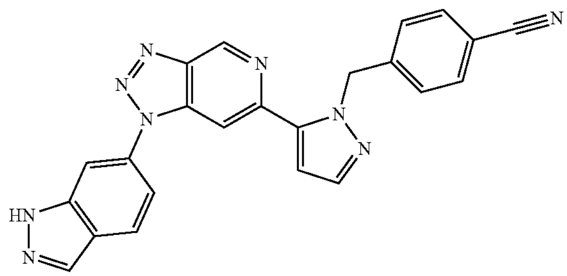 | ++ |
| 142 | 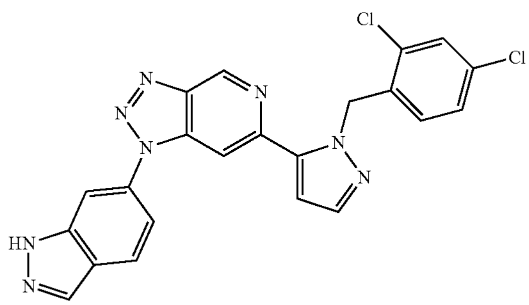 [SMILES: Clc1ccc(Cn2nccc2-c2cc3c(cn2)nnn3-c2ccc3cn[nH]c3c2)c(Cl)c1] | +++ |
| 143 | 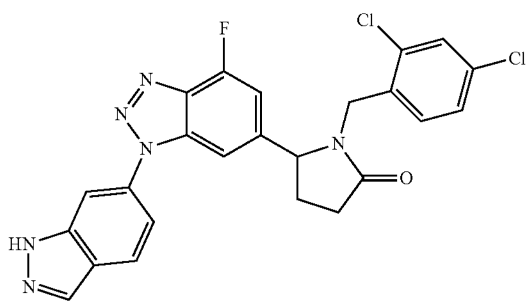 [SMILES: O=C1CCC(c2cc(F)c3nnn(-c4ccc5cn[nH]c5c4)c3c2)N1Cc1ccc(Cl)cc1Cl] | + |
| 144 | 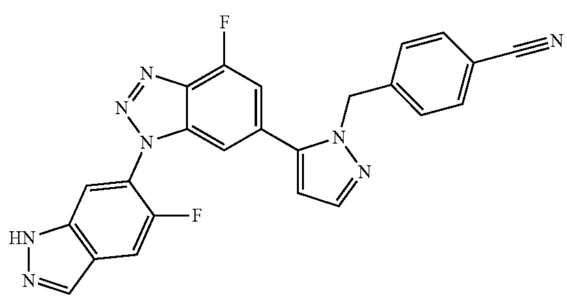 [SMILES: N#Cc1ccc(Cn2nccc2-c2cc(F)c3nnn(-c4cc5[nH]ncc5cc4F)c3c2)cc1] | +++ |
| 145 | 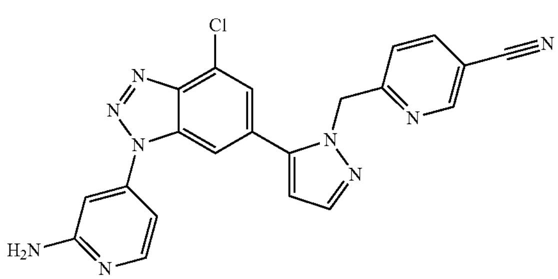 [SMILES: N#Cc1ccc(Cn2nccc2-c2cc(Cl)c3nnn(-c4ccnc(N)c4)c3c2)nc1] | + |

TABLE 1-continued

Specific Examples (Potency: CD73 IC$_{50}$: + means > 1 μM, ++ means 100 nM to 1 μM, +++ means < 100 nM).

| Example | Structure | Potency |
|---|---|---|
| 146 | 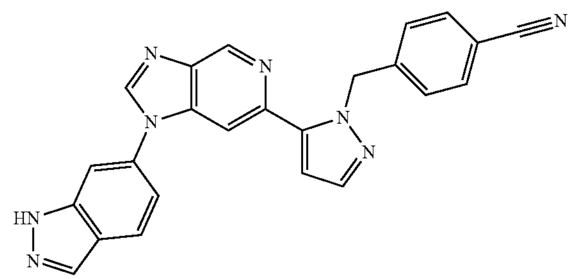 [SMILES: N#Cc1ccc(Cn2nccc2-c2cc3c(cn2)ncn3-c2ccc3cn[nH]c3c2)cc1] | + |
| 147 | 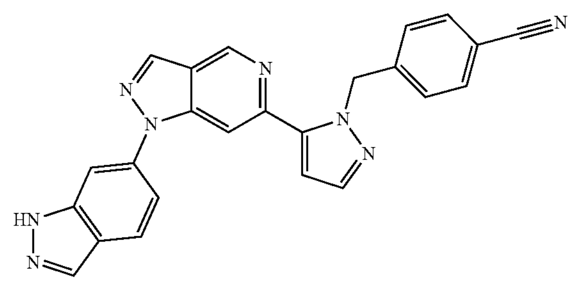 [SMILES: N#Cc1ccc(Cn2nccc2-c2cc3c(cn2)cnn3-c2ccc3cn[nH]c3c2)cc1] | + |
| 148 | 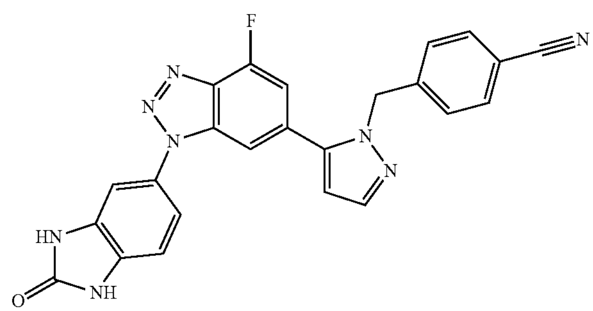 [SMILES: N#Cc1ccc(Cn2nccc2-c2cc(F)c3nnn(-c4ccc5[nH]c(=O)[nH]c5c4)c3c2)cc1] | +++ |
| 149 | 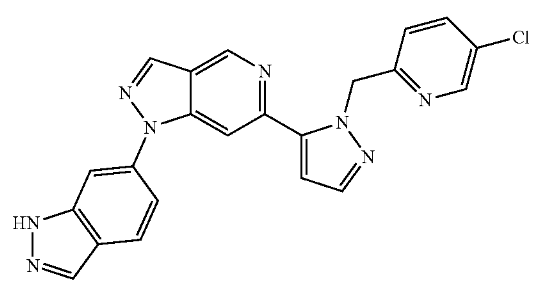 [SMILES: Clc1ccc(Cn2nccc2-c2cc3c(cn2)cnn3-c2ccc3cn[nH]c3c2)nc1] | + |
| 150 | 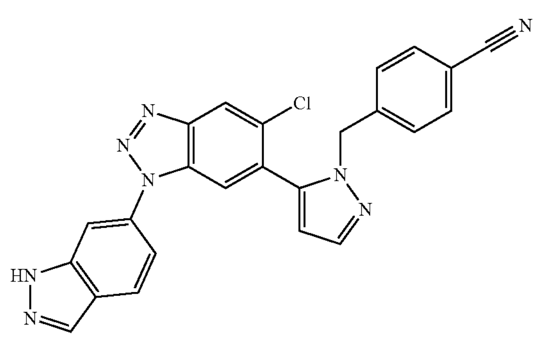 [SMILES: N#Cc1ccc(Cn2nccc2-c2cc3c(cc2Cl)nnn3-c2ccc3cn[nH]c3c2)cc1] | +++ |

TABLE 1-continued

Specific Examples (Potency: CD73 $IC_{50}$: + means > 1 μM, ++ means 100 nM to 1 μM, +++ means < 100 nM).

| Example | Structure | Potency |
|---------|-----------|---------|
| 151 | 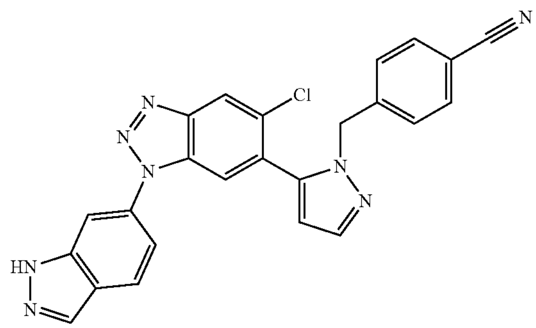 [SMILES: N#Cc1ccc(Cn2nccc2-c2cc3c(cc2Cl)nnn3-c2ccc3cn[nH]c3c2)cc1] | ++ |
| 152 | 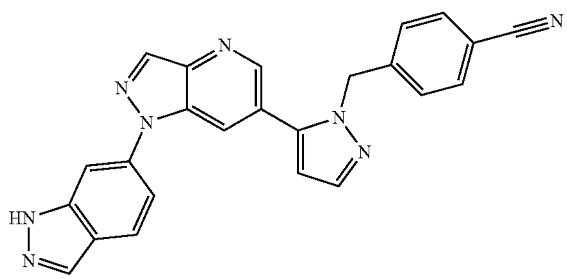 | + |
| 153 | 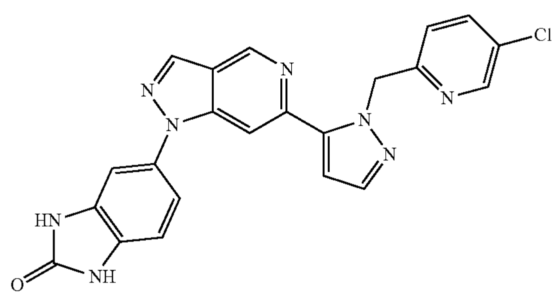 [SMILES: O=c1[nH]c2ccc(-n3ncc4cnc(-c5ccnn5Cc5ccc(Cl)cn5)cc43)cc2[nH]1] | + |
| 154 | 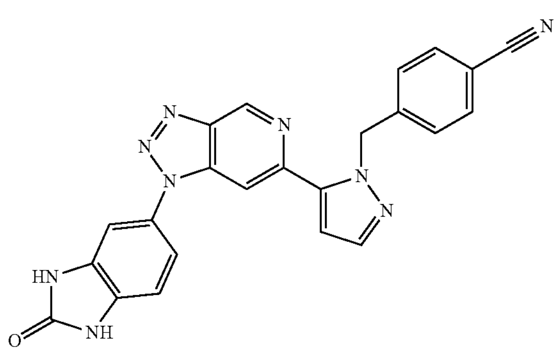 [SMILES: N#Cc1ccc(Cn2nccc2-c2cc3c(cn2)nnn3-c2ccc3[nH]c(=O)[nH]c3c2)cc1] | ++ |

TABLE 1-continued

Specific Examples (Potency: CD73 IC$_{50}$: + means > 1 μM, ++ means 100 nM to 1 μM, +++ means < 100 nM).

| Example | Structure | Potency |
|---------|-----------|---------|
| 155 | 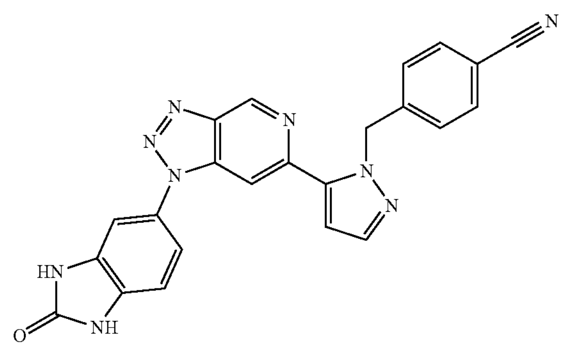 [SMILES: N#Cc1ccc(Cn2nccc2-c2cc3c(cn2)nnn3-c2ccc3[nH]c(=O)[nH]c3c2)cc1] | ++ |
| 156 | 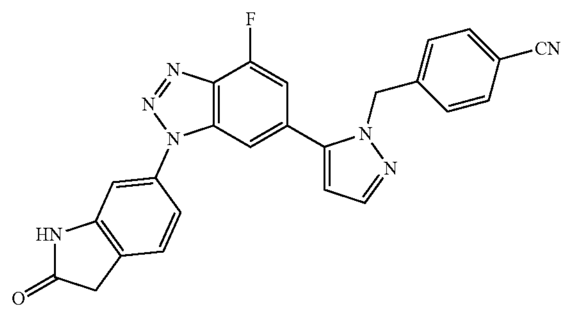 [SMILES: N#Cc1ccc(Cn2nccc2-c2cc(F)c3nnn(-c4ccc5c(c4)NC(=O)C5)c3c2)cc1] | + |
| 157 | 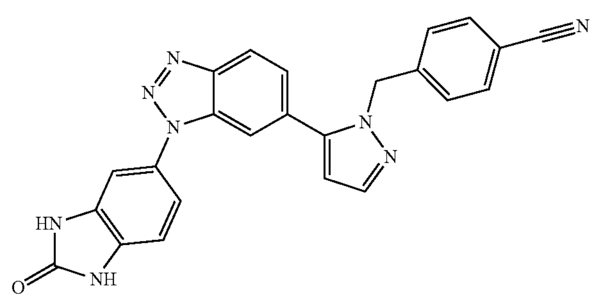 [SMILES: N#Cc1ccc(Cn2nccc2-c2ccc3nnn(-c4ccc5[nH]c(=O)[nH]c5c4)c3c2)cc1] | ++ |
| 158 | 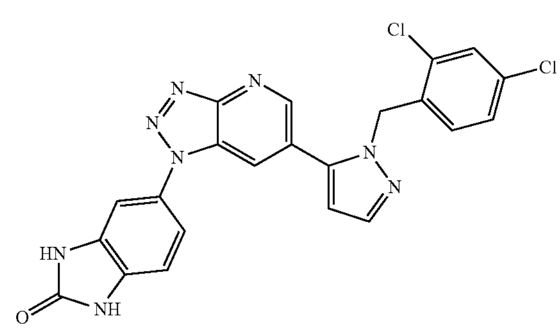 [SMILES: O=c1[nH]c2ccc(-n3nnc4ncc(-c5ccnn5Cc5ccc(Cl)cc5Cl)cc43)cc2[nH]1] | ++ |

TABLE 1-continued

Specific Examples (Potency: CD73 $IC_{50}$: + means > 1 μM, ++ means 100 nM to 1 μM, +++ means < 100 nM).

| Example | Structure | Potency |
|---------|-----------|---------|
| 159 | 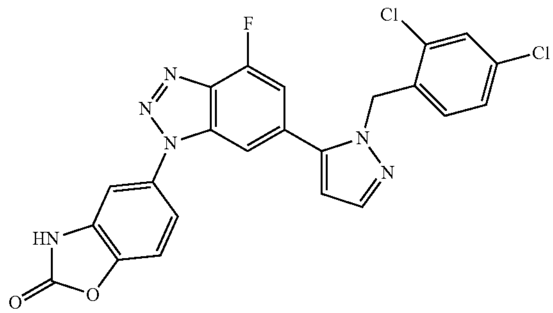 [SMILES: O=c1[nH]c2cc(-n3nnc4c(F)cc(-c5ccnn5Cc5ccc(Cl)cc5Cl)cc43)ccc2o1] | + |
| 160 | 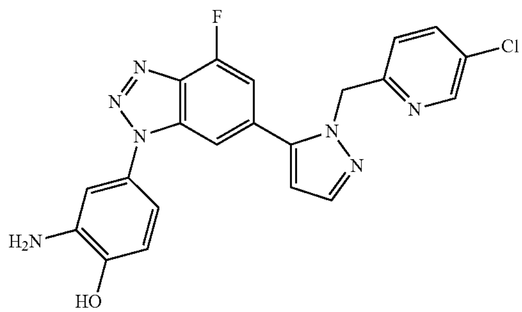 [SMILES: Nc1cc(-n2nnc3c(F)cc(-c4ccnn4Cc4ccc(Cl)cn4)cc32)ccc1O] | + |
| 161 | 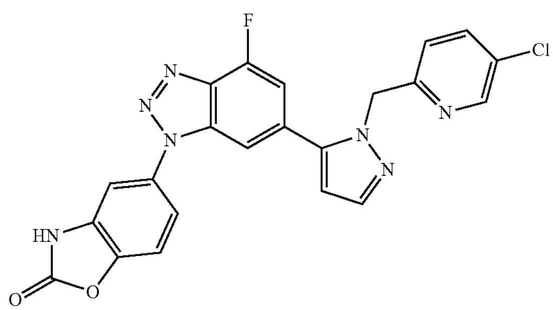 [SMILES: O=c1[nH]c2cc(-n3nnc4c(F)cc(-c5ccnn5Cc5ccc(Cl)cn5)cc43)ccc2o1] | + |
| 162 | 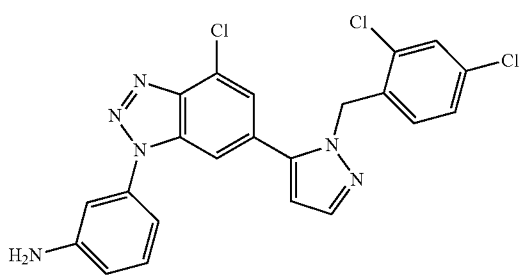 [SMILES: Nc1cccc(-n2nnc3c(Cl)cc(-c4ccnn4Cc4ccc(Cl)cc4Cl)cc32)c1] | + |
| 163 | 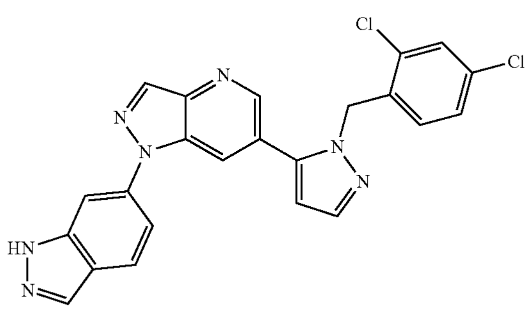 | ++ |

TABLE 1-continued
Specific Examples (Potency: CD73 IC$_{50}$: + means > 1 μM, ++ means 100 nM to 1 μM, +++ means < 100 nM).
| Example | Structure | Potency |
|---------|-----------|---------|
| 164 | 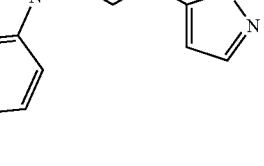 | ++ |
| 165 | 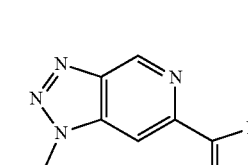 | ++ |
| 166 | 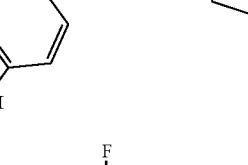 | + |
| 167 | 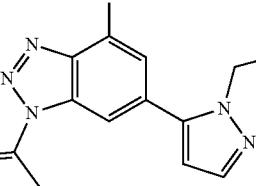 | +++ |
| 168 | 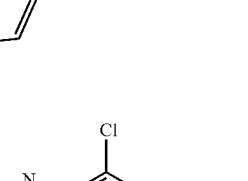 | +++ |

TABLE 1-continued

Specific Examples (Potency: CD73 IC$_{50}$: + means > 1 µM, ++ means 100 nM to 1 µM, +++ means < 100 nM).

| Example | Structure | Potency |
|---|---|---|
| 169 | 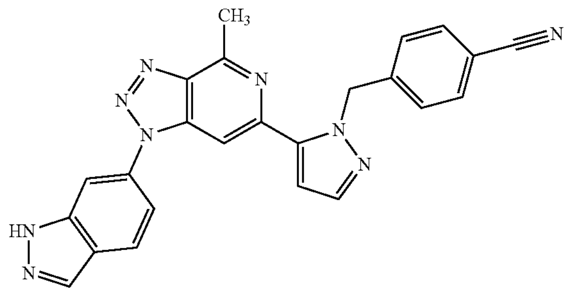 [SMILES: Cc1nc(-c2ccnn2Cc2ccc(C#N)cc2)cc2c1nnn2-c1ccc2cn[nH]c2c1] | ++ |
| 170 | 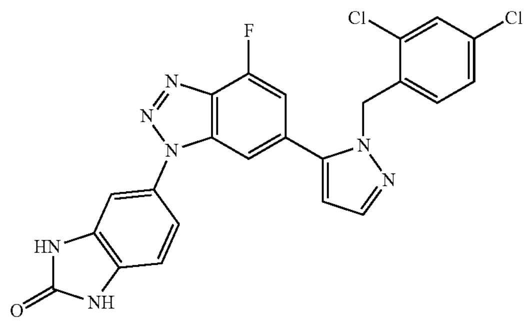 [SMILES: O=c1[nH]c2ccc(-n3nnc4c(F)cc(-c5ccnn5Cc5ccc(Cl)cc5Cl)cc43)cc2[nH]1] | ++ |
| 171 | 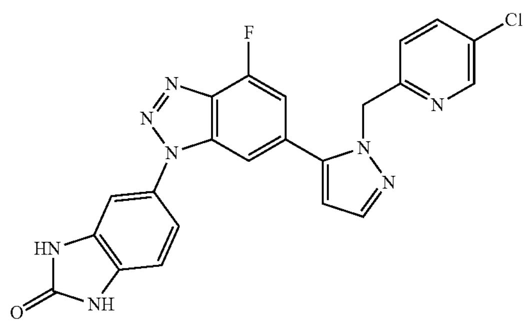 [SMILES: O=c1[nH]c2ccc(-n3nnc4c(F)cc(-c5ccnn5Cc5ccc(Cl)cn5)cc43)cc2[nH]1] | ++ |
| 172 | 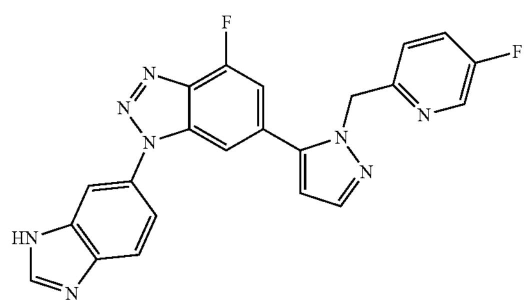 [SMILES: Fc1ccc(Cn2nccc2-c2cc(F)c3nnn(-c4ccc5nc[nH]c5c4)c3c2)nc1] | + |
| 173 | 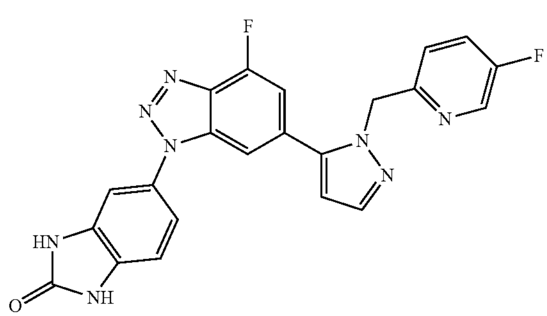 [SMILES: O=c1[nH]c2ccc(-n3nnc4c(F)cc(-c5ccnn5Cc5ccc(F)cn5)cc43)cc2[nH]1] | ++ |

TABLE 1-continued

Specific Examples (Potency: CD73 IC$_{50}$: + means > 1 µM, ++ means 100 nM to 1 µM, +++ means < 100 nM).

| Example | Structure | Potency |
|---|---|---|
| 174 | 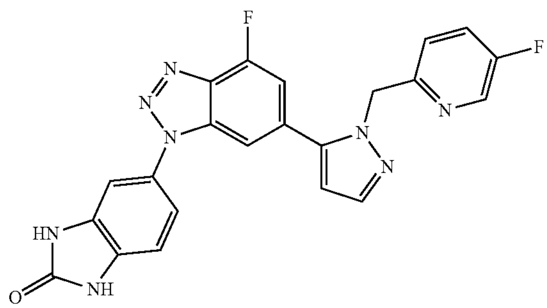 | + |
| 175 | 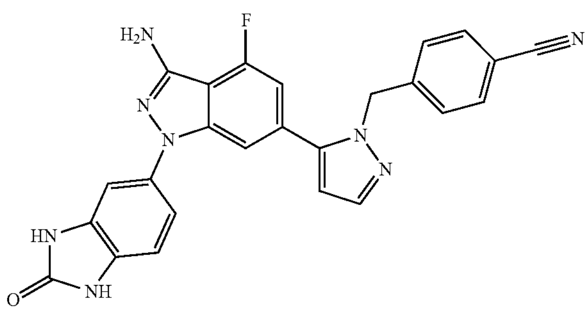 [SMILES: N#Cc1ccc(Cn2nccc2-c2cc(F)c3c(N)nn(-c4ccc5[nH]c(=O)[nH]c5c4)c3c2)cc1] | + |
| 176 | 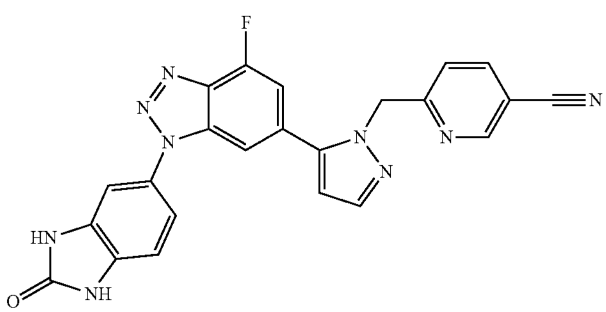 [SMILES: N#Cc1ccc(Cn2nccc2-c2cc(F)c3nnn(-c4ccc5[nH]c(=O)[nH]c5c4)c3c2)nc1] | ++ |
| 177 | 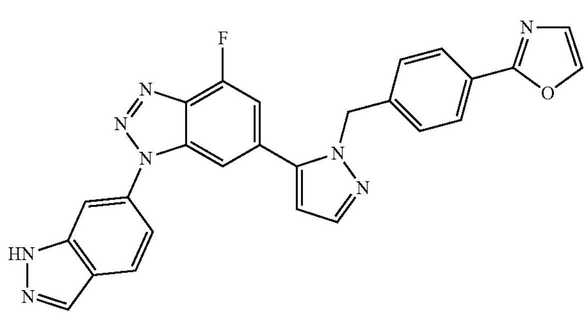 [SMILES: Fc1cc(-c2ccnn2Cc2ccc(-c3ncco3)cc2)cc2c1nnn2-c1ccc2cn[nH]c2c1] | + |
| 178 | 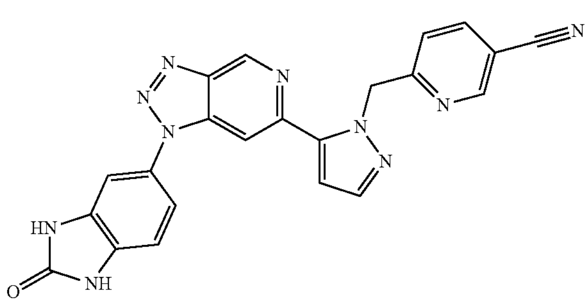 [SMILES: N#Cc1ccc(Cn2nccc2-c2cc3c(cn2)nnn3-c2ccc3[nH]c(=O)[nH]c3c2)nc1] | ++ |

TABLE 1-continued

Specific Examples (Potency: CD73 IC$_{50}$: + means > 1 µM, ++ means 100 nM to 1 µM, +++ means < 100 nM).

| Example | Structure | Potency |
|---------|-----------|---------|
| 179 | 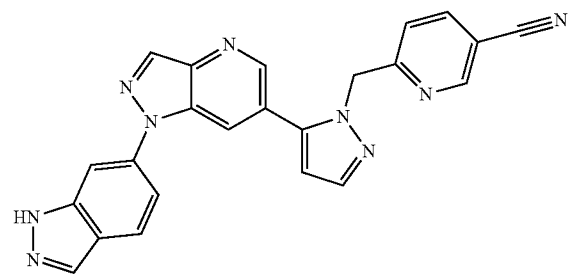 [SMILES: N#Cc1ccc(Cn2nccc2-c2cnc3cnn(-c4ccc5cn[nH]c5c4)c3c2)nc1] | + |
| 180 | 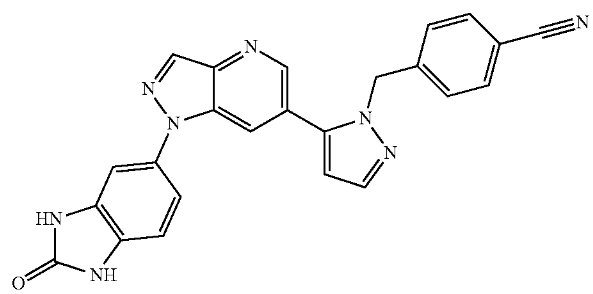 [SMILES: N#Cc1ccc(Cn2nccc2-c2cnc3cnn(-c4ccc5[nH]c(=O)[nH]c5c4)c3c2)cc1] | + |
| 181 | 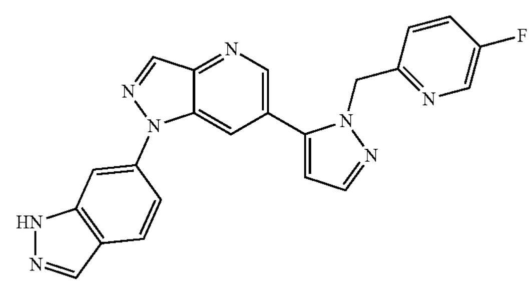 [SMILES: Fc1ccc(Cn2nccc2-c2cnc3cnn(-c4ccc5cn[nH]c5c4)c3c2)nc1] | + |
| 182 | 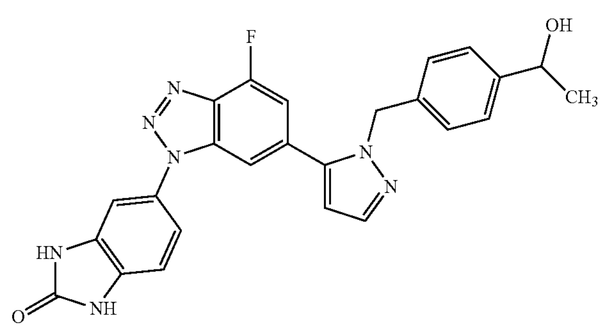 [SMILES: CC(O)c1ccc(Cn2nccc2-c2cc(F)c3nnn(-c4ccc5[nH]c(=O)[nH]c5c4)c3c2)cc1] | + |
| 183 | 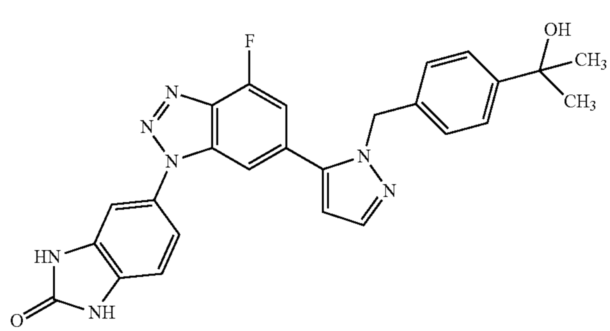 [SMILES: CC(C)(O)c1ccc(Cn2nccc2-c2cc(F)c3nnn(-c4ccc5[nH]c(=O)[nH]c5c4)c3c2)cc1] | + |

TABLE 1-continued

Specific Examples (Potency: CD73 IC$_{50}$: + means > 1 μM, ++ means 100 nM to 1 μM, +++ means < 100 nM).

| Example | Structure | Potency |
| --- | --- | --- |
| 184 | 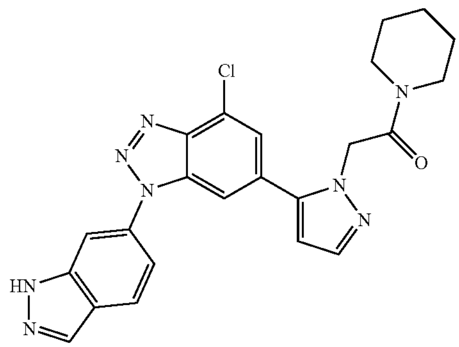 [SMILES: O=C(Cn1nccc1-c1cc(Cl)c2nnn(-c3ccc4cn[nH]c4c3)c2c1)N1CCCCC1] | + |
| 185 | 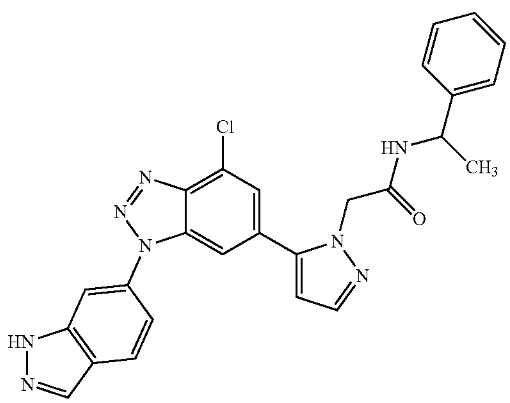 [SMILES: CC(NC(=O)Cn1nccc1-c1cc(Cl)c2nnn(-c3ccc4cn[nH]c4c3)c2c1)c1ccccc1] | + |
| 186 | 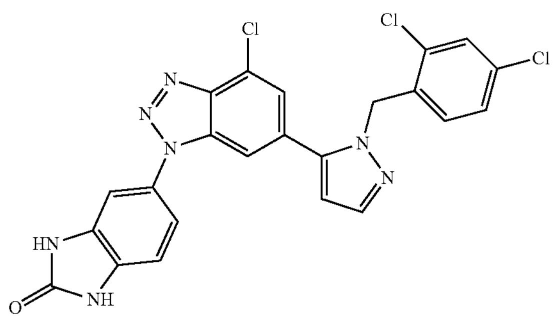 [SMILES: O=c1[nH]c2ccc(-n3nnc4c(Cl)cc(-c5ccnn5Cc5ccc(Cl)cc5Cl)cc43)cc2[nH]1] | ++ |
| 187 | 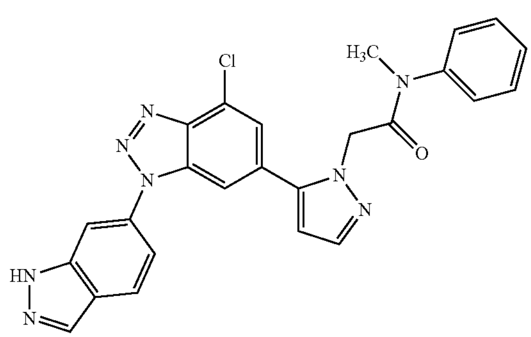 [SMILES: CN(C(=O)Cn1nccc1-c1cc(Cl)c2nnn(-c3ccc4cn[nH]c4c3)c2c1)c1ccccc1] | + |

TABLE 1-continued
Specific Examples (Potency: CD73 IC$_{50}$: + means > 1 μM, ++ means 100 nM to 1 μM, +++ means < 100 nM).
| Example | Structure | Potency |
|---|---|---|
| 188 | 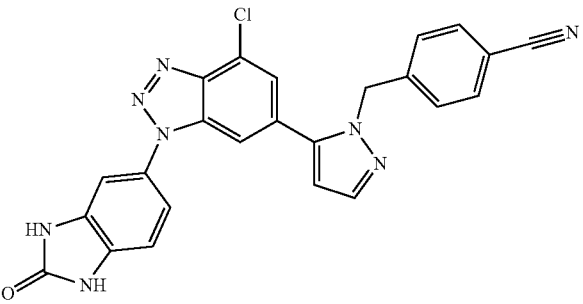 [SMILES: N#Cc1ccc(Cn2nccc2-c2cc(Cl)c3nnn(-c4ccc5[nH]c(=O)[nH]c5c4)c3c2)cc1] | ++ |
| 189 | 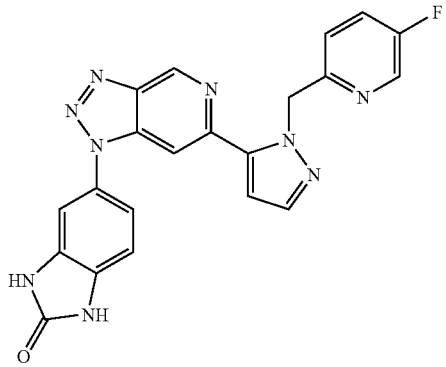 [SMILES: O=c1[nH]c2ccc(-n3nnc4cnc(-c5ccnn5Cc5ccc(F)cn5)cc43)cc2[nH]1] | ++ |
| 190 | 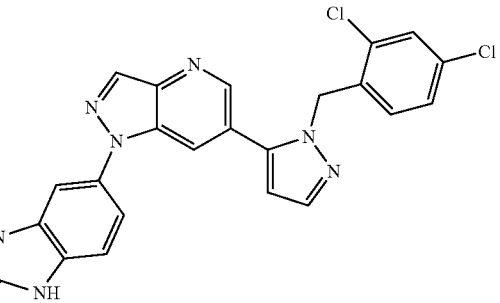 | ++ |
| 191 | 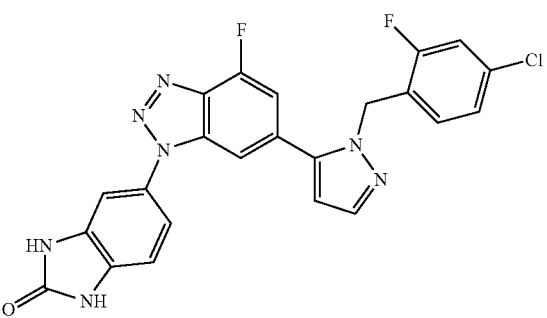 [SMILES: O=c1[nH]c2ccc(-n3nnc4c(F)cc(-c5ccnn5Cc5ccc(Cl)cc5F)cc43)cc2[nH]1] | ++ |

TABLE 1-continued

Specific Examples (Potency: CD73 $IC_{50}$: + means > 1 µM, ++ means 100 nM to 1 µM, +++ means < 100 nM).

| Example | Structure | Potency |
|---|---|---|
| 192 | 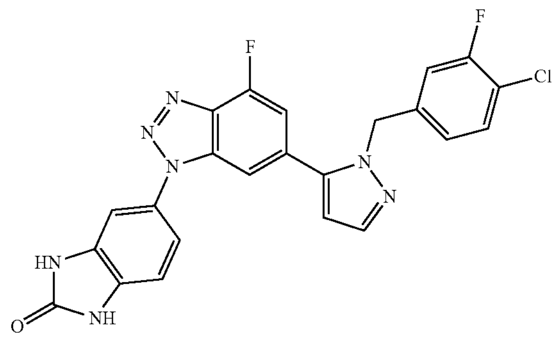 [SMILES: O=c1[nH]c2ccc(-n3nnc4c(F)cc(-c5ccnn5Cc5ccc(Cl)c(F)c5)cc43)cc2[nH]1] | ++ |
| 193 | 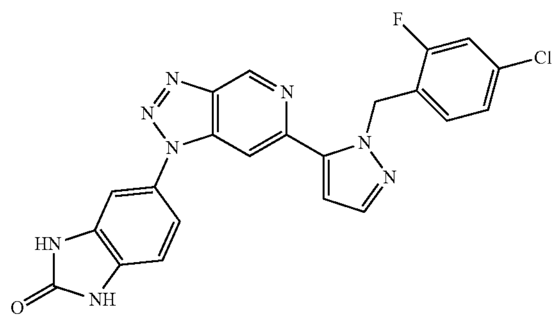 [SMILES: O=c1[nH]c2ccc(-n3nnc4cnc(-c5ccnn5Cc5ccc(Cl)cc5F)cc43)cc2[nH]1] | ++ |
| 194 | 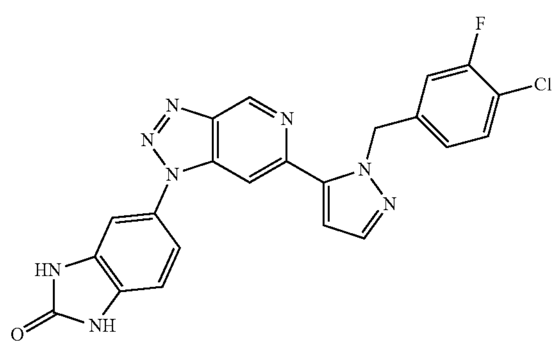 [SMILES: O=c1[nH]c2ccc(-n3nnc4cnc(-c5ccnn5Cc5ccc(Cl)c(F)c5)cc43)cc2[nH]1] | ++ |
| 195 | 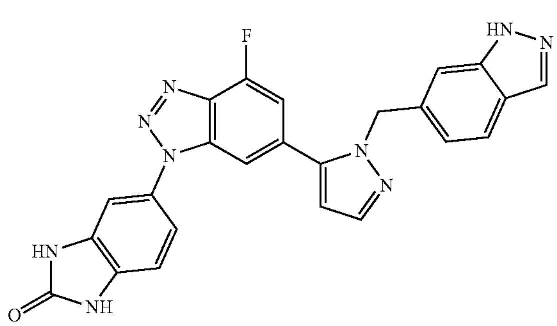 [SMILES: O=c1[nH]c2ccc(-n3nnc4c(F)cc(-c5ccnn5Cc5ccc6cn[nH]c6c5)cc43)cc2[nH]1] | ++ |

TABLE 1-continued

Specific Examples (Potency: CD73 IC$_{50}$: + means > 1 μM, ++ means 100 nM to 1 μM, +++ means < 100 nM).

| Example | Structure | Potency |
|---|---|---|
| 196 | 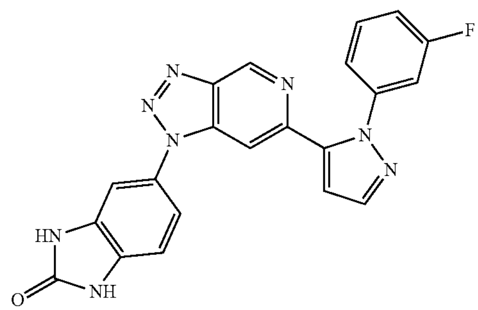 [SMILES: O=c1[nH]c2ccc(-n3nnc4cnc(-c5ccnn5-c5cccc(F)c5)cc43)cc2[nH]1] | + |
| 197 | 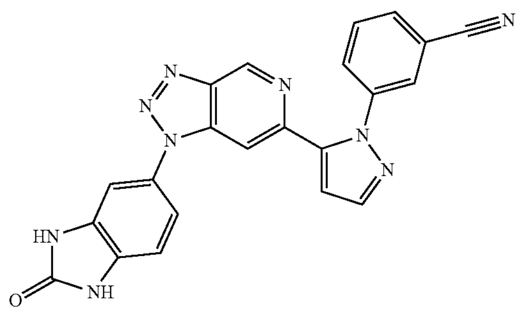 [SMILES: N#Cc1cccc(-n2nccc2-c2cc3c(cn2)nnn3-c2ccc3[nH]c(=O)[nH]c3c2)c1] | + |
| 198 | 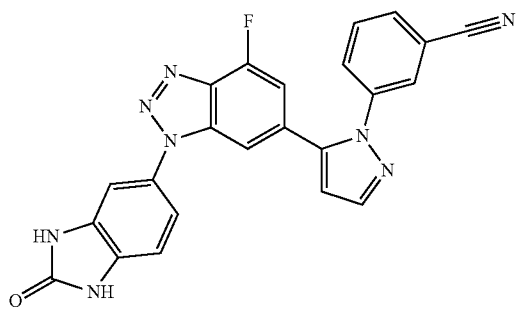 [SMILES: N#Cc1cccc(-n2nccc2-c2cc(F)c3nnn(-c4ccc5[nH]c(=O)[nH]c5c4)c3c2)c1] | + |
| 199 | 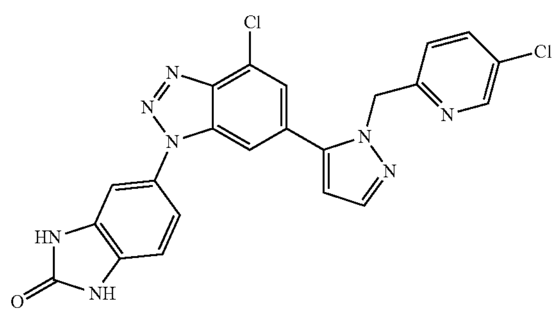 [SMILES: O=c1[nH]c2ccc(-n3nnc4c(Cl)cc(-c5ccnn5Cc5ccc(Cl)cn5)cc43)cc2[nH]1] | +++ |
| 200 | 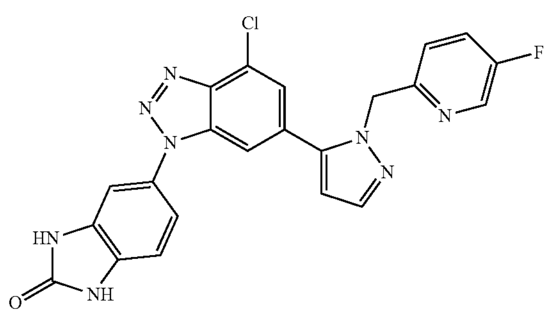 | ++ |

TABLE 1-continued

Specific Examples (Potency: CD73 IC$_{50}$: + means > 1 μM, ++ means 100 nM to 1 μM, +++ means < 100 nM).

| Example | Structure | Potency |
| --- | --- | --- |
| 201 | 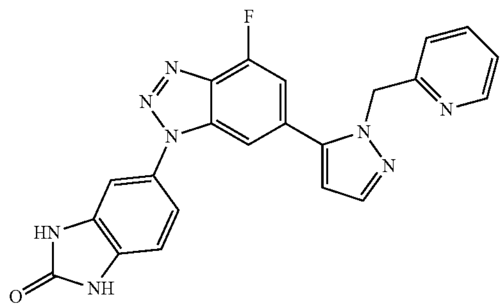 [SMILES: O=c1[nH]c2ccc(-n3nnc4c(F)cc(-c5ccnn5Cc5ccccn5)cc43)cc2[nH]1] | + |
| 202 | 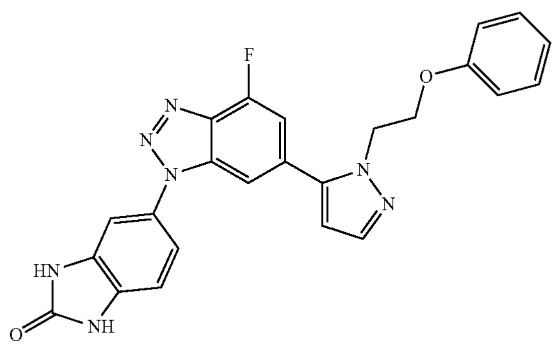 [SMILES: O=c1[nH]c2ccc(-n3nnc4c(F)cc(-c5ccnn5CCOc5ccccc5)cc43)cc2[nH]1] | + |
| 203 | 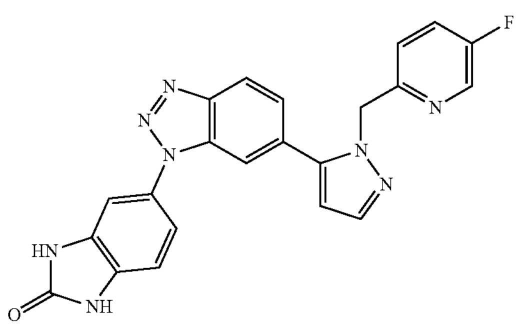 [SMILES: O=c1[nH]c2ccc(-n3nnc4ccc(-c5ccnn5Cc5ccc(F)cn5)cc43)cc2[nH]1] | ++ |
| 204 | 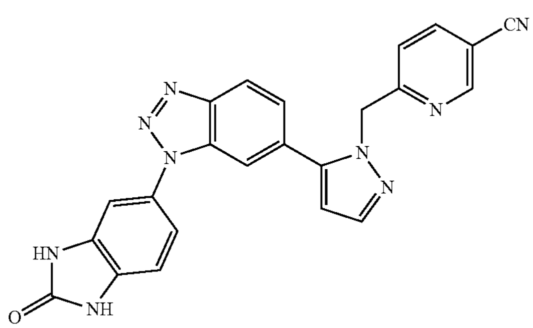 [SMILES: N#Cc1ccc(Cn2nccc2-c2ccc3nnn(-c4ccc5[nH]c(=O)[nH]c5c4)c3c2)nc1] | ++ |

TABLE 1-continued

Specific Examples (Potency: CD73 IC$_{50}$: + means > 1 μM, ++ means 100 nM to 1 μM, +++ means < 100 nM).

| Example | Structure | Potency |
|---------|-----------|---------|
| 205 | 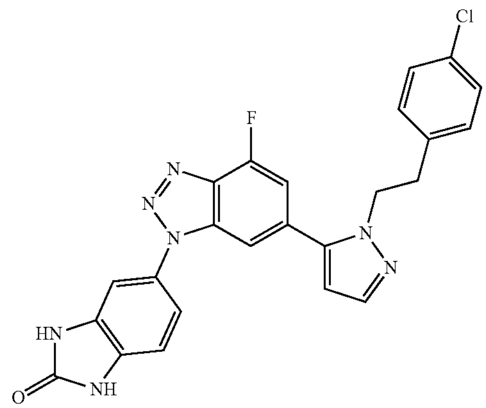 [SMILES: O=c1[nH]c2ccc(-n3nnc4c(F)cc(-c5ccnn5CCc5ccc(Cl)cc5)cc43)cc2[nH]1] | + |
| 206 | 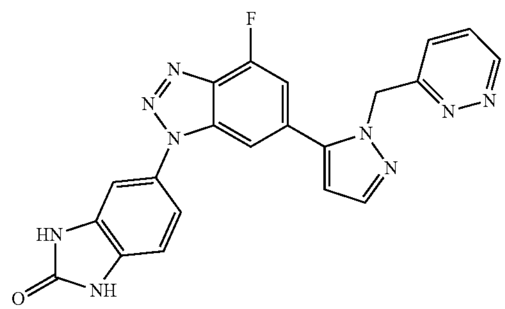 [SMILES: O=c1[nH]c2ccc(-n3nnc4c(F)cc(-c5ccnn5Cc5cccnn5)cc43)cc2[nH]1] | + |
| 207 | 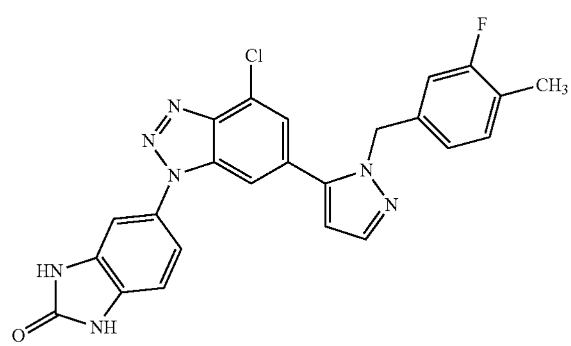 [SMILES: Cc1ccc(Cn2nccc2-c2cc(Cl)c3nnn(-c4ccc5[nH]c(=O)[nH]c5c4)c3c2)cc1F] | ++ |
| 208 | 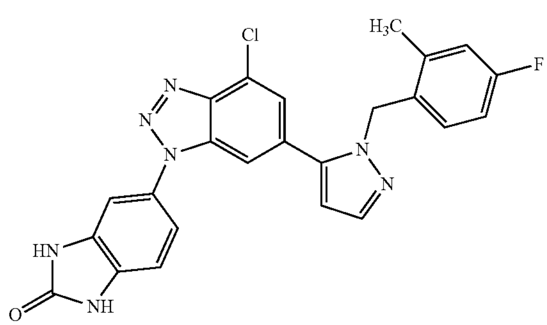 [SMILES: Cc1cc(F)ccc1Cn1nccc1-c1cc(Cl)c2nnn(-c3ccc4[nH]c(=O)[nH]c4c3)c2c1] | ++ |

TABLE 1-continued

Specific Examples (Potency: CD73 IC$_{50}$: + means > 1 μM, ++ means 100 nM to 1 μM, +++ means < 100 nM).

| Example | Structure | Potency |
|---------|-----------|---------|
| 209 | 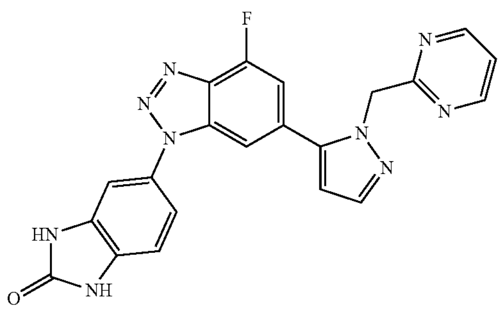 [SMILES: O=c1[nH]c2ccc(-n3nnc4c(F)cc(-c5ccnn5Cc5ncccn5)cc43)cc2[nH]1] | + |
| 210 | 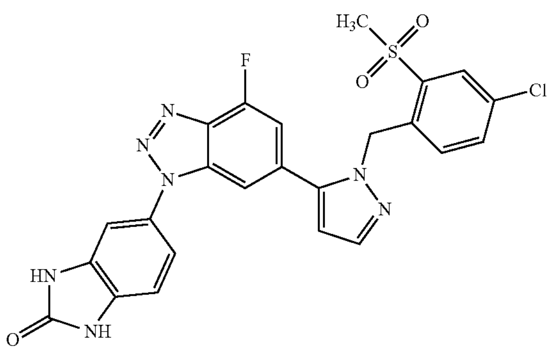 [SMILES: CS(=O)(=O)c1cc(Cl)ccc1Cn1nccc1-c1cc(F)c2nnn(-c3ccc4[nH]c(=O)[nH]c4c3)c2c1] | ++ |
| 211 | 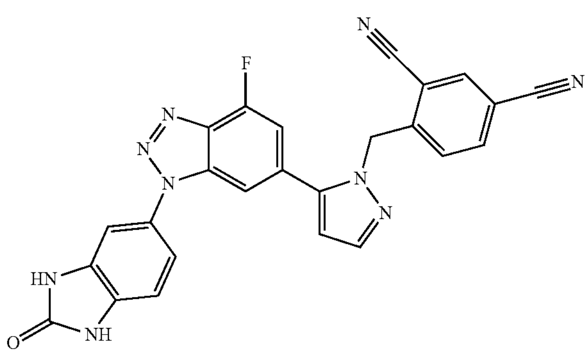 [SMILES: N#Cc1ccc(Cn2nccc2-c2cc(F)c3nnn(-c4ccc5[nH]c(=O)[nH]c5c4)c3c2)c(C#N)c1] | ++ |
| 212 | 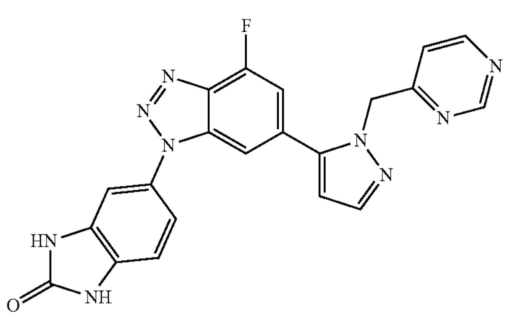 [SMILES: O=c1[nH]c2ccc(-n3nnc4c(F)cc(-c5ccnn5Cc5ccncn5)cc43)cc2[nH]1] | + |

TABLE 1-continued

Specific Examples (Potency: CD73 IC$_{50}$: + means > 1 μM, ++ means 100 nM to 1 μM, +++ means < 100 nM).

| Example | Structure | Potency |
|---------|-----------|---------|
| 213 | 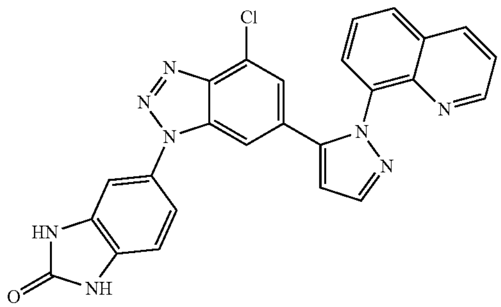 [SMILES: O=c1[nH]c2ccc(-n3nnc4c(Cl)cc(-c5ccnn5-c5cccc6cccnc56)cc43)cc2[nH]1] | + |
| 214 | 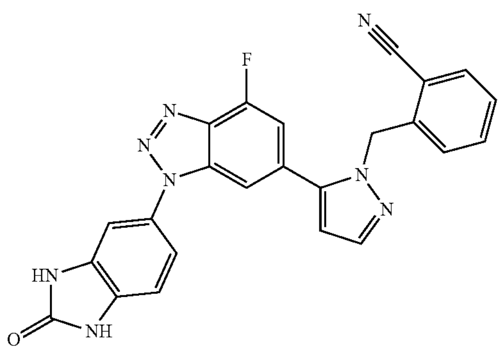 [SMILES: N#Cc1ccccc1Cn1nccc1-c1cc(F)c2nnn(-c3ccc4[nH]c(=O)[nH]c4c3)c2c1] | + |
| 215 | 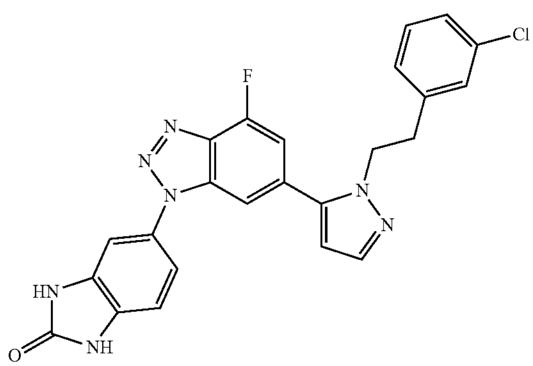 [SMILES: O=c1[nH]c2ccc(-n3nnc4c(F)cc(-c5ccnn5CCc5cccc(Cl)c5)cc43)cc2[nH]1] | + |
| 216 | 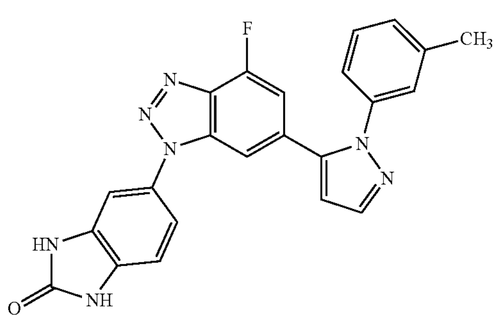 | + |

TABLE 1-continued

Specific Examples (Potency: CD73 IC$_{50}$: + means > 1 μM, ++ means 100 nM to 1 μM, +++ means < 100 nM).

| Example | Structure | Potency |
|---------|-----------|---------|
| 217 | 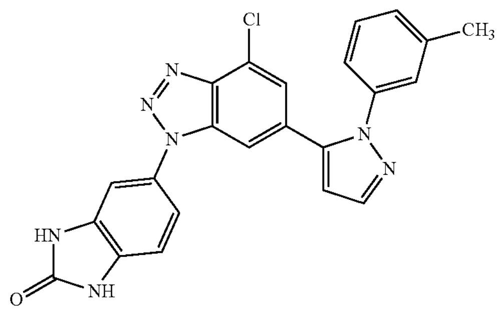 [SMILES: Cc1cccc(-n2nccc2-c2cc(F)c3nnn(-c4ccc5[nH]c(=O)[nH]c5c4)c3c2)c1] | ++ |
| 218 | 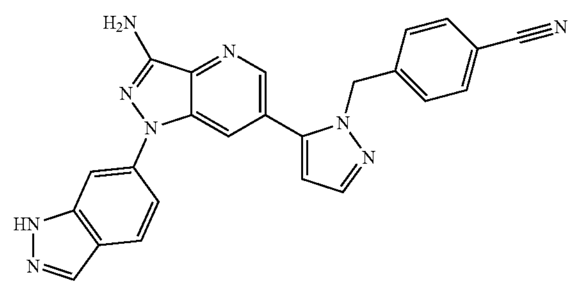 [SMILES: N#Cc1ccc(Cn2nccc2-c2cnc3c(N)nn(-c4ccc5cn[nH]c5c4)c3c2)cc1] | ++ |
| 219 | 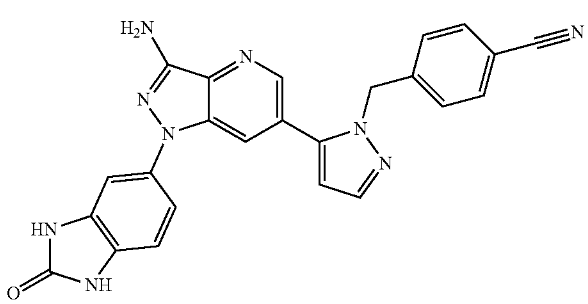 [SMILES: N#Cc1ccc(Cn2nccc2-c2cnc3c(N)nn(-c4ccc5[nH]c(=O)[nH]c5c4)c3c2)cc1] | ++ |
| 220 | 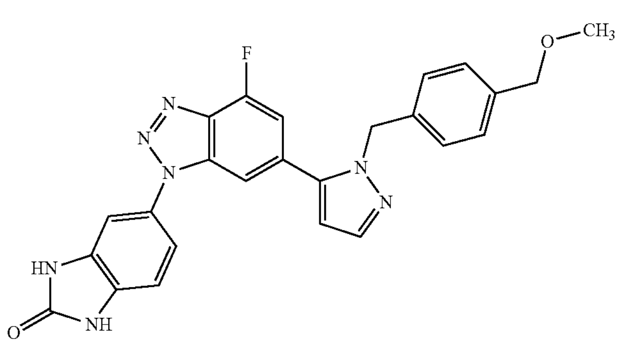 [SMILES: COCc1ccc(Cn2nccc2-c2cc(F)c3nnn(-c4ccc5[nH]c(=O)[nH]c5c4)c3c2)cc1] | + |

TABLE 1-continued

Specific Examples (Potency: CD73 $IC_{50}$: + means > 1 μM, ++ means 100 nM to 1 μM, +++ means < 100 nM).

| Example | Structure | Potency |
|---------|-----------|---------|
| 221 | 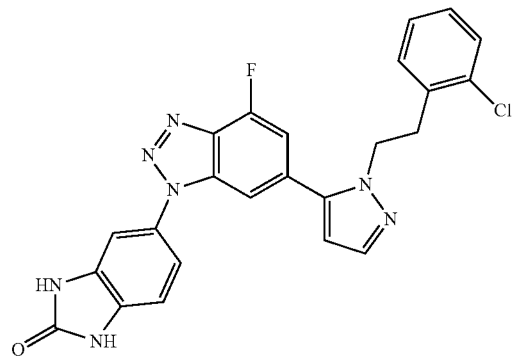 [SMILES: O=c1[nH]c2ccc(-n3nnc4c(F)cc(-c5ccnn5CCc5ccccc5Cl)cc43)cc2[nH]1] | + |
| 222 | 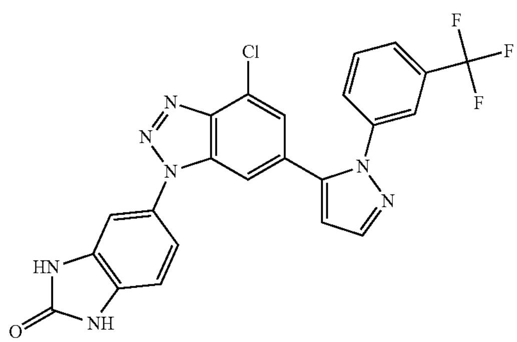 [SMILES: O=c1[nH]c2ccc(-n3nnc4c(Cl)cc(-c5ccnn5-c5cccc(C(F)(F)F)c5)cc43)cc2[nH]1] | ++ |
| 223 | 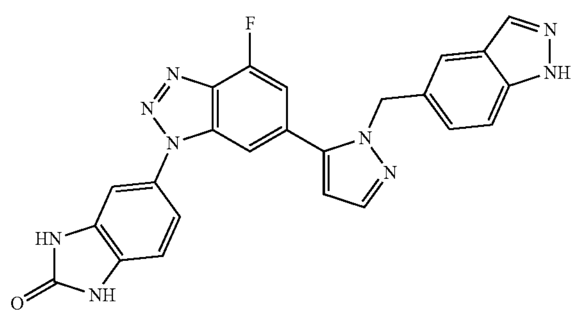 [SMILES: O=c1[nH]c2ccc(-n3nnc4c(F)cc(-c5ccnn5Cc5ccc6[nH]ncc6c5)cc43)cc2[nH]1] | ++ |
| 224 | 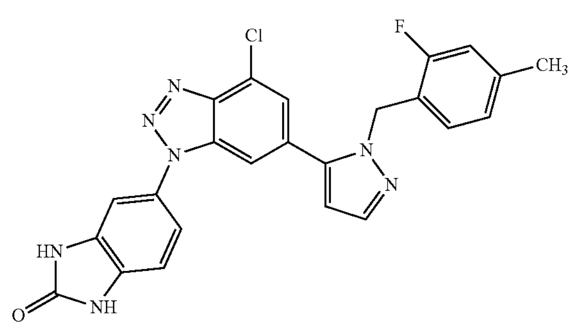 [SMILES: Cc1ccc(Cn2nccc2-c2cc(Cl)c3nnn(-c4ccc5[nH]c(=O)[nH]c5c4)c3c2)c(F)c1] | +++ |

TABLE 1-continued

Specific Examples (Potency: CD73 IC$_{50}$: + means > 1 µM, ++ means 100 nM to 1 µM, +++ means < 100 nM).

| Example | Structure | Potency |
|---------|-----------|---------|
| 225 | 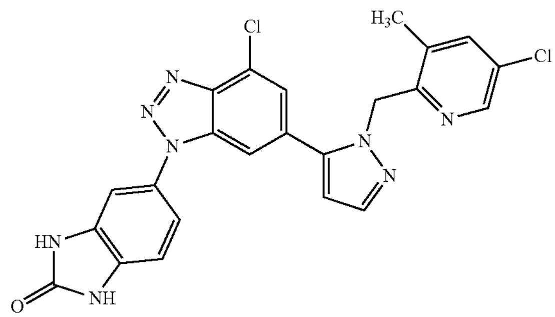 [SMILES: Cc1cc(Cl)cnc1Cn1nccc1-c1cc(Cl)c2nnn(-c3ccc4[nH]c(=O)[nH]c4c3)c2c1] | ++ |
| 226 | 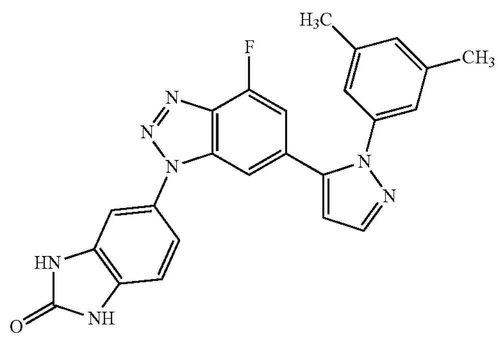 [SMILES: Cc1cc(C)cc(-n2nccc2-c2cc(F)c3nnn(-c4ccc5[nH]c(=O)[nH]c5c4)c3c2)c1] | ++ |
| 227 | 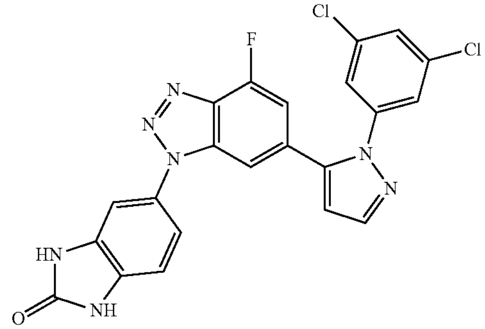 [SMILES: O=c1[nH]c2ccc(-n3nnc4c(F)cc(-c5ccnn5-c5cc(Cl)cc(Cl)c5)cc43)cc2[nH]1] | ++ |
| 228 | 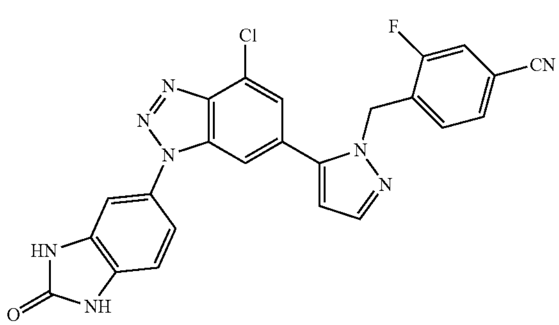 | +++ |

TABLE 1-continued

Specific Examples (Potency: CD73 IC$_{50}$: + means > 1 μM, ++ means 100 nM to 1 μM, +++ means < 100 nM).

| Example | Structure | Potency |
|---|---|---|
| 229 | 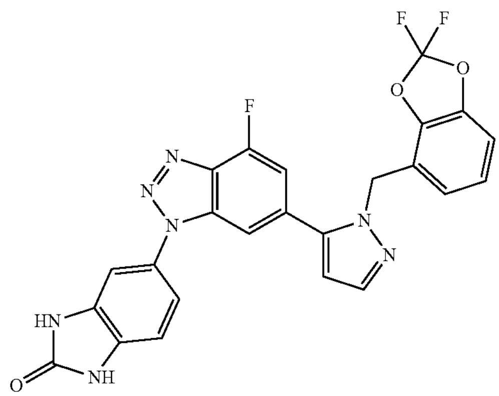 [SMILES: O=c1[nH]c2ccc(-n3nnc4c(F)cc(-c5ccnn5Cc5cccc6c5OC(F)(F)O6)cc43)cc2[nH]1] | + |
| 230 | 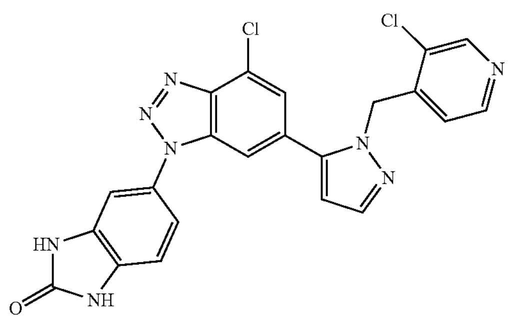 [SMILES: O=c1[nH]c2ccc(-n3nnc4c(Cl)cc(-c5ccnn5Cc5ccncc5Cl)cc43)cc2[nH]1] | ++ |
| 231 | 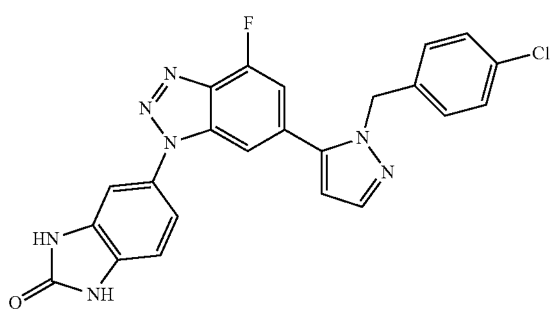 [SMILES: O=c1[nH]c2ccc(-n3nnc4c(F)cc(-c5ccnn5Cc5ccc(Cl)cc5)cc43)cc2[nH]1] | ++ |
| 232 | 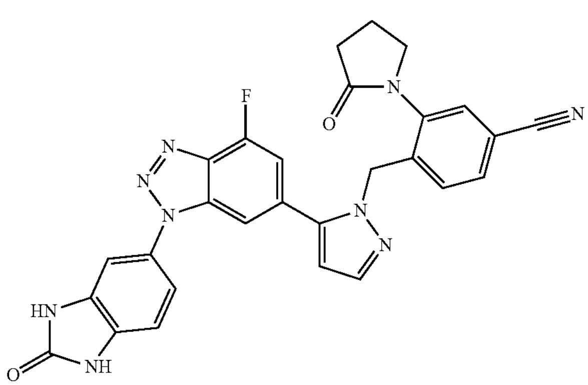 [SMILES: N#Cc1ccc(Cn2nccc2-c2cc(F)c3nnn(-c4ccc5[nH]c(=O)[nH]c5c4)c3c2)c(N2CCCC2=O)c1] | ++ |

TABLE 1-continued

Specific Examples (Potency: CD73 IC$_{50}$: + means > 1 µM, ++ means 100 nM to 1 µM, +++ means < 100 nM).

| Example | Structure | Potency |
|---------|-----------|---------|
| 233 | 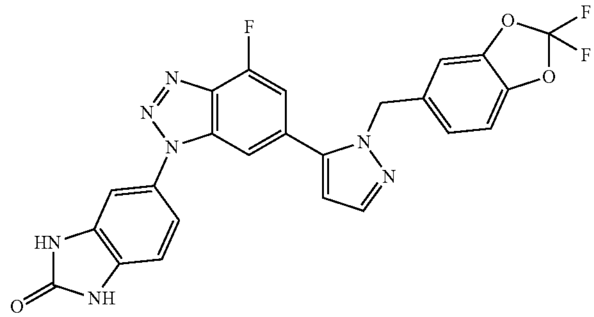 [SMILES: O=c1[nH]c2ccc(-n3nnc4c(F)cc(-c5ccnn5Cc5ccc6c(c5)OC(F)(F)O6)cc43)cc2[nH]1] | + |
| 234 | 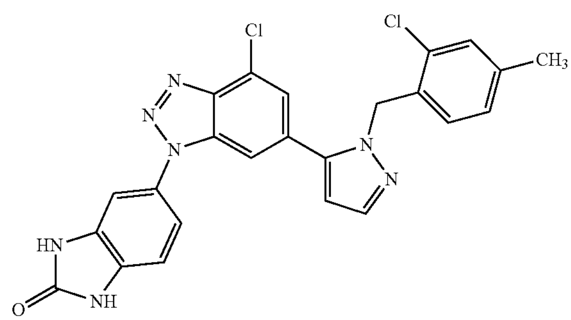 | ++ |
| 235 | 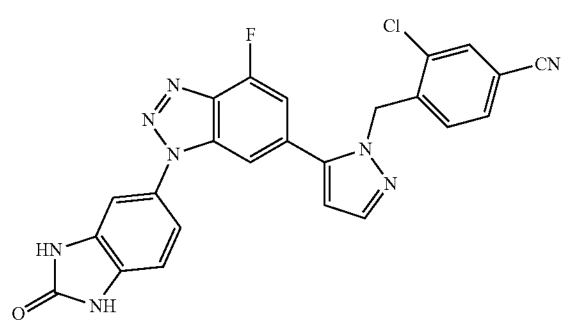 [SMILES: N#Cc1ccc(Cn2nccc2-c2cc(F)c3nnn(-c4ccc5[nH]c(=O)[nH]c5c4)c3c2)c(Cl)c1] | +++ |
| 236 | 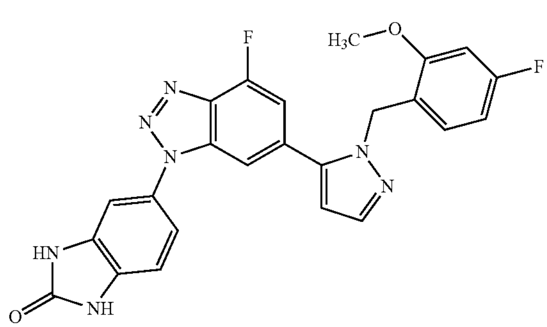 [SMILES: COc1cc(F)ccc1Cn1nccc1-c1cc(F)c2nnn(-c3ccc4[nH]c(=O)[nH]c4c3)c2c1] | + |

TABLE 1-continued
Specific Examples (Potency: CD73 IC$_{50}$: + means > 1 µM, ++ means 100 nM to 1 µM, +++ means < 100 nM).
| Example | Structure | Potency |
|---|---|---|
| 237 | 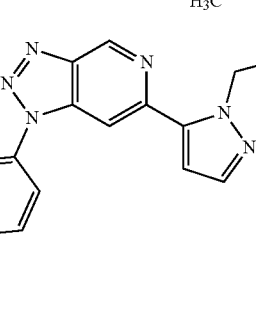 | + |
| 238 | 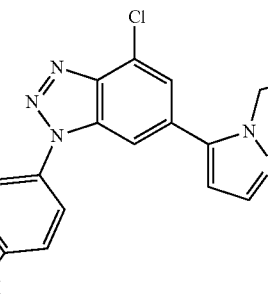 | ++ |
| 239 | 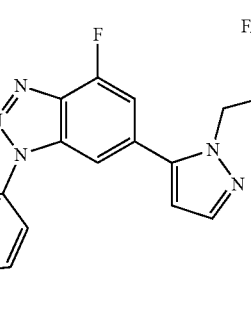 | ++ |
| 240 | 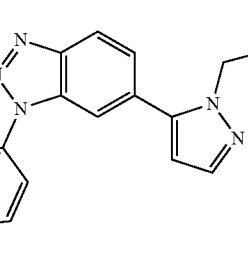 | ++ |

TABLE 1-continued

Specific Examples (Potency: CD73 IC$_{50}$: + means > 1 μM, ++ means 100 nM to 1 μM, +++ means < 100 nM).

| Example | Structure | Potency |
|---------|-----------|---------|
| 241 | 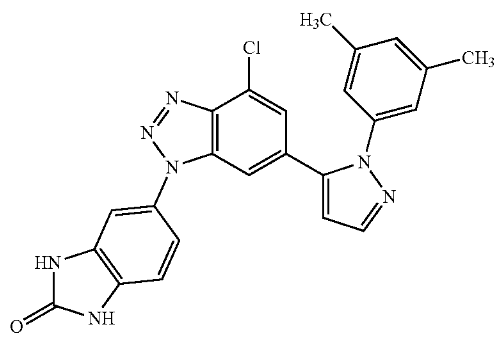 [SMILES: Cc1cc(C)cc(-n2nccc2-c2cc(Cl)c3nnn(-c4ccc5[nH]c(=O)[nH]c5c4)c3c2)c1] | ++ |
| 242 | 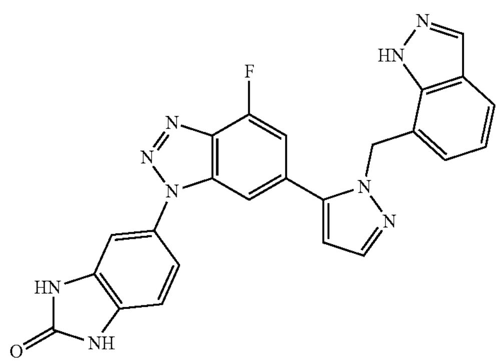 [SMILES: O=c1[nH]c2ccc(-n3nnc4c(F)cc(-c5ccnn5Cc5cccc6cn[nH]c56)cc43)cc2[nH]1] | + |
| 243 | 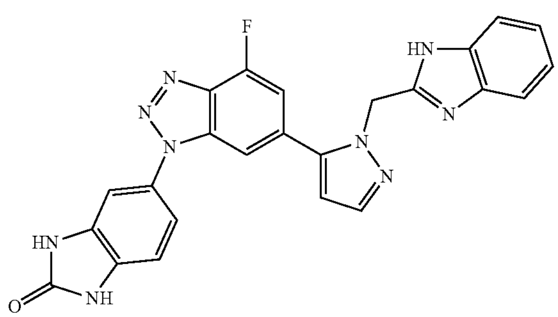 [SMILES: O=c1[nH]c2ccc(-n3nnc4c(F)cc(-c5ccnn5Cc5nc6ccccc6[nH]5)cc43)cc2[nH]1] | ++ |
| 244 | 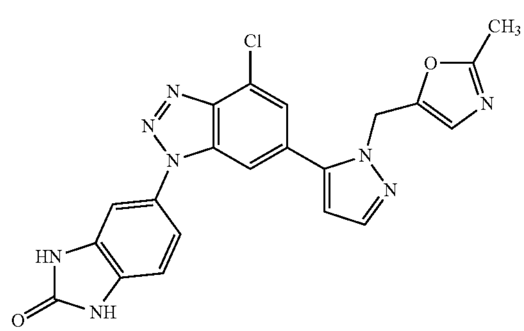 [SMILES: Cc1ncc(Cn2nccc2-c2cc(Cl)c3nnn(-c4ccc5[nH]c(=O)[nH]c5c4)c3c2)o1] | + |

TABLE 1-continued

Specific Examples (Potency: CD73 IC$_{50}$: + means > 1 µM, ++ means 100 nM to 1 µM, +++ means < 100 nM).

| Example | Structure | Potency |
|---------|-----------|---------|
| 245 | 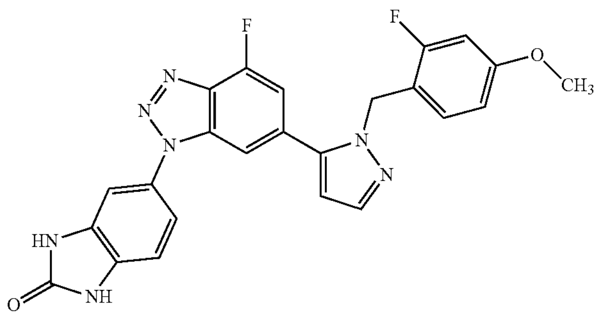 [SMILES: COc1ccc(Cn2nccc2-c2cc(F)c3nnn(-c4ccc5[nH]c(=O)[nH]c5c4)c3c2)c(F)c1] | ++ |
| 246 | 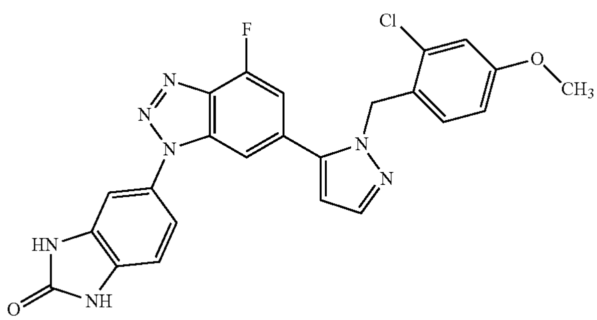 [SMILES: COc1ccc(Cn2nccc2-c2cc(F)c3nnn(-c4ccc5[nH]c(=O)[nH]c5c4)c3c2)c(Cl)c1] | ++ |
| 247 | 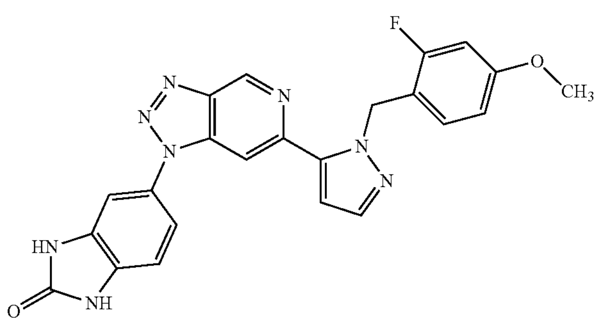 [SMILES: COc1ccc(Cn2nccc2-c2cc3c(cn2)nnn3-c2ccc3[nH]c(=O)[nH]c3c2)c(F)c1] | ++ |
| 248 | 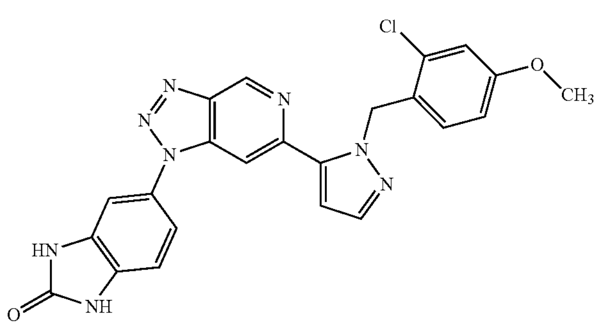 [SMILES: COc1ccc(Cn2nccc2-c2cc3c(cn2)nnn3-c2ccc3[nH]c(=O)[nH]c3c2)c(Cl)c1] | ++ |

TABLE 1-continued

Specific Examples (Potency: CD73 IC$_{50}$: + means > 1 µM, ++ means 100 nM to 1 µM, +++ means < 100 nM).

| Example | Structure | Potency |
|---------|-----------|---------|
| 249 | 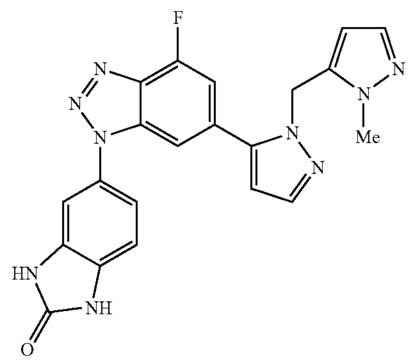 [SMILES: Cn1nccc1Cn1nccc1-c1cc(F)c2nnn(-c3ccc4[nH]c(=O)[nH]c4c3)c2c1] | + |
| 250 | 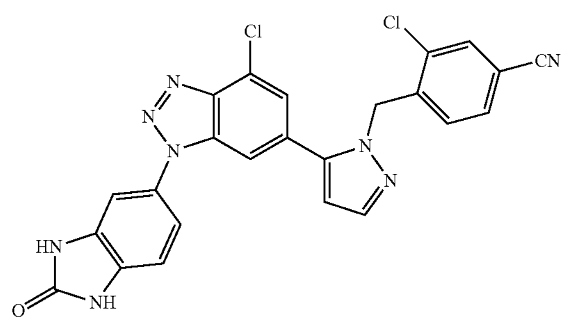 [SMILES: N#Cc1ccc(Cn2nccc2-c2cc(Cl)c3nnn(-c4ccc5[nH]c(=O)[nH]c5c4)c3c2)c(Cl)c1] | +++ |
| 251 | 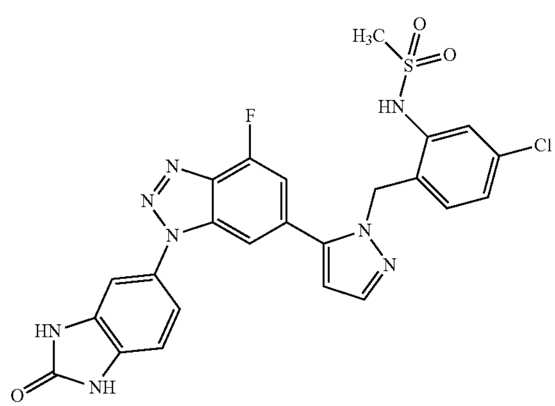 [SMILES: CS(=O)(=O)Nc1cc(Cl)ccc1Cn1nccc1-c1cc(F)c2nnn(-c3ccc4[nH]c(=O)[nH]c4c3)c2c1] | + |
| 252 | 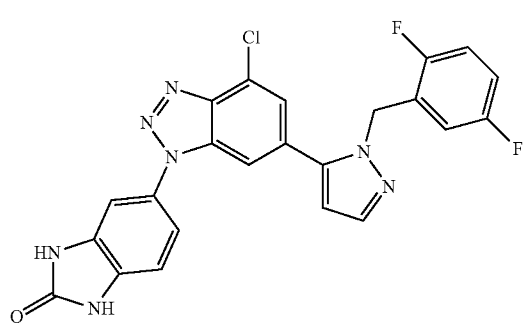 [SMILES: O=c1[nH]c2ccc(-n3nnc4c(Cl)cc(-c5ccnn5Cc5cc(F)ccc5F)cc43)cc2[nH]1] | + |

TABLE 1-continued

Specific Examples (Potency: CD73 IC$_{50}$: + means > 1 μM, ++ means 100 nM to 1 μM, +++ means < 100 nM).

| Example | Structure | Potency |
|---|---|---|
| 253 | 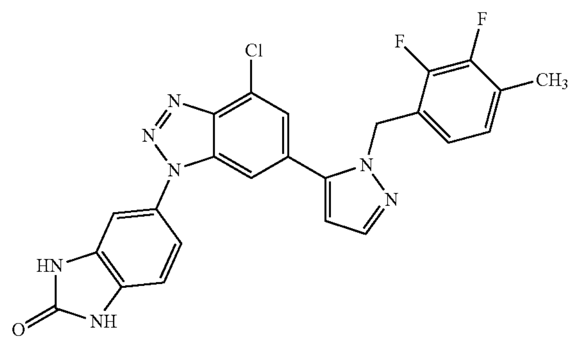 [SMILES: Cc1ccc(Cn2nccc2-c2cc(Cl)c3nnn(-c4ccc5[nH]c(=O)[nH]c5c4)c3c2)c(F)c1F] | ++ |
| 254 | 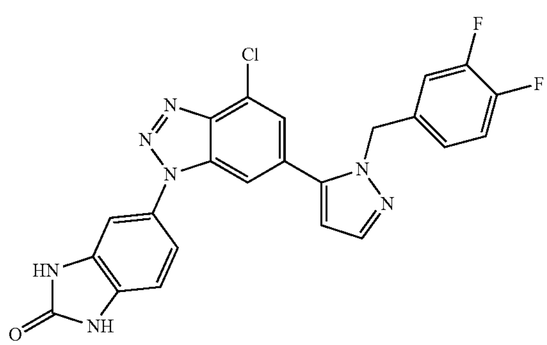 [SMILES: O=c1[nH]c2ccc(-n3nnc4c(Cl)cc(-c5ccnn5Cc5ccc(F)c(F)c5)cc43)cc2[nH]1] | ++ |
| 255 | 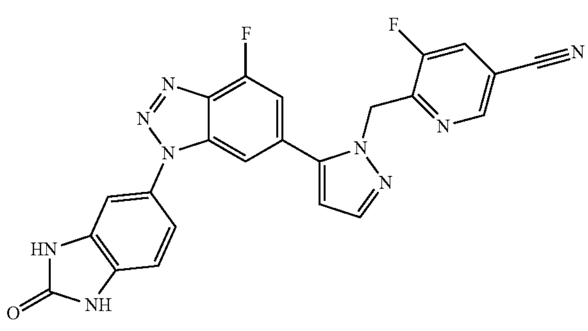 [SMILES: N#Cc1cnc(Cn2nccc2-c2cc(F)c3nnn(-c4ccc5[nH]c(=O)[nH]c5c4)c3c2)c(F)c1] | ++ |
| 256 | 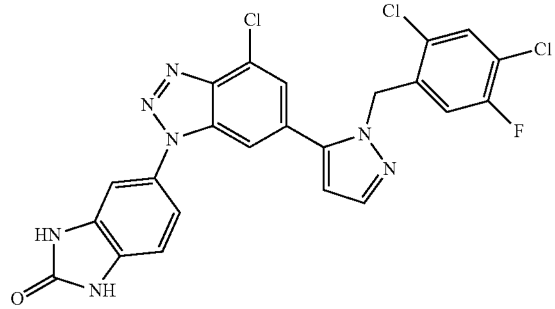 [SMILES: O=c1[nH]c2ccc(-n3nnc4c(Cl)cc(-c5ccnn5Cc5cc(F)c(Cl)cc5Cl)cc43)cc2[nH]1] | ++ |

TABLE 1-continued

Specific Examples (Potency: CD73 IC$_{50}$: + means > 1 μM, ++ means 100 nM to 1 μM, +++ means < 100 nM).

| Example | Structure | Potency |
|---|---|---|
| 257 | 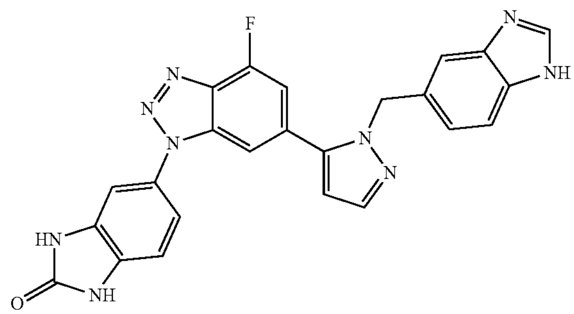 [SMILES: O=c1[nH]c2ccc(-n3nnc4c(F)cc(-c5ccnn5Cc5ccc6[nH]cnc6c5)cc43)cc2[nH]1] | + |
| 258 | 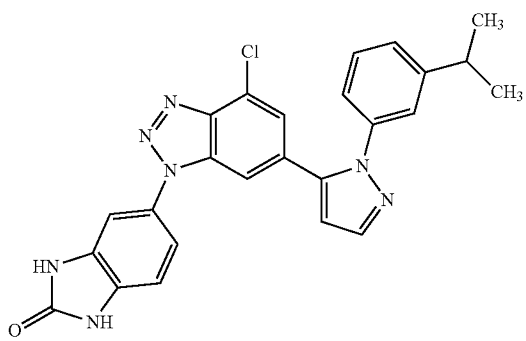 [SMILES: CC(C)c1cccc(-n2nccc2-c2cc(Cl)c3nnn(-c4ccc5[nH]c(=O)[nH]c5c4)c3c2)c1] | ++ |
| 259 | 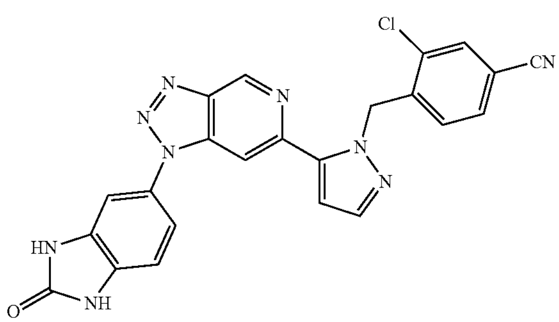 [SMILES: N#Cc1ccc(Cn2nccc2-c2cc3c(cn2)nnn3-c2ccc3[nH]c(=O)[nH]c3c2)c(Cl)c1] | +++ |
| 260 | 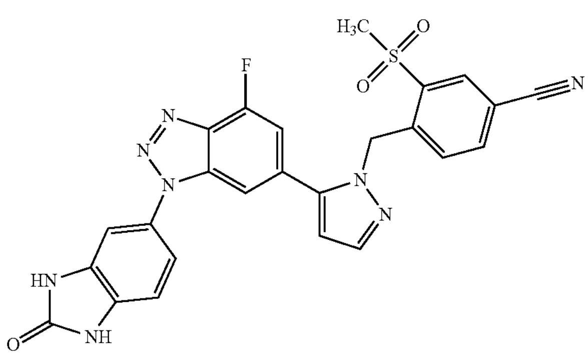 [SMILES: CS(=O)(=O)c1cc(C#N)ccc1Cn1nccc1-c1cc(F)c2nnn(-c3ccc4[nH]c(=O)[nH]c4c3)c2c1] | ++ |

TABLE 1-continued

Specific Examples (Potency: CD73 IC$_{50}$: + means > 1 μM, ++ means 100 nM to 1 μM, +++ means < 100 nM).

| Example | Structure | Potency |
|---------|-----------|---------|
| 261 | 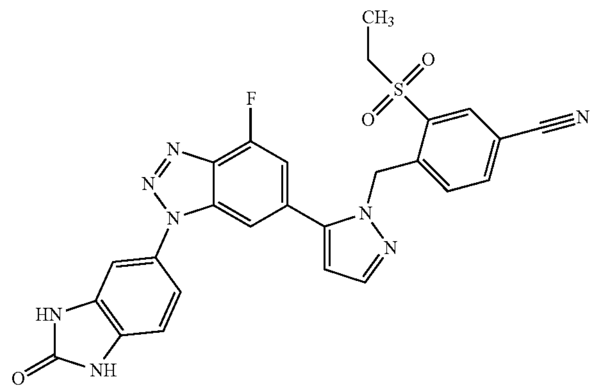 [SMILES: CCS(=O)(=O)c1cc(C#N)ccc1Cn1nccc1-c1cc(F)c2nnn(-c3ccc4[nH]c(=O)[nH]c4c3)c2c1] | ++ |
| 262 | 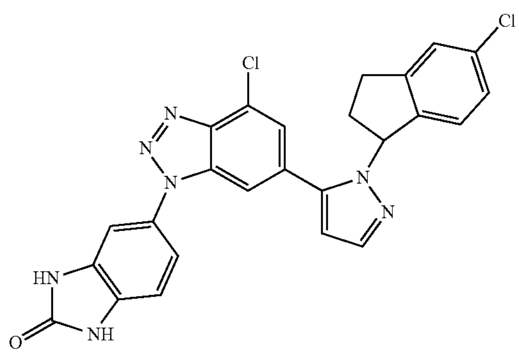 [SMILES: O=c1[nH]c2ccc(-n3nnc4c(Cl)cc(-c5ccnn5C5CCc6cc(Cl)ccc65)cc43)cc2[nH]1] | ++ |
| 263 | 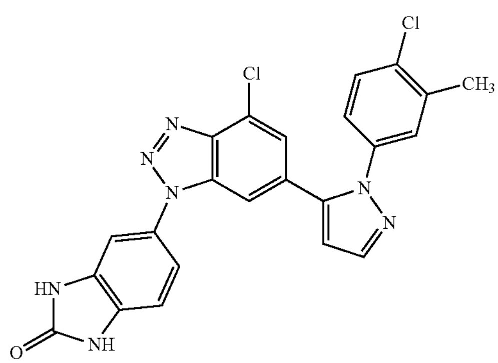 [SMILES: Cc1cc(-n2nccc2-c2cc(Cl)c3nnn(-c4ccc5[nH]c(=O)[nH]c5c4)c3c2)ccc1Cl] | + |
| 264 | 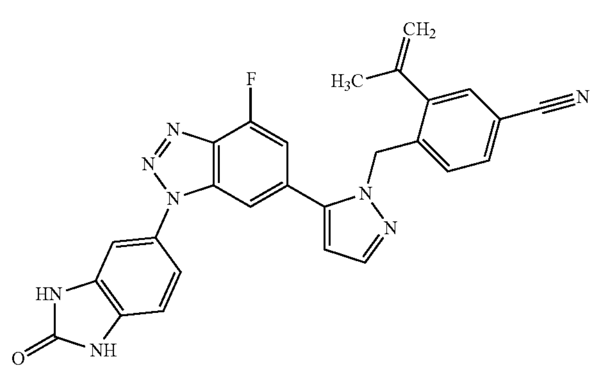 [SMILES: C=C(C)c1cc(C#N)ccc1Cn1nccc1-c1cc(F)c2nnn(-c3ccc4[nH]c(=O)[nH]c4c3)c2c1] | ++ |

TABLE 1-continued

Specific Examples (Potency: CD73 IC$_{50}$: + means > 1 µM, ++ means 100 nM to 1 µM, +++ means < 100 nM).

| Example | Structure | Potency |
|---------|-----------|---------|
| 265 | 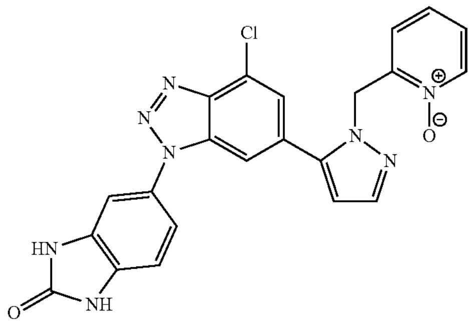 [SMILES: O=c1[nH]c2ccc(-n3nnc4c(Cl)cc(-c5ccnn5Cc5cccc[n+]5[O-])cc43)cc2[nH]1] | + |
| 266 | 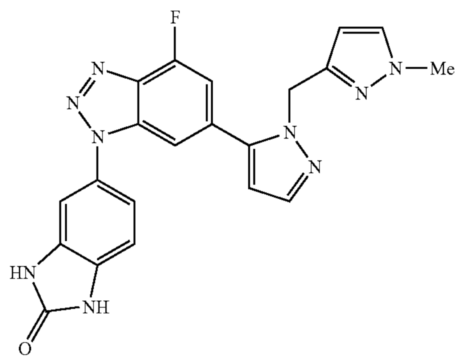 [SMILES: Cn1ccc(Cn2nccc2-c2cc(F)c3nnn(-c4ccc5[nH]c(=O)[nH]c5c4)c3c2)n1] | + |
| 267 | 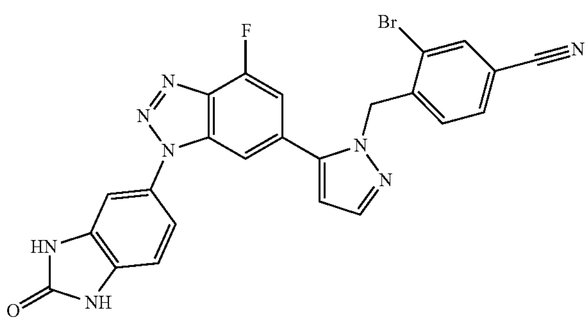 [SMILES: N#Cc1ccc(Cn2nccc2-c2cc(F)c3nnn(-c4ccc5[nH]c(=O)[nH]c5c4)c3c2)c(Br)c1] | ++ |
| 268 | 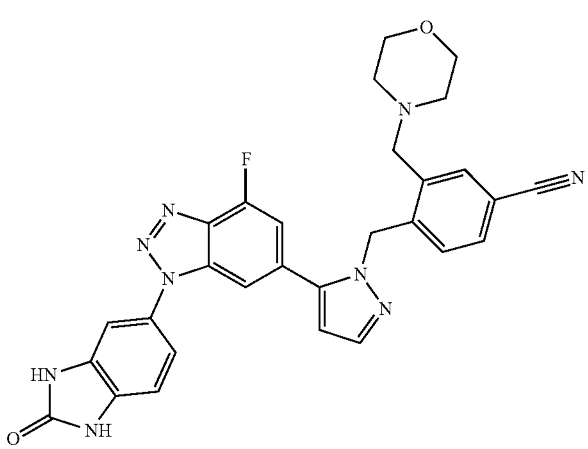 [SMILES: N#Cc1ccc(Cn2nccc2-c2cc(F)c3nnn(-c4ccc5[nH]c(=O)[nH]c5c4)c3c2)c(CN2CCOCC2)c1] | + |

TABLE 1-continued

Specific Examples (Potency: CD73 IC$_{50}$: + means > 1 μM, ++ means 100 nM to 1 μM, +++ means < 100 nM).

| Example | Structure | Potency |
|---------|-----------|---------|
| 269 | 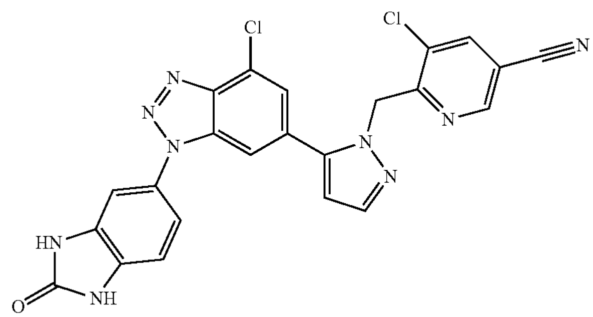 [SMILES: N#Cc1cnc(Cn2nccc2-c2cc(Cl)c3nnn(-c4ccc5[nH]c(=O)[nH]c5c4)c3c2)c(Cl)c1] | ++ |
| 270 | 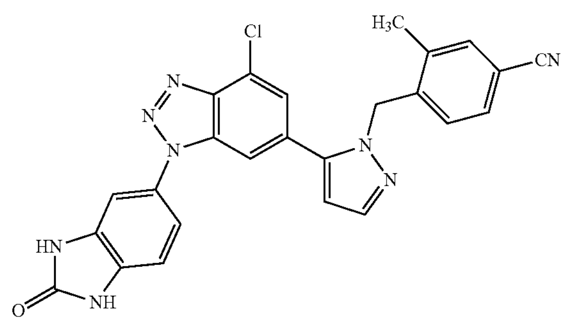 [SMILES: Cc1cc(C#N)ccc1Cn1nccc1-c1cc(Cl)c2nnn(-c3ccc4[nH]c(=O)[nH]c4c3)c2c1] | +++ |
| 271 | 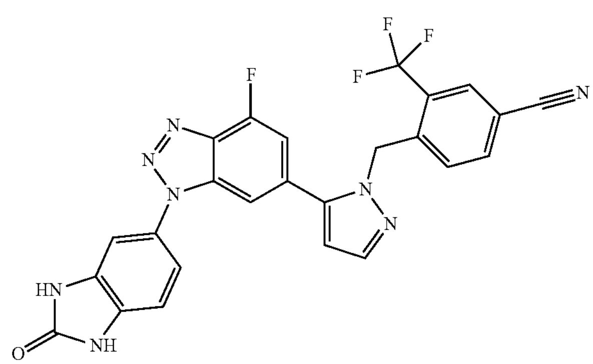 [SMILES: N#Cc1ccc(Cn2nccc2-c2cc(F)c3nnn(-c4ccc5[nH]c(=O)[nH]c5c4)c3c2)c(C(F)(F)F)c1] | ++ |
| 272 | 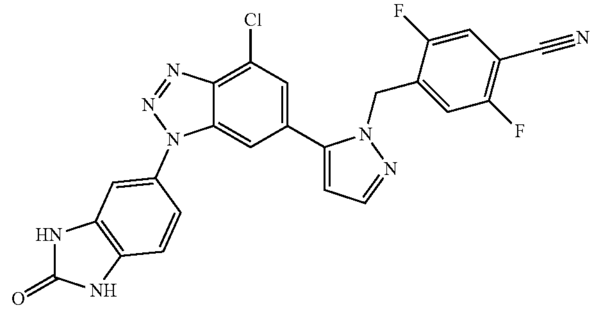 [SMILES: N#Cc1cc(F)c(Cn2nccc2-c2cc(Cl)c3nnn(-c4ccc5[nH]c(=O)[nH]c5c4)c3c2)cc1F] | ++ |

TABLE 1-continued

Specific Examples (Potency: CD73 IC$_{50}$: + means > 1 μM, ++ means 100 nM to 1 μM, +++ means < 100 nM).

| Example | Structure | Potency |
|---------|-----------|---------|
| 273 | 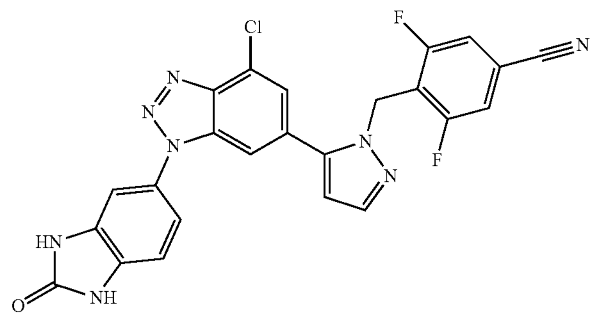 | ++ |
| 274 | 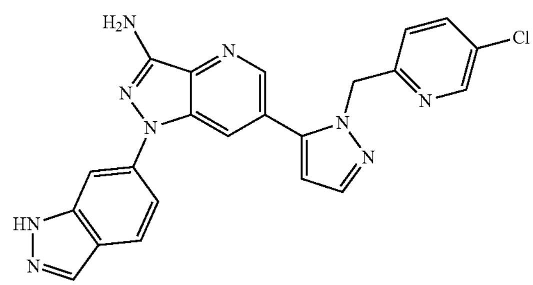 [SMILES: Nc1nn(-c2ccc3cn[nH]c3c2)c2cc(-c3ccnn3Cc3ccc(Cl)cn3)cnc12] | ++ |
| 275 | 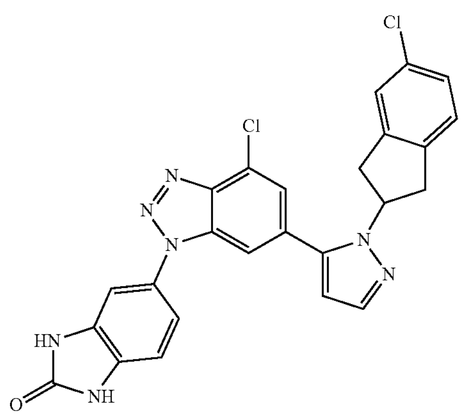 [SMILES: O=c1[nH]c2ccc(-n3nnc4c(Cl)cc(-c5ccnn5C5Cc6ccc(Cl)cc6C5)cc43)cc2[nH]1] | ++ |
| 276 | 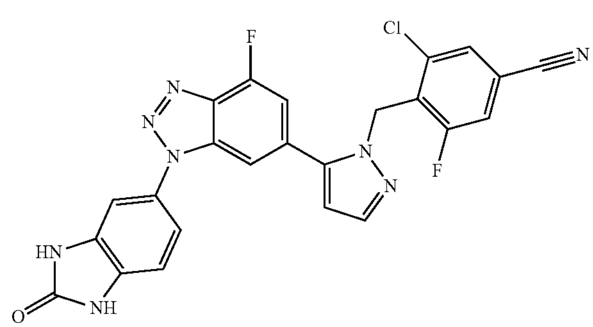 [SMILES: N#Cc1cc(F)c(Cn2nccc2-c2cc(F)c3nnn(-c4ccc5[nH]c(=O)[nH]c5c4)c3c2)c(Cl)c1] | + |

TABLE 1-continued
Specific Examples (Potency: CD73 IC$_{50}$: + means > 1 μM, ++ means 100 nM to 1 μM, +++ means < 100 nM).
| Example | Structure | Potency |
|---|---|---|
| 277 | 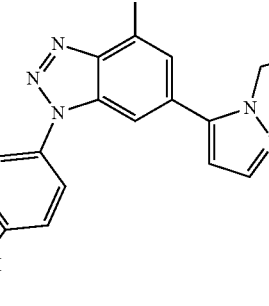 | + |
| 278 | 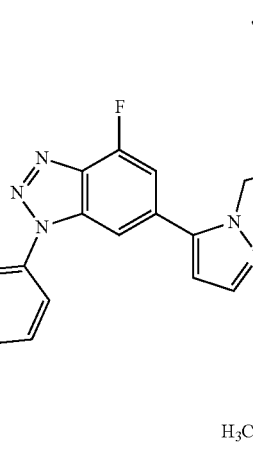 | + |
| 279 | 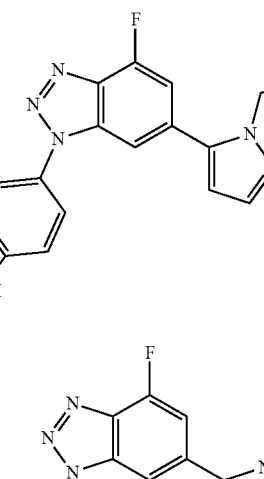 | ++ |
| 280 | 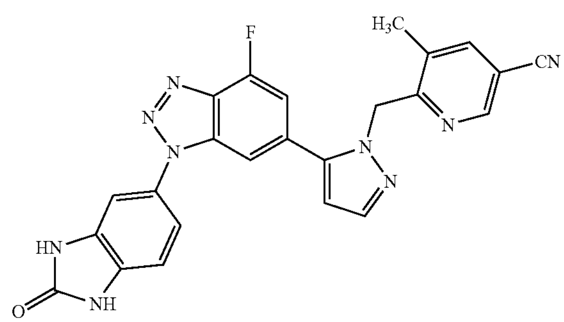 [SMILES: Cc1cc(C#N)cnc1Cn1nccc1-c1cc(F)c2nnn(-c3ccc4[nH]c(=O)[nH]c4c3)c2c1] | + |

TABLE 1-continued

Specific Examples (Potency: CD73 IC$_{50}$: + means > 1 µM, ++ means 100 nM to 1 µM, +++ means < 100 nM).

| Example | Structure | Potency |
|---------|-----------|---------|
| 281 | 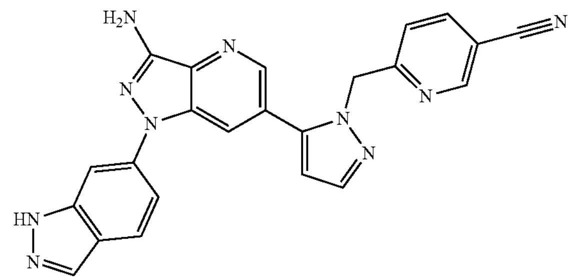 [SMILES: N#Cc1ccc(Cn2nccc2-c2cnc3c(N)nn(-c4ccc5cn[nH]c5c4)c3c2)nc1] | ++ |
| 282 | 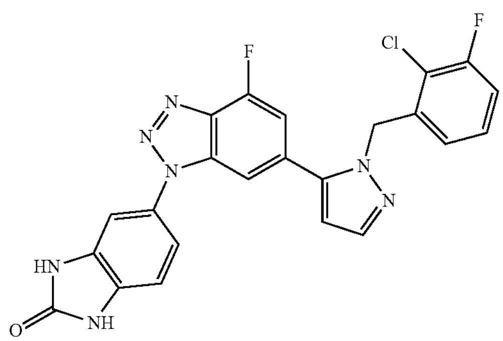 | ++ |
| 283 | 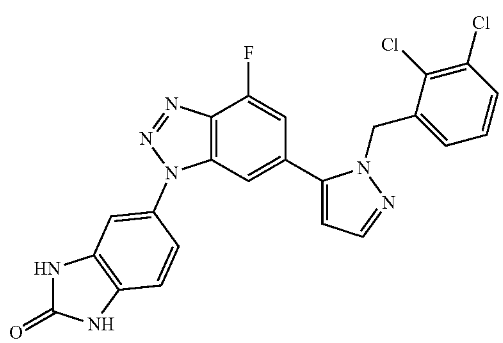 [SMILES: O=c1[nH]c2ccc(-n3nnc4c(F)cc(-c5ccnn5Cc5cccc(F)c5Cl)cc43)cc2[nH]1] | ++ |
| 284 | 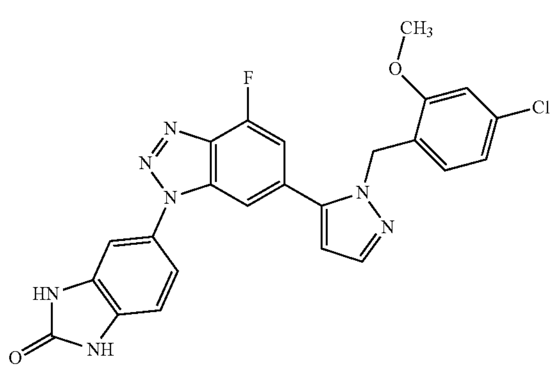 [SMILES: COc1cc(Cl)ccc1Cn1nccc1-c1cc(F)c2nnn(-c3ccc4[nH]c(=O)[nH]c4c3)c2c1] | ++ |

TABLE 1-continued

Specific Examples (Potency: CD73 IC$_{50}$: + means > 1 µM, ++ means 100 nM to 1 µM, +++ means < 100 nM).

| Example | Structure | Potency |
|---------|-----------|---------|
| 285 | 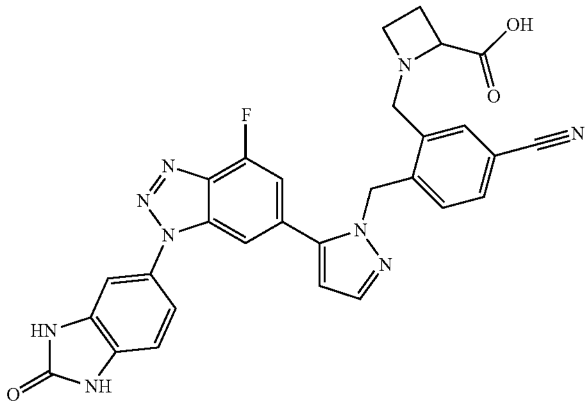 [SMILES: N#Cc1ccc(Cn2nccc2-c2cc(F)c3nnn(-c4ccc5[nH]c(=O)[nH]c5c4)c3c2)c(CN2CCC2C(=O)O)c1] | + |
| 286 | 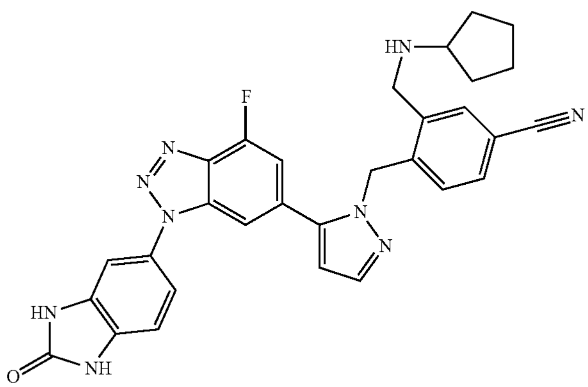 [SMILES: N#Cc1ccc(Cn2nccc2-c2cc(F)c3nnn(-c4ccc5[nH]c(=O)[nH]c5c4)c3c2)c(CNC2CCCC2)c1] | ++ |
| 287 | 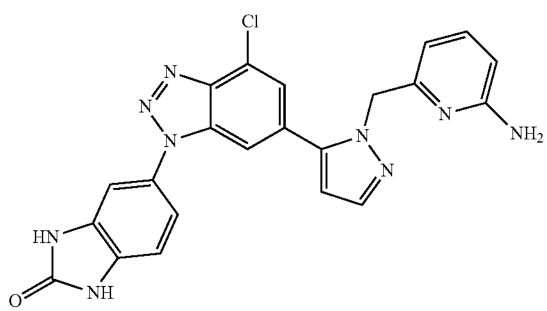 [SMILES: Nc1cccc(Cn2nccc2-c2cc(Cl)c3nnn(-c4ccc5[nH]c(=O)[nH]c5c4)c3c2)n1] | + |
| 288 | 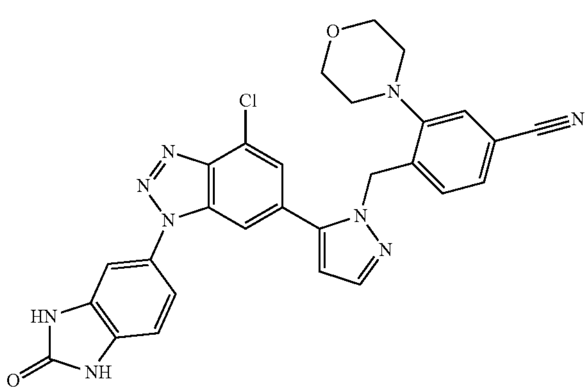 [SMILES: N#Cc1ccc(Cn2nccc2-c2cc(Cl)c3nnn(-c4ccc5[nH]c(=O)[nH]c5c4)c3c2)c(N2CCOCC2)c1] | + |

TABLE 1-continued

Specific Examples (Potency: CD73 IC$_{50}$: + means > 1 μM, ++ means 100 nM to 1 μM, +++ means < 100 nM).

| Example | Structure | Potency |
|---------|-----------|---------|
| 289 | 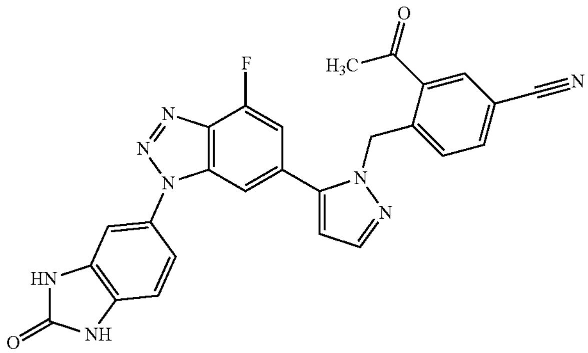 [SMILES: CC(=O)c1cc(C#N)ccc1Cn1nccc1-c1cc(F)c2nnn(-c3ccc4[nH]c(=O)[nH]c4c3)c2c1] | ++ |
| 290 | 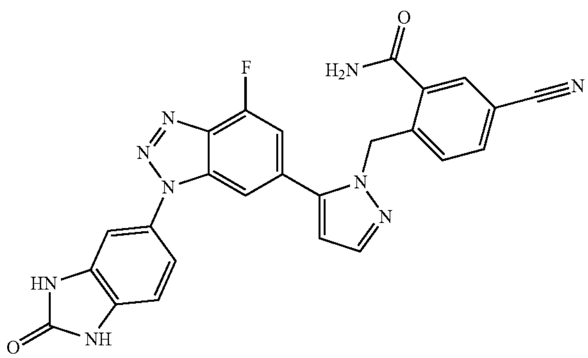 [SMILES: N#Cc1ccc(Cn2nccc2-c2cc(F)c3nnn(-c4ccc5[nH]c(=O)[nH]c5c4)c3c2)c(C(N)=O)c1] | ++ |
| 291 | 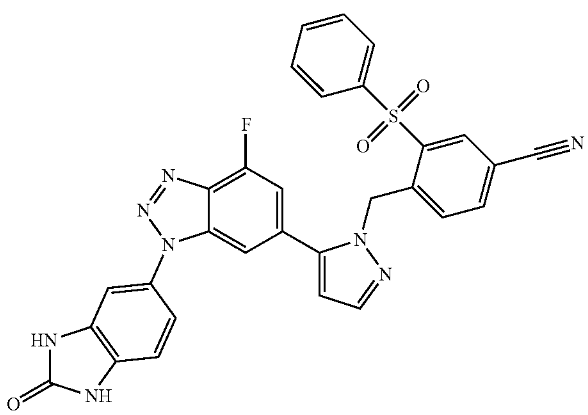 [SMILES: N#Cc1ccc(Cn2nccc2-c2cc(F)c3nnn(-c4ccc5[nH]c(=O)[nH]c5c4)c3c2)c(S(=O)(=O)c2ccccc2)c1] | ++ |
| 292 | 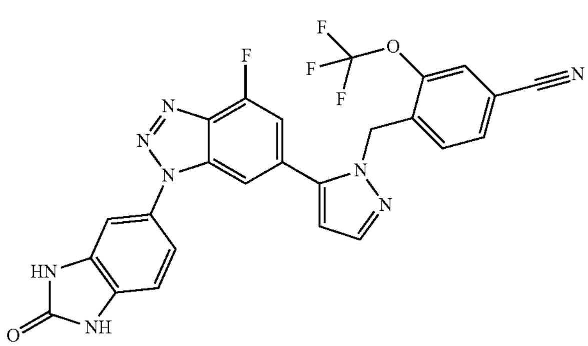 [SMILES: N#Cc1ccc(Cn2nccc2-c2cc(F)c3nnn(-c4ccc5[nH]c(=O)[nH]c5c4)c3c2)c(OC(F)(F)F)c1] | ++ |

TABLE 1-continued
Specific Examples (Potency: CD73 $IC_{50}$: + means > 1 μM, ++ means 100 nM to 1 μM, +++ means < 100 nM).
| Example | Structure | Potency |
|---------|-----------|---------|
| 293 | 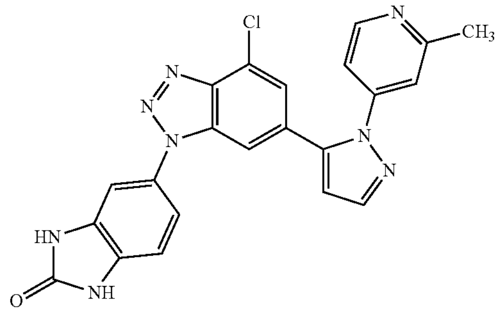 [SMILES: Cc1cc(-n2nccc2-c2cc(Cl)c3nnn(-c4ccc5[nH]c(=O)[nH]c5c4)c3c2)ccn1] | ++ |
| 294 | 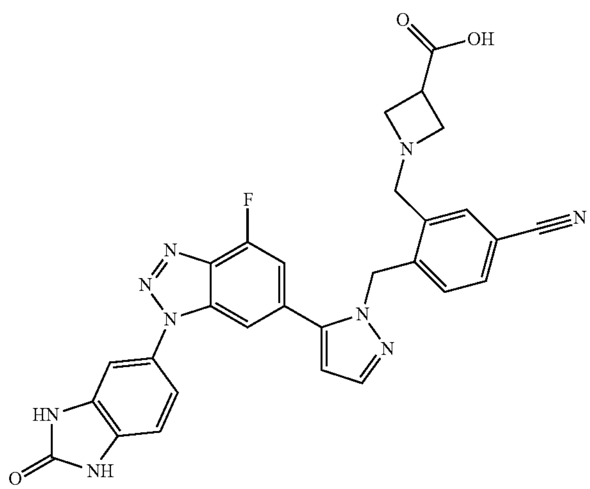 [SMILES: N#Cc1ccc(Cn2nccc2-c2cc(F)c3nnn(-c4ccc5[nH]c(=O)[nH]c5c4)c3c2)c(CN2CC(C(=O)O)C2)c1] | ++ |
| 295 | 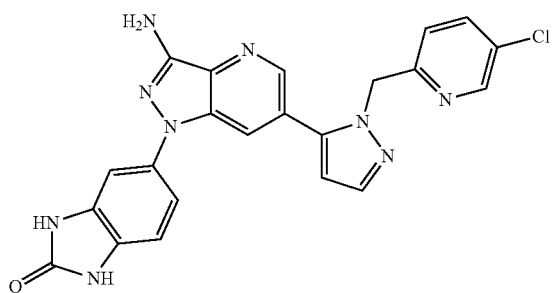 [SMILES: Nc1nn(-c2ccc3[nH]c(=O)[nH]c3c2)c2cc(-c3ccnn3Cc3ccc(Cl)cn3)cnc12] | + |

TABLE 1-continued

Specific Examples (Potency: CD73 IC$_{50}$: + means > 1 μM, ++ means 100 nM to 1 μM, +++ means < 100 nM).

| Example | Structure | Potency |
| --- | --- | --- |
| 296 | 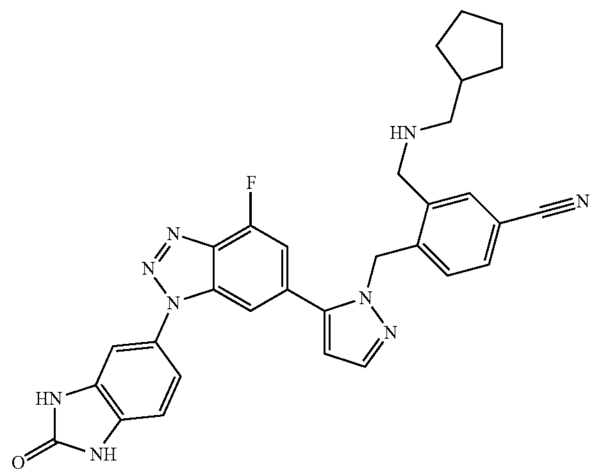 [SMILES: N#Cc1ccc(Cn2nccc2-c2cc(F)c3nnn(-c4ccc5[nH]c(=O)[nH]c5c4)c3c2)c(CNCC2CCCC2)c1] | ++ |
| 297 | 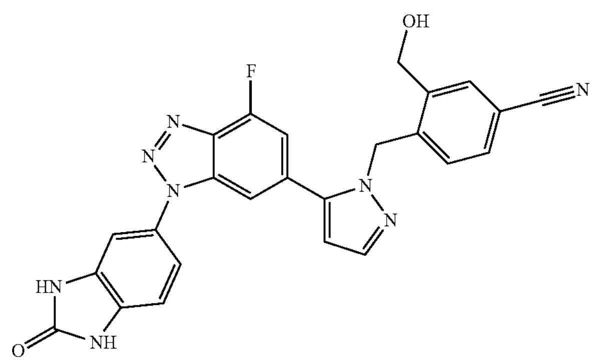 [SMILES: N#Cc1ccc(Cn2nccc2-c2cc(F)c3nnn(-c4ccc5[nH]c(=O)[nH]c5c4)c3c2)c(CO)c1] | +++ |
| 298 | 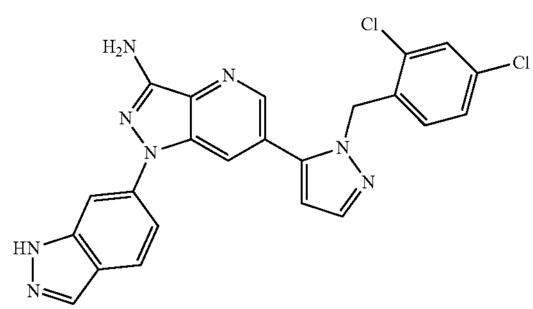 [SMILES: Nc1nn(-c2ccc3cn[nH]c3c2)c2cc(-c3ccnn3Cc3ccc(Cl)cc3Cl)cnc12] | +++ |
| 299 | 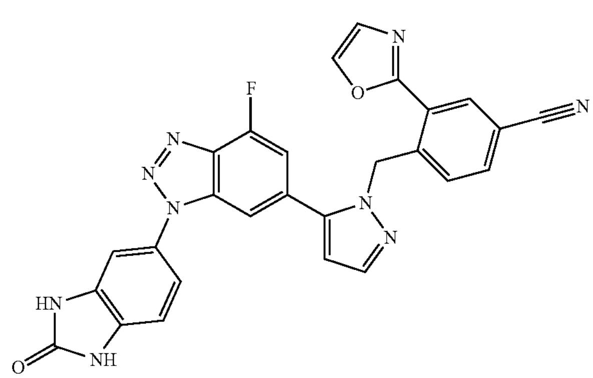 [SMILES: N#Cc1ccc(Cn2nccc2-c2cc(F)c3nnn(-c4ccc5[nH]c(=O)[nH]c5c4)c3c2)c(-c2ncco2)c1] | ++ |

TABLE 1-continued

Specific Examples (Potency: CD73 IC$_{50}$: + means > 1 μM, ++ means 100 nM to 1 μM, +++ means < 100 nM).

| Example | Structure | Potency |
|---------|-----------|---------|
| 300 | 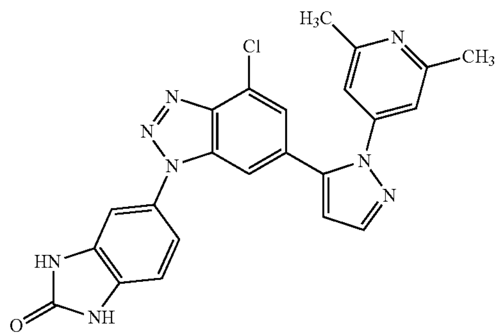 [SMILES: Cc1cc(-n2nccc2-c2cc(Cl)c3nnn(-c4ccc5[nH]c(=O)[nH]c5c4)c3c2)cc(C)n1] | ++ |
| 301 | 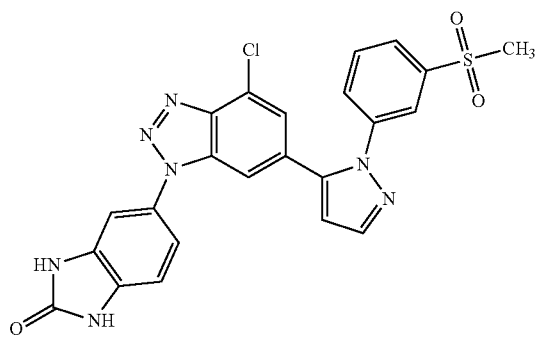 [SMILES: CS(=O)(=O)c1cccc(-n2nccc2-c2cc(Cl)c3nnn(-c4ccc5[nH]c(=O)[nH]c5c4)c3c2)c1] | ++ |
| 302 | 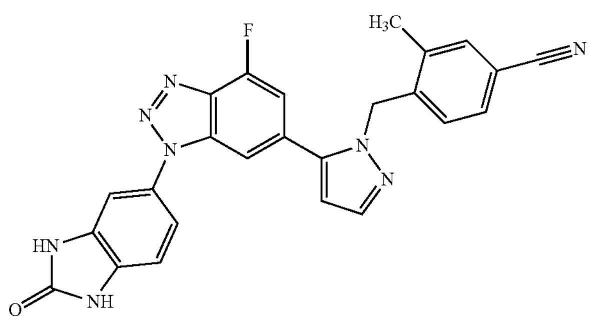 [SMILES: Cc1cc(C#N)ccc1Cn1nccc1-c1cc(F)c2nnn(-c3ccc4[nH]c(=O)[nH]c4c3)c2c1] | ++ |
| 303 | 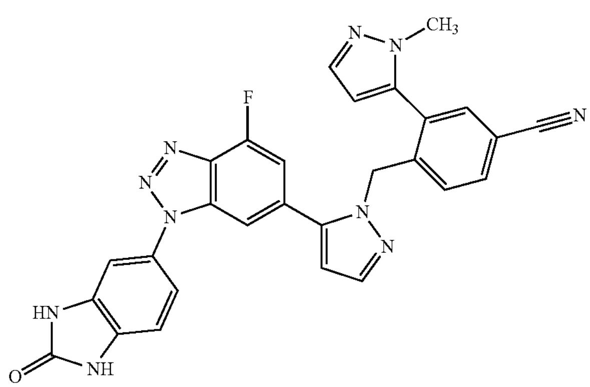 [SMILES: Cn1nccc1-c1cc(C#N)ccc1Cn1nccc1-c1cc(F)c2nnn(-c3ccc4[nH]c(=O)[nH]c4c3)c2c1] | ++ |

TABLE 1-continued

Specific Examples (Potency: CD73 IC$_{50}$: + means > 1 μM, ++ means 100 nM to 1 μM, +++ means < 100 nM).

| Example | Structure | Potency |
|---------|-----------|---------|
| 304 | 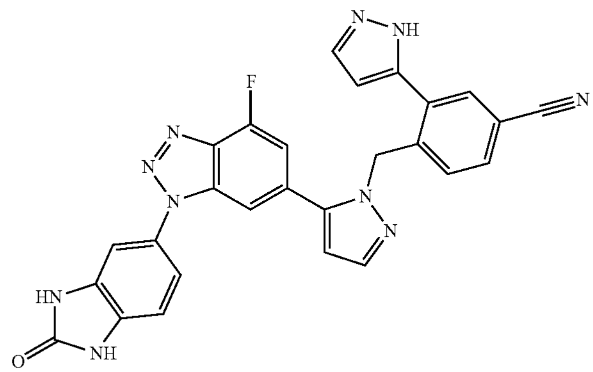 [SMILES: N#Cc1ccc(Cn2nccc2-c2cc(F)c3nnn(-c4ccc5[nH]c(=O)[nH]c5c4)c3c2)c(-c2ccn[nH]2)c1] | ++ |
| 305 | 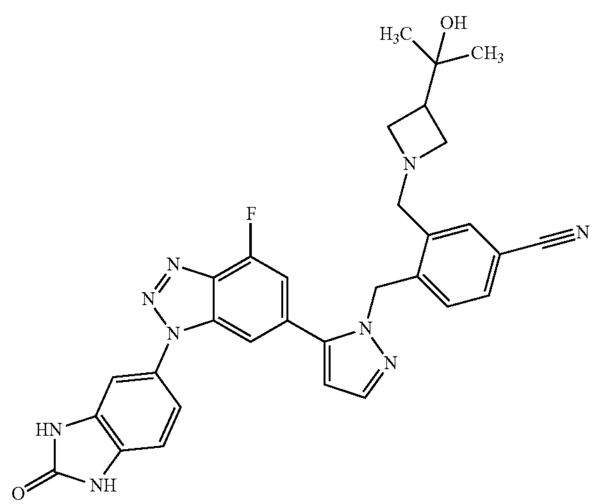 [SMILES: CC(C)(O)C1CN(Cc2cc(C#N)ccc2Cn2nccc2-c2cc(F)c3nnn(-c4ccc5[nH]c(=O)[nH]c5c4)c3c2)C1] | ++ |
| 306 | 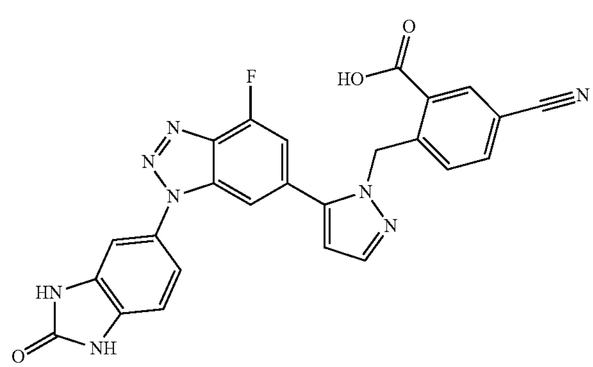 [SMILES: N#Cc1ccc(Cn2nccc2-c2cc(F)c3nnn(-c4ccc5[nH]c(=O)[nH]c5c4)c3c2)c(C(=O)O)c1] | ++ |

TABLE 1-continued

Specific Examples (Potency: CD73 IC$_{50}$: + means > 1 μM, ++ means 100 nM to 1 μM, +++ means < 100 nM).

| Example | Structure | Potency |
|---------|-----------|---------|
| 307 | 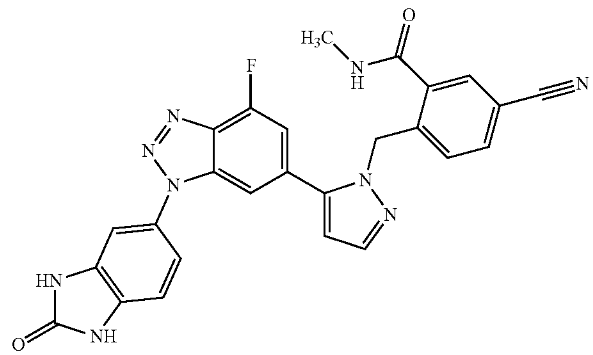 [SMILES: CNC(=O)c1cc(C#N)ccc1Cn1nccc1-c1cc(F)c2nnn(-c3ccc4[nH]c(=O)[nH]c4c3)c2c1] | ++ |
| 308 | 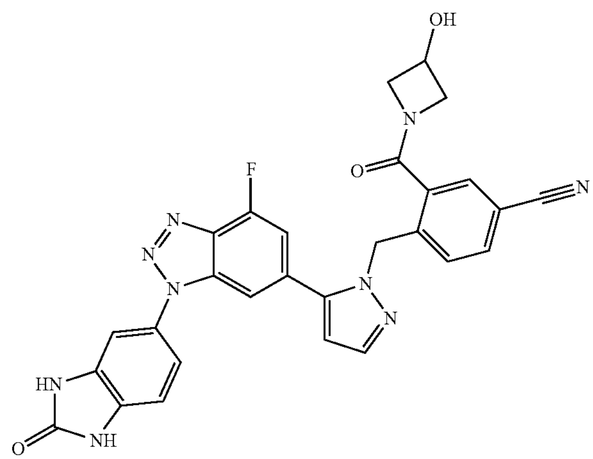 [SMILES: N#Cc1ccc(Cn2nccc2-c2cc(F)c3nnn(-c4ccc5[nH]c(=O)[nH]c5c4)c3c2)c(C(=O)N2CC(O)C2)c1] | + |
| 309 | 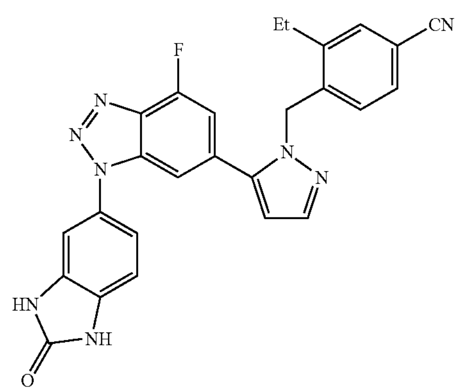 [SMILES: CCc1cc(C#N)ccc1Cn1nccc1-c1cc(F)c2nnn(-c3ccc4[nH]c(=O)[nH]c4c3)c2c1] | ++ |
| 310 | 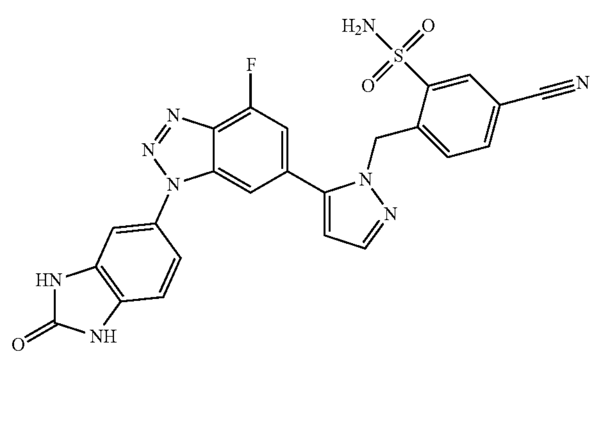 [SMILES: N#Cc1ccc(Cn2nccc2-c2cc(F)c3nnn(-c4ccc5[nH]c(=O)[nH]c5c4)c3c2)c(S(N)(=O)=O)c1] | ++ |

TABLE 1-continued

Specific Examples (Potency: CD73 IC$_{50}$: + means > 1 μM, ++ means 100 nM to 1 μM, +++ means < 100 nM).

| Example | Structure | Potency |
|---------|-----------|---------|
| 311 | 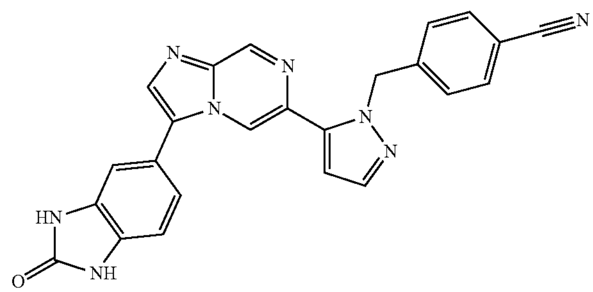 [SMILES: N#Cc1ccc(Cn2nccc2-c2cn3c(-c4ccc5[nH]c(=O)[nH]c5c4)cnc3cn2)cc1] | + |
| 312 | 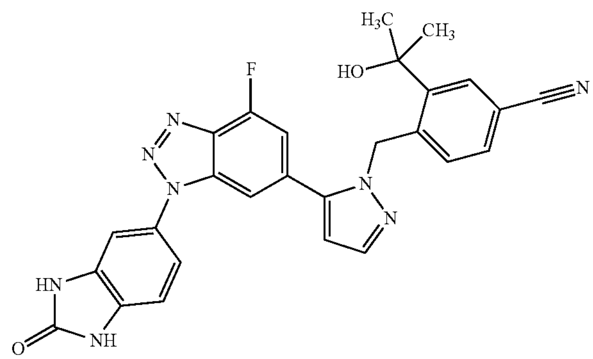 [SMILES: CC(C)(O)c1cc(C#N)ccc1Cn1nccc1-c1cc(F)c2nnn(-c3ccc4[nH]c(=O)[nH]c4c3)c2c1] | + |
| 313 | 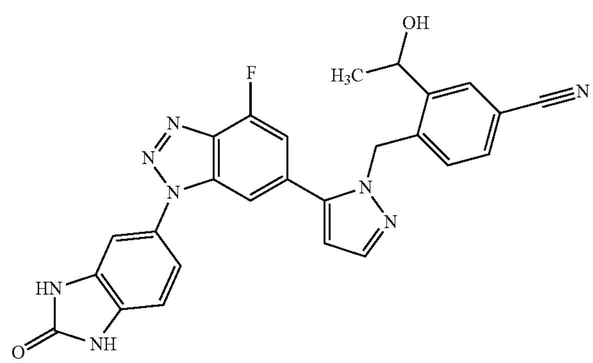 [SMILES: CC(O)c1cc(C#N)ccc1Cn1nccc1-c1cc(F)c2nnn(-c3ccc4[nH]c(=O)[nH]c4c3)c2c1] | ++ |
| 314 | 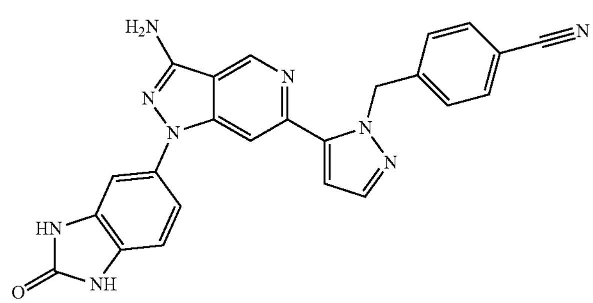 [SMILES: N#Cc1ccc(Cn2nccc2-c2cc3c(cn2)c(N)nn3-c2ccc3[nH]c(=O)[nH]c3c2)cc1] | ++ |

TABLE 1-continued

Specific Examples (Potency: CD73 IC$_{50}$: + means > 1 µM, ++ means 100 nM to 1 µM, +++ means < 100 nM).

| Example | Structure | Potency |
|---------|-----------|---------|
| 315 | 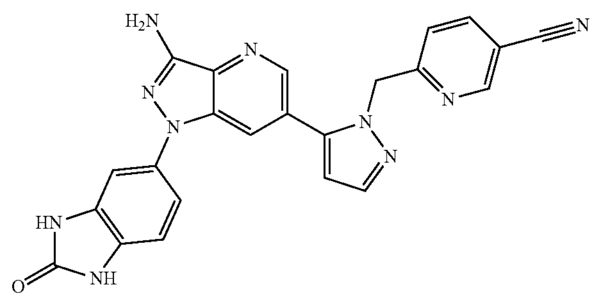 [SMILES: N#Cc1ccc(Cn2nccc2-c2cnc3c(N)nn(-c4ccc5[nH]c(=O)[nH]c5c4)c3c2)nc1] | ++ |
| 316 | 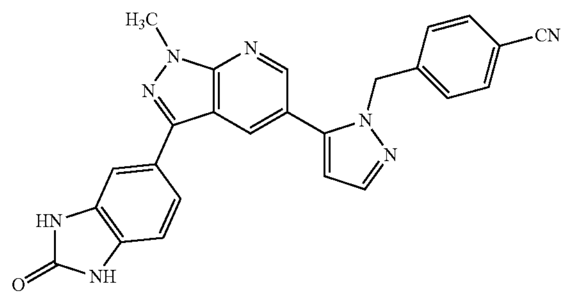 [SMILES: Cn1nc(-c2ccc3[nH]c(=O)[nH]c3c2)c2cc(-c3ccnn3Cc3ccc(C#N)cc3)cnc21] | ++ |
| 317 | 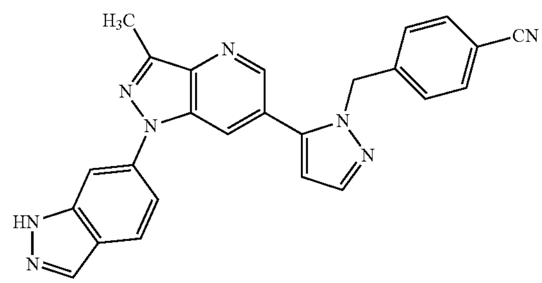 [SMILES: Cc1nn(-c2ccc3cn[nH]c3c2)c2cc(-c3ccnn3Cc3ccc(C#N)cc3)cnc12] | ++ |
| 318 | 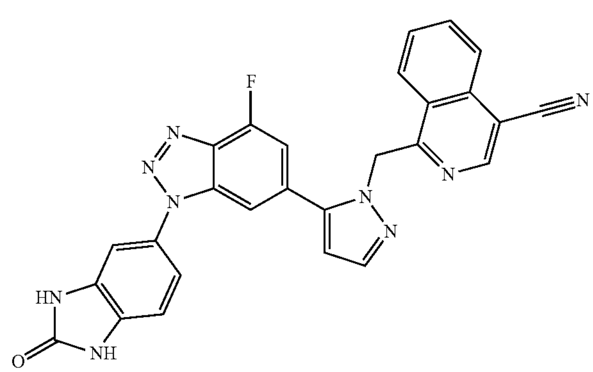 [SMILES: N#Cc1cnc(Cn2nccc2-c2cc(F)c3nnn(-c4ccc5[nH]c(=O)[nH]c5c4)c3c2)c2ccccc12] | + |

TABLE 1-continued

Specific Examples (Potency: CD73 IC$_{50}$: + means > 1 μM, ++ means 100 nM to 1 μM, +++ means < 100 nM).

| Example | Structure | Potency |
|---|---|---|
| 319 | 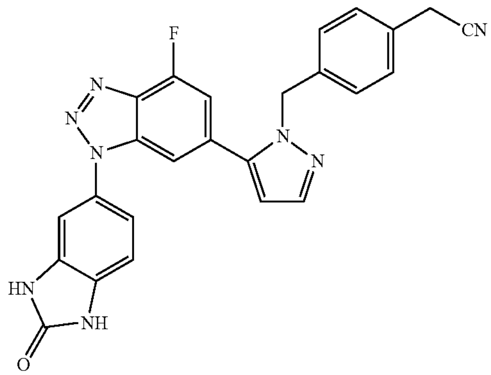 [SMILES: N#CCc1ccc(Cn2nccc2-c2cc(F)c3nnn(-c4ccc5[nH]c(=O)[nH]c5c4)c3c2)cc1] | + |
| 320 | 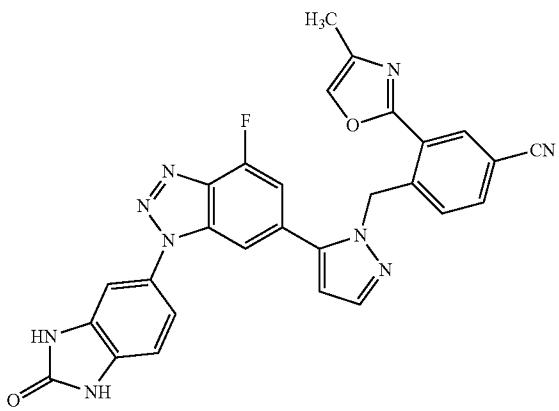 [SMILES: Cc1coc(-c2cc(C#N)ccc2Cn2nccc2-c2cc(F)c3nnn(-c4ccc5[nH]c(=O)[nH]c5c4)c3c2)n1] | ++ |
| 321 | 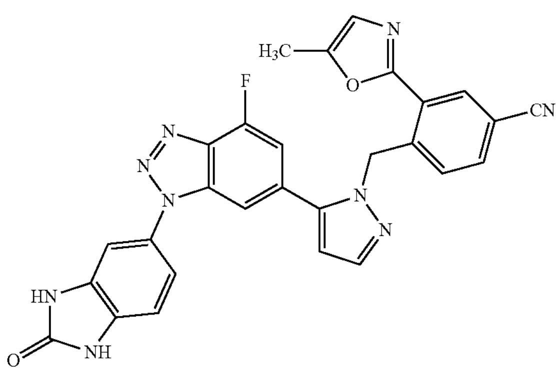 [SMILES: Cc1cnc(-c2cc(C#N)ccc2Cn2nccc2-c2cc(F)c3nnn(-c4ccc5[nH]c(=O)[nH]c5c4)c3c2)o1] | ++ |
| 322 | 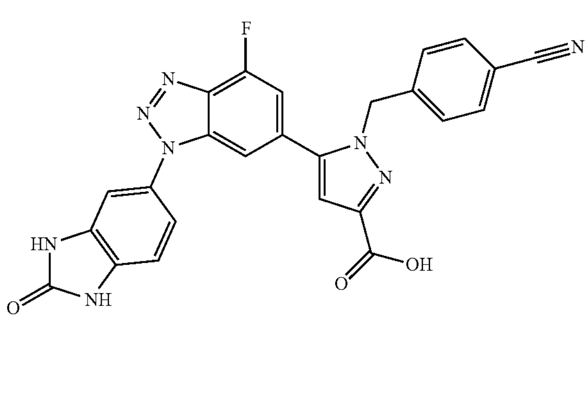 [SMILES: N#Cc1ccc(Cn2nc(C(=O)O)cc2-c2cc(F)c3nnn(-c4ccc5[nH]c(=O)[nH]c5c4)c3c2)cc1] | + |

TABLE 1-continued

Specific Examples (Potency: CD73 IC$_{50}$: + means > 1 μM, ++ means 100 nM to 1 μM,
+++ means < 100 nM).

| Example | Structure | Potency |
|---------|-----------|---------|
| 323 | 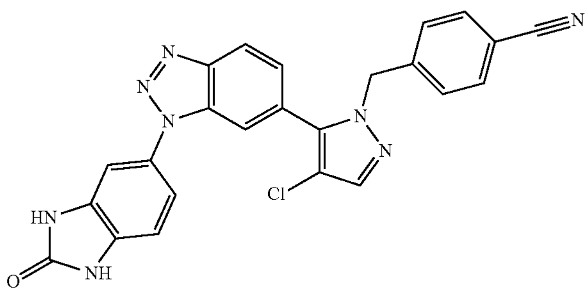 [SMILES: N#Cc1ccc(Cn2ncc(Cl)c2-c2ccc3nnn(-c4ccc5[nH]c(=O)[nH]c5c4)c3c2)cc1] | ++ |
| 324 | 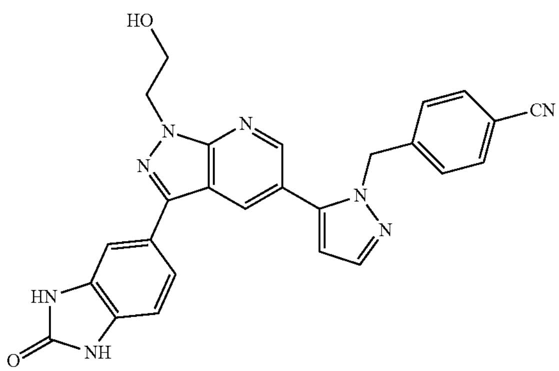 [SMILES: N#Cc1ccc(Cn2nccc2-c2cnc3c(c2)c(-c2ccc4[nH]c(=O)[nH]c4c2)nn3CCO)cc1] | + |
| 325 | 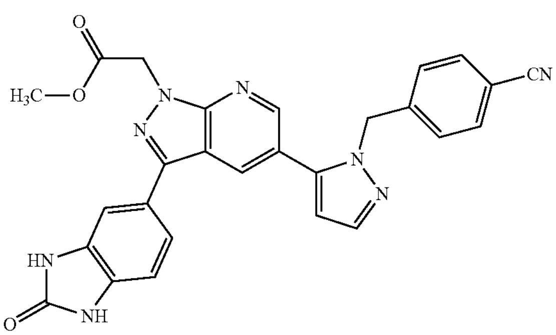 [SMILES: COC(=O)Cn1nc(-c2ccc3[nH]c(=O)[nH]c3c2)c2cc(-c3ccnn3Cc3ccc(C#N)cc3)cnc21] | + |
| 326 | 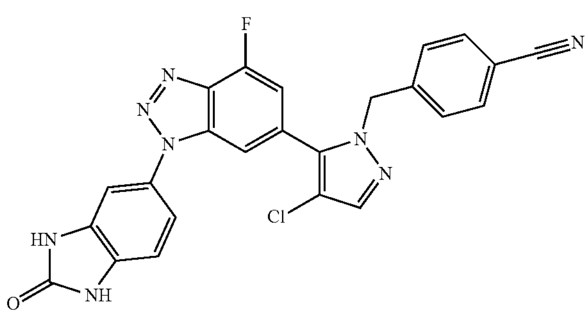 [SMILES: N#Cc1ccc(Cn2ncc(Cl)c2-c2cc(F)c3nnn(-c4ccc5[nH]c(=O)[nH]c5c4)c3c2)cc1] | ++ |

TABLE 1-continued

Specific Examples (Potency: CD73 IC$_{50}$: + means > 1 μM, ++ means 100 nM to 1 μM, +++ means < 100 nM).

| Example | Structure | Potency |
|---------|-----------|---------|
| 327 | 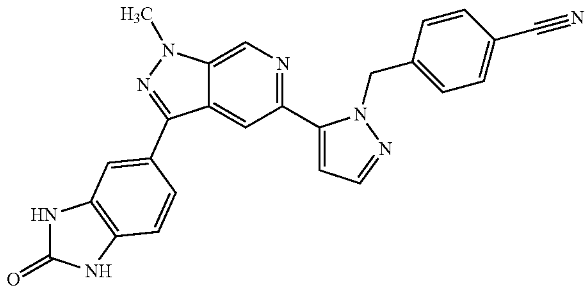 [SMILES: Cn1nc(-c2ccc3[nH]c(=O)[nH]c3c2)c2cc(-c3ccnn3Cc3ccc(C#N)cc3)ncc21] | ++ |
| 328 | 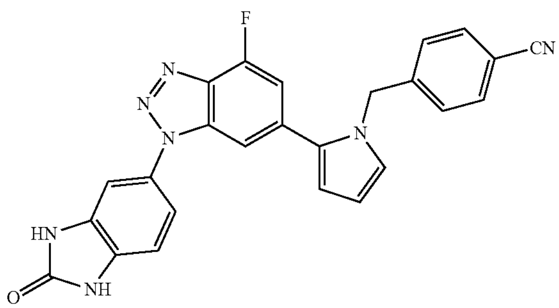 [SMILES: N#Cc1ccc(Cn2cccc2-c2cc(F)c3nnn(-c4ccc5[nH]c(=O)[nH]c5c4)c3c2)cc1] | ++ |
| 329 | 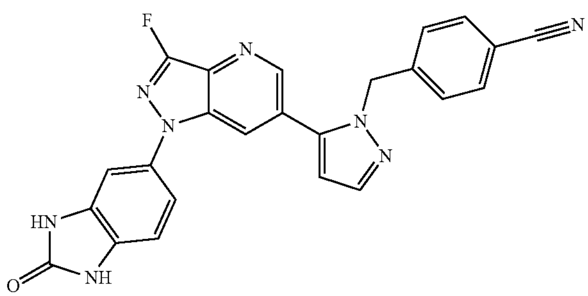 [SMILES: N#Cc1ccc(Cn2nccc2-c2cnc3c(F)nn(-c4ccc5[nH]c(=O)[nH]c5c4)c3c2)cc1] | ++ |
| 330 | 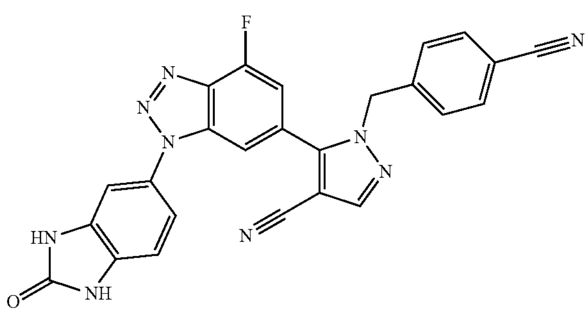 [SMILES: N#Cc1ccc(Cn2ncc(C#N)c2-c2cc(F)c3nnn(-c4ccc5[nH]c(=O)[nH]c5c4)c3c2)cc1] | + |
| 331 | 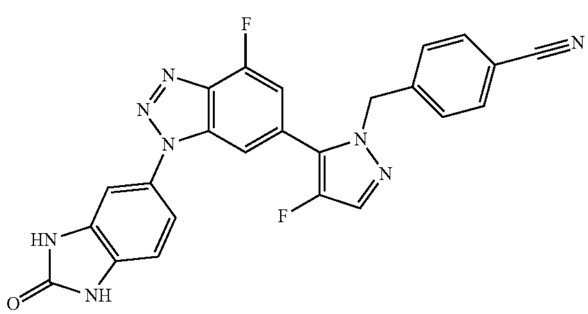 [SMILES: N#Cc1ccc(Cn2ncc(F)c2-c2cc(F)c3nnn(-c4ccc5[nH]c(=O)[nH]c5c4)c3c2)cc1] | ++ |

TABLE 1-continued
Specific Examples (Potency: CD73 $IC_{50}$: + means > 1 μM, ++ means 100 nM to 1 μM, +++ means < 100 nM).
| Example | Structure | Potency |
|---------|-----------|---------|
| 332 | 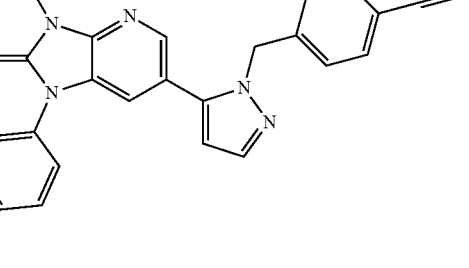 | + |
| 333 | 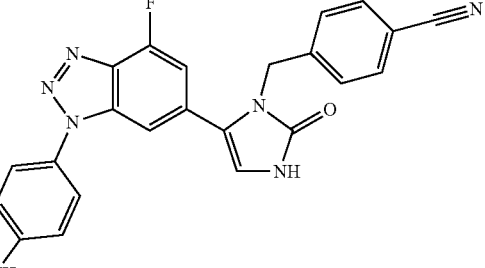 | ++ |
| 334 | 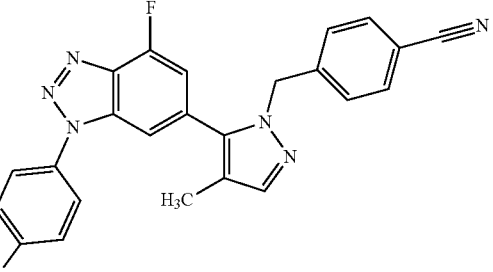 | ++ |
| 335 | 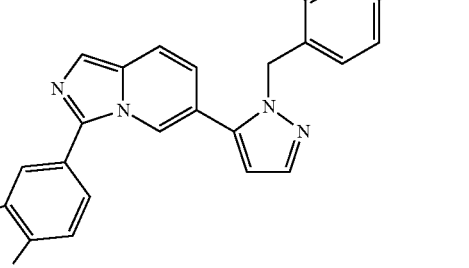 | + |

TABLE 1-continued

Specific Examples (Potency: CD73 IC$_{50}$: + means > 1 μM, ++ means 100 nM to 1 μM,
+++ means < 100 nM).

| Example | Structure | Potency |
|---------|-----------|---------|
| 336 | 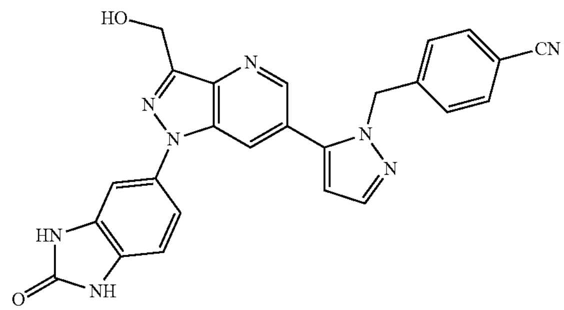 [SMILES: N#Cc1ccc(Cn2nccc2-c2cnc3c(CO)nn(-c4ccc5[nH]c(=O)[nH]c5c4)c3c2)cc1] | ++ |
| 337 | 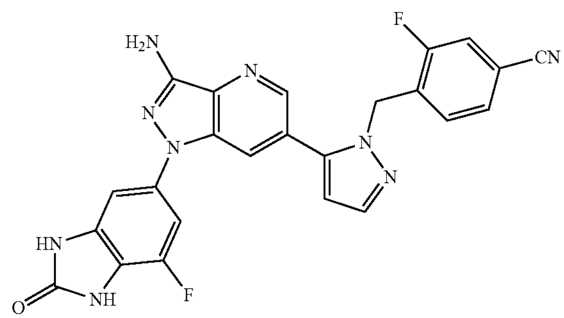 [SMILES: N#Cc1ccc(Cn2nccc2-c2cnc3c(N)nn(-c4cc(F)c5[nH]c(=O)[nH]c5c4)c3c2)c(F)c1] | ++ |
| 338 | 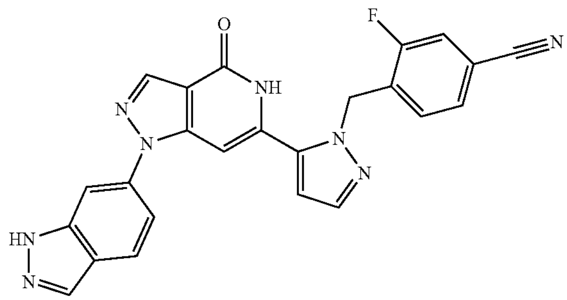 [SMILES: N#Cc1ccc(Cn2nccc2-c2cc3c(cnn3-c3ccc4cn[nH]c4c3)c(=O)[nH]2)c(F)c1] | ++ |
| 339 | 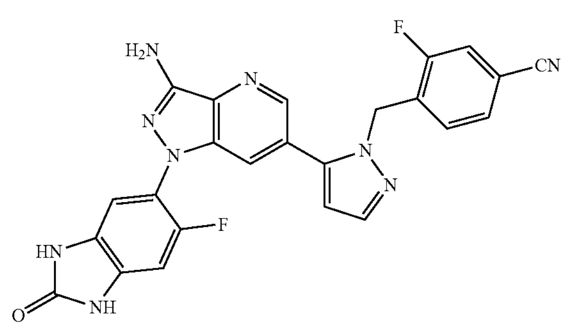 [SMILES: N#Cc1ccc(Cn2nccc2-c2cnc3c(N)nn(-c4cc5[nH]c(=O)[nH]c5cc4F)c3c2)c(F)c1] | +++ |

TABLE 1-continued

Specific Examples (Potency: CD73 IC$_{50}$: + means > 1 µM, ++ means 100 nM to 1 µM, +++ means < 100 nM).

| Example | Structure | Potency |
|---------|-----------|---------|
| 340 | 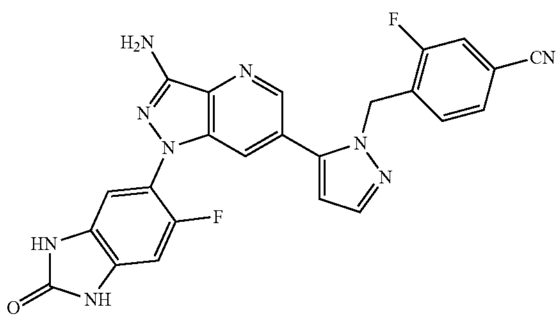 [SMILES: N#Cc1ccc(Cn2nccc2-c2cnc3c(N)nn(-c4cc5[nH]c(=O)[nH]c5cc4F)c3c2)c(F)c1] | +++ |
| 341 | 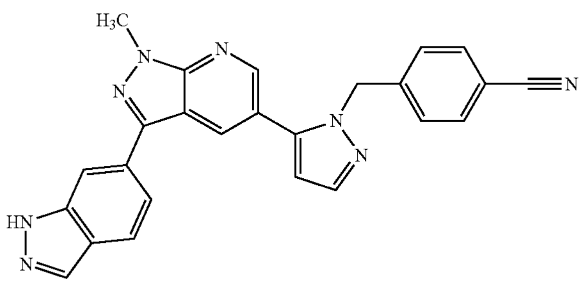 [SMILES: Cn1nc(-c2ccc3cn[nH]c3c2)c2cc(-c3ccnn3Cc3ccc(C#N)cc3)cnc21] | ++ |
| 342 | 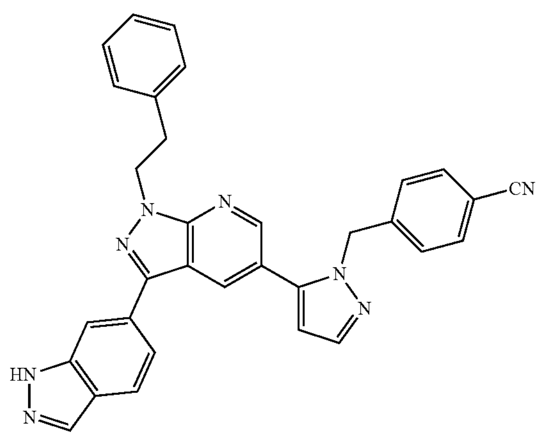 [SMILES: N#Cc1ccc(Cn2nccc2-c2cnc3c(c2)c(-c2ccc4cn[nH]c4c2)nn3CCc2ccccc2)cc1] | + |
| 343 | 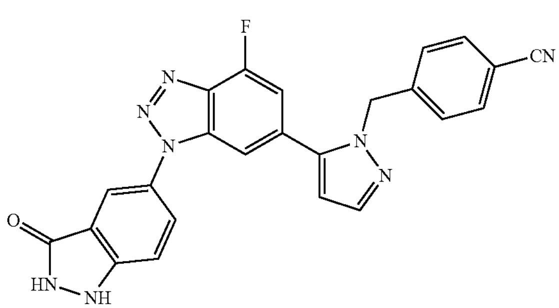 [SMILES: N#Cc1ccc(Cn2nccc2-c2cc(F)c3nnn(-c4ccc5[nH][nH]c(=O)c5c4)c3c2)cc1] | ++ |

TABLE 1-continued

Specific Examples (Potency: CD73 IC$_{50}$: + means > 1 μM, ++ means 100 nM to 1 μM, +++ means < 100 nM).

| Example | Structure | Potency |
|---------|-----------|---------|
| 344 | 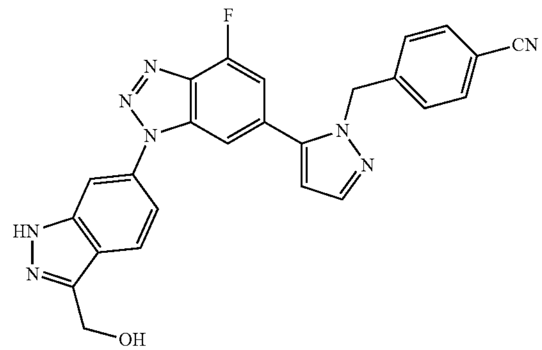 [SMILES: N#Cc1ccc(Cn2nccc2-c2cc(F)c3nnn(-c4ccc5c(CO)n[nH]c5c4)c3c2)cc1] | ++ |
| 345 | 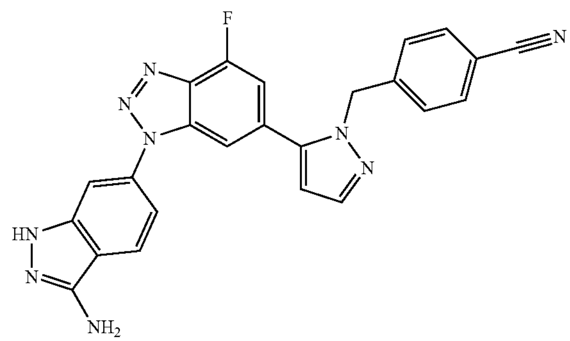 [SMILES: N#Cc1ccc(Cn2nccc2-c2cc(F)c3nnn(-c4ccc5c(N)n[nH]c5c4)c3c2)cc1] | ++ |
| 346 | 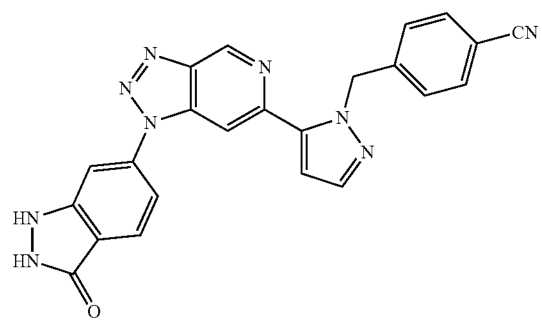 [SMILES: N#Cc1ccc(Cn2nccc2-c2cc3c(cn2)nnn3-c2ccc3c(=O)[nH][nH]c3c2)cc1] | ++ |
| 347 | 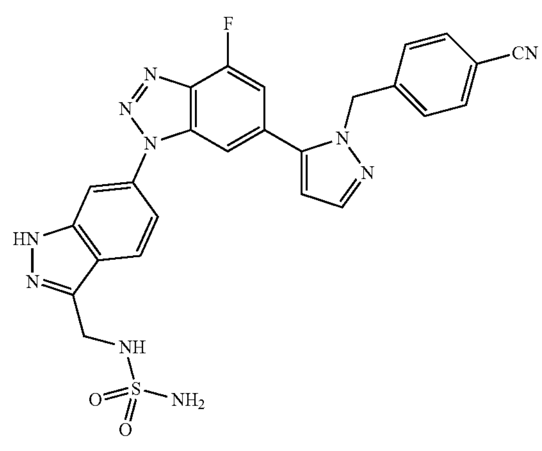 [SMILES: N#Cc1ccc(Cn2nccc2-c2cc(F)c3nnn(-c4ccc5c(CNS(N)(=O)=O)n[nH]c5c4)c3c2)cc1] | + |

TABLE 1-continued

Specific Examples (Potency: CD73 IC$_{50}$: + means > 1 μM, ++ means 100 nM to 1 μM, +++ means < 100 nM).

| Example | Structure | Potency |
|---|---|---|
| 348 | 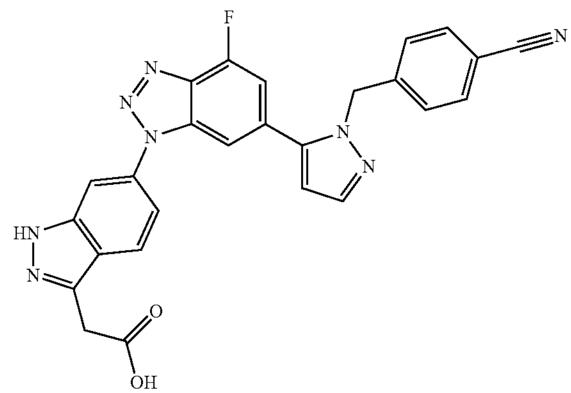 [SMILES: N#Cc1ccc(Cn2nccc2-c2cc(F)c3nnn(-c4ccc5c(CC(=O)O)n[nH]c5c4)c3c2)cc1] | + |
| 349 | 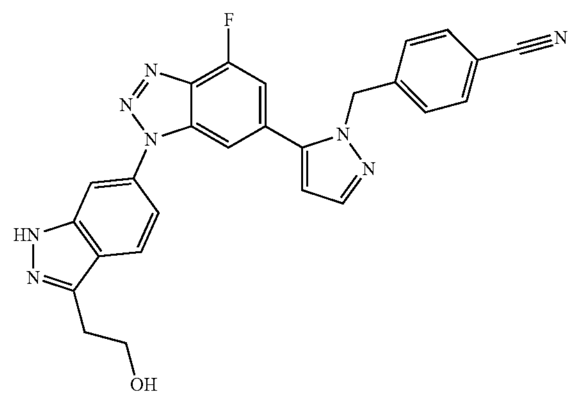 [SMILES: N#Cc1ccc(Cn2nccc2-c2cc(F)c3nnn(-c4ccc5c(CCO)n[nH]c5c4)c3c2)cc1] | + |
| 350 | 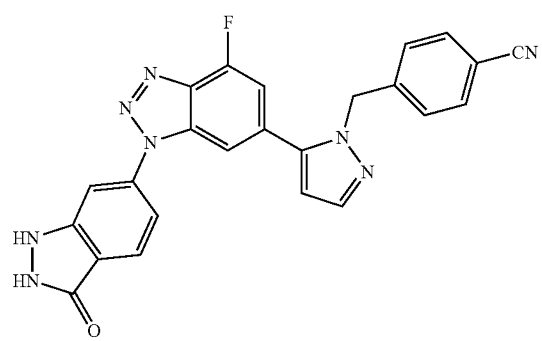 [SMILES: N#Cc1ccc(Cn2nccc2-c2cc(F)c3nnn(-c4ccc5c(=O)[nH][nH]c5c4)c3c2)cc1] | ++ |
| 351 | 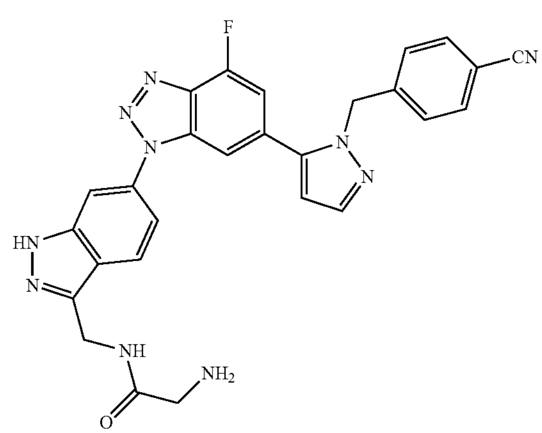 [SMILES: N#Cc1ccc(Cn2nccc2-c2cc(F)c3nnn(-c4ccc5c(CNC(=O)CN)n[nH]c5c4)c3c2)cc1] | + |

TABLE 1-continued

Specific Examples (Potency: CD73 IC$_{50}$: + means > 1 µM, ++ means 100 nM to 1 µM, +++ means < 100 nM).

| Example | Structure | Potency |
|---|---|---|
| 352 | 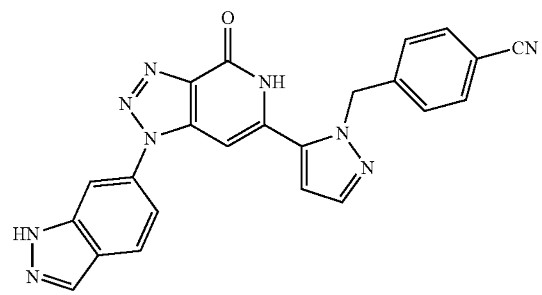 [SMILES: N#Cc1ccc(Cn2nccc2-c2cc3c(nnn3-c3ccc4cn[nH]c4c3)c(=O)[nH]2)cc1] | +++ |
| 353 | 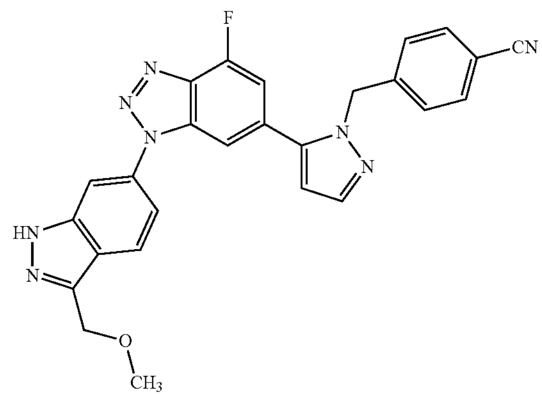 [SMILES: COCc1n[nH]c2cc(-n3nnc4c(F)cc(-c5ccnn5Cc5ccc(C#N)cc5)cc43)ccc12] | + |
| 354 | 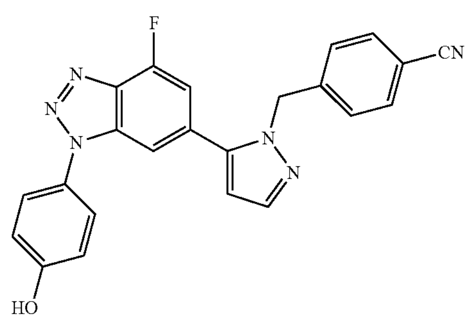 [SMILES: N#Cc1ccc(Cn2nccc2-c2cc(F)c3nnn(-c4ccc(O)cc4)c3c2)cc1] | + |
| 355 | 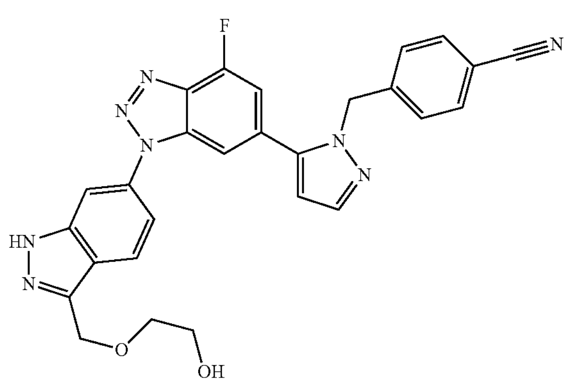 [SMILES: N#Cc1ccc(Cn2nccc2-c2cc(F)c3nnn(-c4ccc5c(COCCO)n[nH]c5c4)c3c2)cc1] | + |

TABLE 1-continued

Specific Examples (Potency: CD73 IC$_{50}$: + means > 1 μM, ++ means 100 nM to 1 μM, +++ means < 100 nM).

| Example | Structure | Potency |
|---------|-----------|---------|
| 356 | 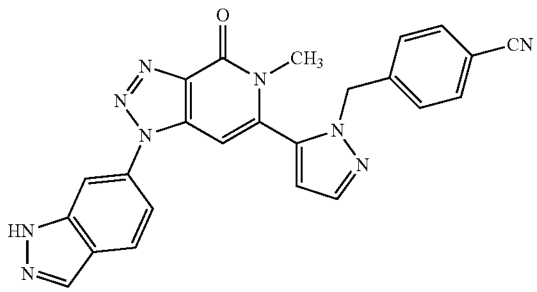 [SMILES: Cn1c(-c2ccnn2Cc2ccc(C#N)cc2)cc2c(nnn2-c2ccc3cn[nH]c3c2)c1=O] | ++ |
| 357 | 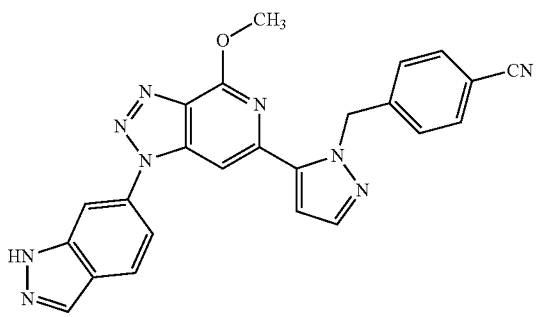 [SMILES: COc1nc(-c2ccnn2Cc2ccc(C#N)cc2)cc2c1nnn2-c1ccc2cn[nH]c2c1] | ++ |
| 358 | 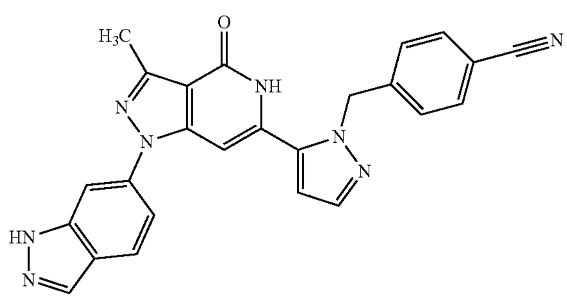 [SMILES: Cc1nn(-c2ccc3cn[nH]c3c2)c2cc(-c3ccnn3Cc3ccc(C#N)cc3)[nH]c(=O)c12] | ++ |
| 359 | 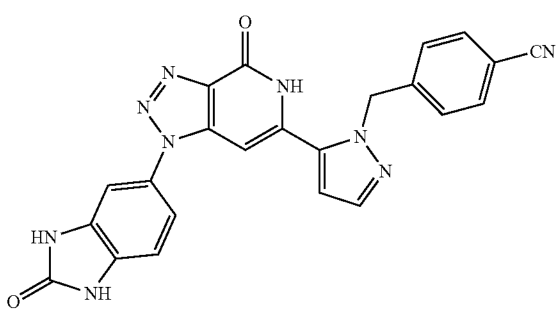 [SMILES: N#Cc1ccc(Cn2nccc2-c2cc3c(nnn3-c3ccc4[nH]c(=O)[nH]c4c3)c(=O)[nH]2)cc1] | ++ |
| 360 | 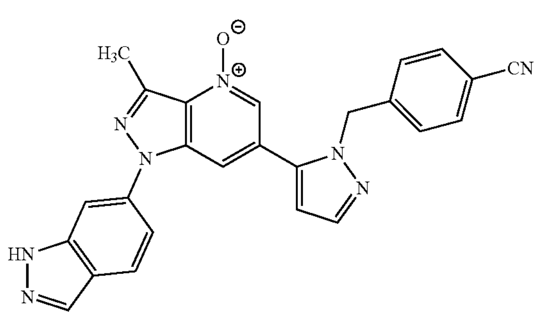 [SMILES: Cc1nn(-c2ccc3cn[nH]c3c2)c2cc(-c3ccnn3Cc3ccc(C#N)cc3)c[n+]([O-])c12] | ++ |

TABLE 1-continued
Specific Examples (Potency: CD73 IC$_{50}$: + means > 1 µM, ++ means 100 nM to 1 µM, +++ means < 100 nM).
| Example | Structure | Potency |
|---|---|---|
| 361 | 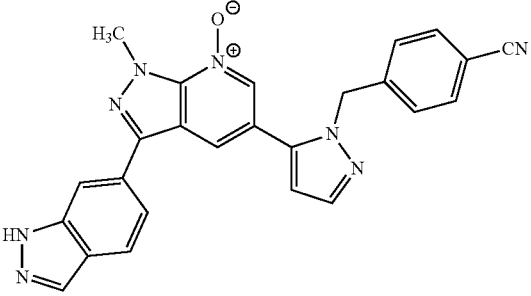 [SMILES: Cn1nc(-c2ccc3cn[nH]c3c2)c2cc(-c3ccnn3Cc3ccc(C#N)cc3)c[n+]([O-])c21] | + |
| 362 | 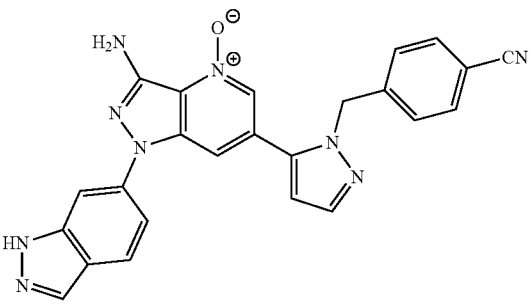 [SMILES: N#Cc1ccc(Cn2nccc2-c2cc3c(c(N)nn3-c3ccc4cn[nH]c4c3)[n+]([O-])c2)cc1] | ++ |
| 363 | 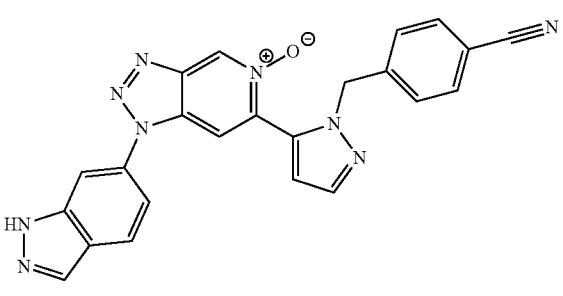 [SMILES: N#Cc1ccc(Cn2nccc2-c2cc3c(c[n+]2[O-])nnn3-c2ccc3cn[nH]c3c2)cc1] | ++ |
| 364 | 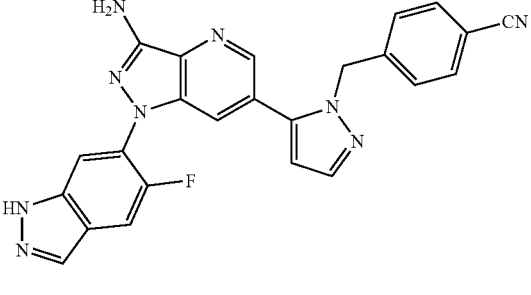 [SMILES: N#Cc1ccc(Cn2nccc2-c2cnc3c(N)nn(-c4cc5[nH]ncc5cc4F)c3c2)cc1] | +++ |
| 365 | 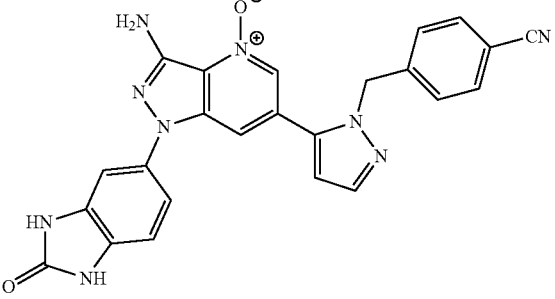 | + |

TABLE 1-continued

Specific Examples (Potency: CD73 IC$_{50}$: + means > 1 µM, ++ means 100 nM to 1 µM, +++ means < 100 nM).

| Example | Structure | Potency |
|---------|-----------|---------|
| 366 | 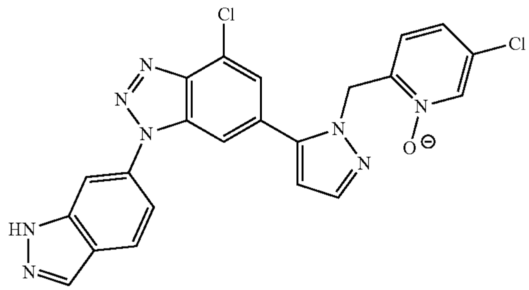 | +++ |
| 367 | 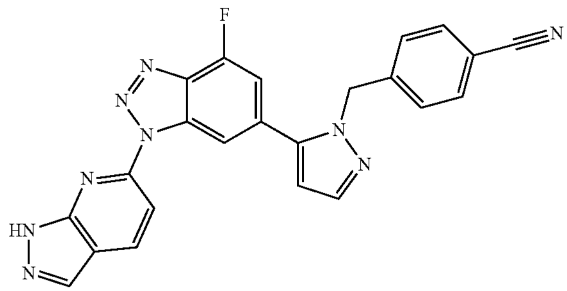 [SMILES: N#Cc1ccc(Cn2nccc2-c2cc(F)c3nnn(-c4ccc5cn[nH]c5n4)c3c2)cc1] | +++ |
| 368 | 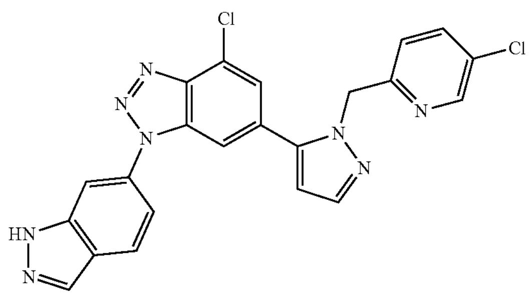 [SMILES: Clc1ccc(Cn2nccc2-c2cc(Cl)c3nnn(-c4ccc5cn[nH]c5c4)c3c2)nc1] | +++ |
| 369 | 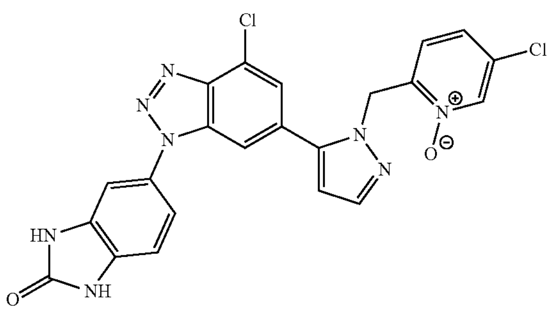 [SMILES: O=c1[nH]c2ccc(-n3nnc4c(Cl)cc(-c5ccnn5Cc5ccc(Cl)c[n+]5[O-])cc43)cc2[nH]1] | ++ |
| 370 | 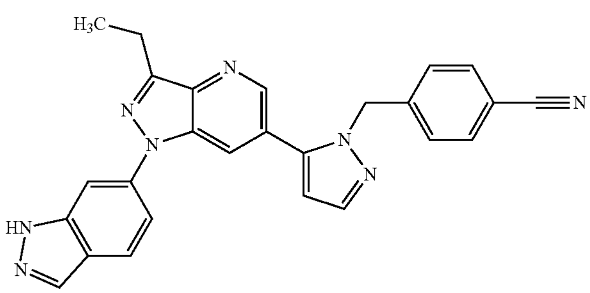 [SMILES: CCc1nn(-c2ccc3cn[nH]c3c2)c2cc(-c3ccnn3Cc3ccc(C#N)cc3)cnc12] | + |

TABLE 1-continued

Specific Examples (Potency: CD73 IC$_{50}$: + means > 1 μM, ++ means 100 nM to 1 μM, +++ means < 100 nM).

| Example | Structure | Potency |
|---------|-----------|---------|
| 371 | 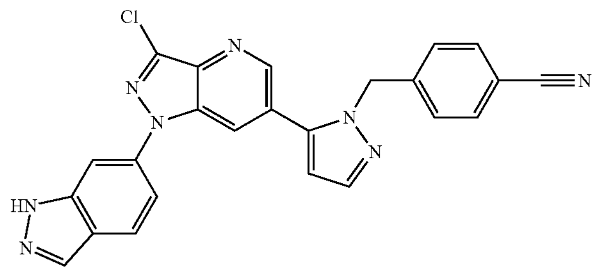 [SMILES: N#Cc1ccc(Cn2nccc2-c2cnc3c(Cl)nn(-c4ccc5cn[nH]c5c4)c3c2)cc1] | ++ |
| 372 | 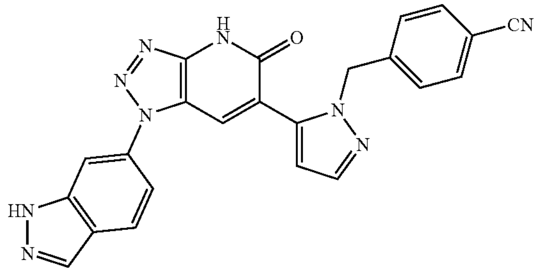 [SMILES: N#Cc1ccc(Cn2nccc2-c2cc3c(nnn3-c3ccc4cn[nH]c4c3)[nH]c2=O)cc1] | ++ |
| 373 | 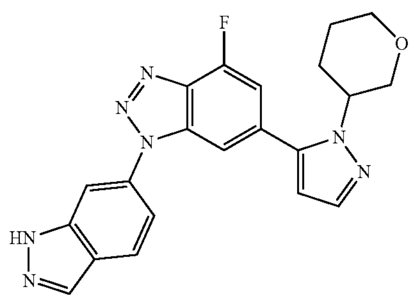 [SMILES: Fc1cc(-c2ccnn2C2CCCOC2)cc2c1nnn2-c1ccc2cn[nH]c2c1] | + |
| 374 | 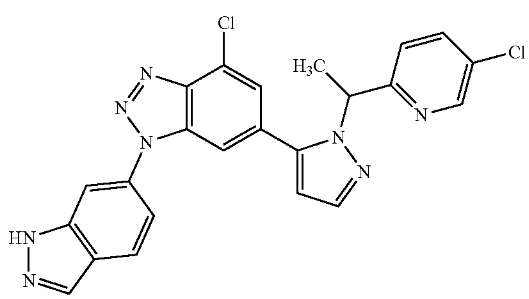 | ++ |
| 375 | 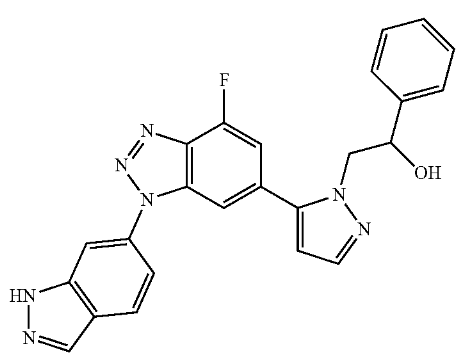 | + |

TABLE 1-continued

Specific Examples (Potency: CD73 IC$_{50}$: + means > 1 μM, ++ means 100 nM to 1 μM, +++ means < 100 nM).

| Example | Structure | Potency |
|---|---|---|
| 376 | 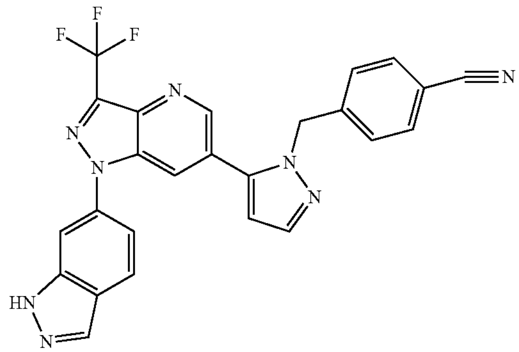 [SMILES: N#Cc1ccc(Cn2nccc2-c2cnc3c(C(F)(F)F)nn(-c4ccc5cn[nH]c5c4)c3c2)cc1] | + |
| 377 | 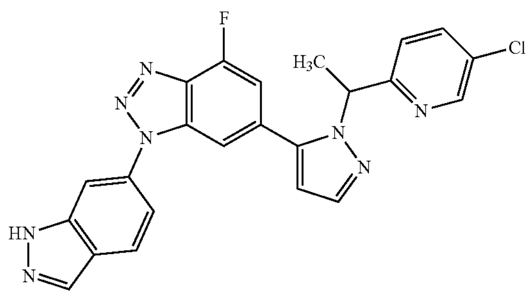 [SMILES: CC(c1ccc(Cl)cn1)n1nccc1-c1cc(F)c2nnn(-c3ccc4cn[nH]c4c3)c2c1] | ++ |
| 378 | 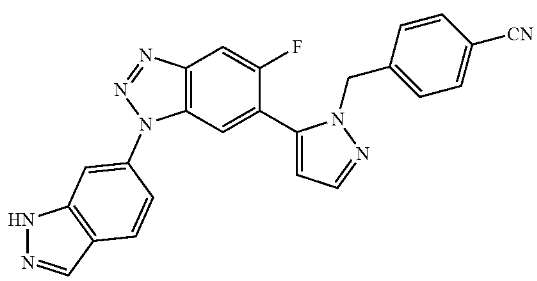 [SMILES: N#Cc1ccc(Cn2nccc2-c2cc3c(cc2F)nnn3-c2ccc3cn[nH]c3c2)cc1] | +++ |
| 379 | 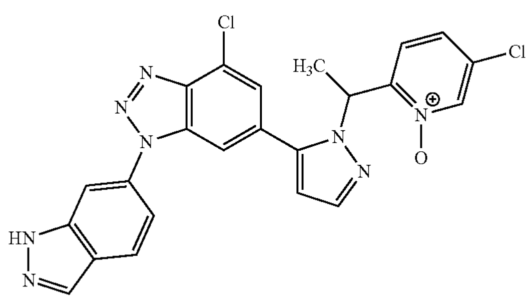 [SMILES: CC(c1ccc(Cl)c[n+]1O)n1nccc1-c1cc(Cl)c2nnn(-c3ccc4cn[nH]c4c3)c2c1] | ++ |
| 380 | 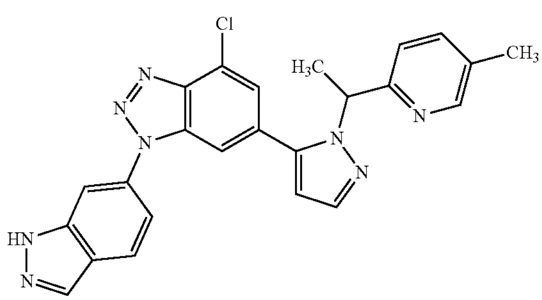 [SMILES: Cc1ccc(C(C)n2nccc2-c2cc(Cl)c3nnn(-c4ccc5cn[nH]c5c4)c3c2)nc1] | ++ |

TABLE 1-continued

Specific Examples (Potency: CD73 IC$_{50}$: + means > 1 μM, ++ means 100 nM to 1 μM, +++ means < 100 nM).

| Example | Structure | Potency |
|---------|-----------|---------|
| 381 | 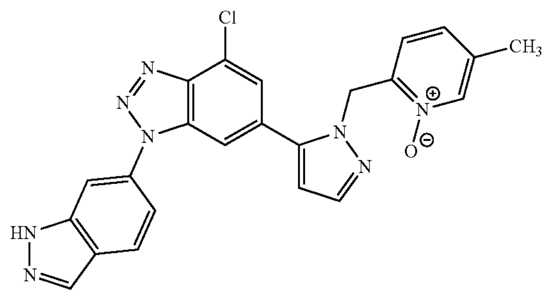 [SMILES: Cc1ccc(Cn2nccc2-c2cc(Cl)c3nnn(-c4ccc5cn[nH]c5c4)c3c2)[n+]([O-])c1] | +++ |
| 382 | 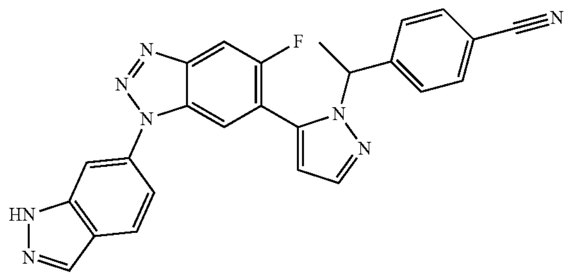 [SMILES: CC(c1ccc(C#N)cc1)n1nccc1-c1cc2c(cc1F)nnn2-c1ccc2cn[nH]c2c1] | ++ |
| 383 | 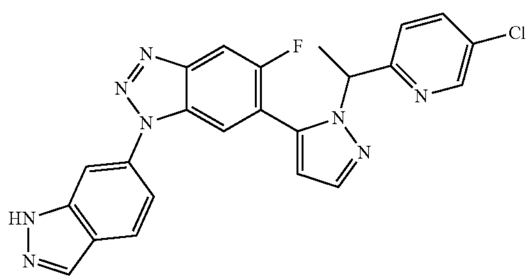 [SMILES: CC(c1ccc(Cl)cn1)n1nccc1-c1cc2c(cc1F)nnn2-c1ccc2cn[nH]c2c1] | ++ |
| 384 | 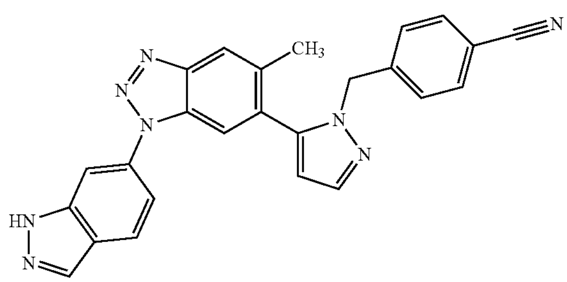 [SMILES: Cc1cc2nnn(-c3ccc4cn[nH]c4c3)c2cc1-c1ccnn1Cc1ccc(C#N)cc1] | ++ |
| 385 | 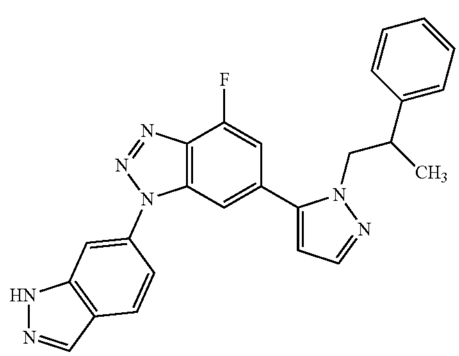 [SMILES: CC(Cn1nccc1-c1cc(F)c2nnn(-c3ccc4cn[nH]c4c3)c2c1)c1ccccc1] | + |

TABLE 1-continued

Specific Examples (Potency: CD73 IC$_{50}$: + means > 1 μM, ++ means 100 nM to 1 μM, +++ means < 100 nM).

| Example | Structure | Potency |
|---------|-----------|---------|
| 386 | 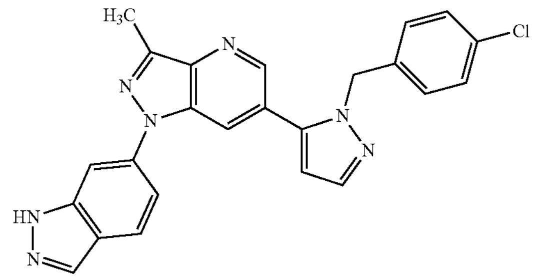 [SMILES: Cc1nn(-c2ccc3cn[nH]c3c2)c2cc(-c3ccnn3Cc3ccc(Cl)cc3)cnc12] | ++ |
| 387 | 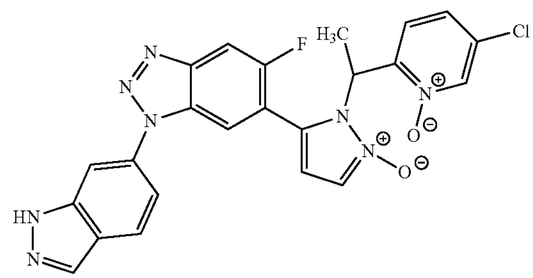 [SMILES: CC(c1ccc(Cl)c[n+]1[O-])n1c(-c2cc3c(cc2F)nnn3-c2ccc3cn[nH]c3c2)cc[n+]1[O-]] | ++ |
| 388 | 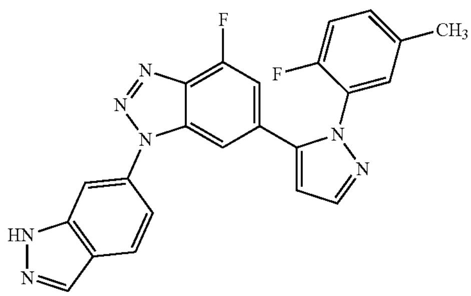 [SMILES: Cc1ccc(F)c(-n2nccc2-c2cc(F)c3nnn(-c4ccc5cn[nH]c5c4)c3c2)c1] | + |
| 389 | 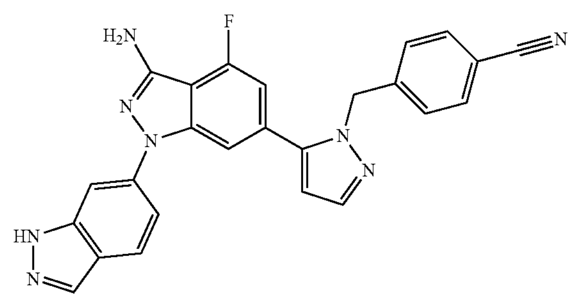 [SMILES: N#Cc1ccc(Cn2nccc2-c2cc(F)c3c(N)nn(-c4ccc5cn[nH]c5c4)c3c2)cc1] | ++ |
| 390 | 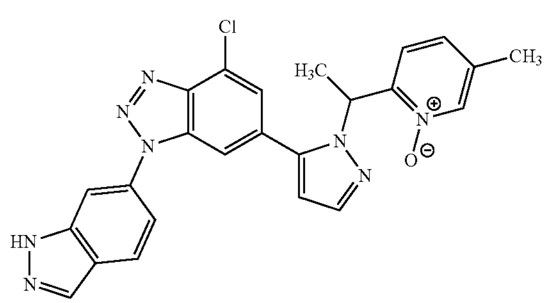 [SMILES: Cc1ccc(C(C)n2nccc2-c2cc(Cl)c3nnn(-c4ccc5cn[nH]c5c4)c3c2)[n+]([O-])c1] | ++ |

TABLE 1-continued
Specific Examples (Potency: CD73 IC$_{50}$: + means > 1 µM, ++ means 100 nM to 1 µM, +++ means < 100 nM).
| Example | Structure | Potency |
|---|---|---|
| 391 | 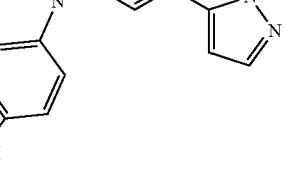 | + |
| 392 | 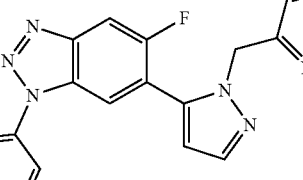 | +++ |
| 393 | 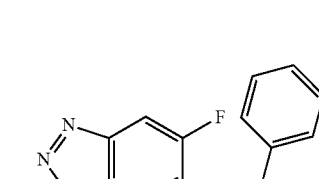 | ++ |
| 394 | 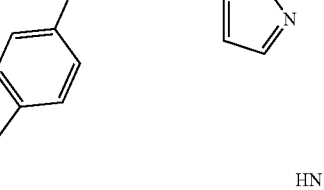 | + |
| 395 | 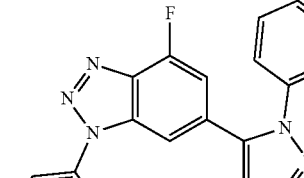 | ++ |

TABLE 1-continued
Specific Examples (Potency: CD73 IC$_{50}$: + means > 1 μM, ++ means 100 nM to 1 μM, +++ means < 100 nM).
| Example | Structure | Potency |
|---|---|---|
| 396 | 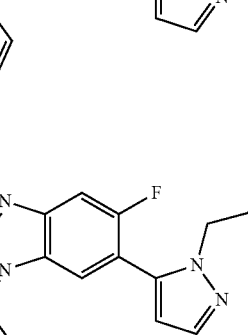 | ++ |
| 397 | 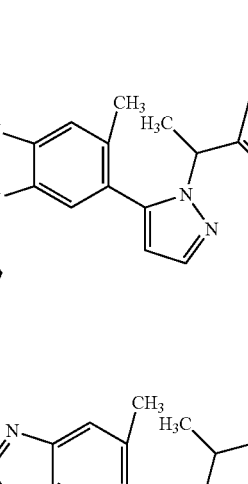 | ++ |
| 398 | 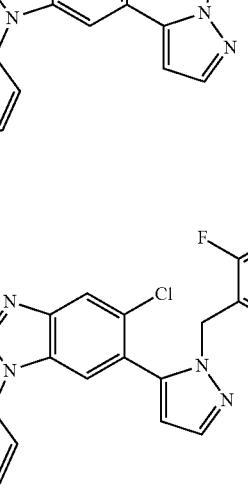 | + |
| 399 | 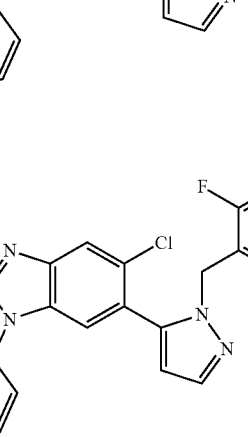 | + |
| 400 | 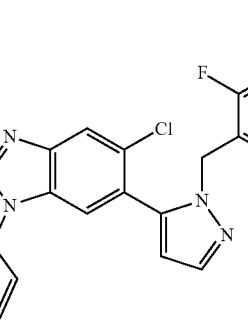 | +++ |

TABLE 1-continued
Specific Examples (Potency: CD73 IC$_{50}$: + means > 1 μM, ++ means 100 nM to 1 μM, +++ means < 100 nM).
| Example | Structure | Potency |
|---|---|---|
| 401 | 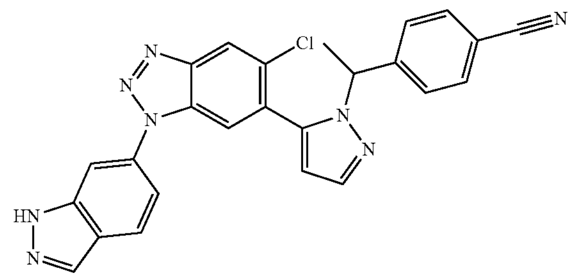 | ++ |
| 402 | 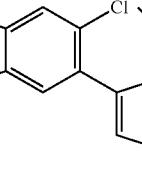 | ++ |
| 403 | 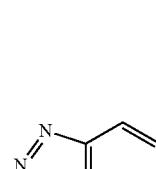 | + |
| 404 | 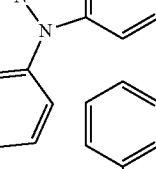 | ++ |
| 405 | 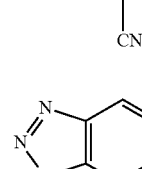 | ++ |

TABLE 1-continued

Specific Examples (Potency: CD73 IC$_{50}$: + means > 1 µM, ++ means 100 nM to 1 µM, +++ means < 100 nM).

| Example | Structure | Potency |
|---------|-----------|---------|
| 406 | 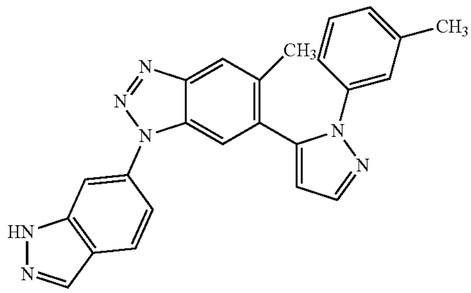 [SMILES: Cc1cccc(-n2nccc2-c2cc3c(cc2C)nnn3-c2ccc3cn[nH]c3c2)c1] | + |
| 407 | 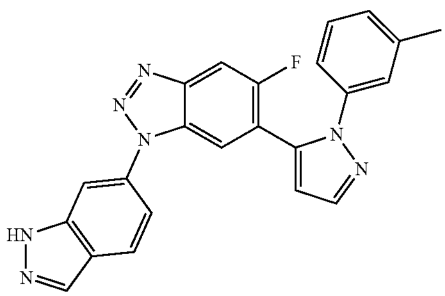 [SMILES: Cc1cccc(-n2nccc2-c2cc3c(cc2F)nnn3-c2ccc3cn[nH]c3c2)c1] | ++ |
| 408 | 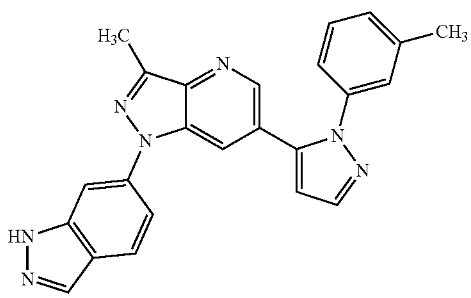 [SMILES: Cc1cccc(-n2nccc2-c2cnc3c(C)nn(-c4ccc5cn[nH]c5c4)c3c2)c1] | ++ |
| 409 | 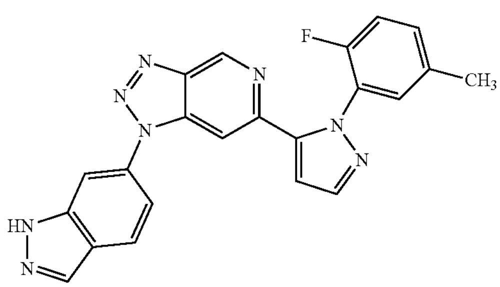 [SMILES: Cc1ccc(F)c(-n2nccc2-c2cc3c(cn2)nnn3-c2ccc3cn[nH]c3c2)c1] | + |
| 410 | 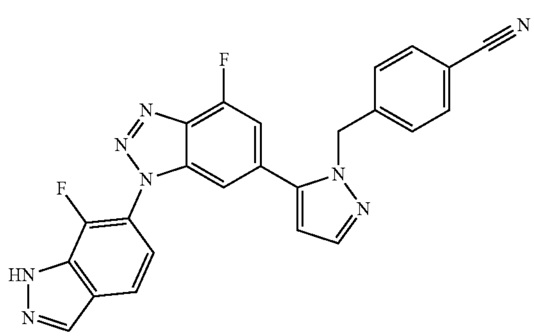 [SMILES: N#Cc1ccc(Cn2nccc2-c2cc(F)c3nnn(-c4ccc5cn[nH]c5c4F)c3c2)cc1] | ++ |

TABLE 1-continued

Specific Examples (Potency: CD73 IC$_{50}$: + means > 1 μM, ++ means 100 nM to 1 μM, +++ means < 100 nM).

| Example | Structure | Potency |
|---|---|---|
| 411 | 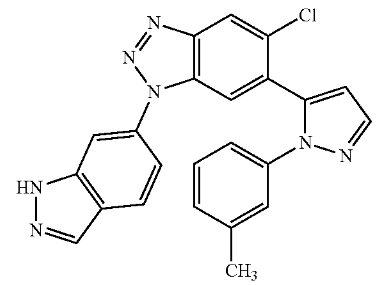 [SMILES: Cc1cccc(-n2nccc2-c2cc3c(cc2Cl)nnn3-c2ccc3cn[nH]c3c2)c1] | ++ |
| 412 | 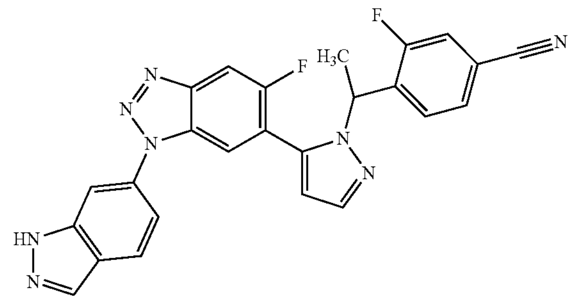 [SMILES: CC(c1ccc(C#N)cc1F)n1nccc1-c1cc2c(cc1F)nnn2-c1ccc2cn[nH]c2c1] | ++ |
| 413 | 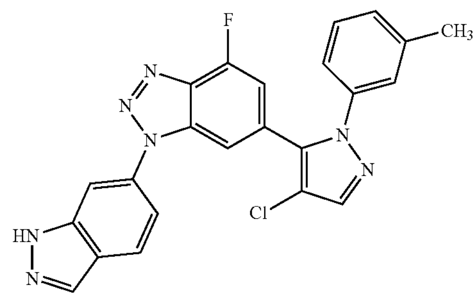 [SMILES: Cc1cccc(-n2ncc(Cl)c2-c2cc(F)c3nnn(-c4ccc5cn[nH]c5c4)c3c2)c1] | ++ |
| 414 | 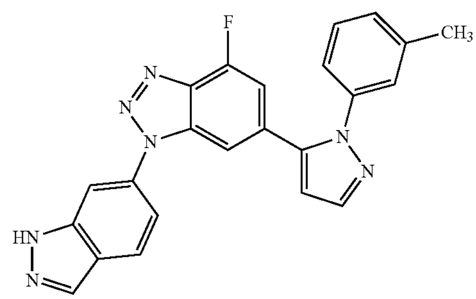 [SMILES: Cc1cccc(-n2nccc2-c2cc(F)c3nnn(-c4ccc5cn[nH]c5c4)c3c2)c1] | ++ |
| 415 | 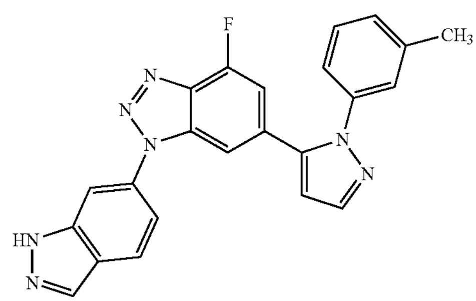 | + |

TABLE 1-continued

Specific Examples (Potency: CD73 $IC_{50}$: + means > 1 μM, ++ means 100 nM to 1 μM, +++ means < 100 nM).

| Example | Structure | Potency |
|---------|-----------|---------|
| 416 | 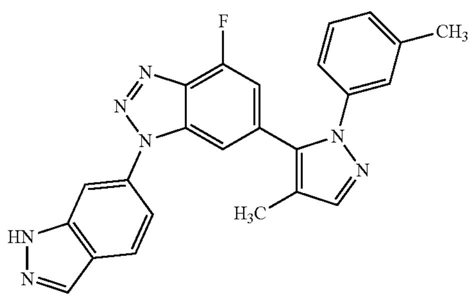 | + |
| 417 | 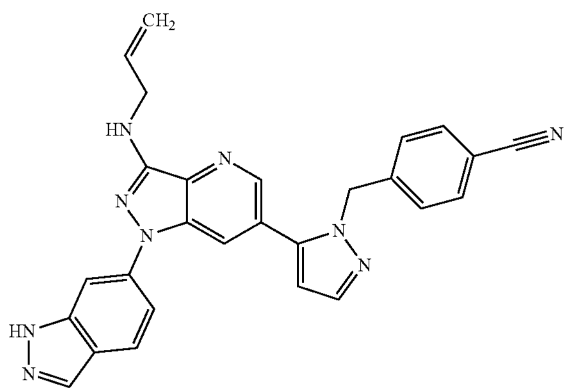 [SMILES: C=CCNc1nn(-c2ccc3cn[nH]c3c2)c2cc(-c3ccnn3Cc3ccc(C#N)cc3)cnc12] | + |
| 418 | 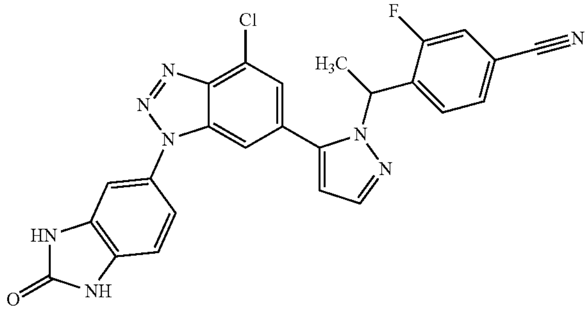 [SMILES: CC(c1ccc(C#N)cc1F)n1nccc1-c1cc(Cl)c2nnn(-c3ccc4[nH]c(=O)[nH]c4c3)c2c1] | ++ |
| 419 | 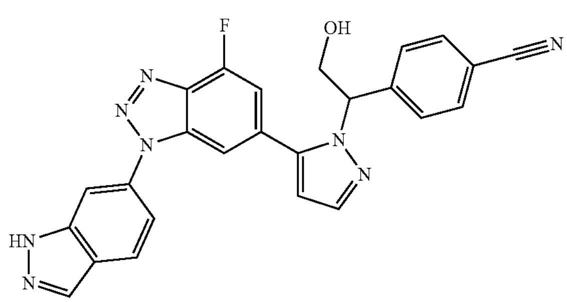 [SMILES: N#Cc1ccc(C(CO)n2nccc2-c2cc(F)c3nnn(-c4ccc5cn[nH]c5c4)c3c2)cc1] | ++ |

TABLE 1-continued

Specific Examples (Potency: CD73 IC$_{50}$: + means > 1 μM, ++ means 100 nM to 1 μM, +++ means < 100 nM).

| Example | Structure | Potency |
|---------|-----------|---------|
| 420 | 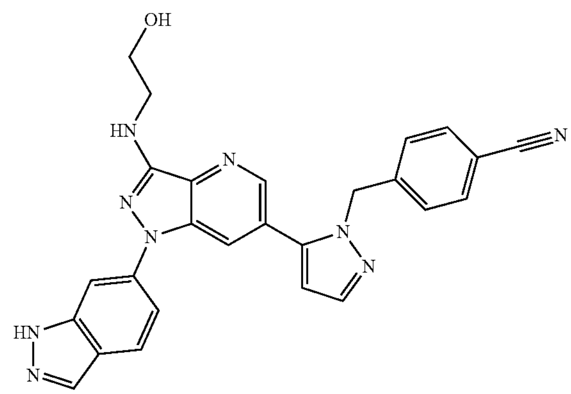 [SMILES: N#Cc1ccc(Cn2nccc2-c2cnc3c(NCCO)nn(-c4ccc5cn[nH]c5c4)c3c2)cc1] | + |
| 421 | 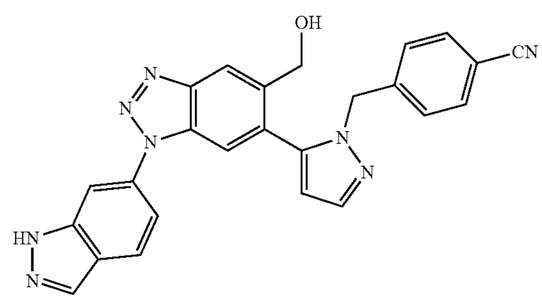 [SMILES: N#Cc1ccc(Cn2nccc2-c2cc3c(cc2CO)nnn3-c2ccc3cn[nH]c3c2)cc1] | ++ |
| 422 | 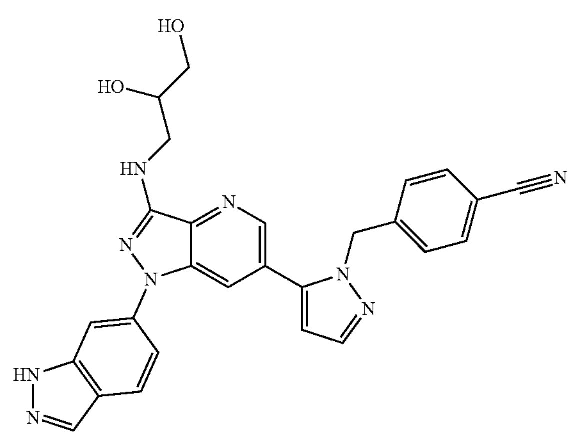 [SMILES: N#Cc1ccc(Cn2nccc2-c2cnc3c(NCC(O)CO)nn(-c4ccc5cn[nH]c5c4)c3c2)cc1] | + |
| 423 | 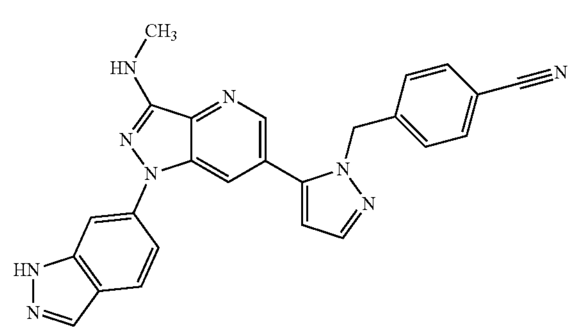 [SMILES: CNc1nn(-c2ccc3cn[nH]c3c2)c2cc(-c3ccnn3Cc3ccc(C#N)cc3)cnc12] | + |

TABLE 1-continued

Specific Examples (Potency: CD73 IC$_{50}$: + means > 1 µM, ++ means 100 nM to 1 µM, +++ means < 100 nM).

| Example | Structure | Potency |
|---|---|---|
| 424 | [structure] | + |
| 425 | [structure] | + |

Biological Examples

Materials and Methods

The following general materials and methods were used, where indicated, or may be used in the Examples below:

Standard methods in molecular biology are described in the scientific literature (see, e.g., Sambrook and Russell (2001) Molecular Cloning, 3$^{rd}$ ed., Cold Spring Harbor Laboratory Press, Cold Spring Harbor, N.Y.; and Ausubel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4)).

The scientific literature describes methods for protein purification, including immunoprecipitation, chromatography, electrophoresis, centrifugation, and crystallization, as well as chemical analysis, chemical modification, post-translational modification, production of fusion proteins, and glycosylation of proteins (see, e.g., Coligan, et al. (2000) Current Protocols in Protein Science, Vols. 1-2, John Wiley and Sons, Inc., NY).

Software packages and databases for determining, e.g., antigenic fragments, leader sequences, protein folding, functional domains, glycosylation sites, and sequence alignments, are available (see, e.g., GCG Wisconsin Package (Accelrys, Inc., San Diego, CA); and DeCypher™ (TimeLogic Corp., Crystal Bay, NV).

The literature is replete with assays and other experimental techniques that can serve as a basis for evaluation of the compounds described herein.

Inhibition of Ecto-5'-nucleotidase Activity. Compounds were evaluated to determine their ecto-5'-nucleotidase (CD73) inhibitory activity. Briefly, CHO-K1 cells stably transfected with human CD73 were generated by LakePharma (Belmont, CA) using molecular cloning of human CD73 (http://www.uniprot.org/uniprot/P21589) and mammalian transient expression vector (P21589.1). After antibiotic selection in CD OptiCHO cell media (Invitrogen, Catalog #12681-011) containing 5 µg/mL Puromycin and 200 µg/mL Hygromycin B, a suspension pool of CHO-CD73 cells was collected and frozen in 7.5% DMSO in cell media without antibiotics.

On the day of the experiment, one vial of CHO-CD73 cells was thawed and suspended in assay media which consisted of 20 mM HEPES, pH 7.4, 137 mM NaCl, 5.4 mM KCl, 1.3 mM CaCl$_2$, 4.2 mM NaHCO$_3$ and 0.1% glucose. To test the ability of compounds to inhibit CD73 enzymatic activity, 2 µL of 500 µM of compounds dissolved in DMSO (50×) were added to a 96-well polystyrene plate containing 58 µL of assay buffer. Next, 20 µL of CHO-CD73 cells in assay buffer were added to assay plate followed by 20 µL of 125 µM AMP (Adenosine 5'-monophosphate monohydrate) in assay buffer. Final assay conditions consisted of 2500 cells per well in 2% DMSO and 25 µM of AMP substrate. After 50 minutes of incubation (37° C. and 5% CO$_2$) and centrifugation at 225×g for 5 mins, 80 µL of supernatant were transferred to a 96-well Spectra Plate (PerkinElmer, cat #6005640) which was pre-dispensed with 20 µL of PiColorLock Gold colorimetric assay reagents (Thermo, cat #30 300 30). The amount of inorganic phosphate was determined by reading the absorbance at 620 nm on an EnVision Multilabel Plate Reader (PerkinElmer). Enzymatic activity of CD73 was based on the amount of phosphate generated. Percentage of activity was calculated based on DMSO and no cells control wells. IC$_{50}$ values of compounds were determined by four parameter non-linear regression fitting of percentage of activity in GraphPad Prism software.

Pharmacodynamic and Pharmacokinetic Evaluation. A pharmacodynamic assay can be based on measuring CD73 mediated serum levels of adenosine. Adenosine levels can be determined by HPLC analysis, and serum compound levels can optionally also be determined in the same HPLC run.

Particular embodiments of this invention are described herein, including the best mode known to the inventors for carrying out the invention. Upon reading the foregoing, description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference as if each individual publication or patent application were specifically and individually indicated to be incorporated by reference.

What is claimed is:
1. A compound represented by formula (Ia) or (Ib):

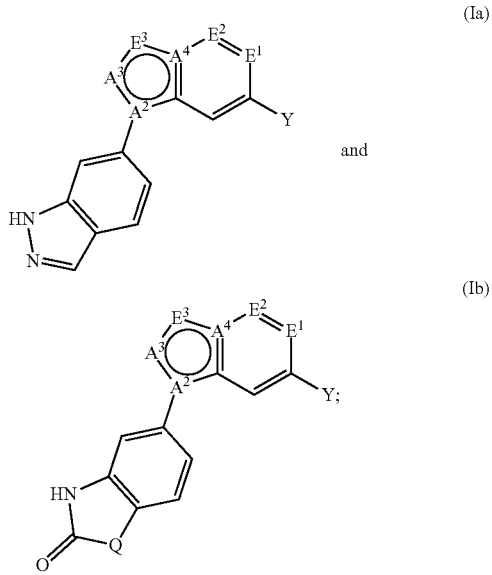

or a pharmaceutically acceptable salt, hydrate, N-oxide, or solvate thereof, wherein,
each of $A^2$ and $A^4$ is independently selected from the group consisting of C, CH and N;
$A^3$ is selected from the group consisting of C(O), CH and N;
each $E^1$ and $E^2$ is independently selected from the group consisting of N, C(O) and $CR^1$;
$E^3$ is selected from the group consisting of N, $NR^1$ and $CR^1$;
at least two of $A^2$, $A^3$, $A^4$, $E^1$, $E^2$ and $E^3$ are N or $NR^1$;

each $R^1$ is independently selected from the group consisting of hydrogen, halogen, CN, $NH_2$, $NH—C_1$-$C_6$ alkyl, $C_1$-$C_6$ alkyl, $C_1$-$C_6$ haloalkyl, $C_1$-$C_6$ alkoxy, and $C_1$-$C_6$ haloalkoxy, wherein $NH_2$, $NH—C_1$-$C_6$ alkyl, $C_1$-$C_6$ alkyl, $C_1$-$C_6$ haloalkyl, $C_1$-$C_6$ alkoxy, and $C_1$-$C_6$ haloalkoxy are each substituted with from 0 to 3 R;

Y is an optionally substituted 5-6 membered heteroaryl or an optionally substituted 4-7 membered heterocycle, wherein said 5-6 membered heteroaryl and 4-7 membered heterocycle have from 1 to 3 ring heteroatoms independently selected from N, O, S, SO, and $SO_2$;

Q is selected from the group consisting of NH, $CH_2$, and O;

each R is independently selected from the group consisting of H, halogen, CN, $NH_2$, $NHR^a$, $NR^aR^b$, $R^c$, OH, $OR^a$, $SR^a$, $S(O)_2R^a$, —$X^a$—$NH_2$, —$X^a$—$NHR^a$, —$X^a$—$NR^aR^b$, —$X^a$—OH, —$X^a$—$OR^a$, —$X^a$—$R^a$, —$X^a$—$SR^a$, and —$X^a$—$S(O)_2R^a$;

each $R^a$, $R^b$ and $R^c$ is independently selected from the group consisting of $C_1$-$C_6$ alkyl, $C_1$-$C_6$ haloalkyl, $C_1$-$C_6$ hydroxyalkyl, $C_{3-7}$ cycloalkyl, $C_2$-$C_6$ alkenyl, and $C_2$-$C_6$ alkynyl, or $R^a$ and $R^b$ attached to N form a 4- to 7-membered ring; and each $X^a$ is independently selected from the group consisting of C(O), $C_1$-$C_4$ alkylene, —O—$C_1$-$C_4$ alkylene, and $C_1$-$C_4$ alkylene-O—.

2. The compound of claim 1, or a pharmaceutically acceptable salt, hydrate, N-oxide, or solvate thereof, having a formula selected from the group consisting of (Ia1) and (Ib1):

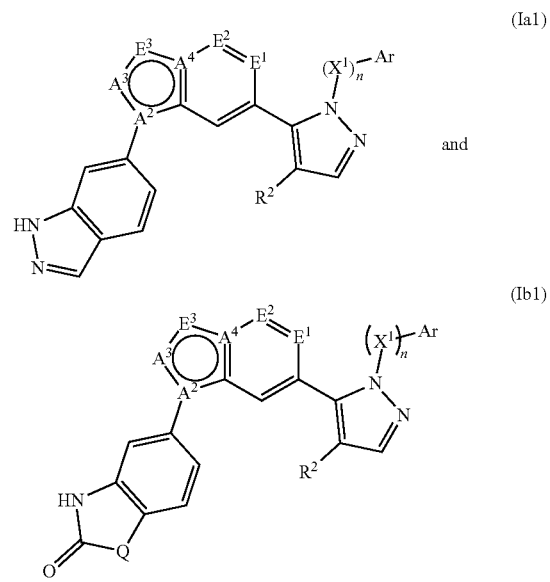

wherein Ar is an unsubstituted or substituted aryl or heteroaryl;
n is 0, 1, or 2;
each $X^1$ is independently —$CHR^3$—;
$R^2$ is selected from the group consisting of H, halogen, CN, $C_1$-$C_4$ alkyl, and $C_1$-$C_4$ haloalkyl; and
each $R^3$ is independently selected from the group consisting of H and unsubstituted or substituted $C_1$-$C_4$ alkyl.

3. The compound of claim 2, or a pharmaceutically acceptable salt, hydrate, N-oxide, or solvate thereof, having a formula selected from the group consisting of (Ia2) and (Ib2):

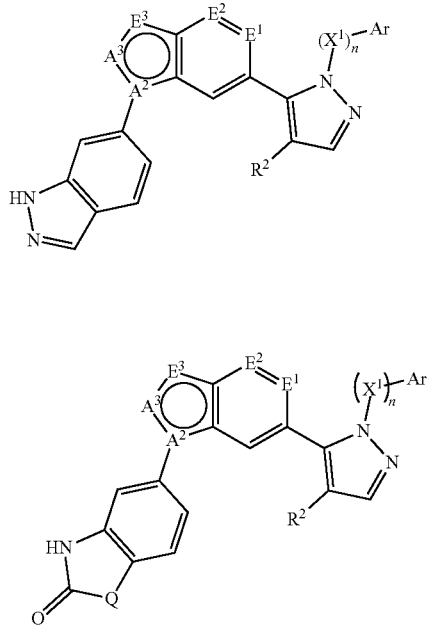

(Ia2)

and (Ib2)

4. The compound of claim 3, or a pharmaceutically acceptable salt, hydrate, N-oxide, or solvate thereof, having a formula selected from the group consisting of (Ia3) and (Ib3):

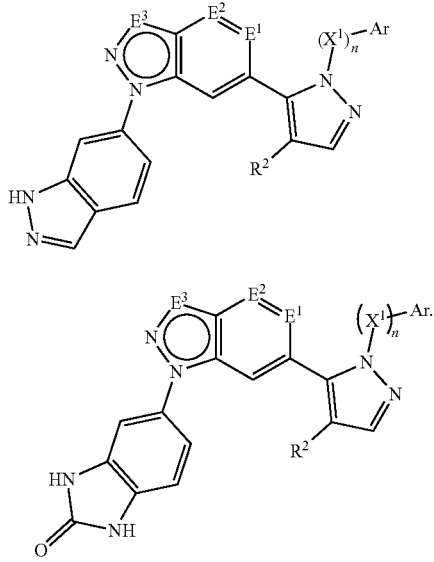

(Ia3)

and (Ib3)

5. The compound of claim 4, or a pharmaceutically acceptable salt, hydrate, N-oxide, or solvate thereof, having a formula selected from the group consisting of (Ia4) and (Ib4):

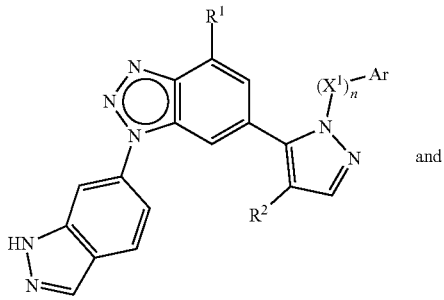

(Ia4)

and (Ib4)

6. The compound of claim 5, or a pharmaceutically acceptable salt, hydrate, N-oxide, or solvate thereof, having a formula selected from the group consisting of (Ia5) and (Ib5):

(Ia5)

and (Ib5)

wherein each E is independently selected from the group consisting of CH, CR$^1$, and N.

7. The compound of claim 5, or a pharmaceutically acceptable salt, hydrate, N-oxide, or solvate thereof, having a formula selected from the group consisting of (Ia6) and (Ib6):

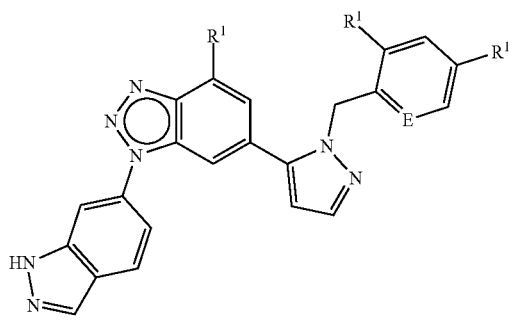

(Ia6)

and (Ib6)

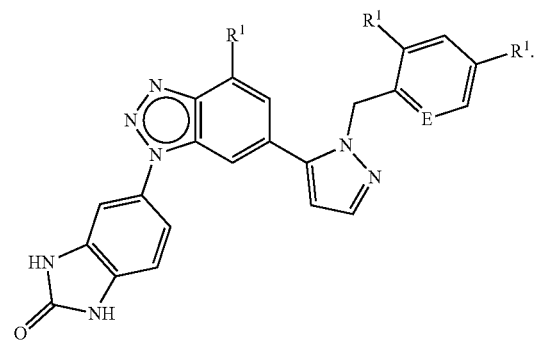

8. The compound of claim 7, or a pharmaceutically acceptable salt, hydrate, N-oxide, or solvate thereof, having a formula selected from the group consisting of (Ia7) and (Ib7):

(Ia7)

and

-continued (Ib7)

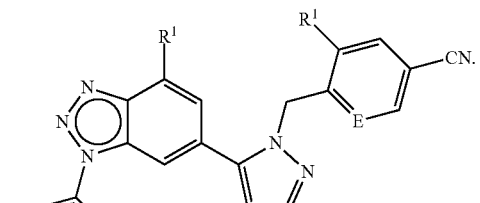

9. The compound of claim 4, or a pharmaceutically acceptable salt, hydrate, N-oxide, or solvate thereof, having a formula selected from the group consisting of (Ia8) and (Ib8):

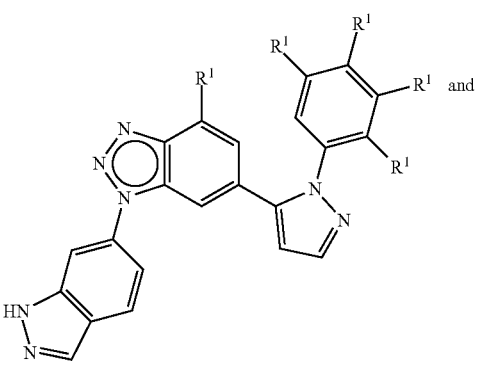

(Ia8)

and (Ib8)

10. A compound selected from:
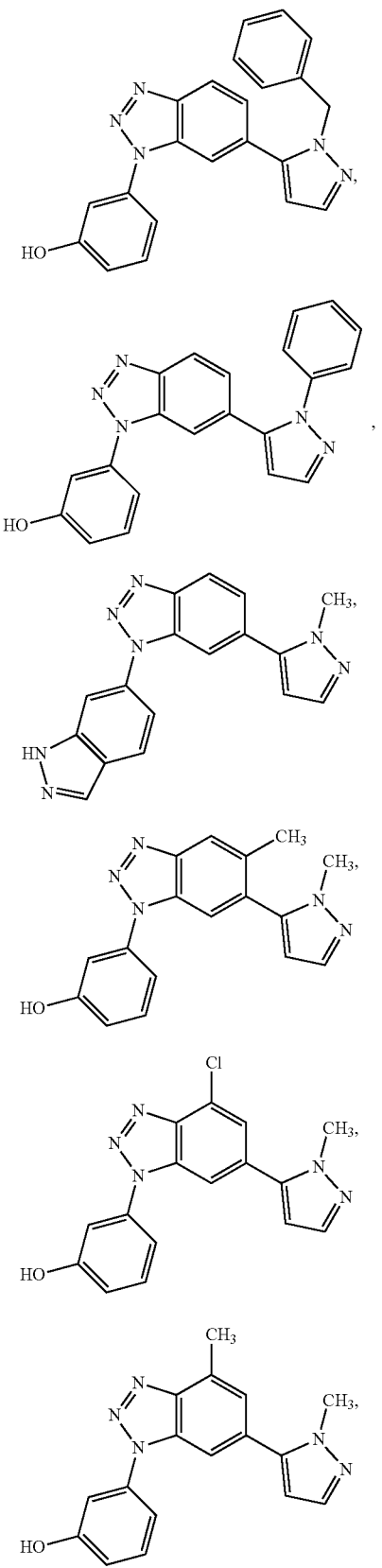
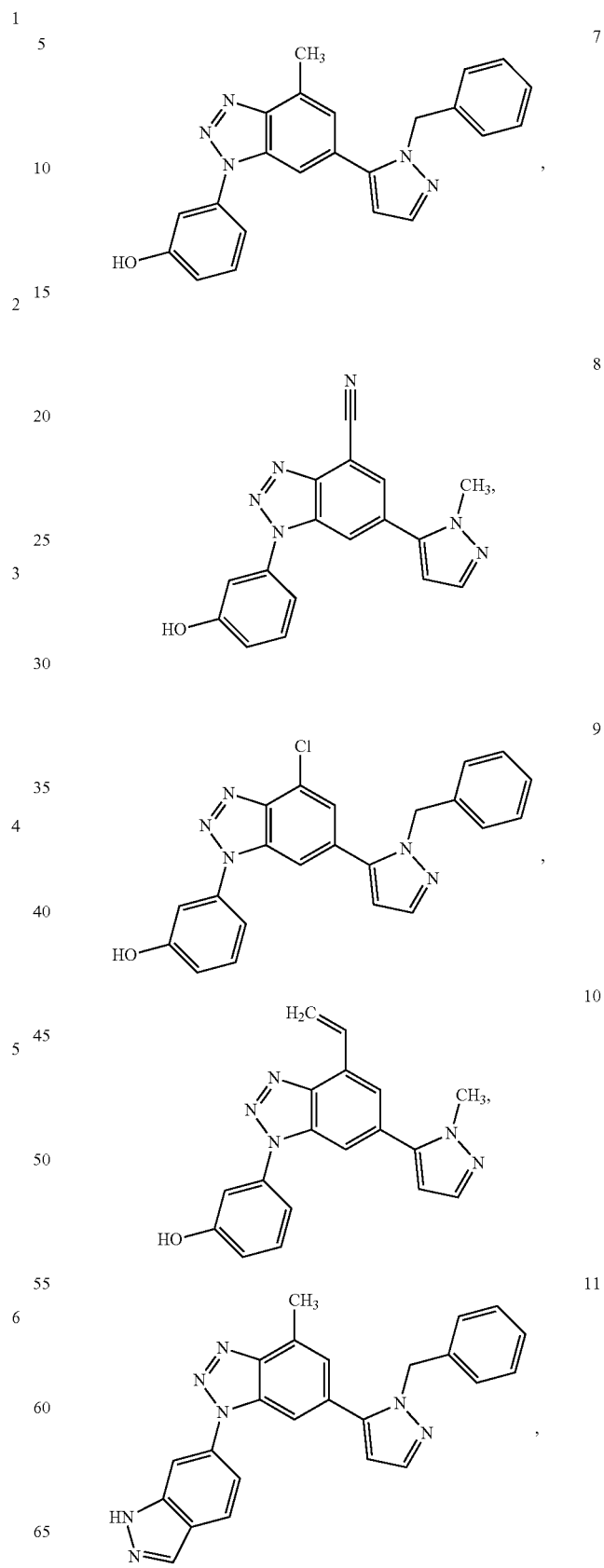

281
-continued
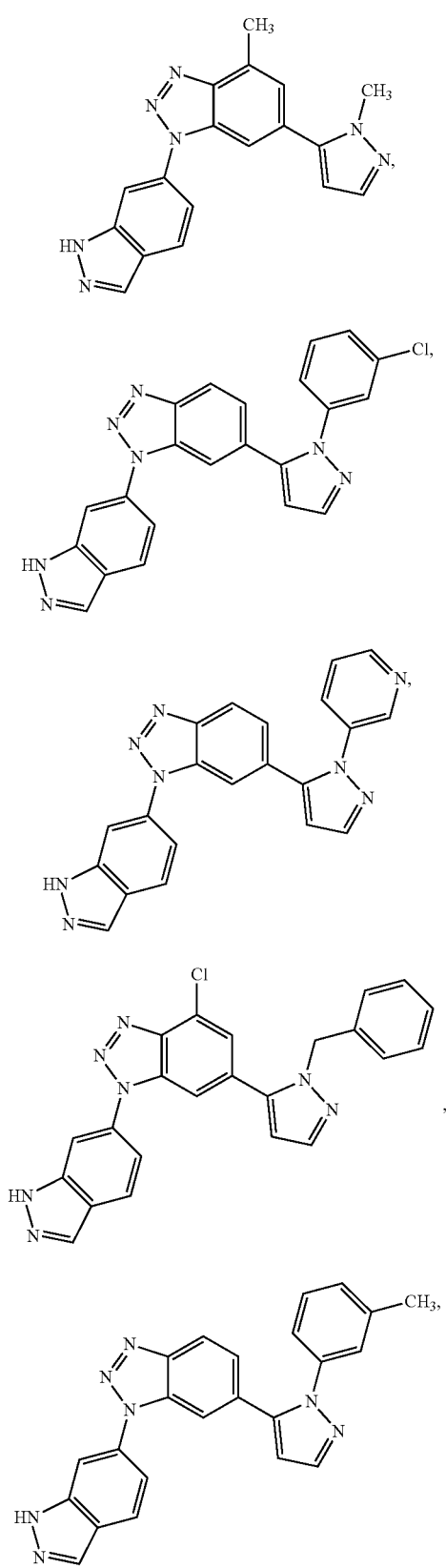
282
-continued
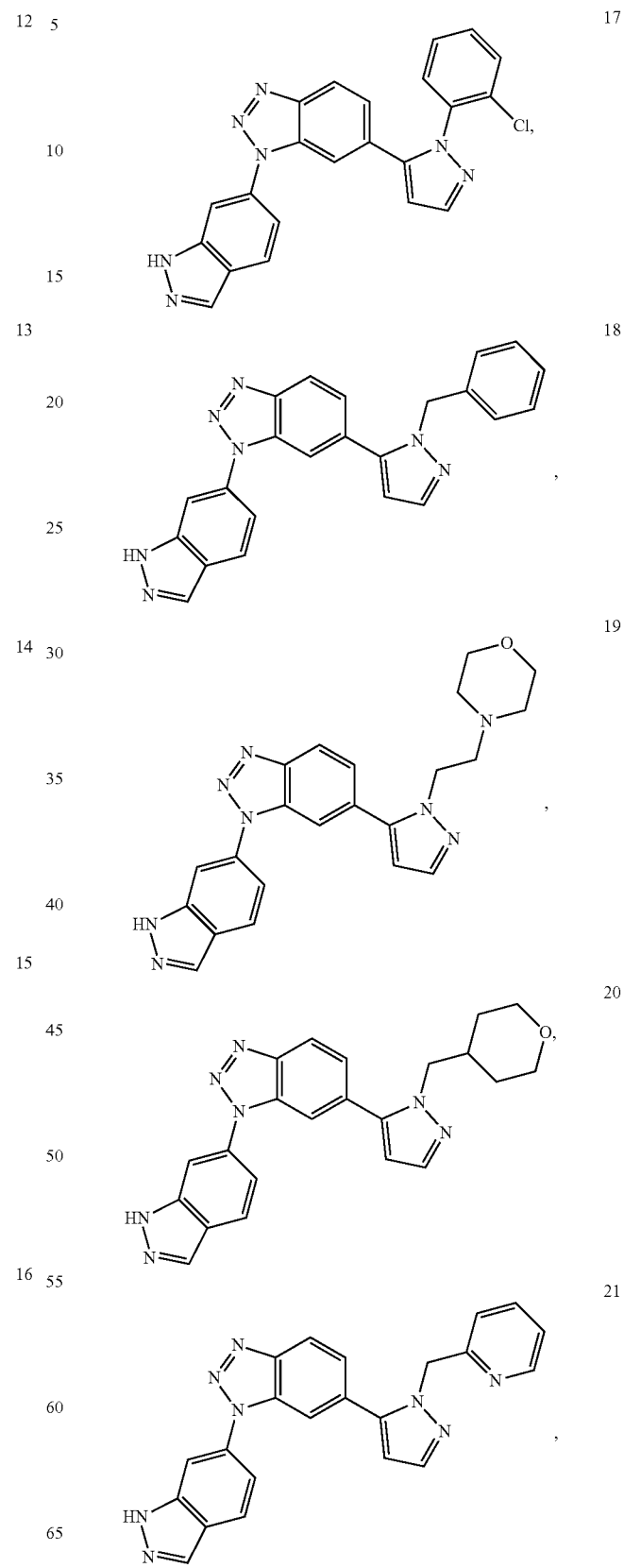

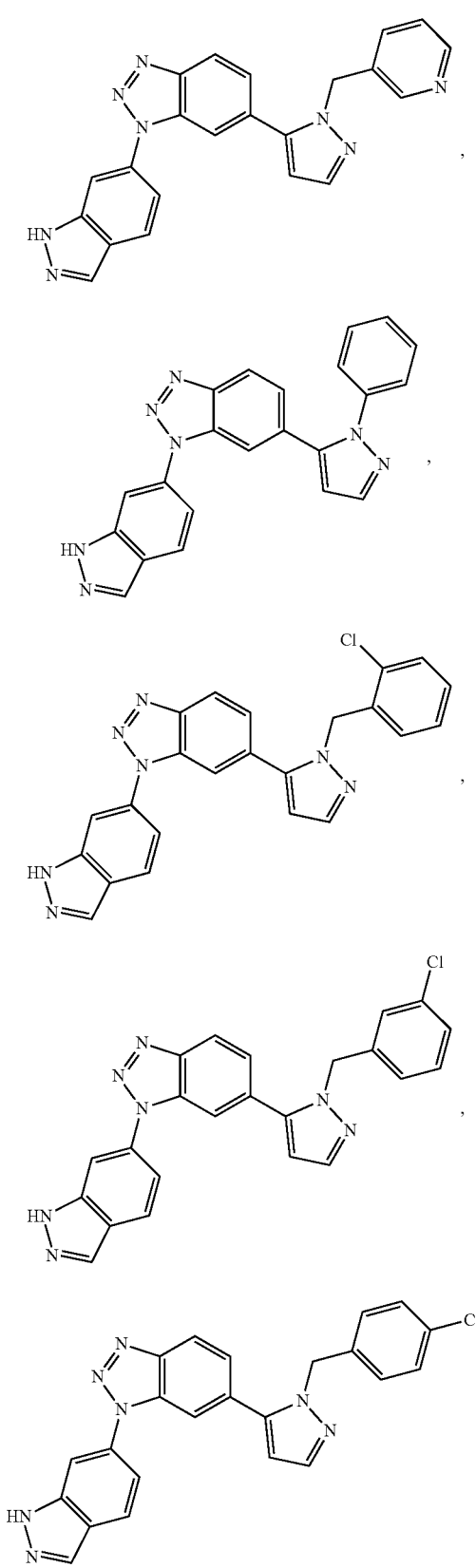
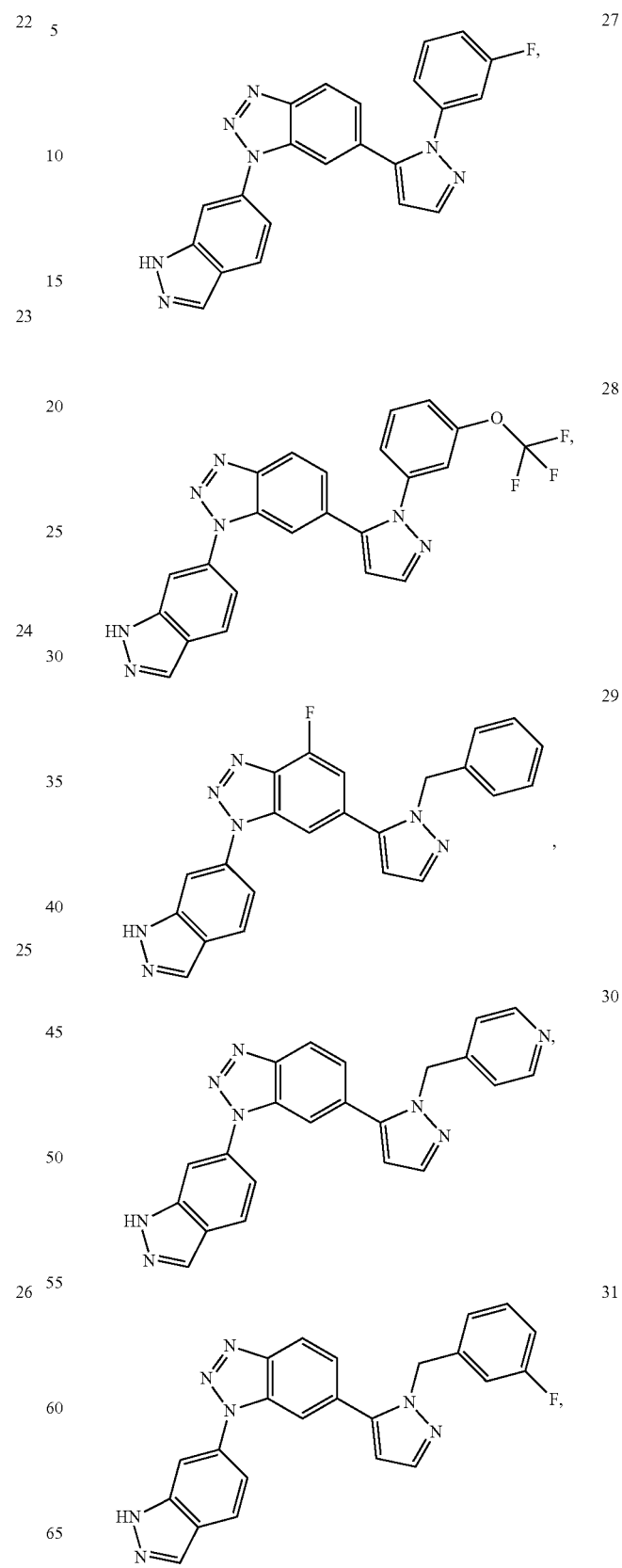

32
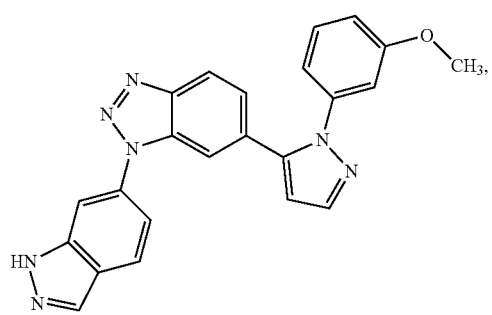
33
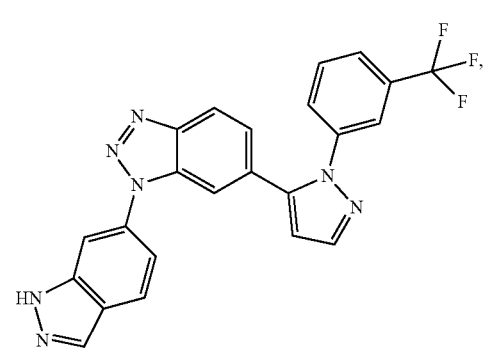
34
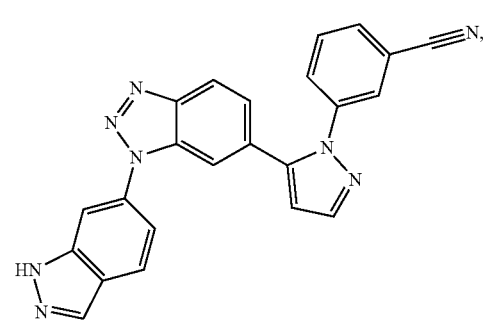
35
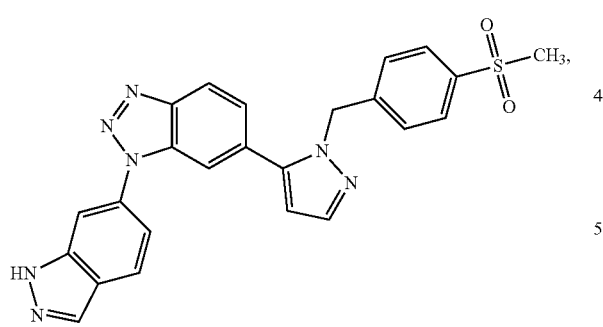
36
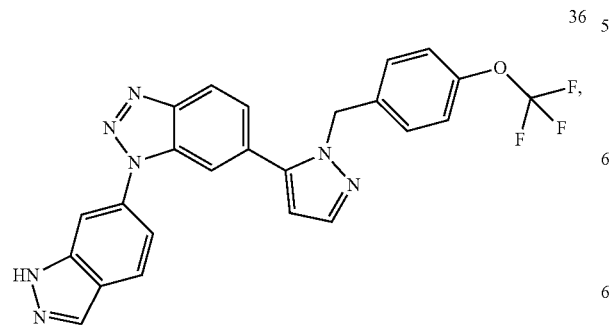
37
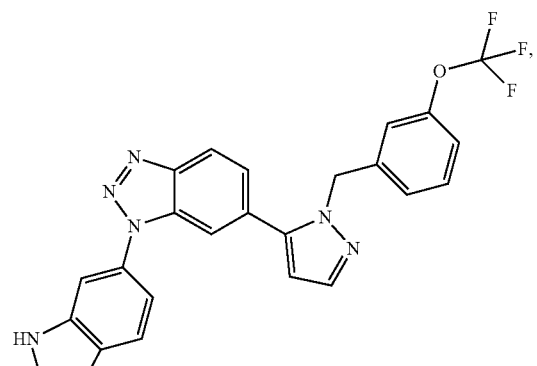
38
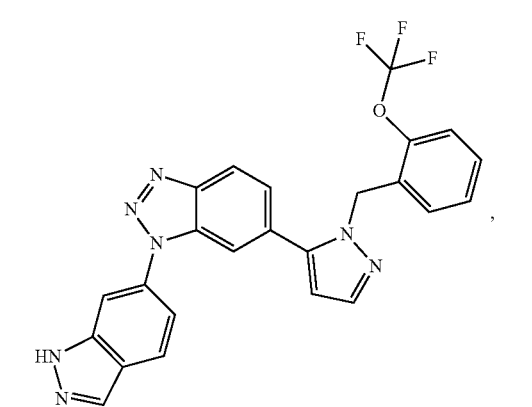
39
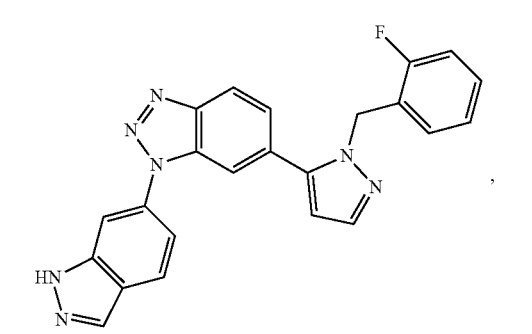
40
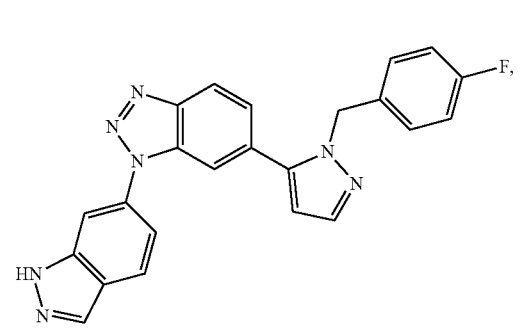

41
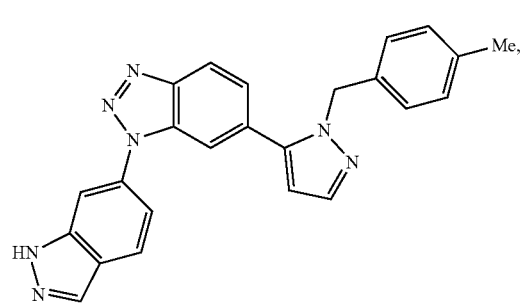
42
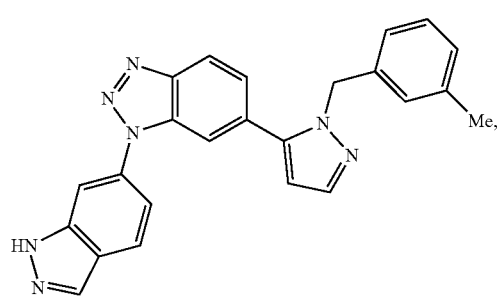
43
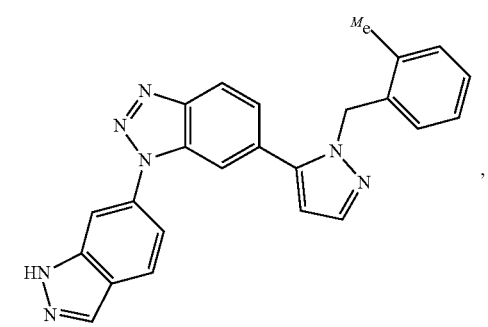
44
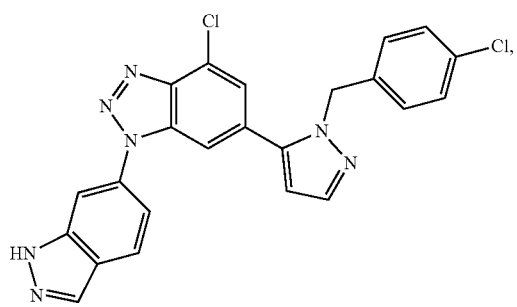
45
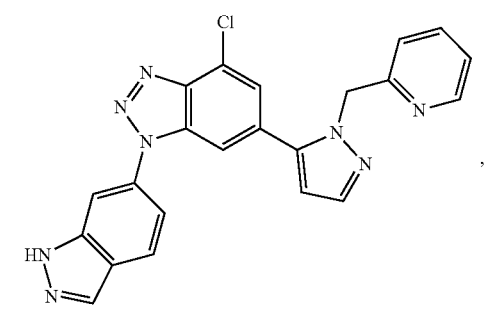
46
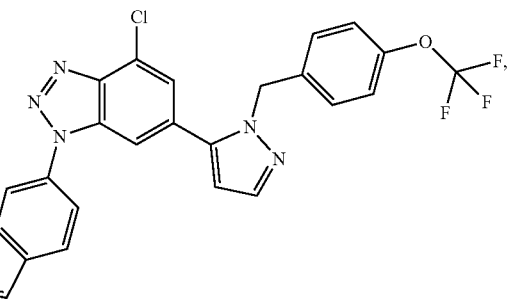
47
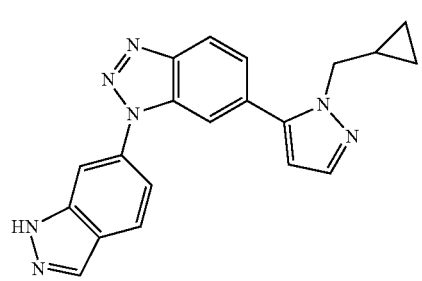
48
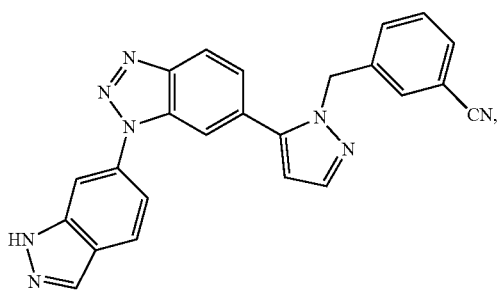
49
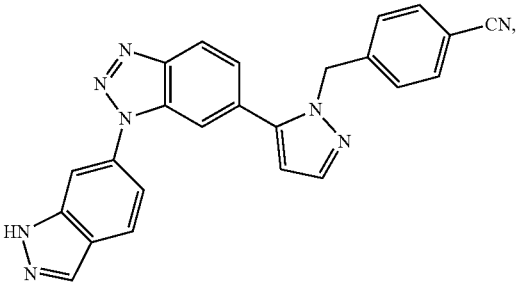
50
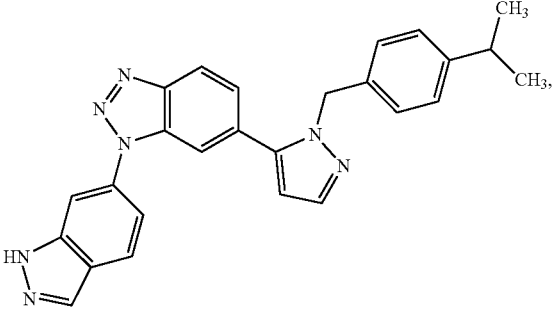

51 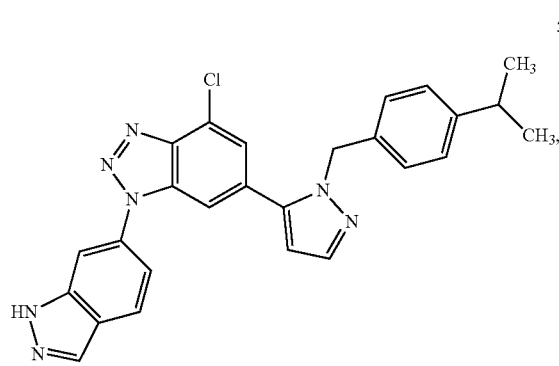
52 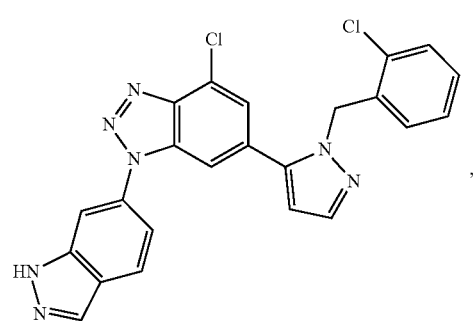
53 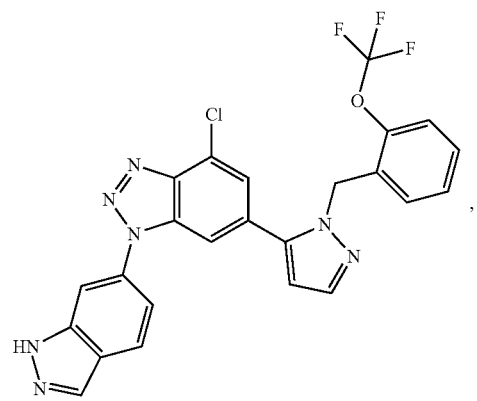
54 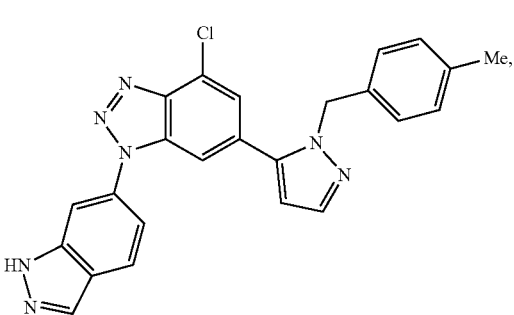
55 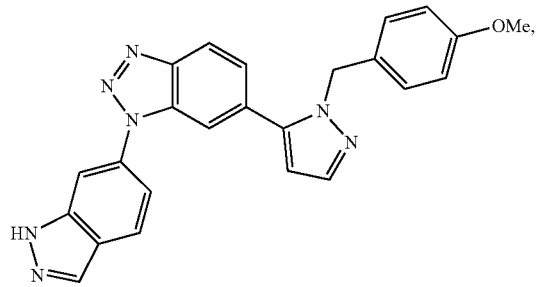
56 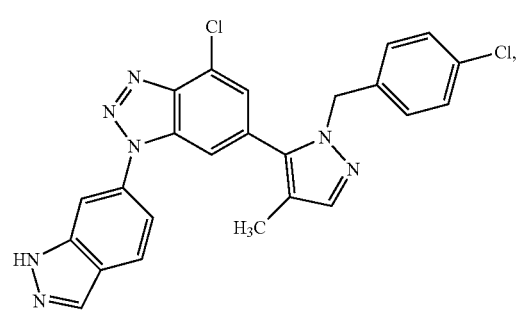
57 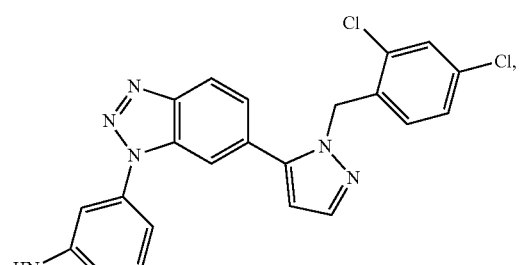
58 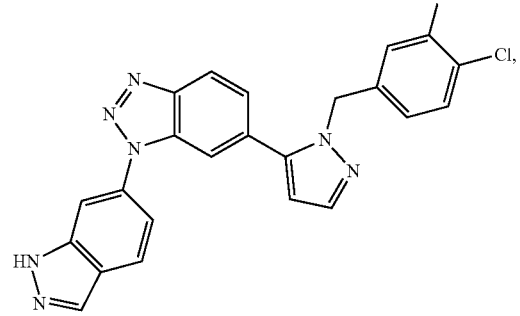
59 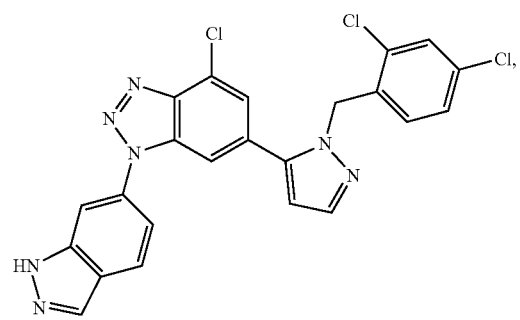

60 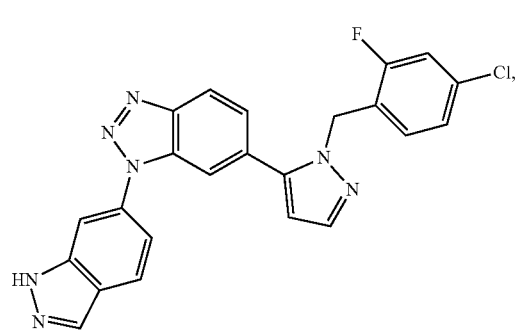
61 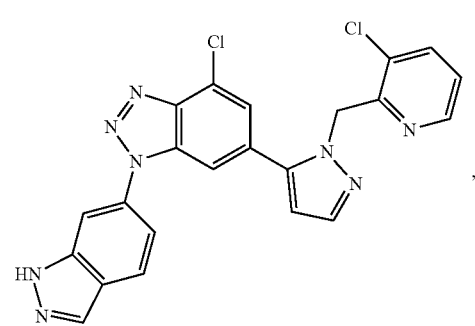
62 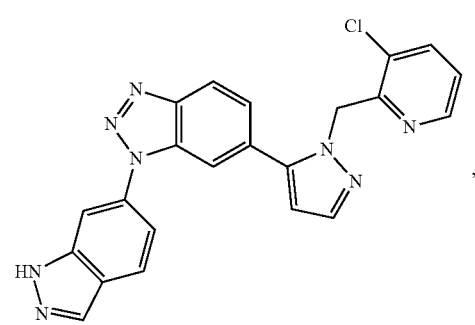
63 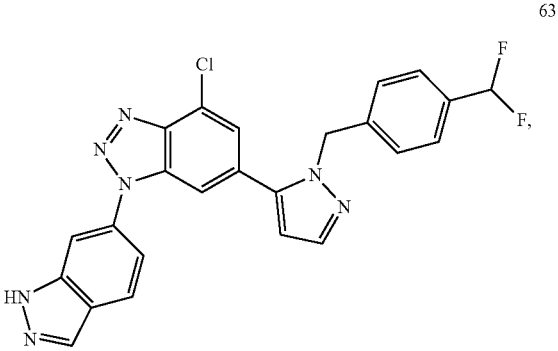
64 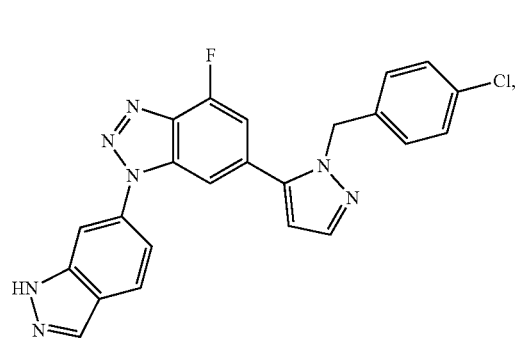
65 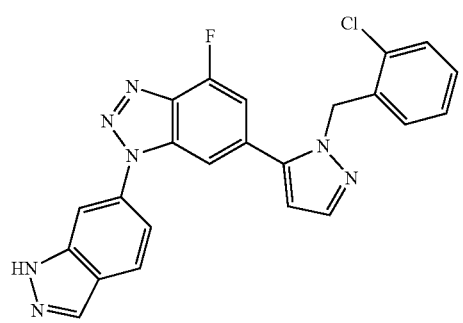
66 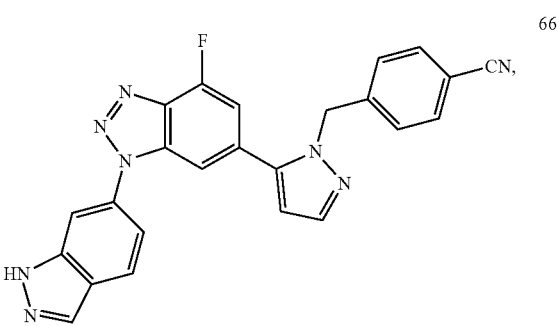
67 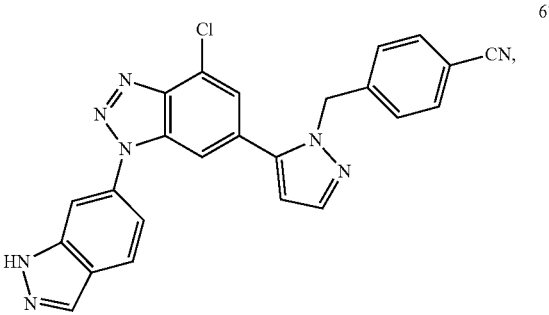
68 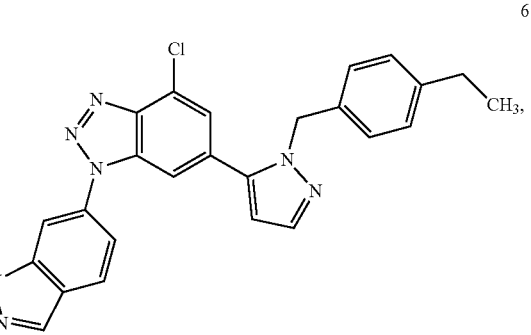
69 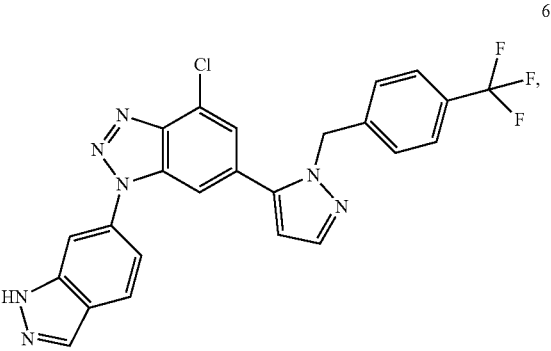

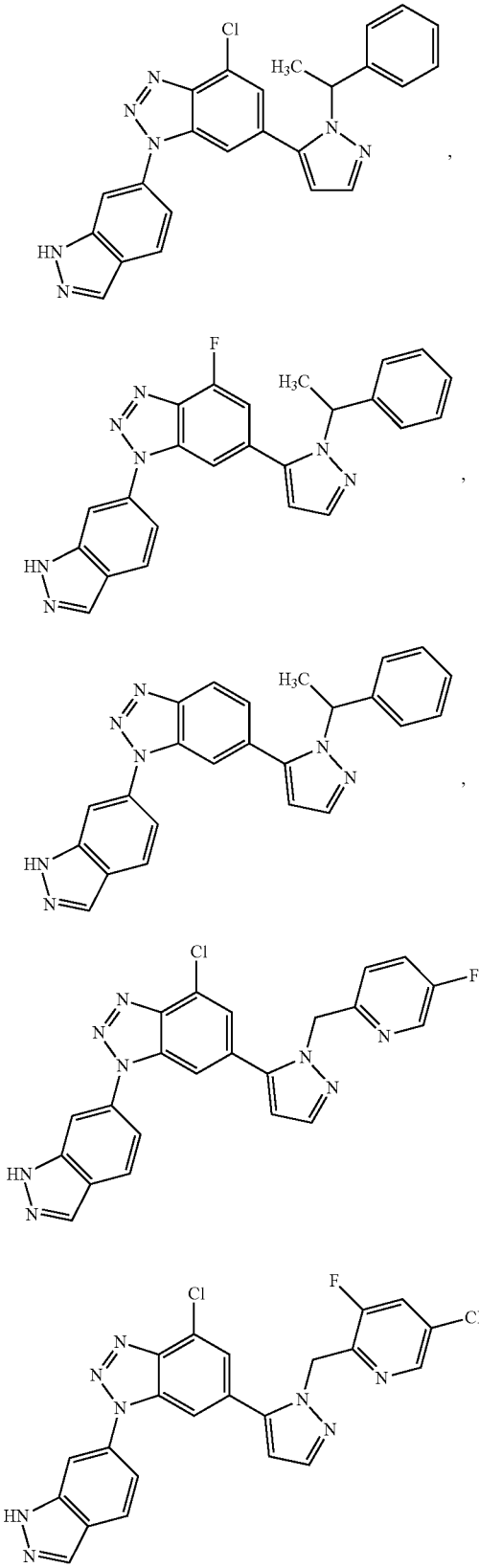
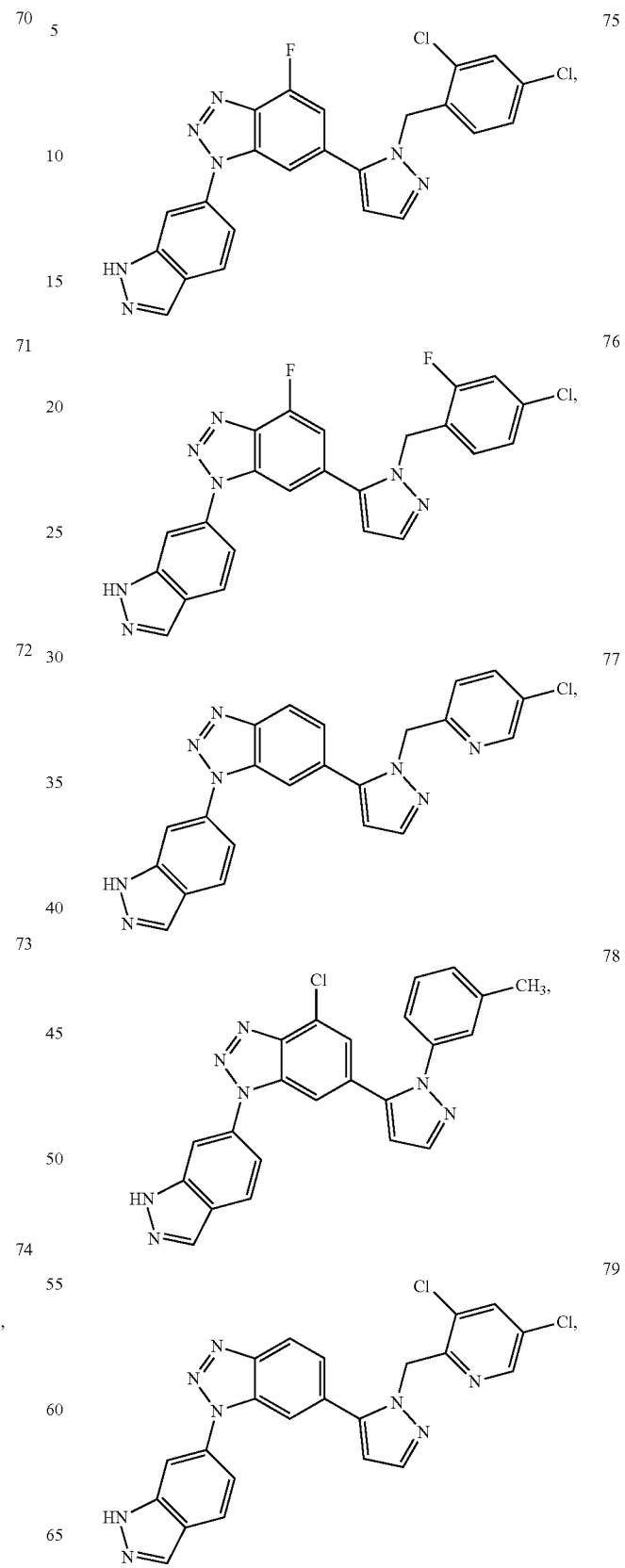

80
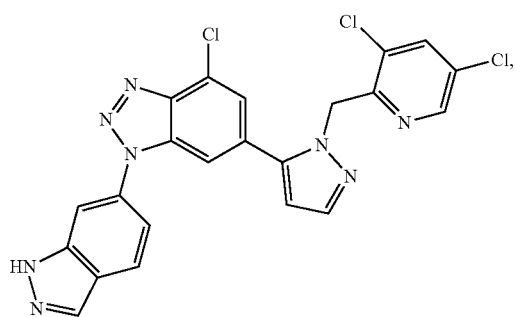
81
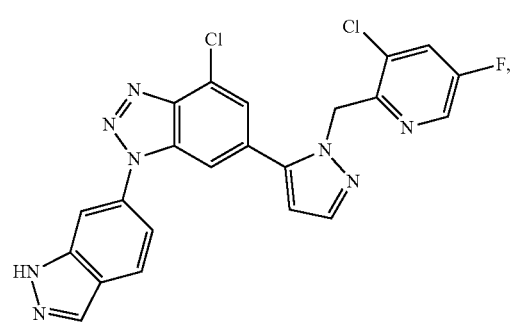
82
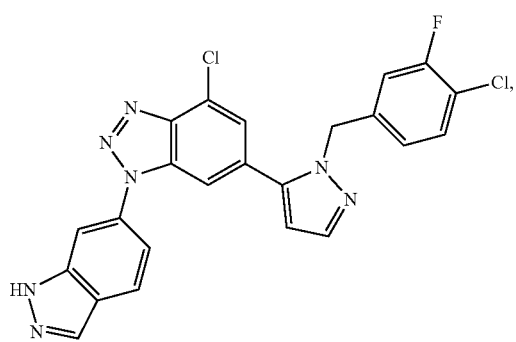
83
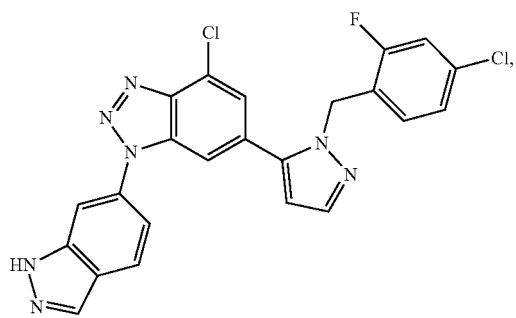
84
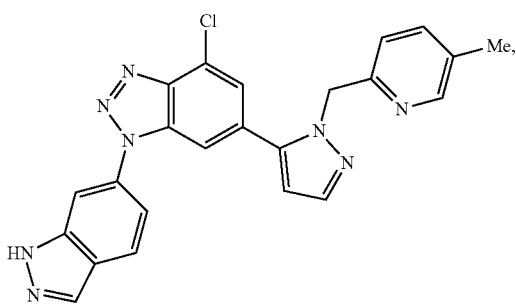
85
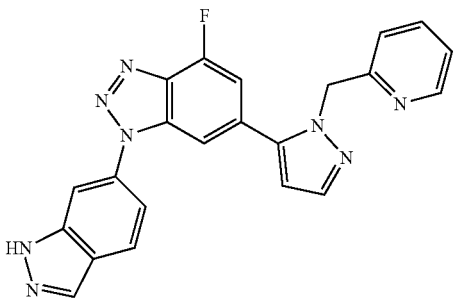
86
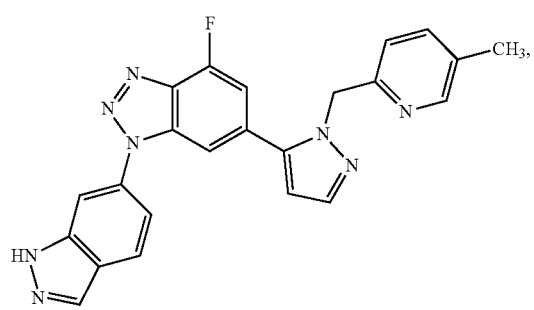
87
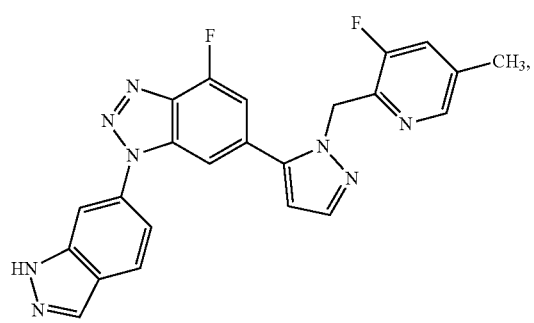
88
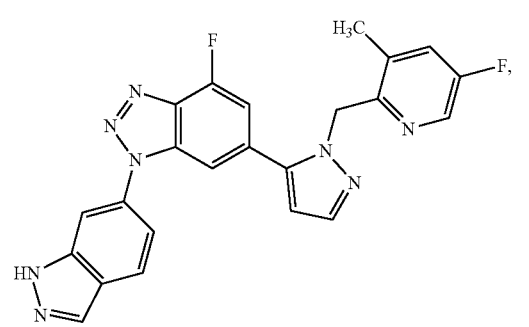
89
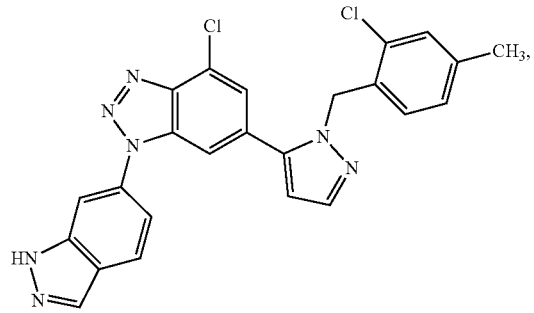

90 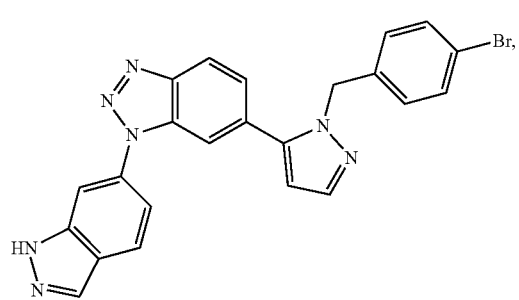
91 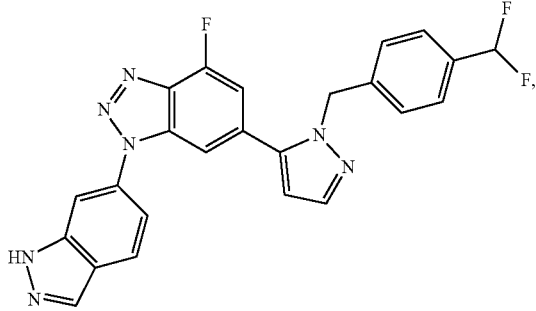
92 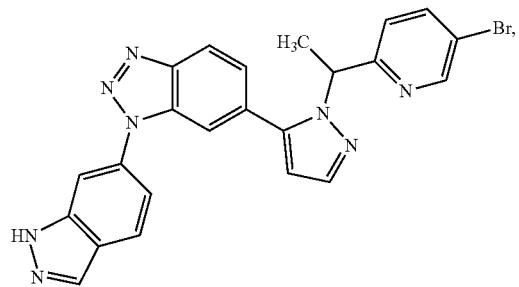
93 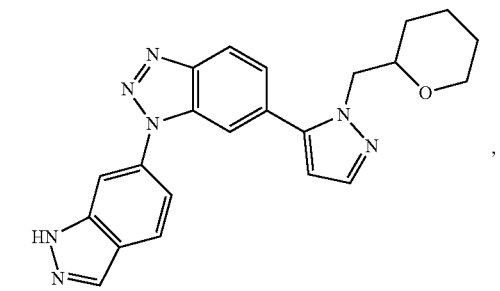
94 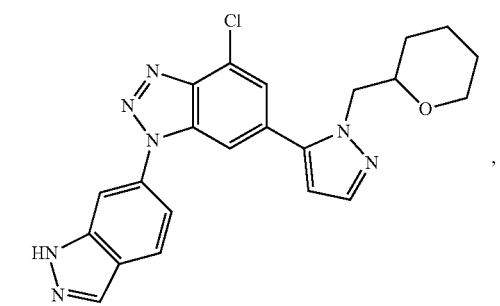
95 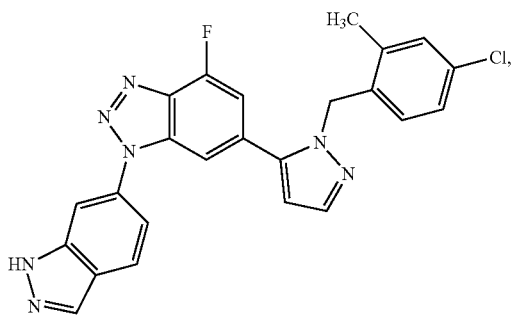
96 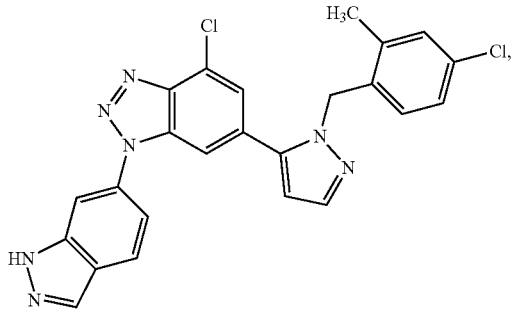
97 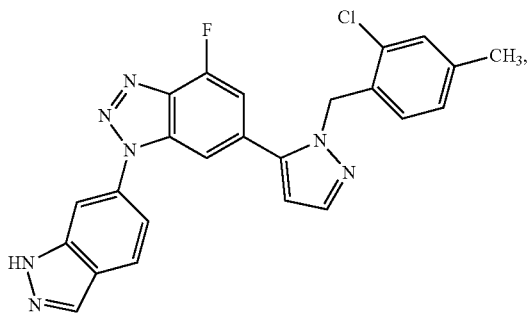
98 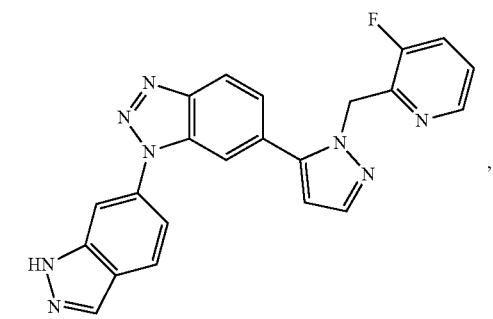
99 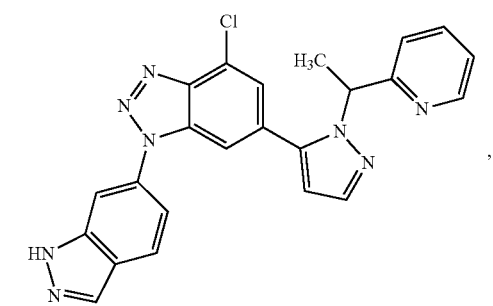

100 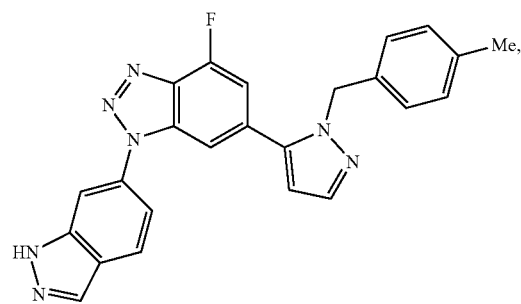
101 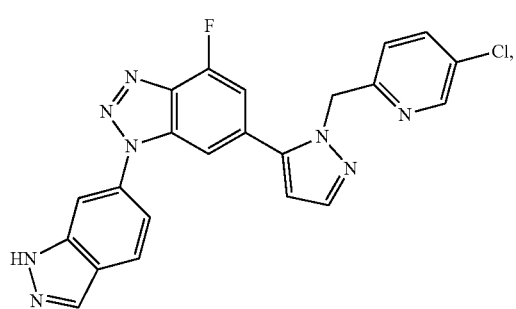
102 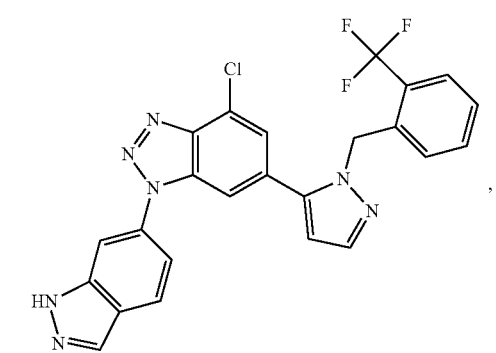
103 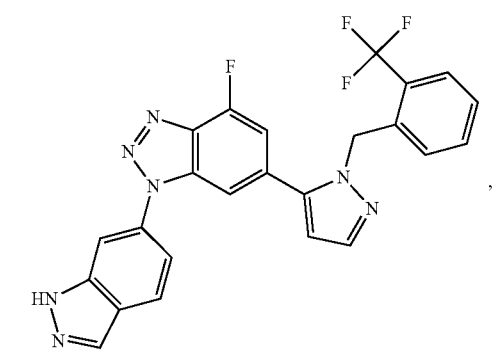
104 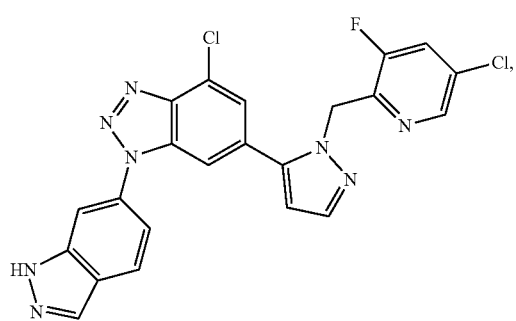
105 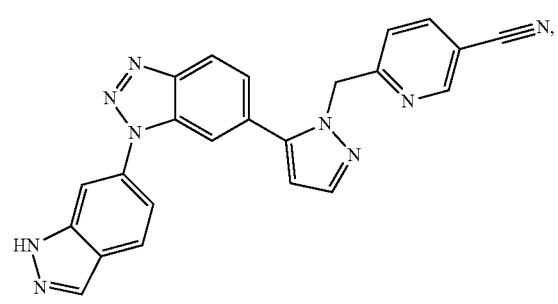
106 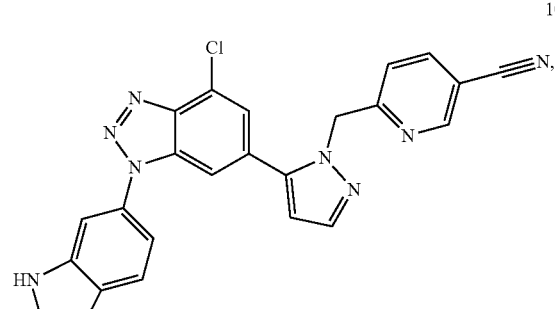
107 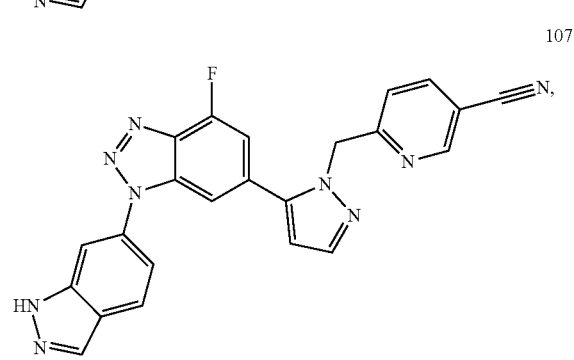
108 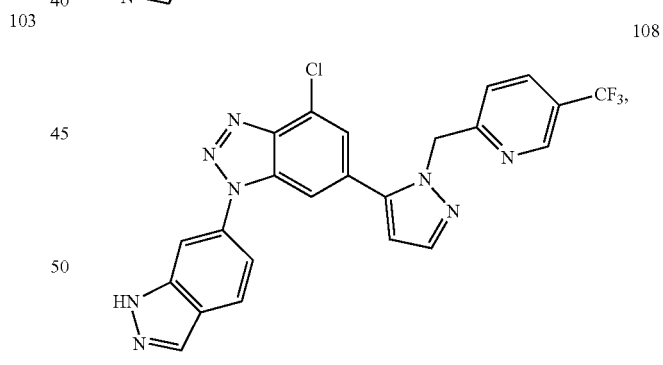
109 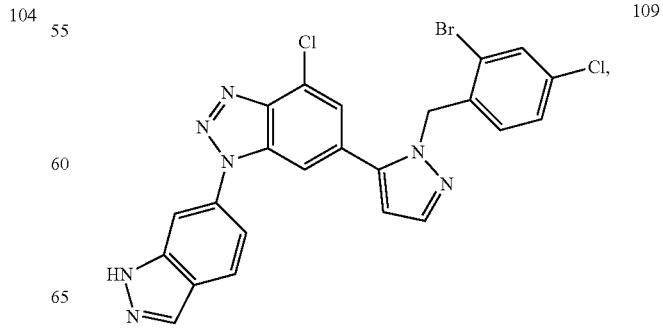

301
-continued
110
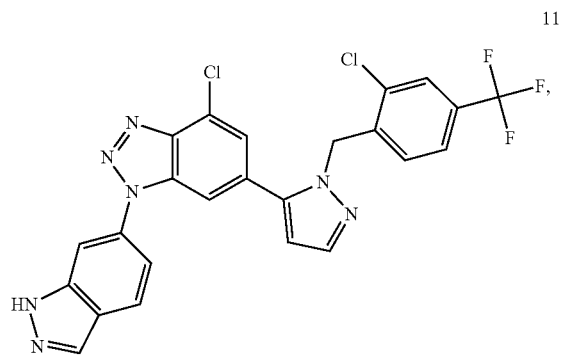
111
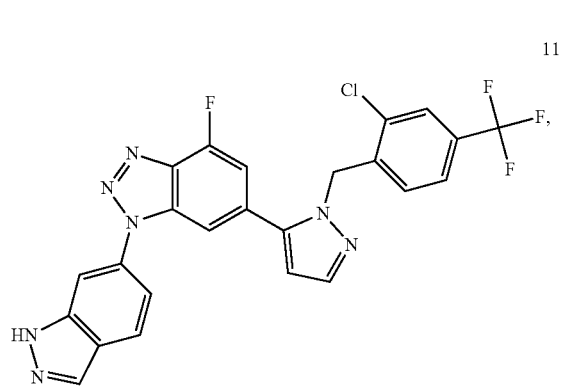
112
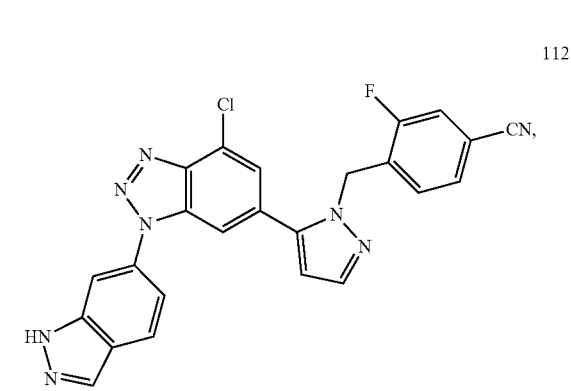
113
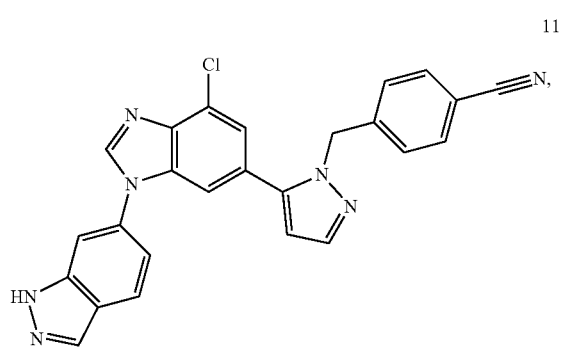
302
-continued
114
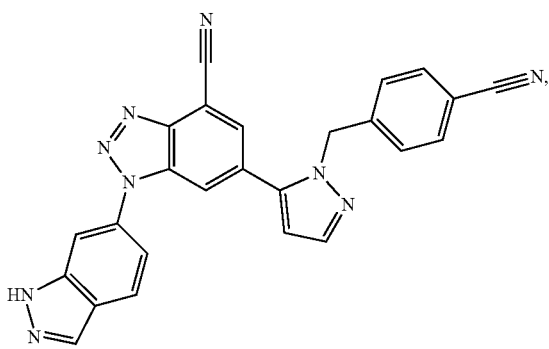
115
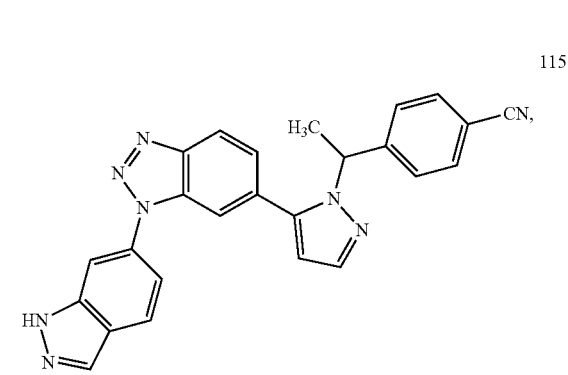
116
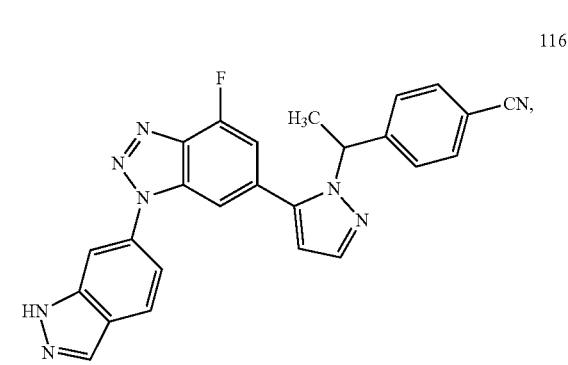
117
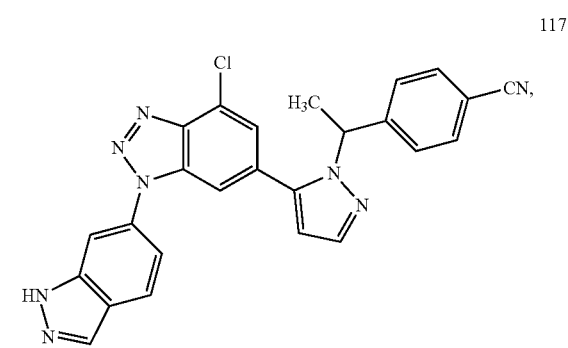

118
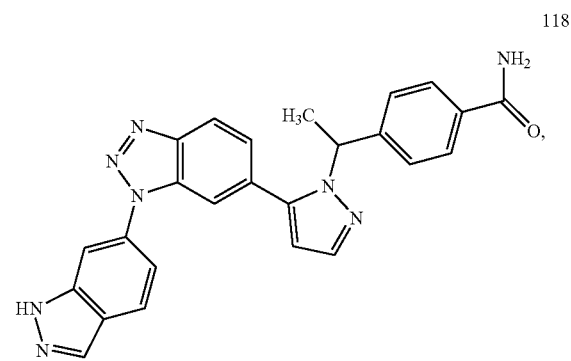
119
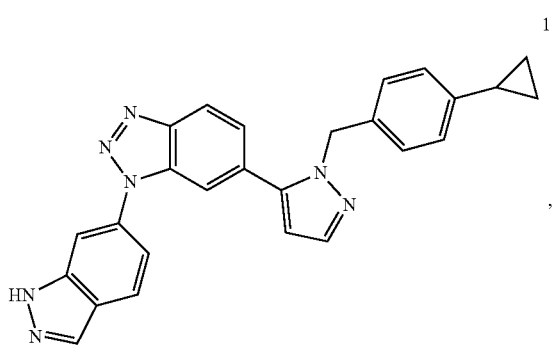
120
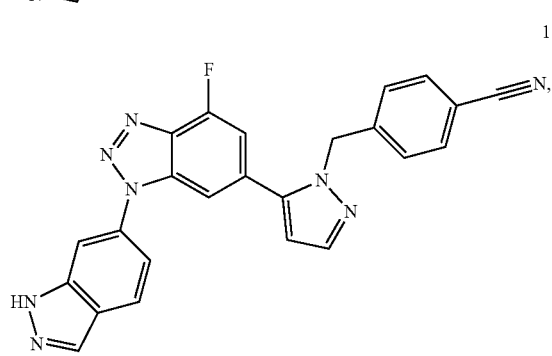
121
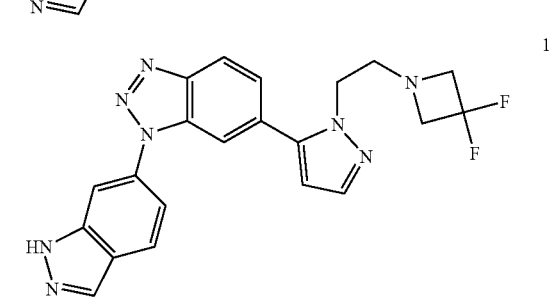
122
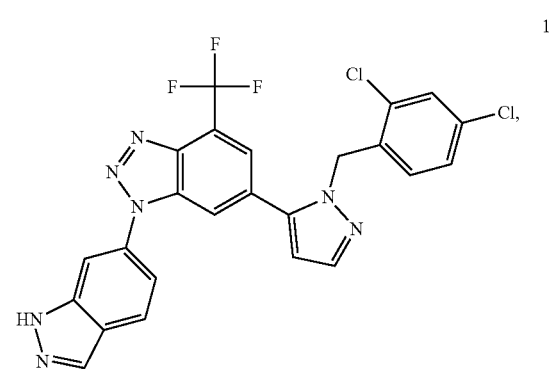
123
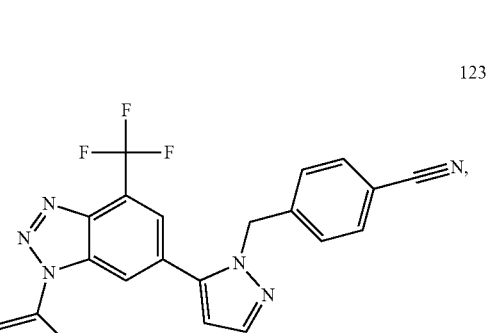
124
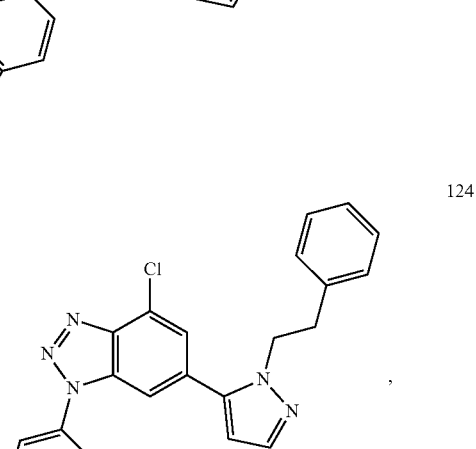
125
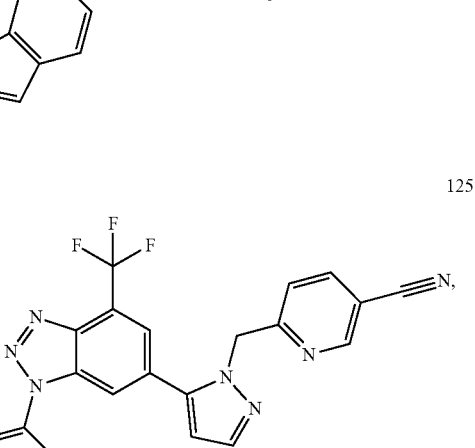
126
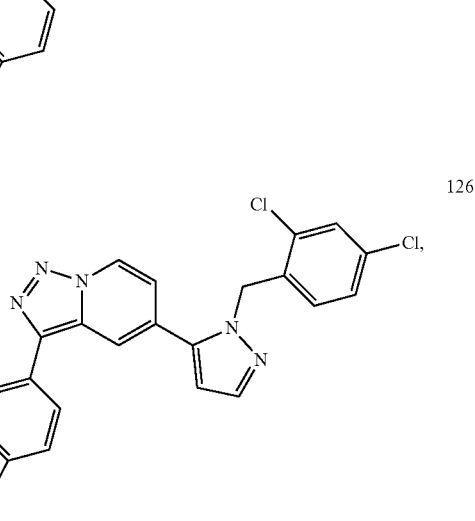

127
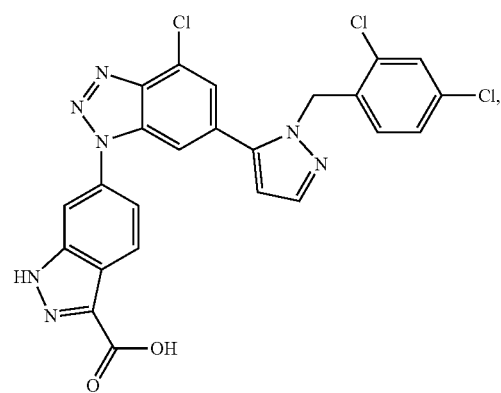
128
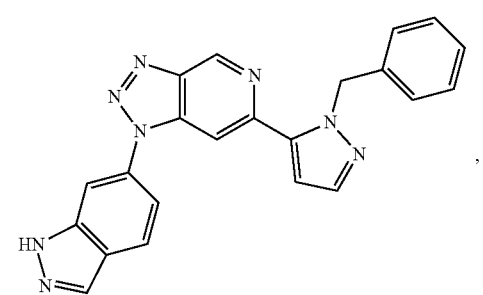
129
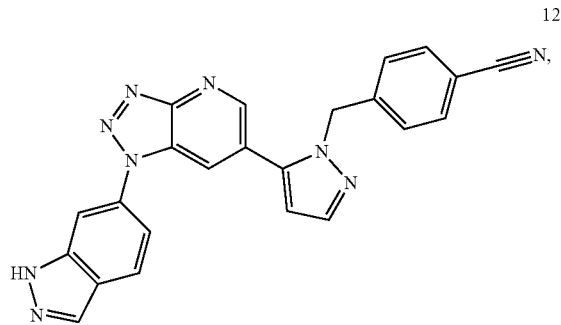
130
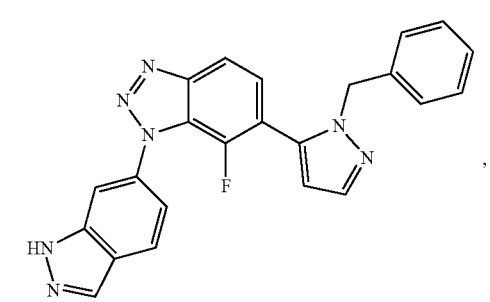
131
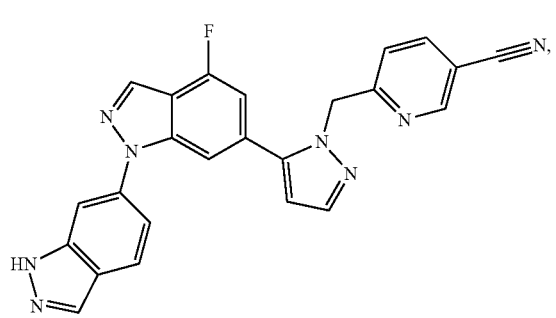
132
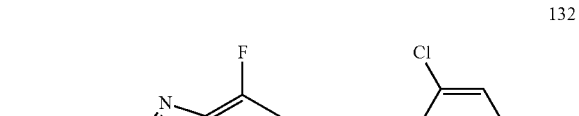
133
134
135
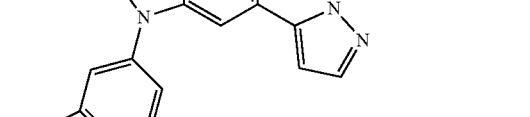
136

| 137 | 142 |
| --- | --- |
| 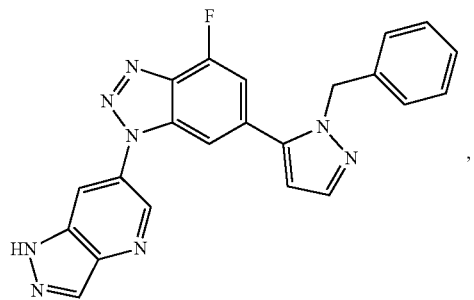 | 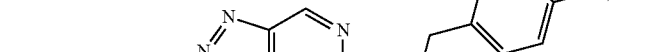 |
| 138 | 143 |
| 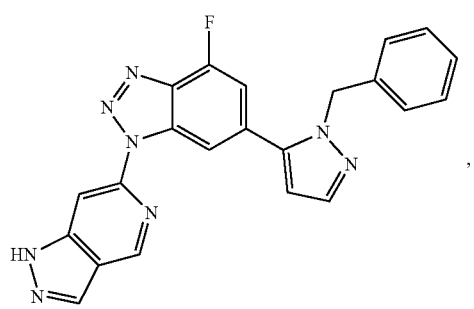 | 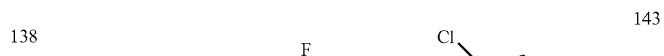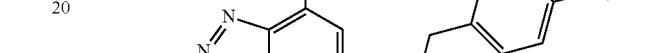 |
| 139 | 144 |
| 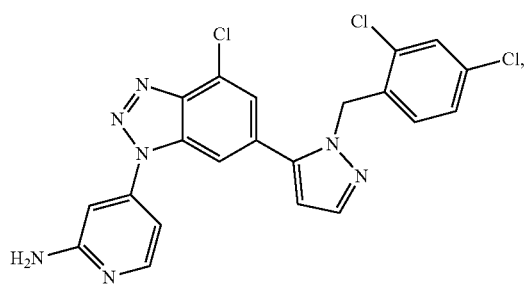 |  |
| 140 | 145 |
| 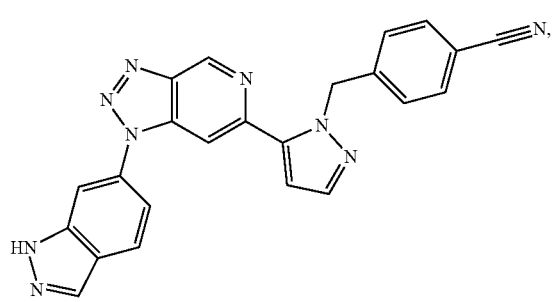 | 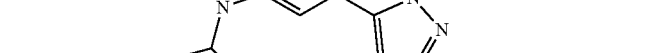 |
| 141 | 146 |
| 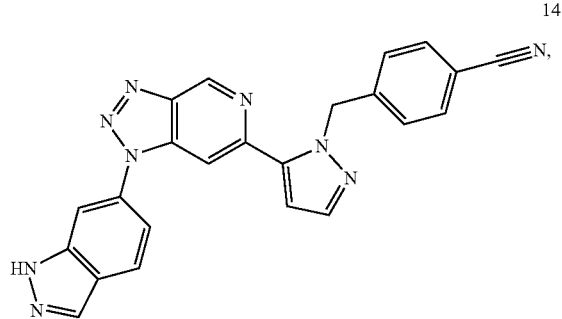 | 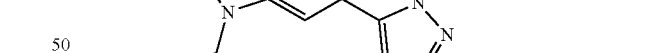 |

147 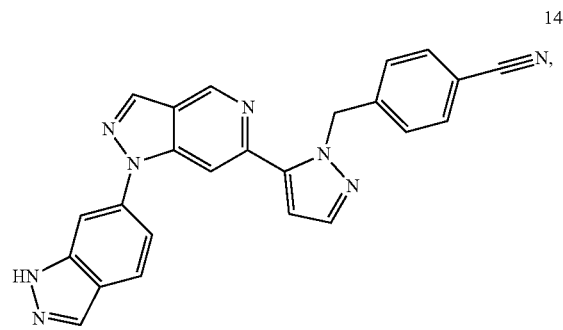
148 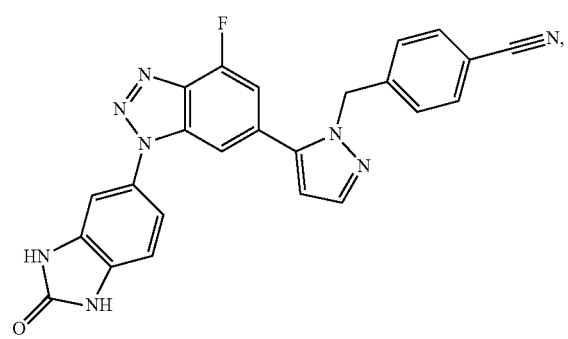
149 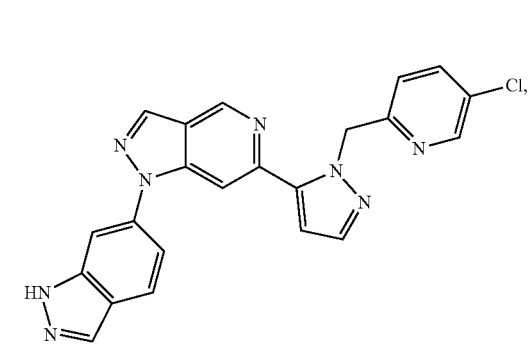
150 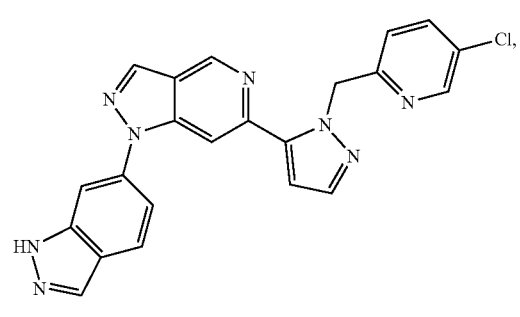
151 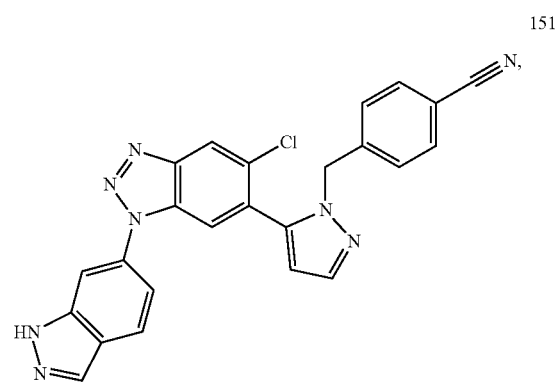
152 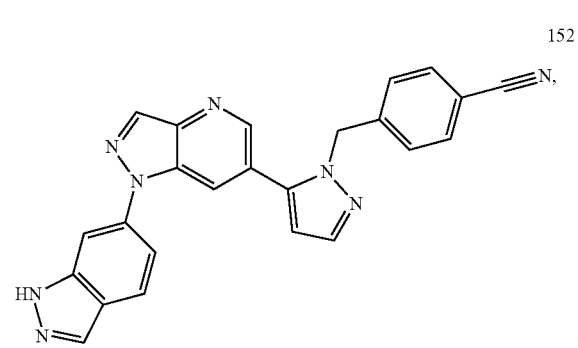
153 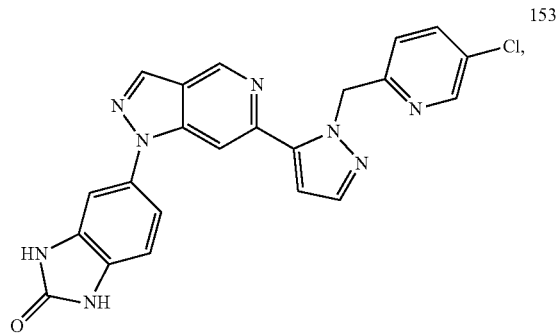
154 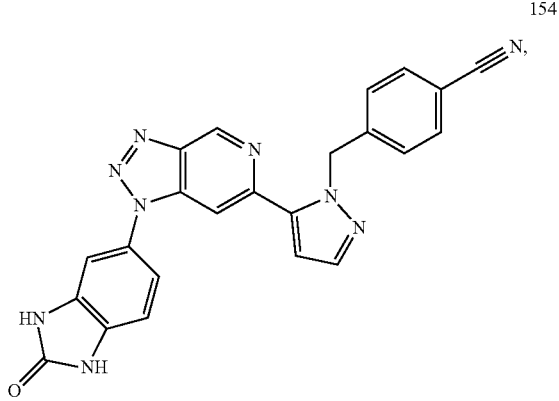

311
-continued
312
-continued
155
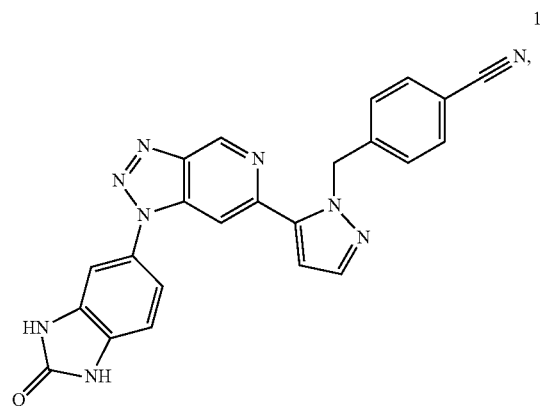
159
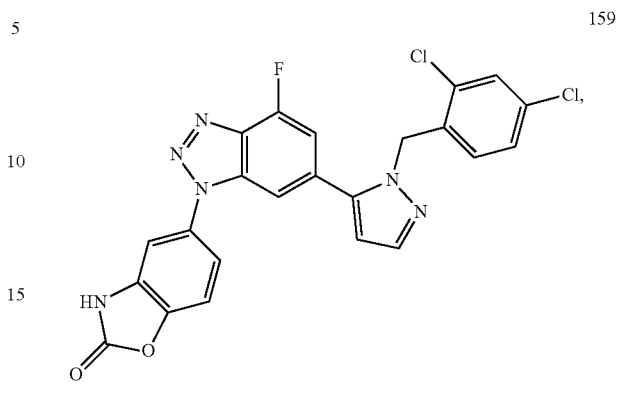
156
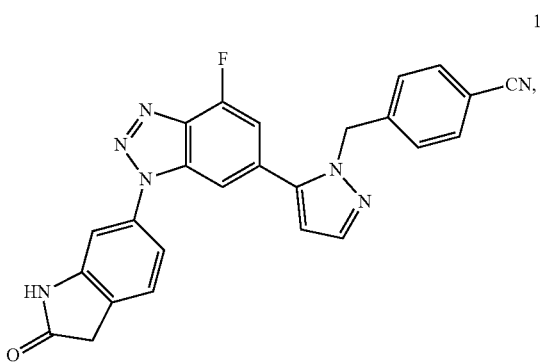
160
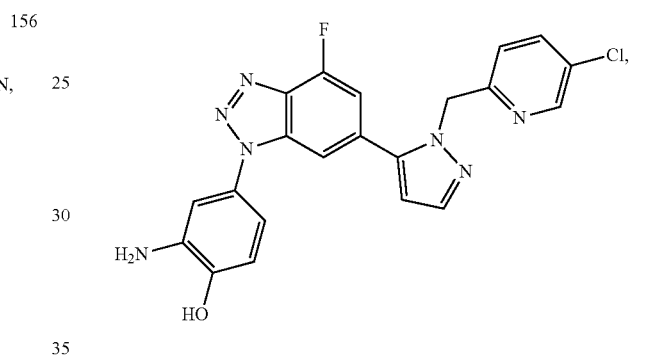
157
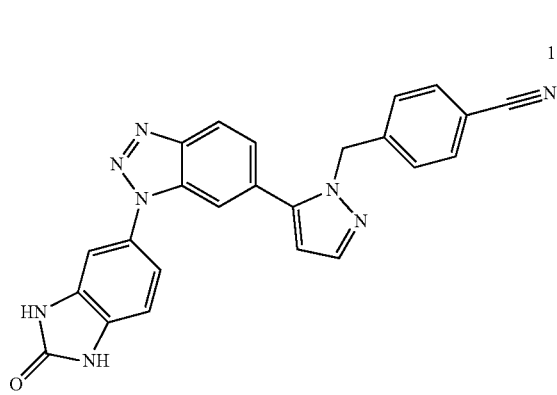
161
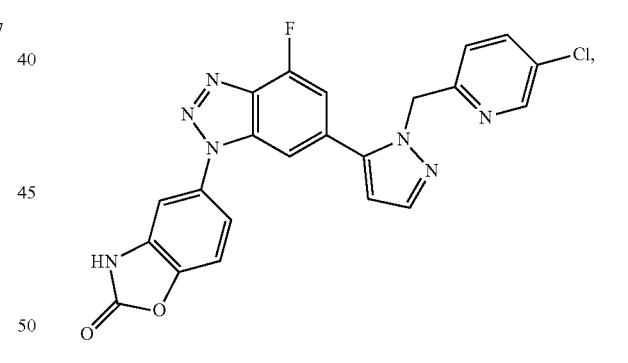
158
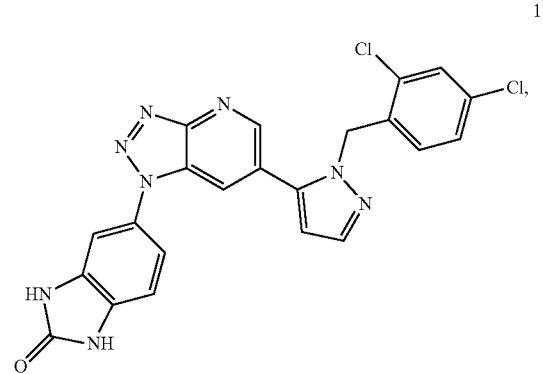
162
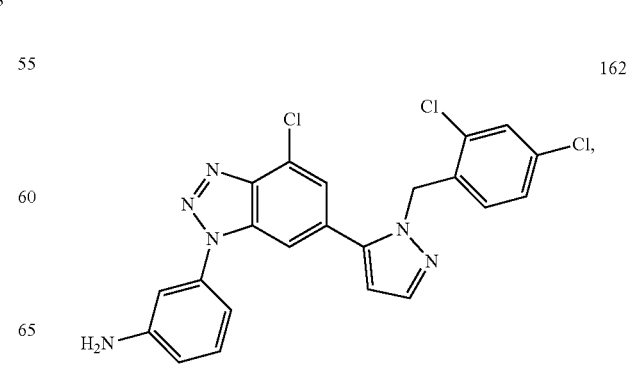

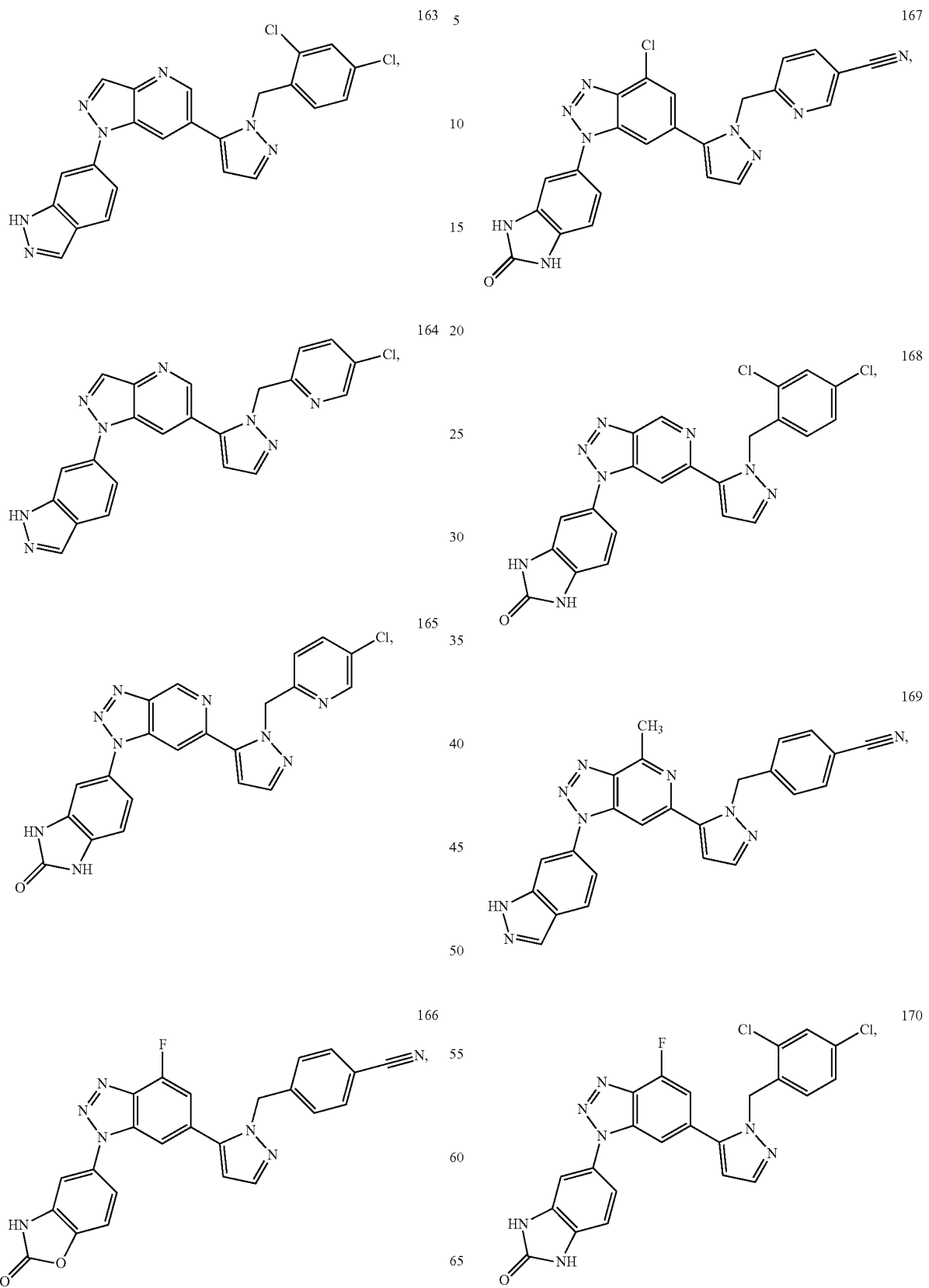

171 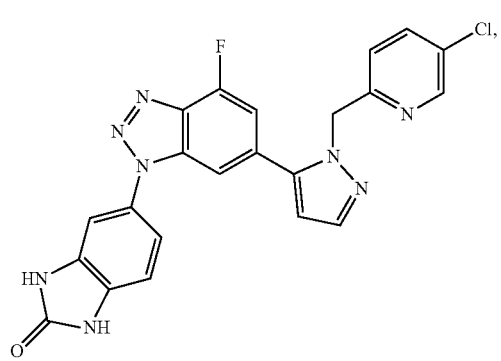
172 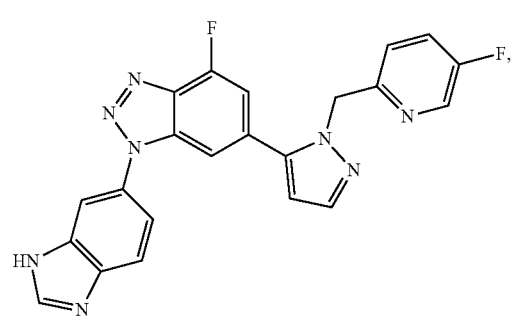
173 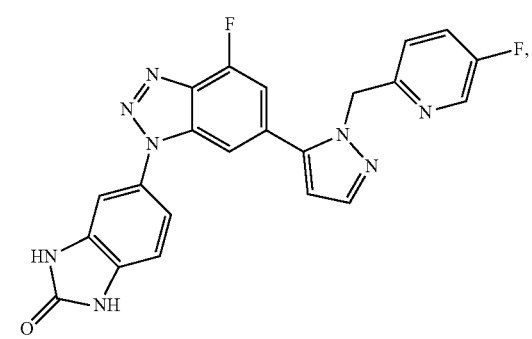
174 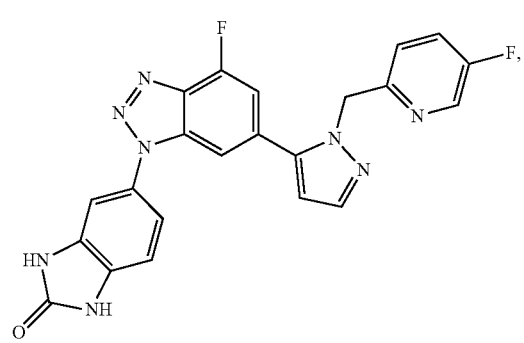
175 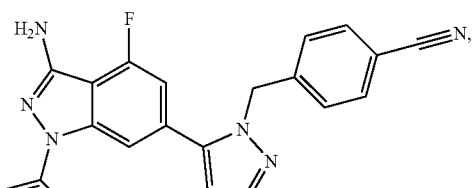
176 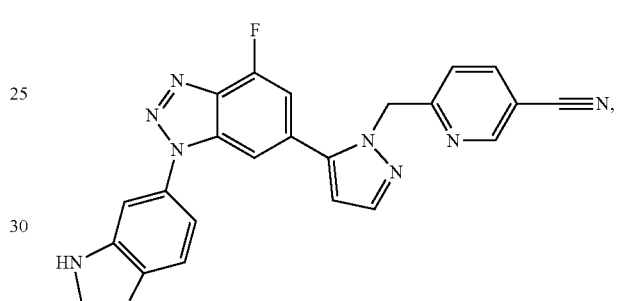
177 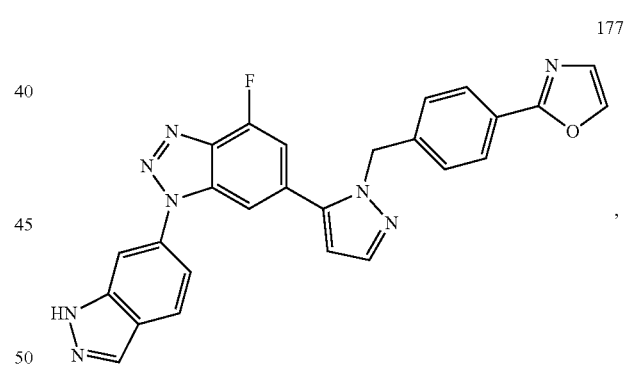
178 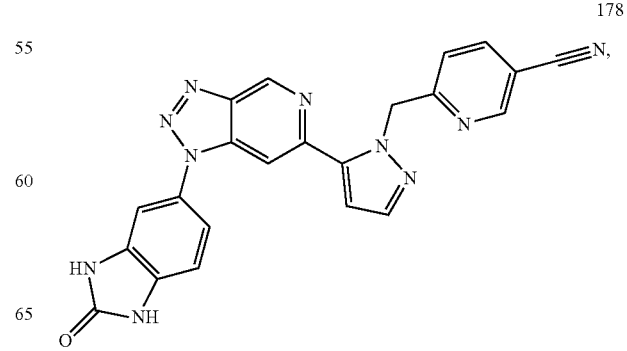

179
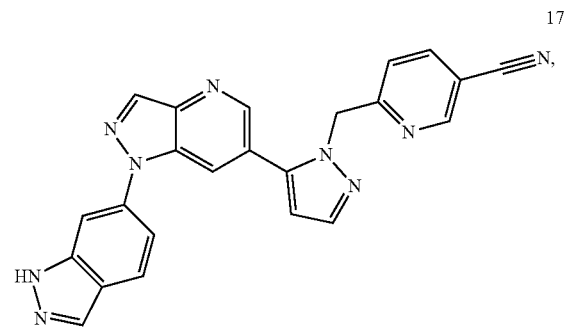
183
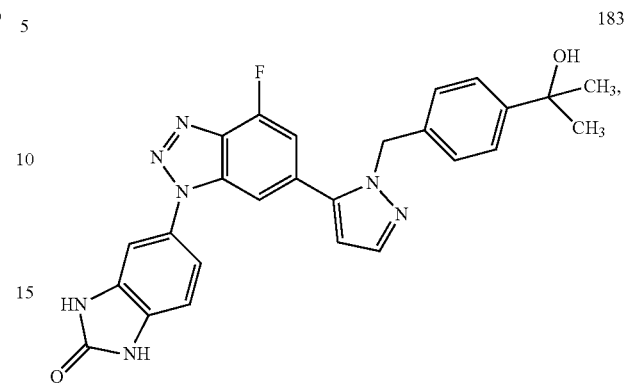
180
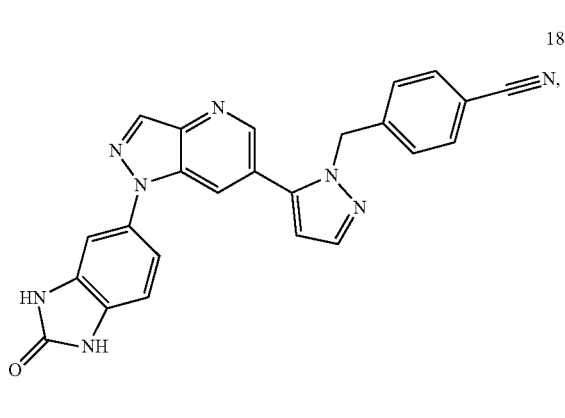
184
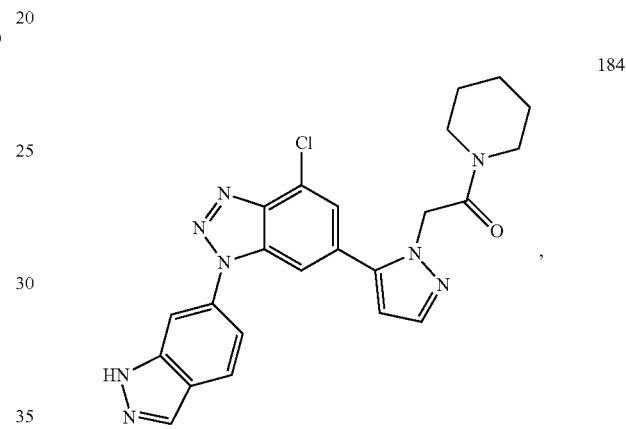
181
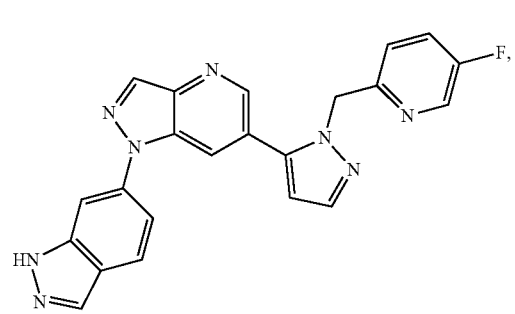
185
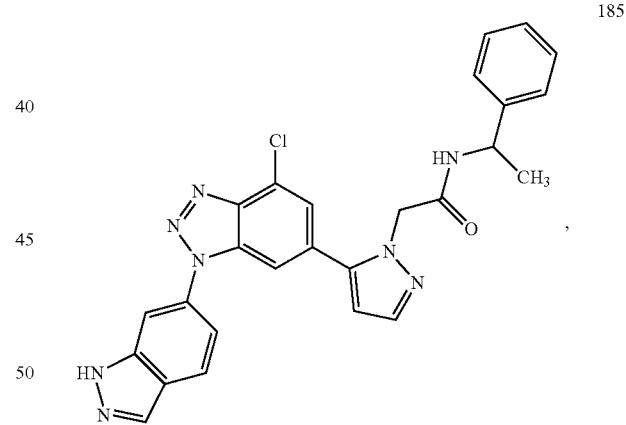
182
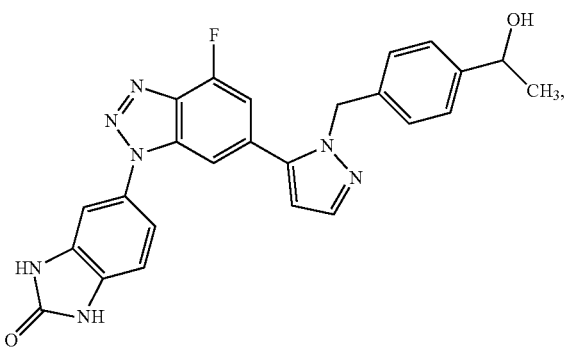
186
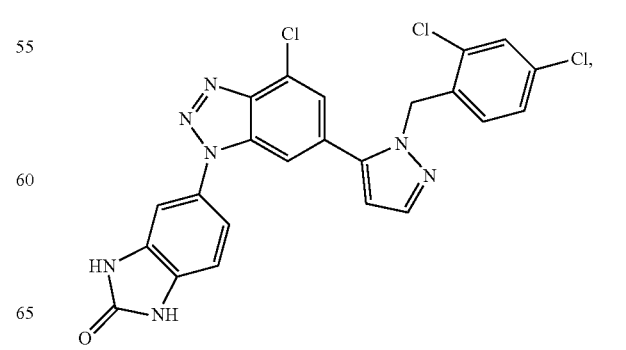

319
-continued
187
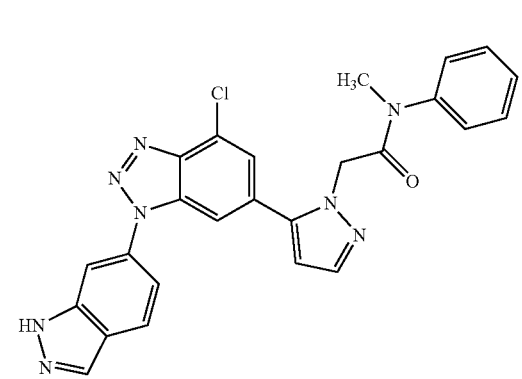
188
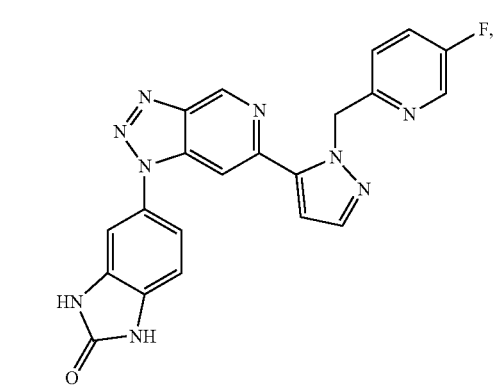
189
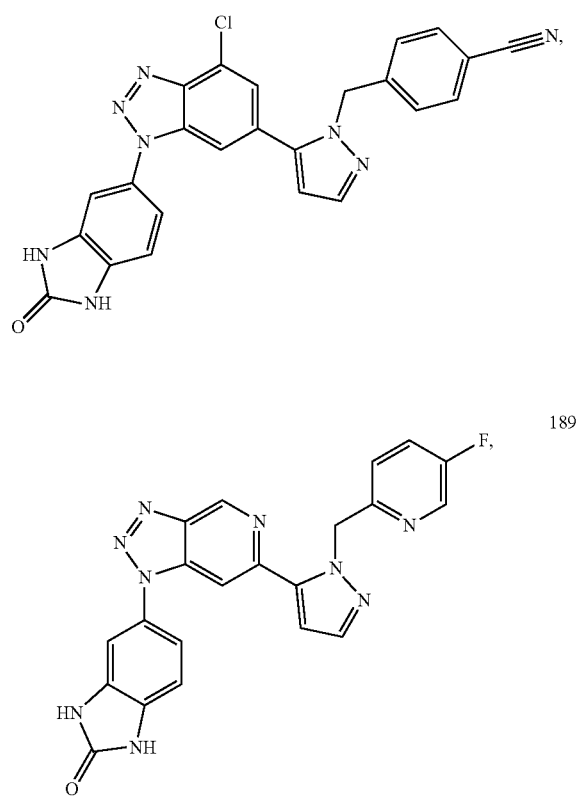
190
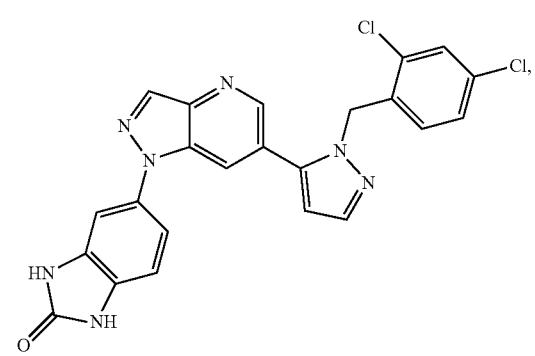
320
-continued
191
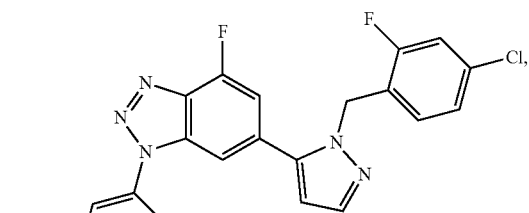
192
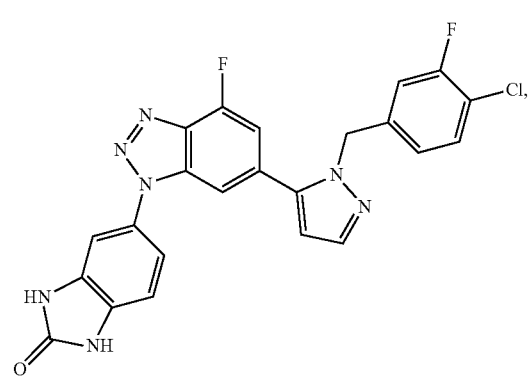
193
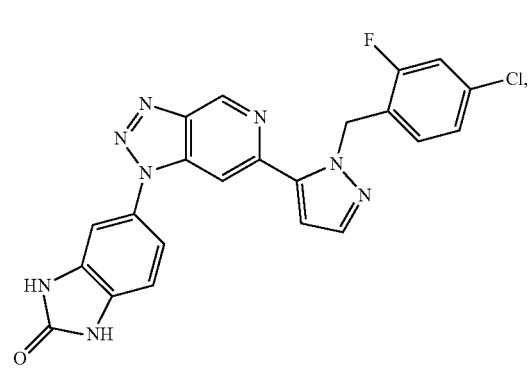
194
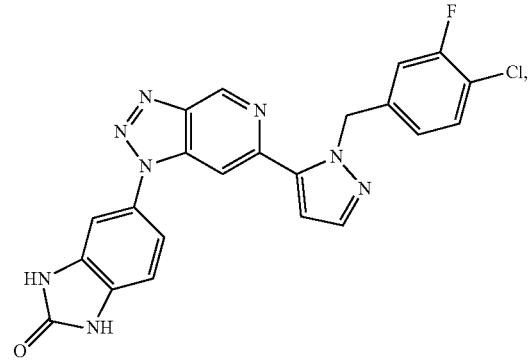

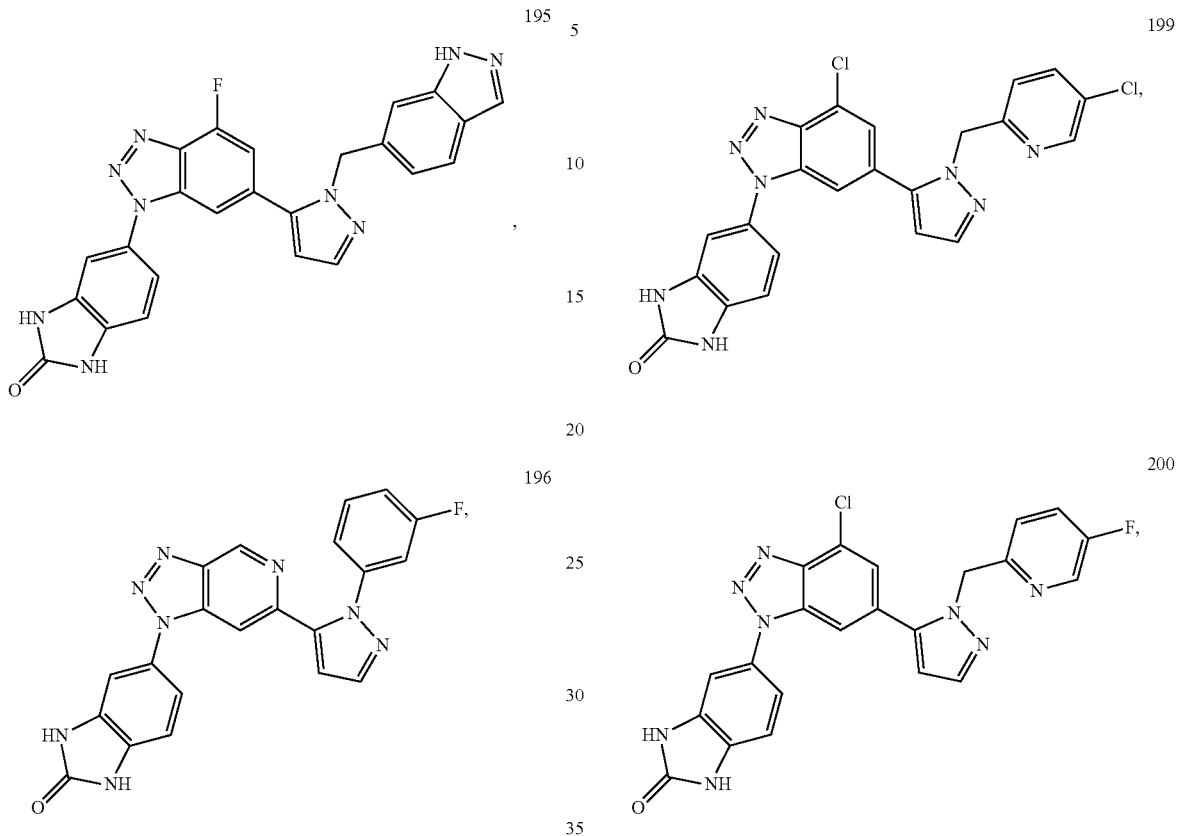
195
196
197
198
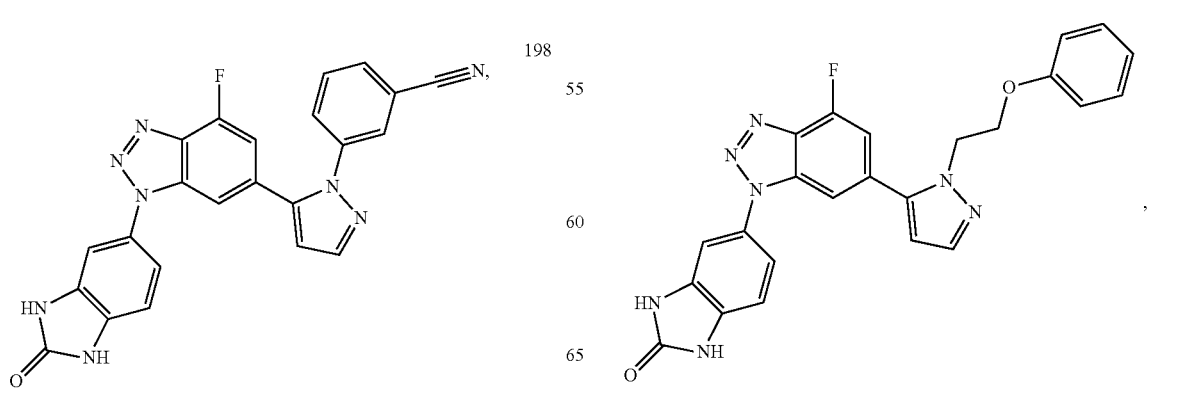
199
200
201
202

323
-continued
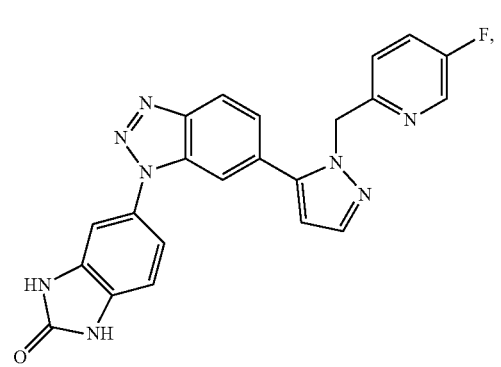
203
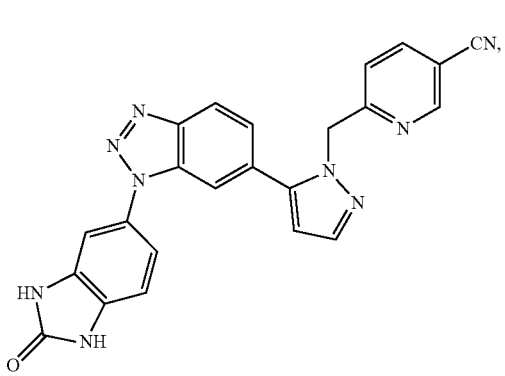
204
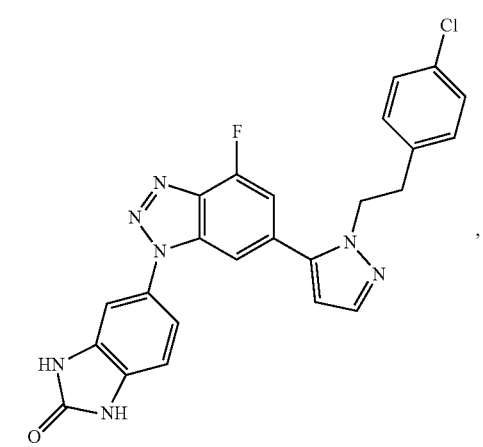
205
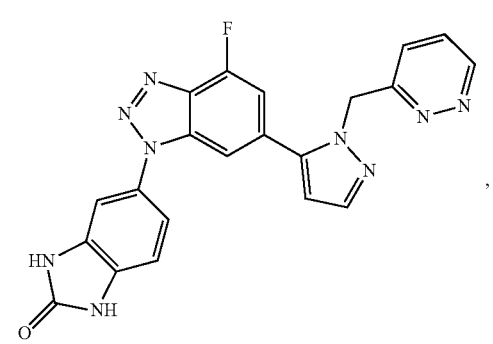
206
324
-continued
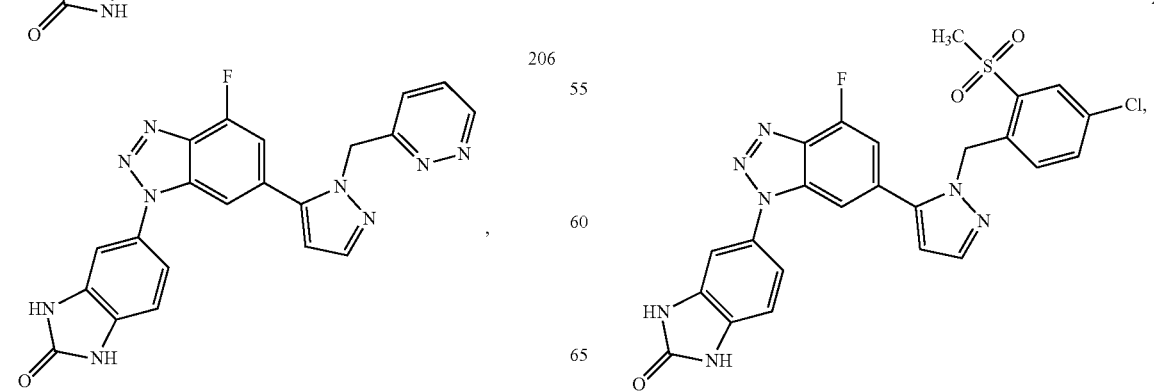

325
-continued
326
-continued
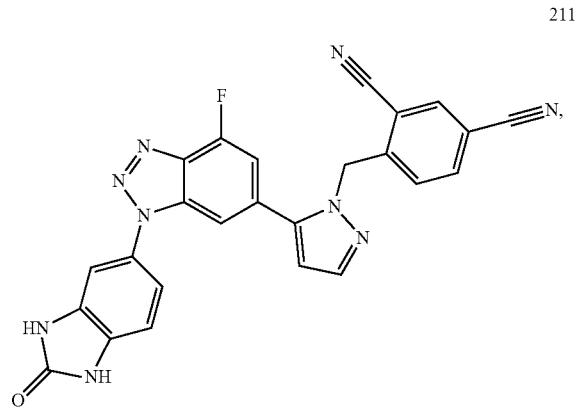
211
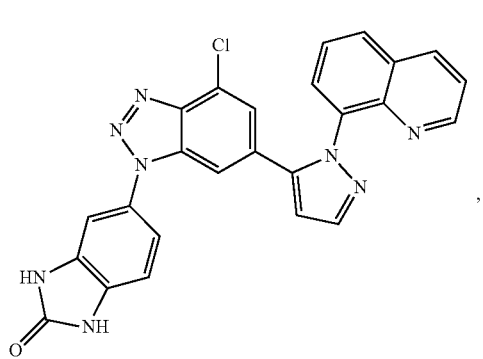
212
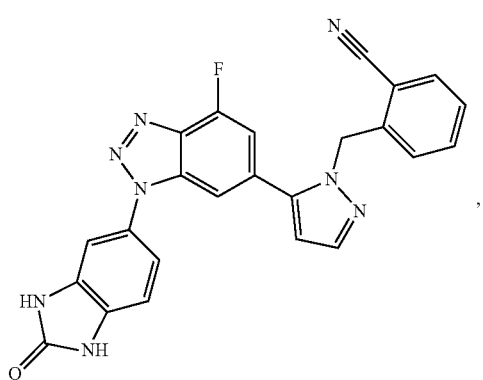
213
214
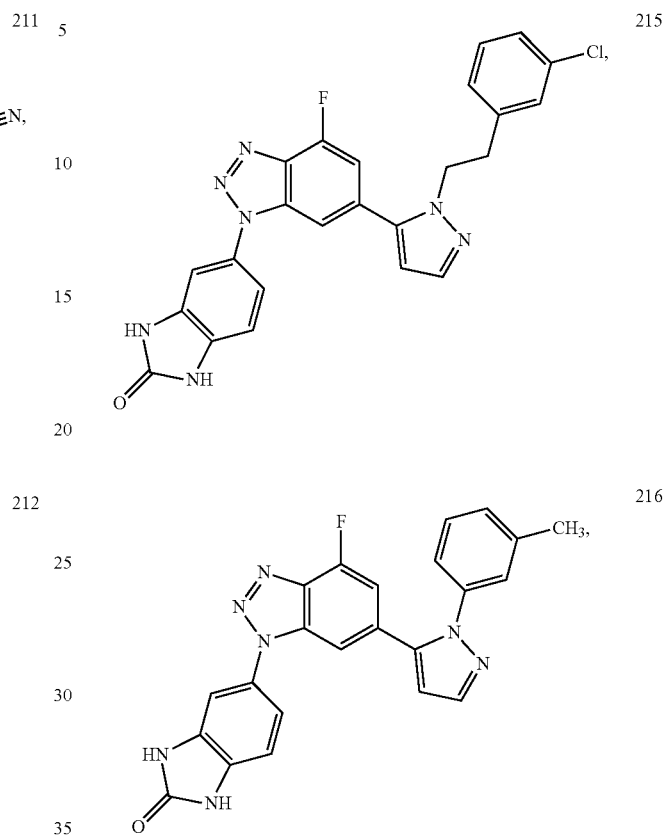
215
216
217
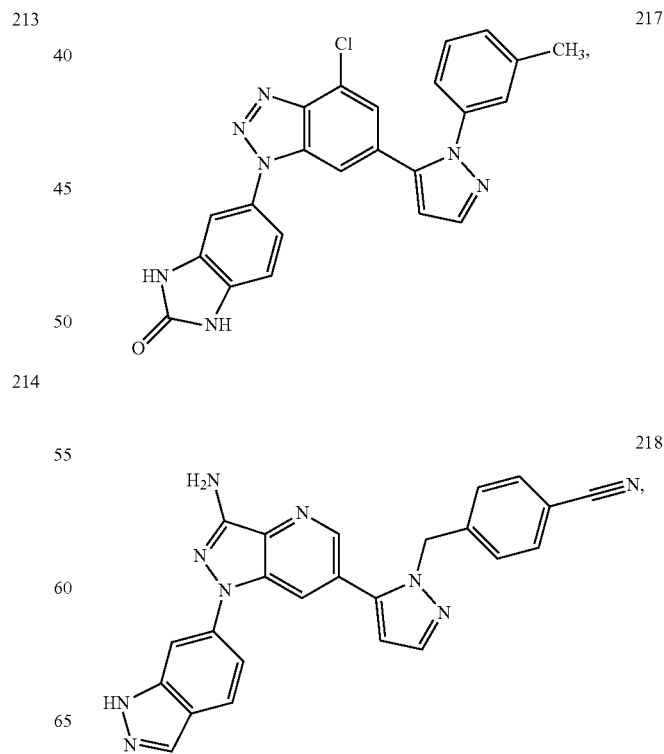
218

327
-continued
219
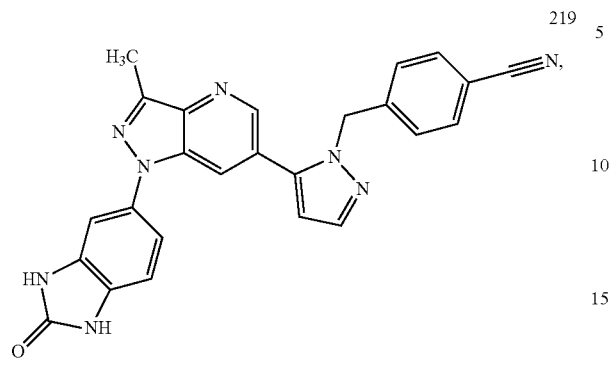
220
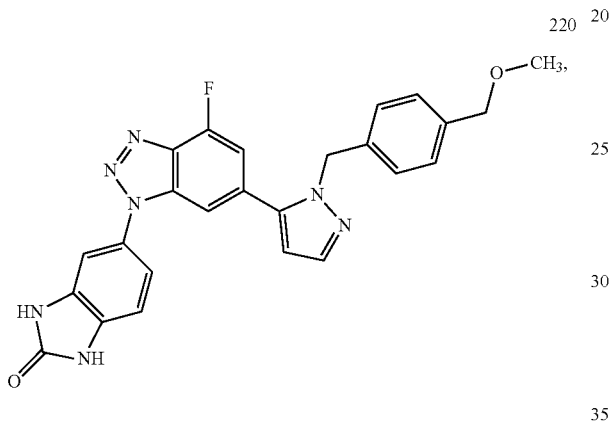
221
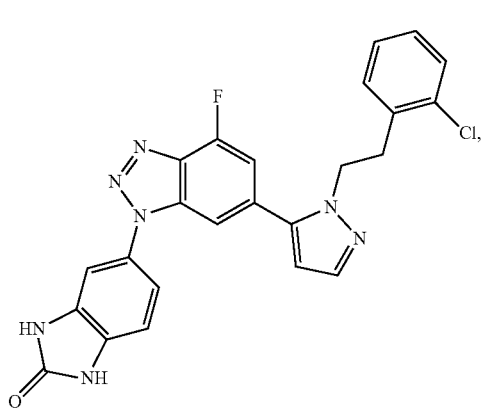
222
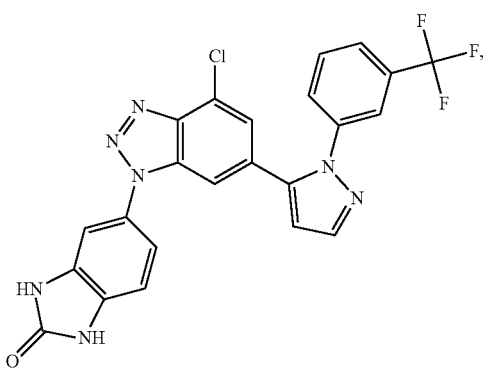
328
-continued
223
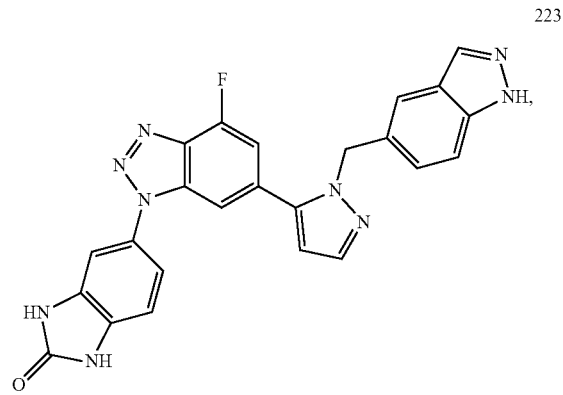
224
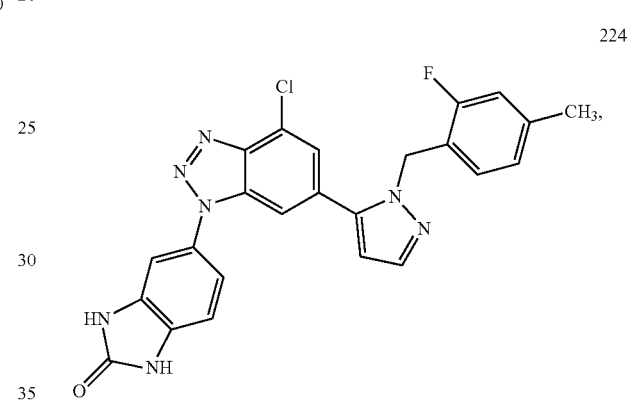
225
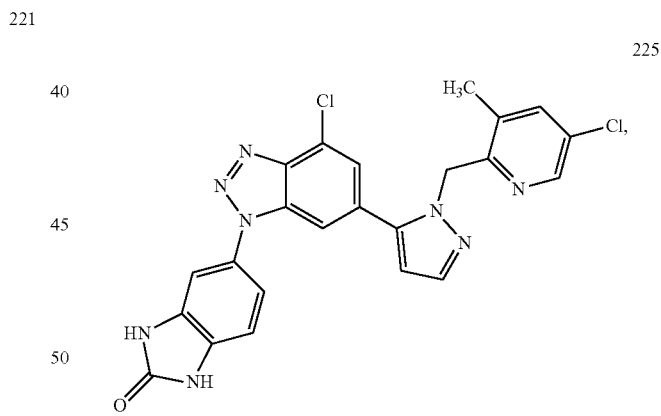
226
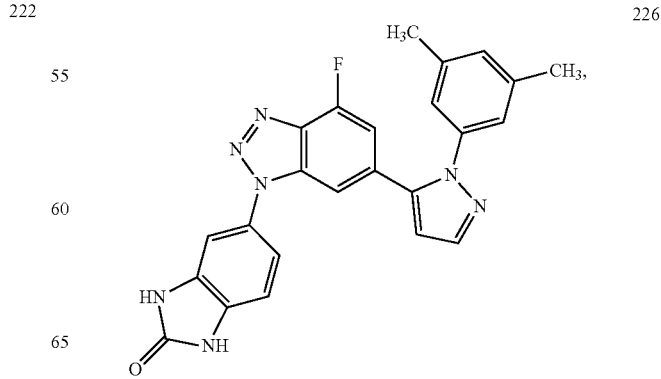

329 -continued
227 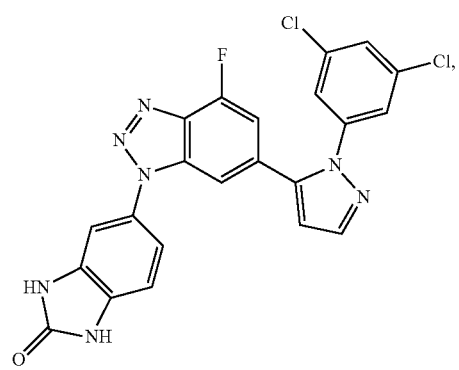
228 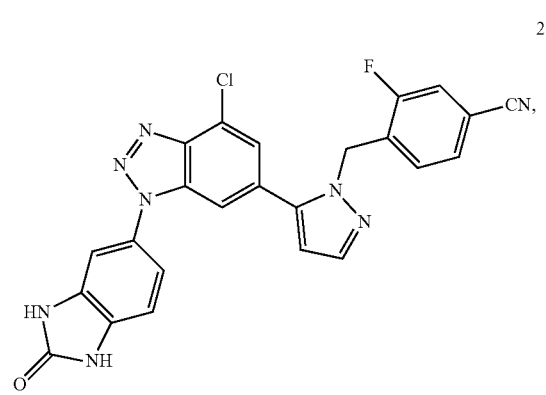
229 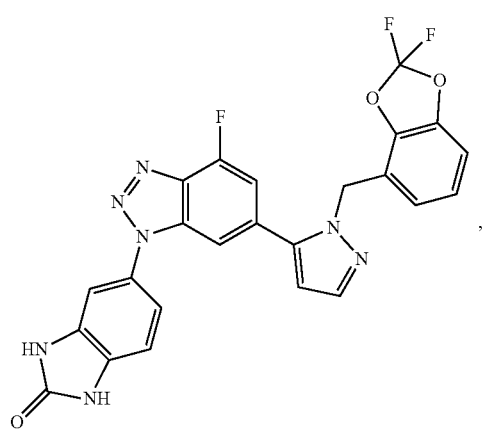
230 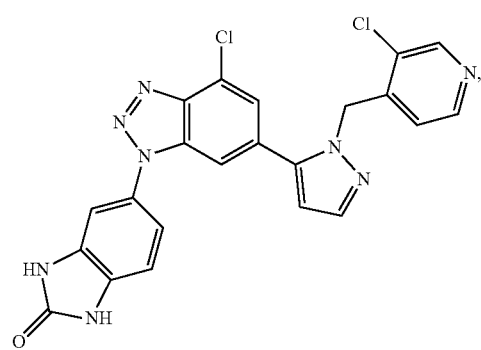
330 -continued
231 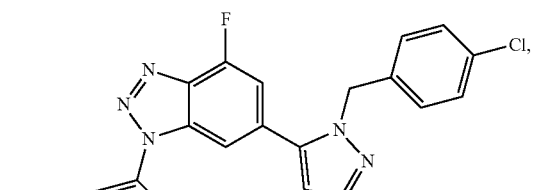
232 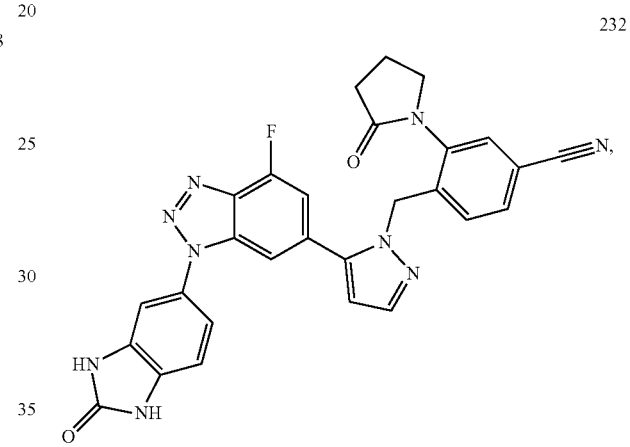
233 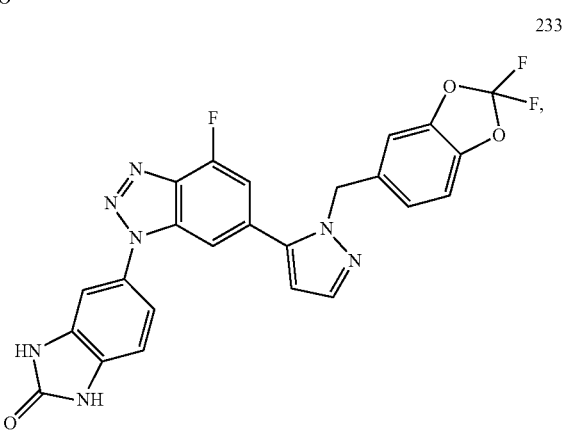
234 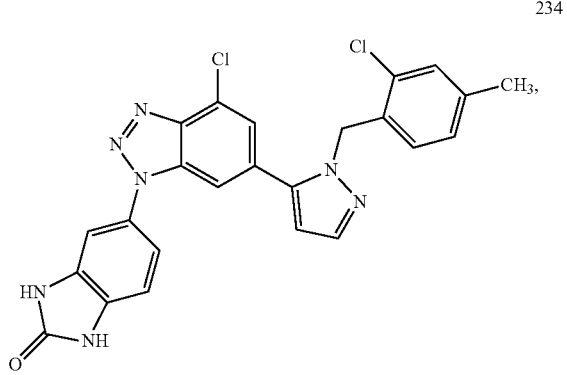

235
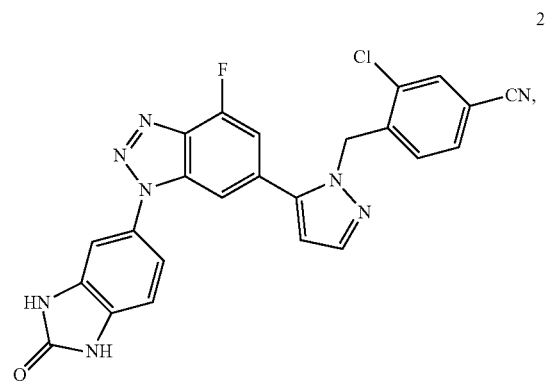
236
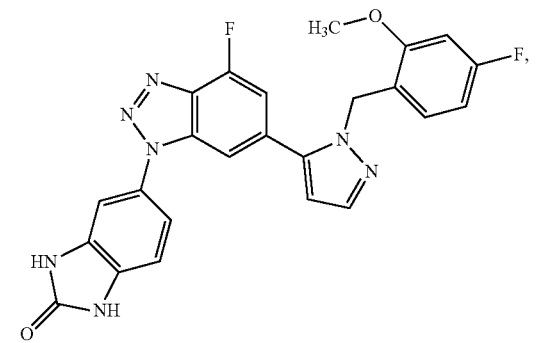
237
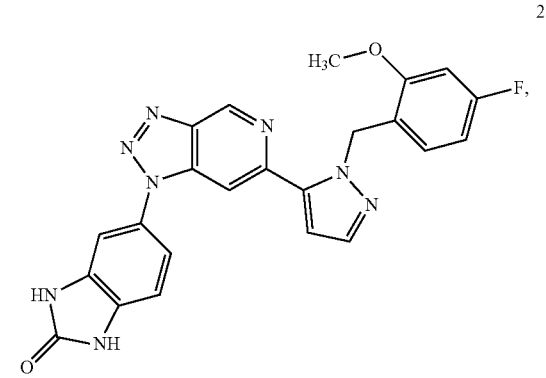
238
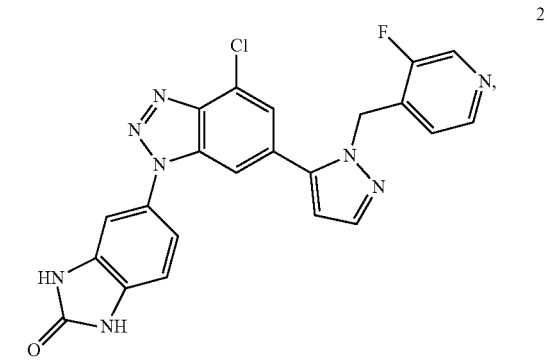
239
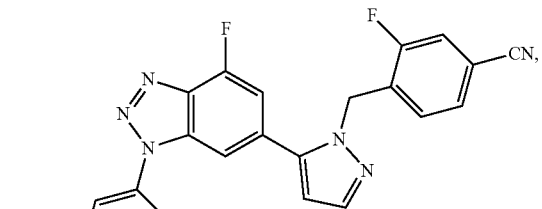
240
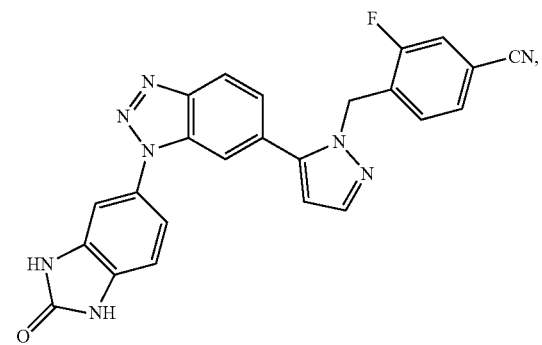
241
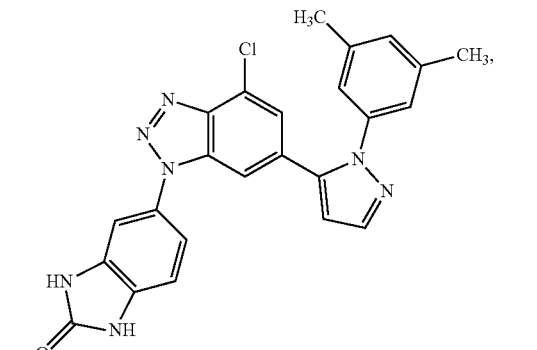
242
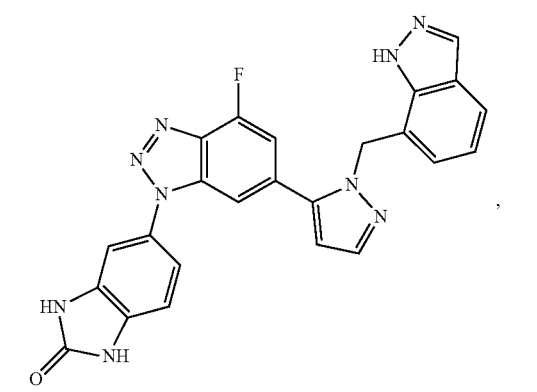

333
-continued
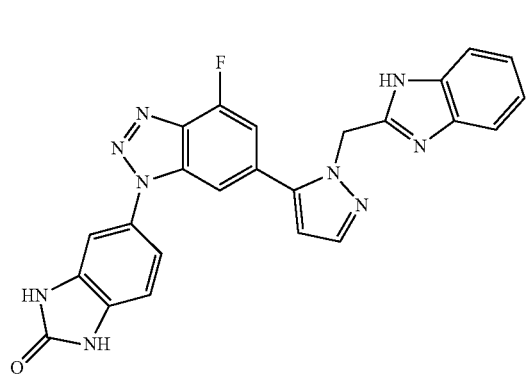
243
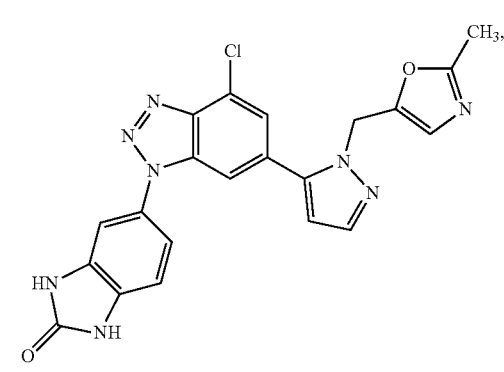
244
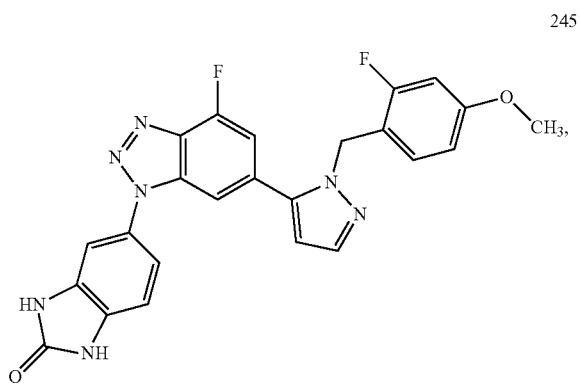
245
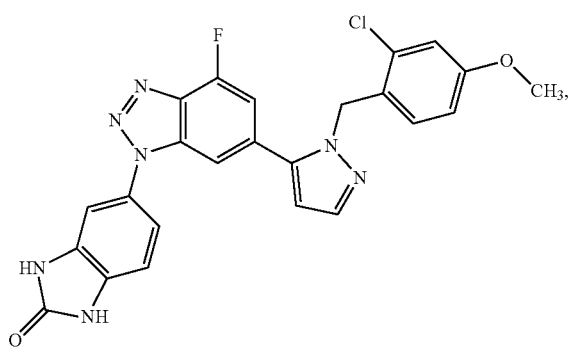
246
334
-continued
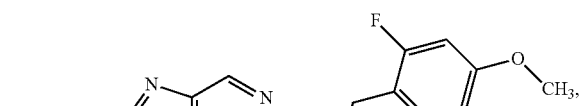
247
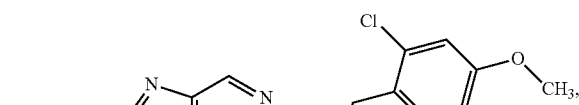
248
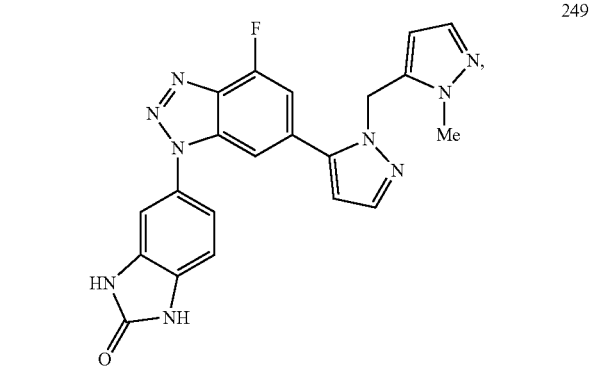
249
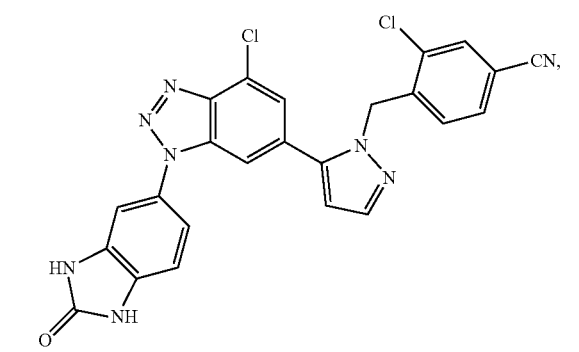
250

251 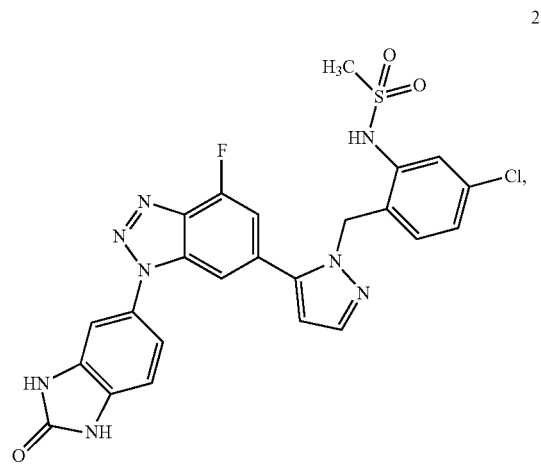
252 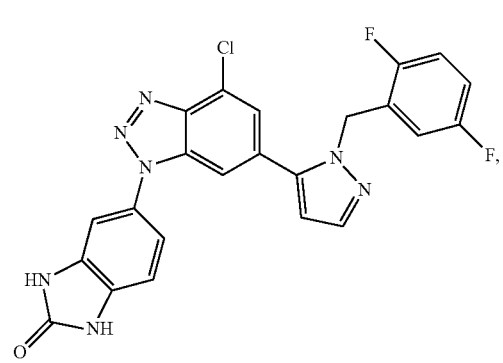
253 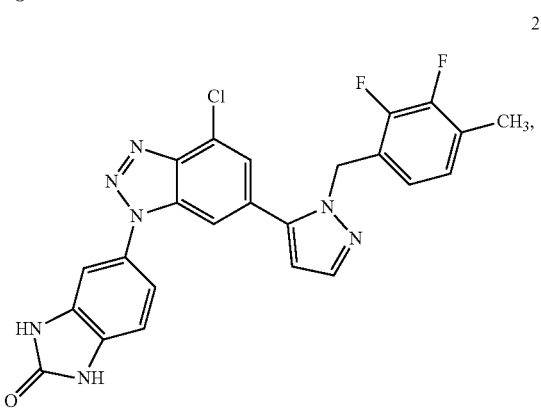
254 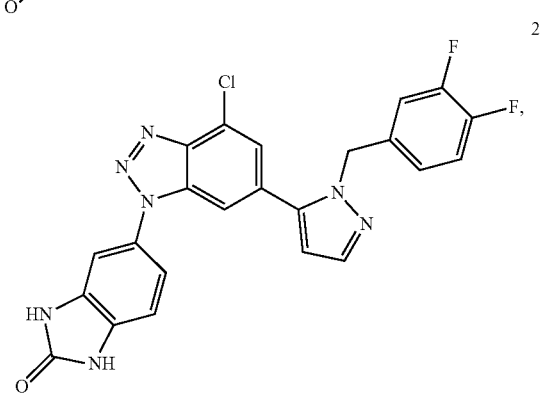
255 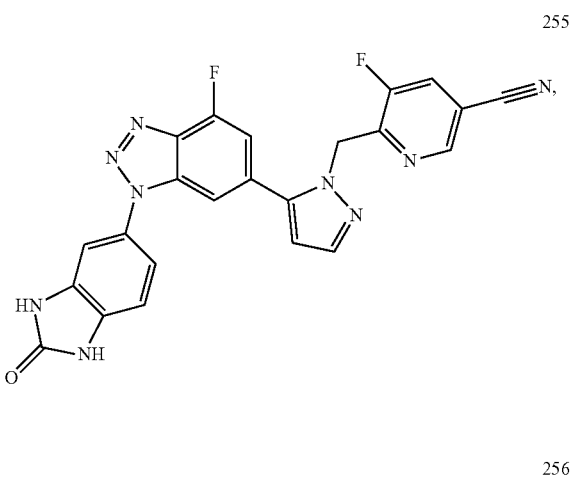
256 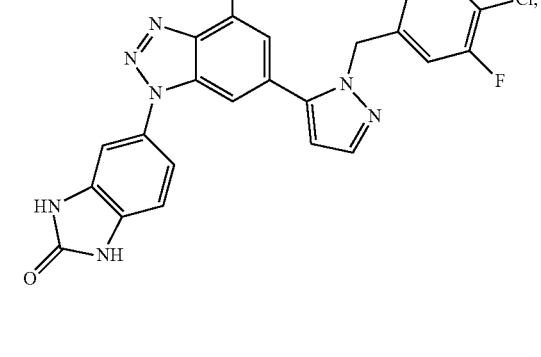
257 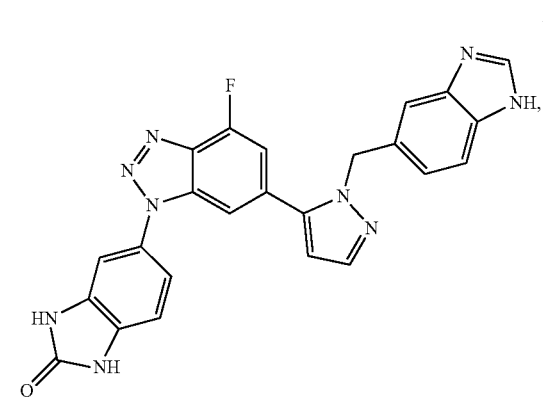
258 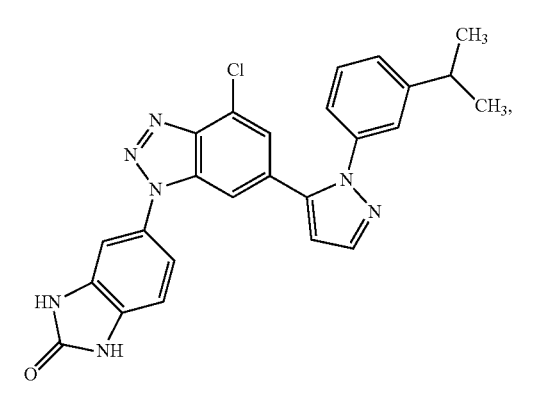

259 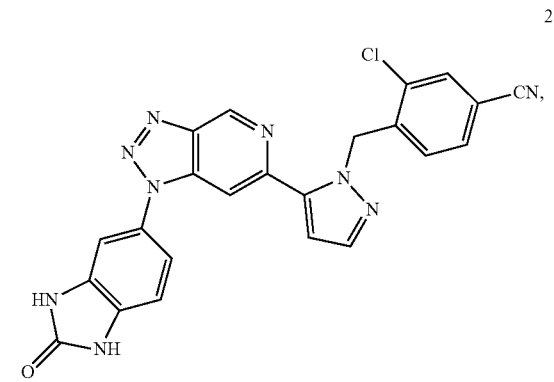
260 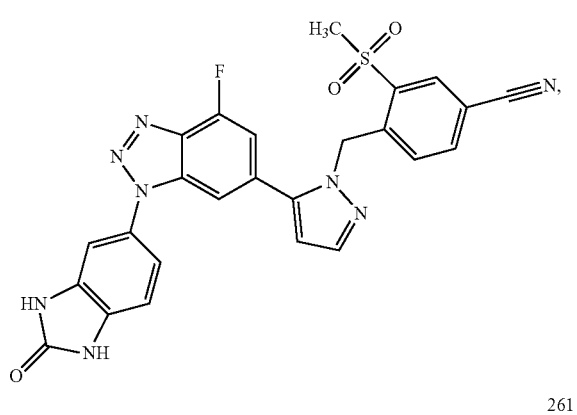
261 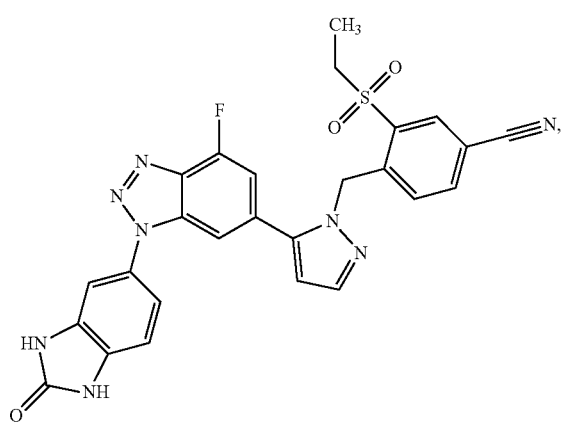
262 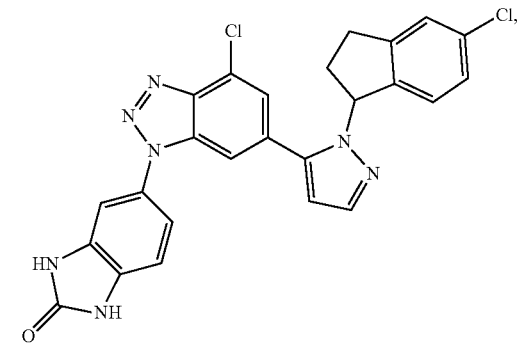
263 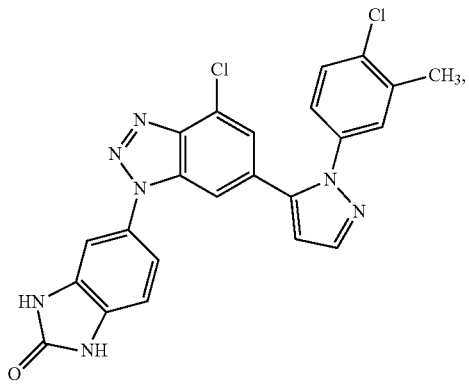
264 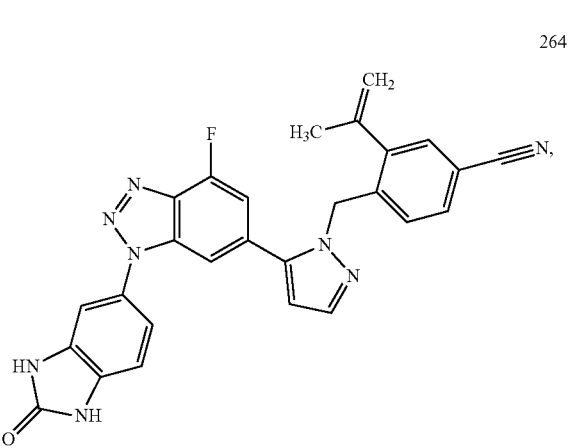
265 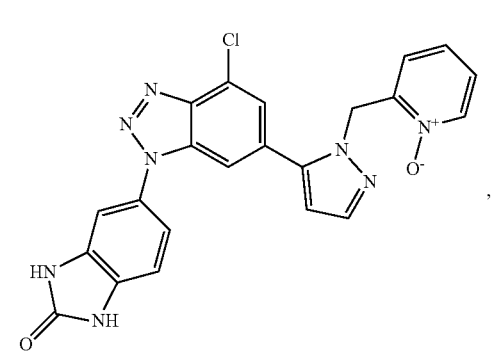
266 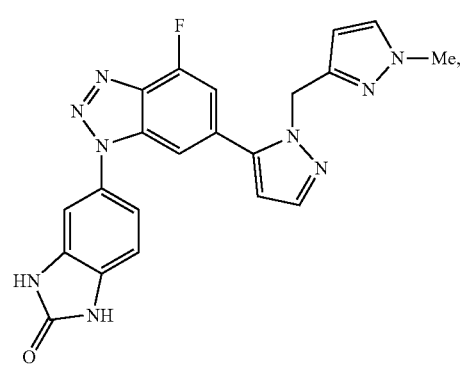

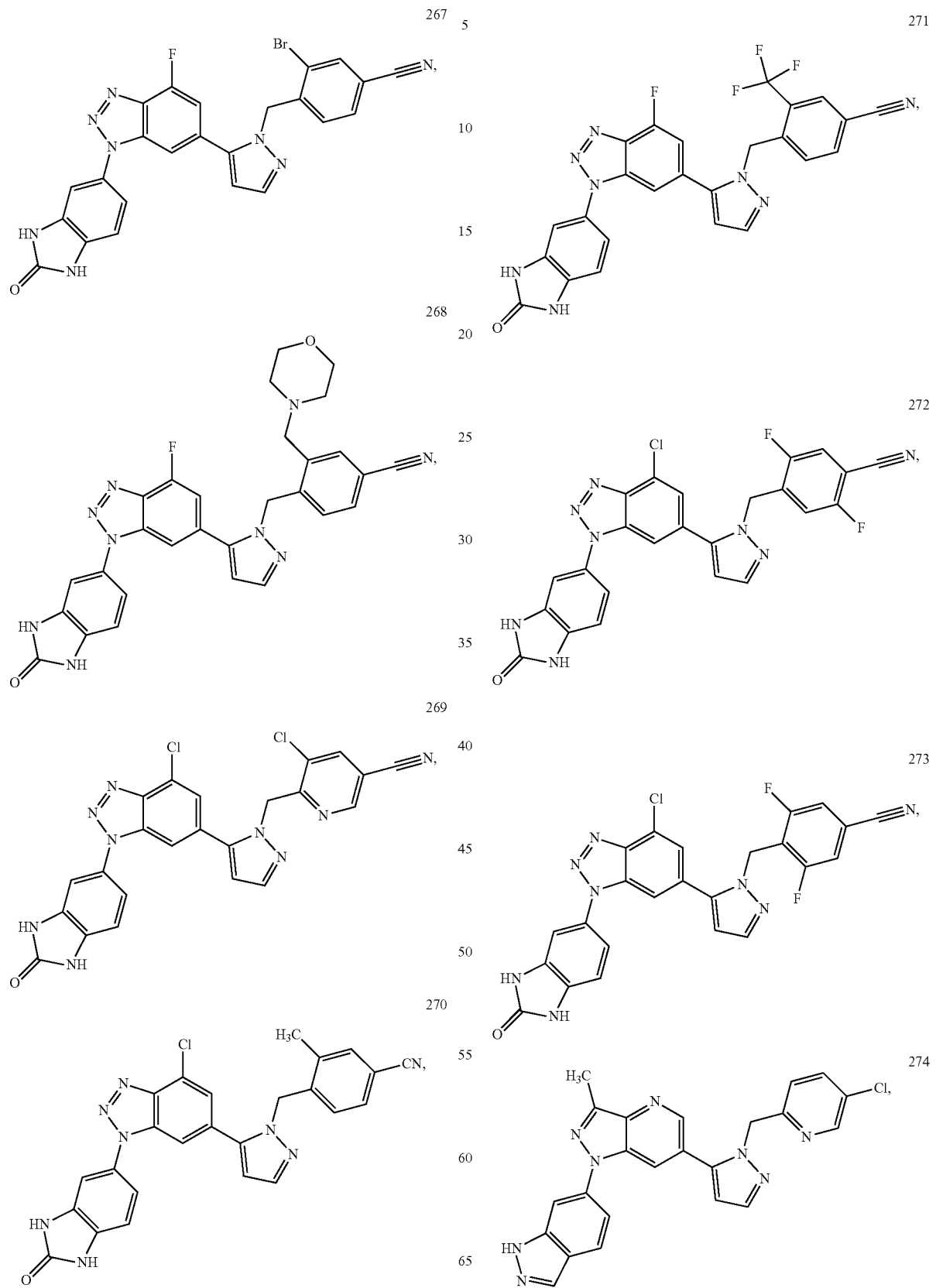

341
-continued
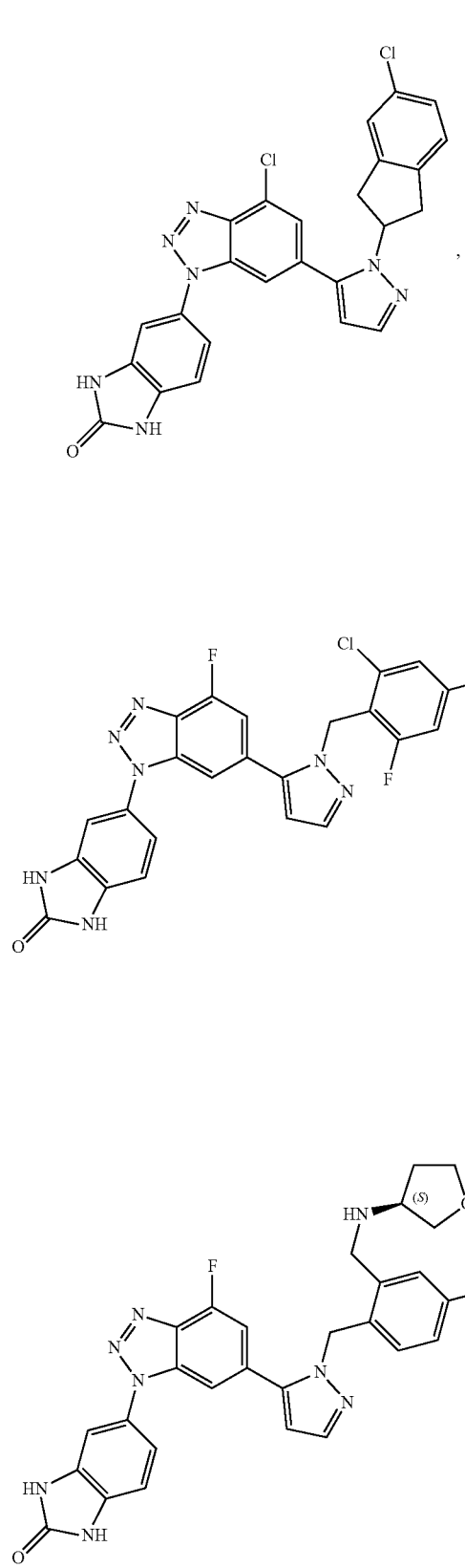
342
-continued
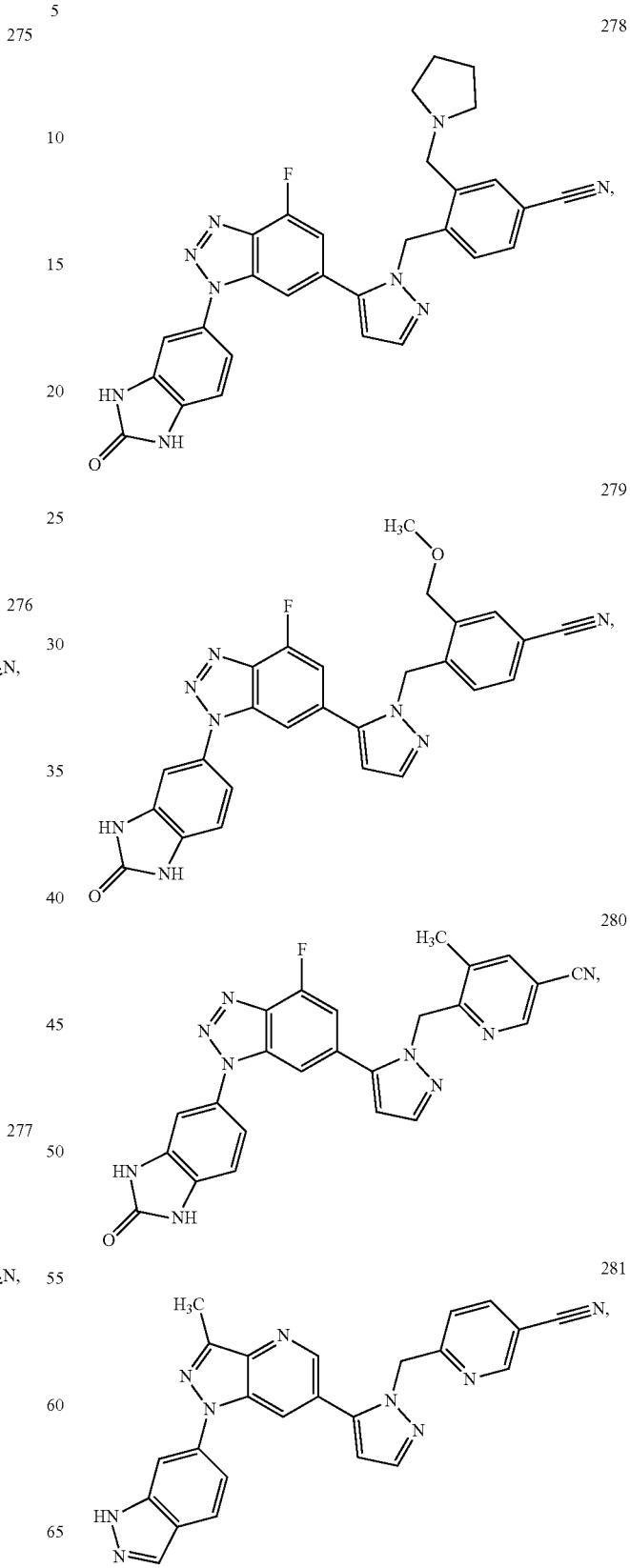

-continued
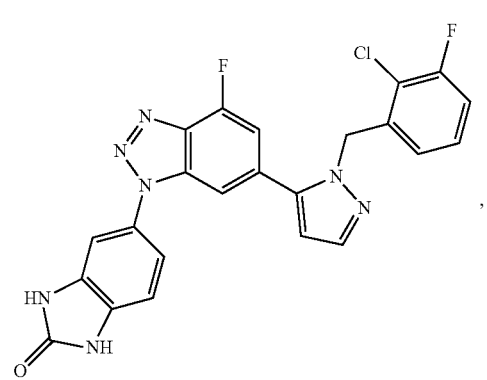
282
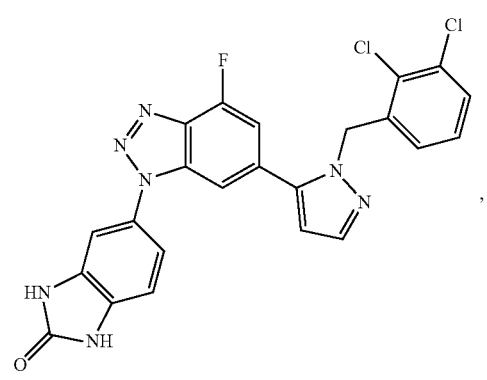
283
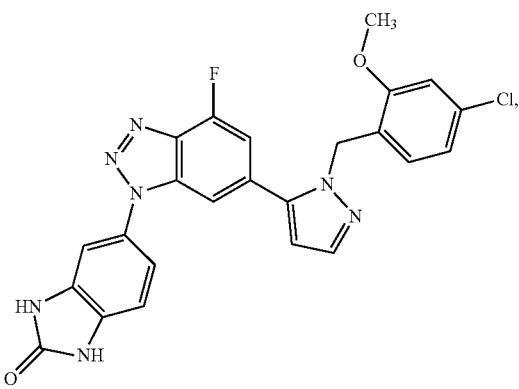
284
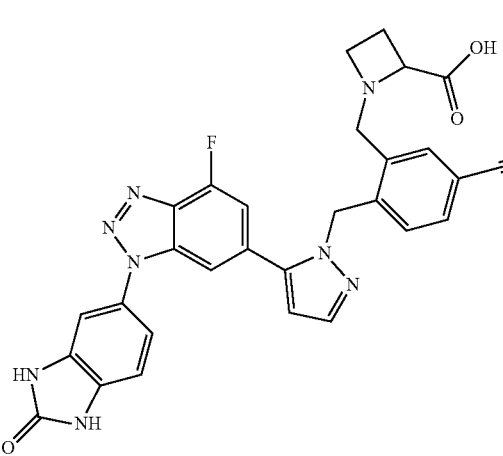
285
-continued
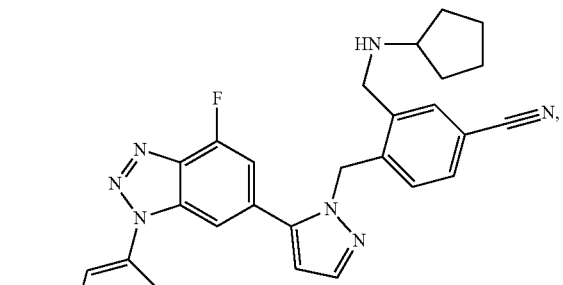
286
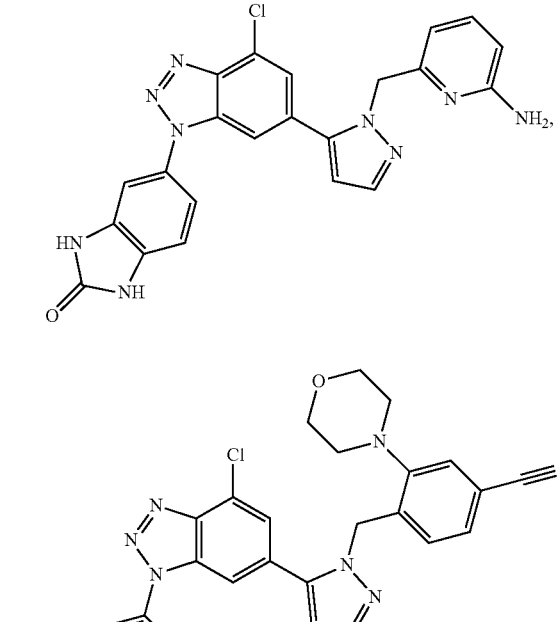
287
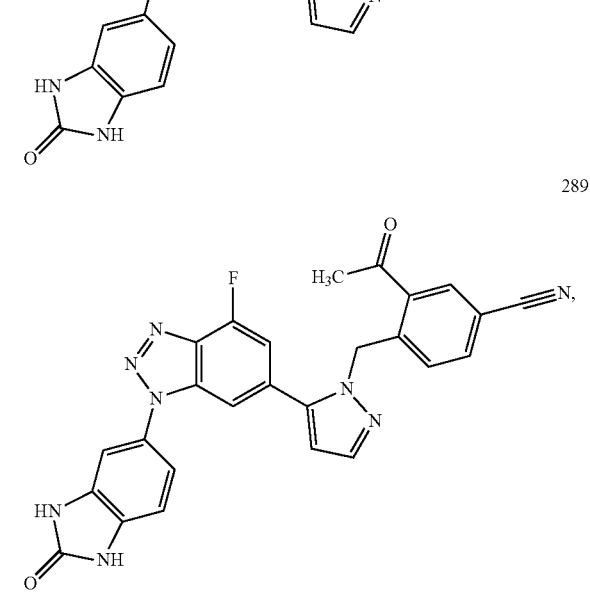
288
289

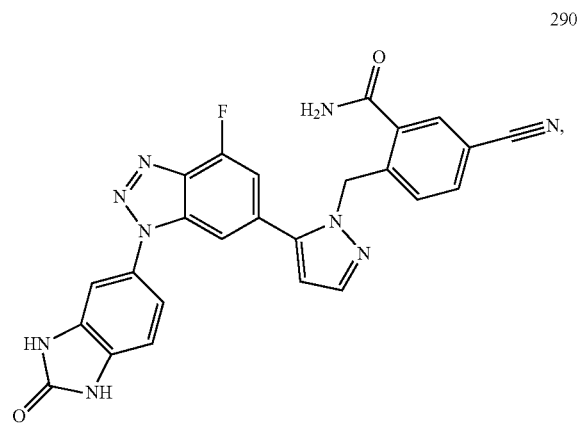
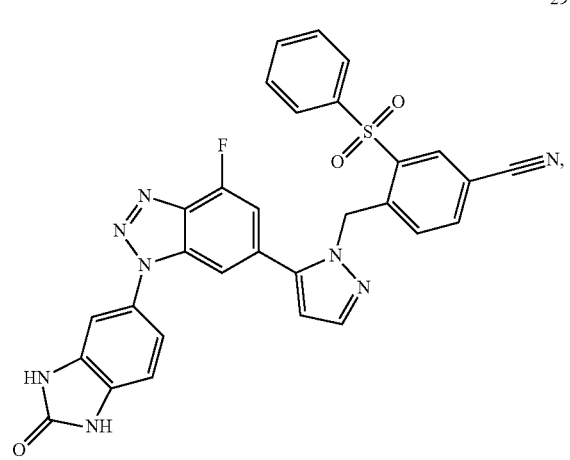
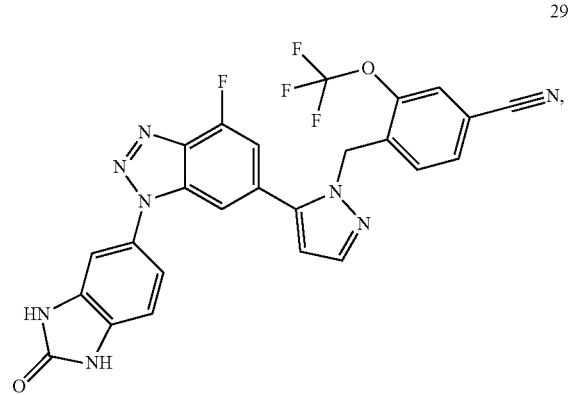
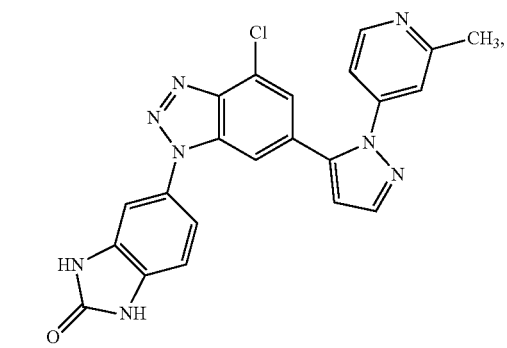
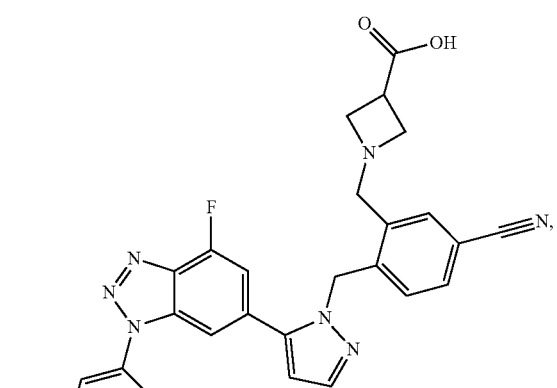
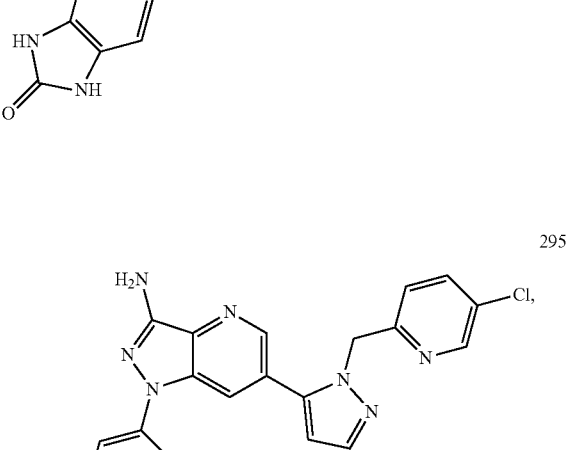
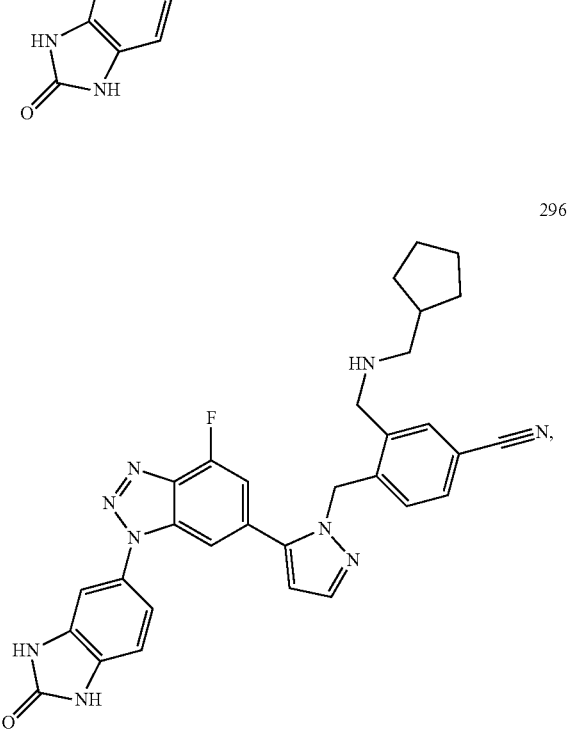

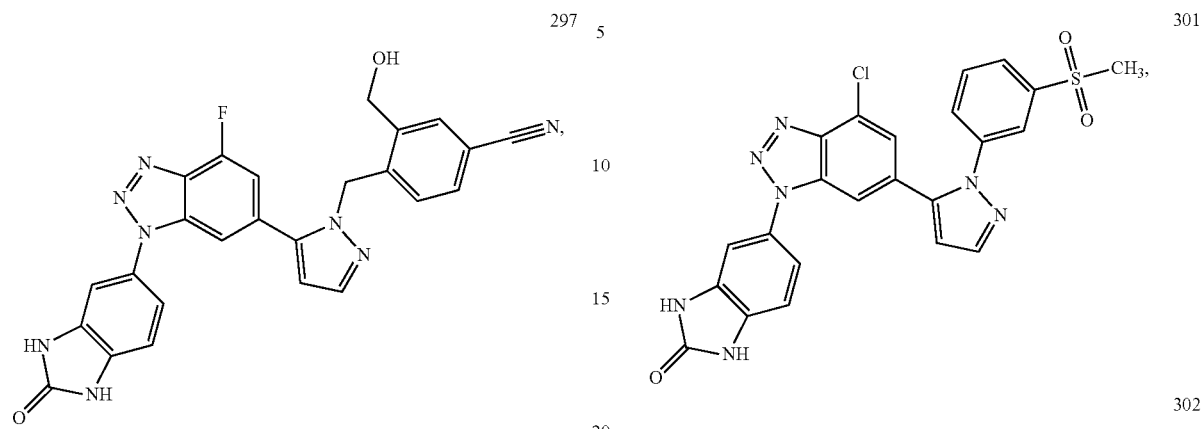
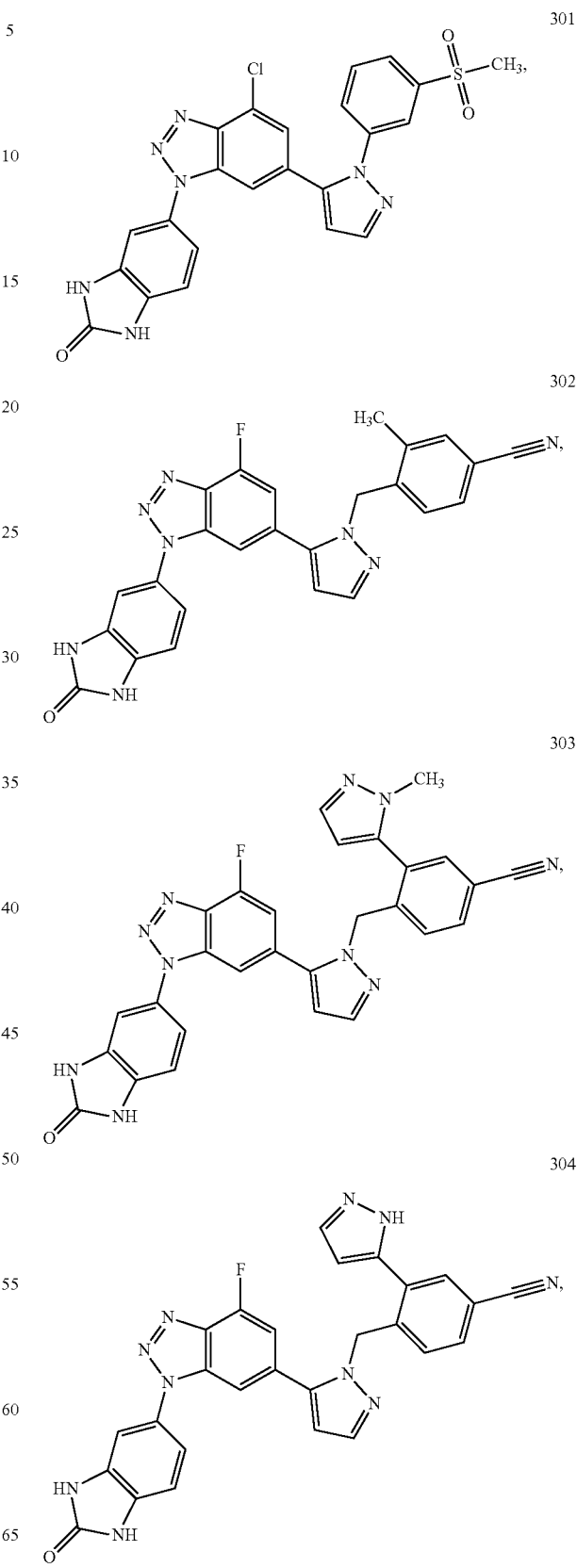

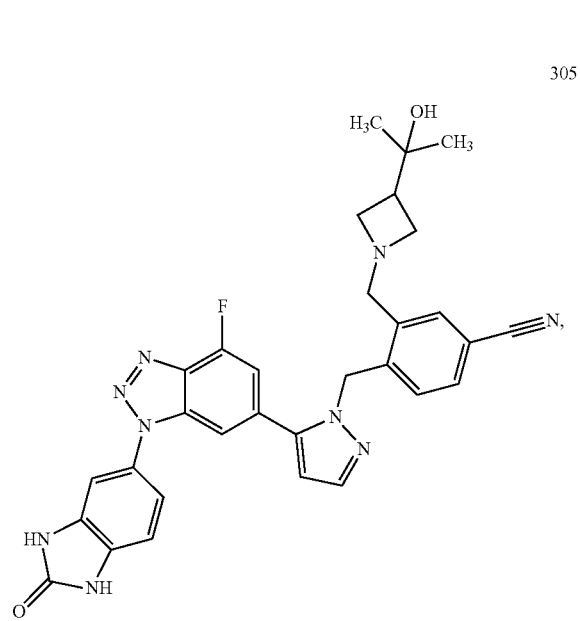
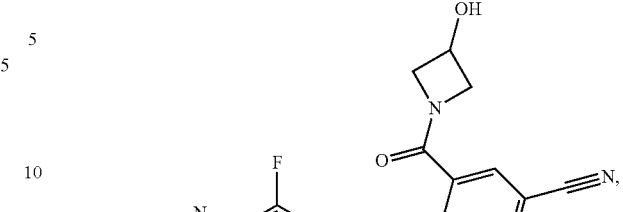
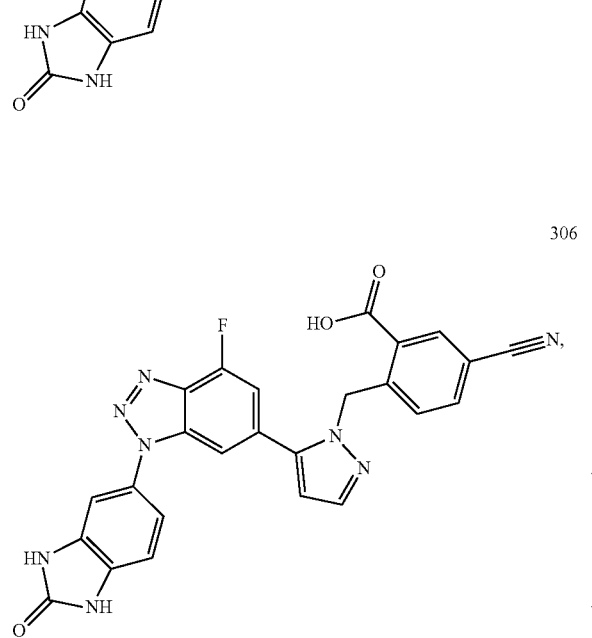
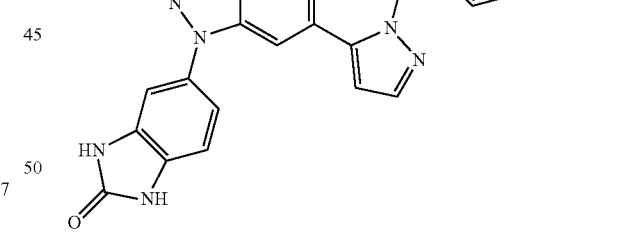
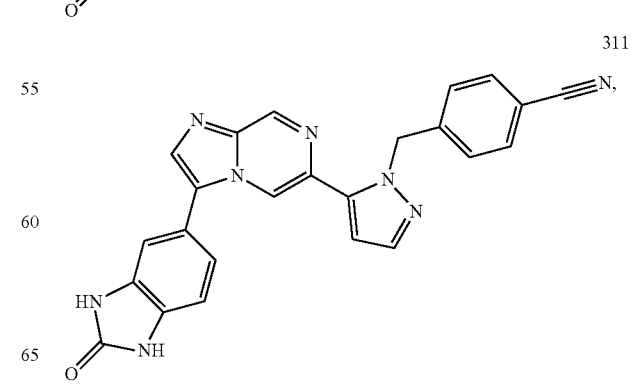

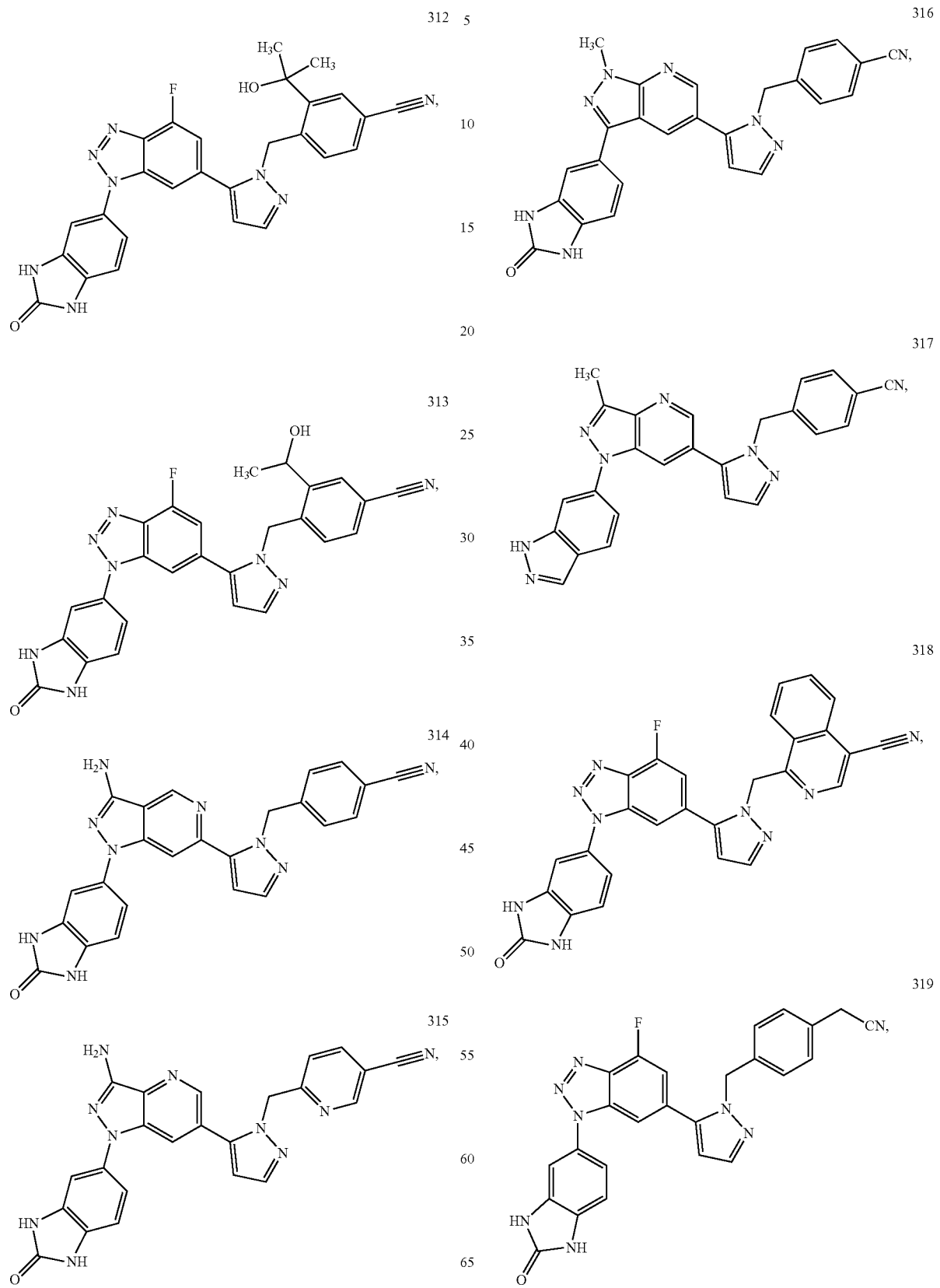

353
-continued
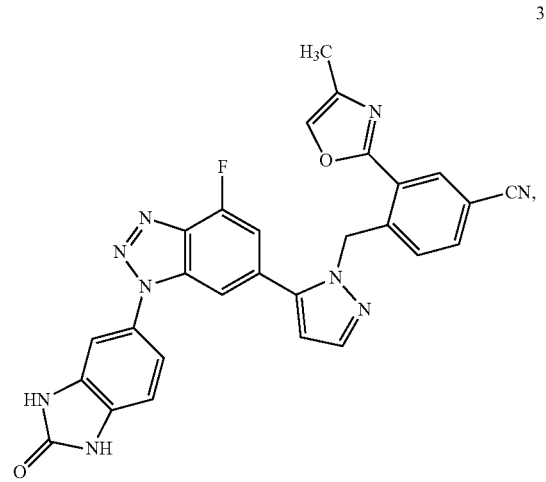
320
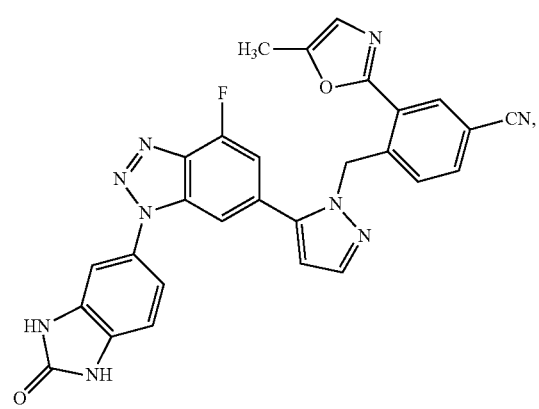
321
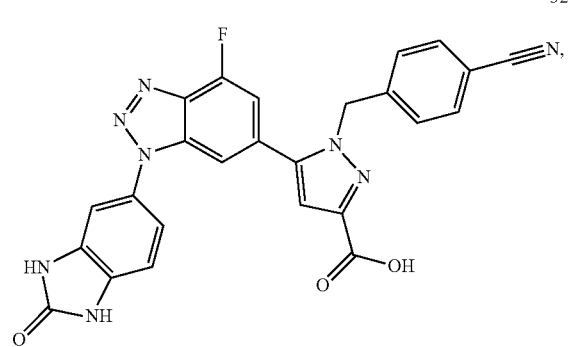
322
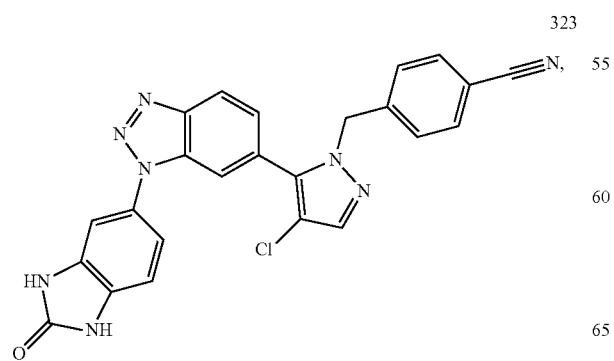
323
354
-continued
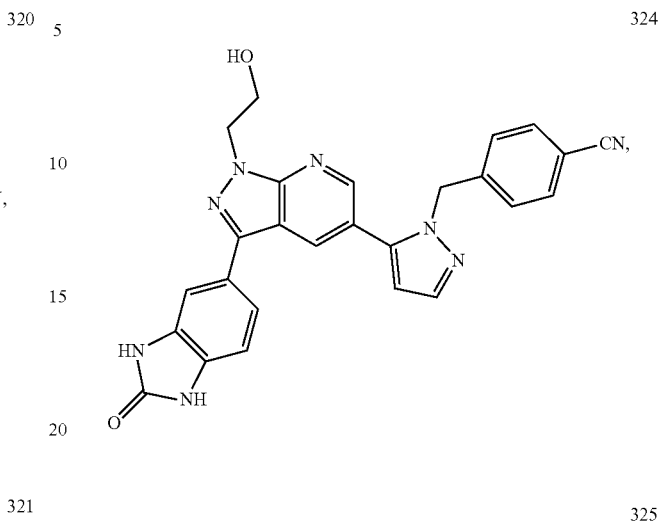
324
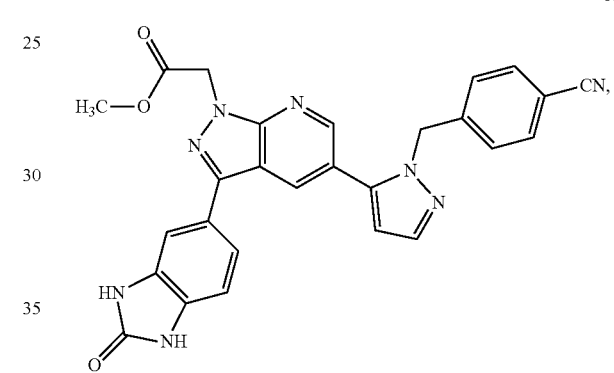
325
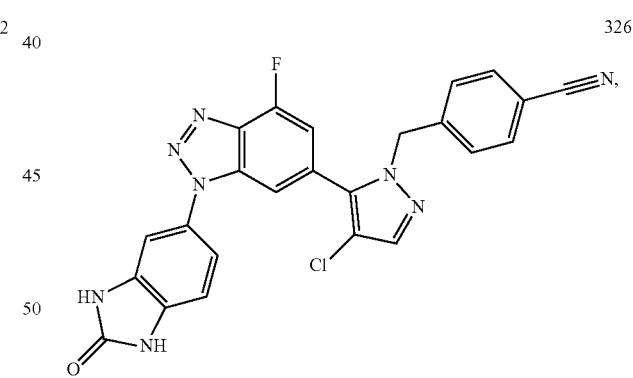
326
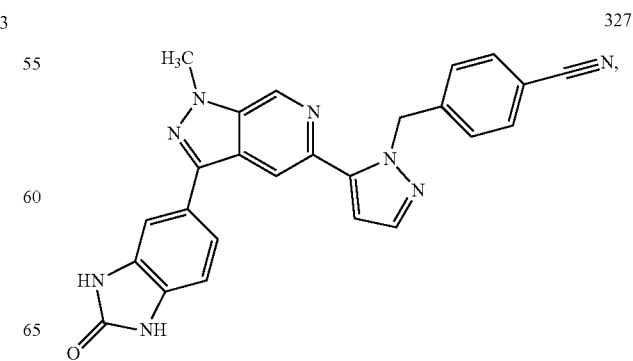
327

328 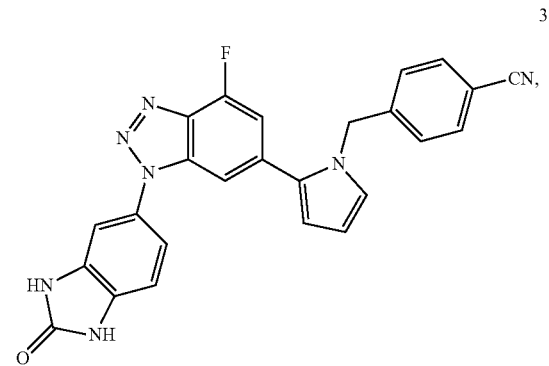
329 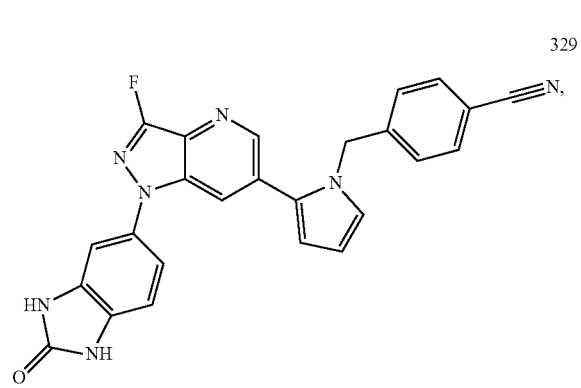
330 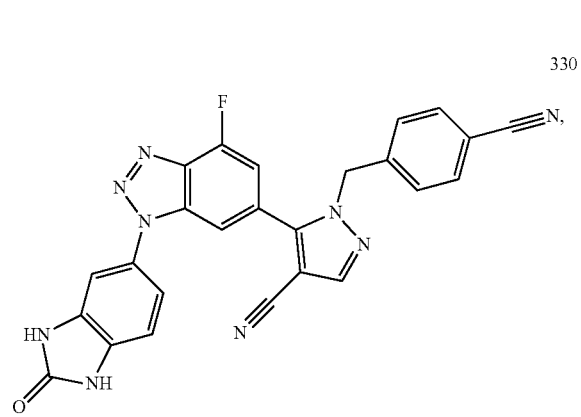
331 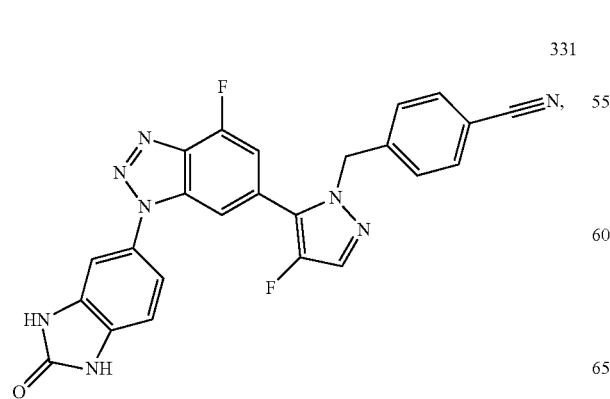
332 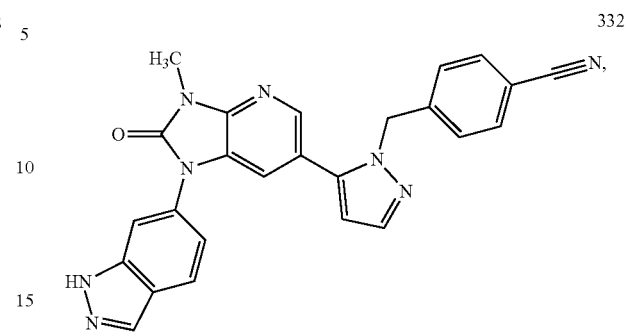
333 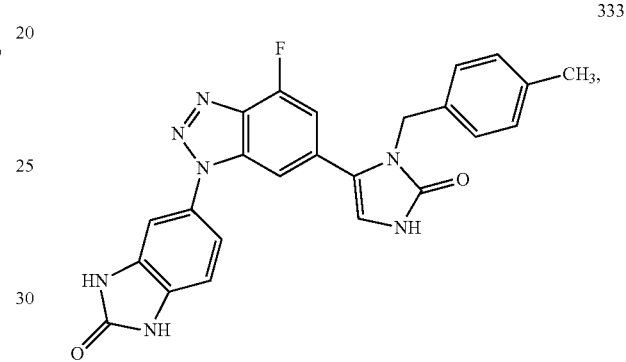
334 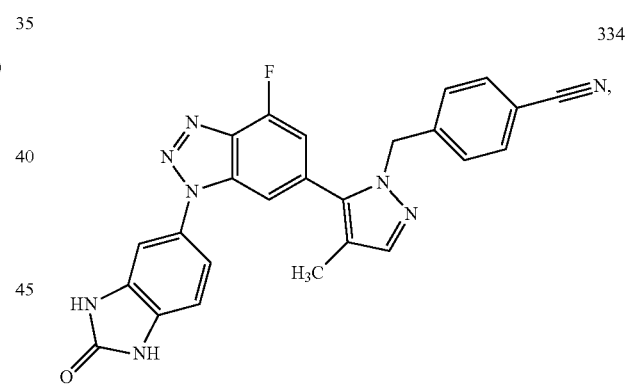
335 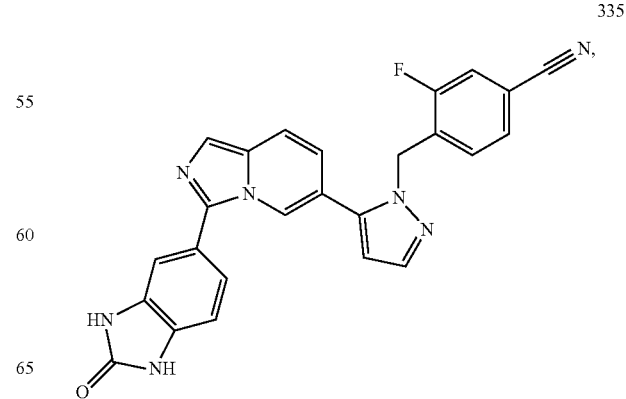

357
-continued
336
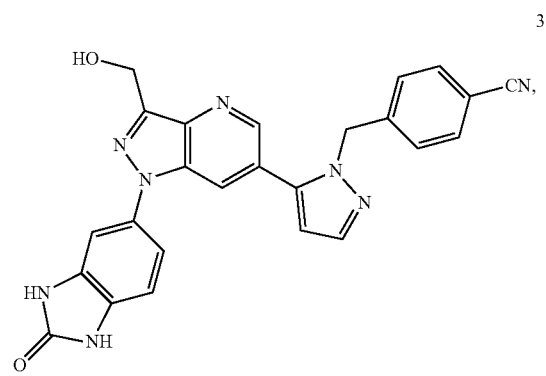
337
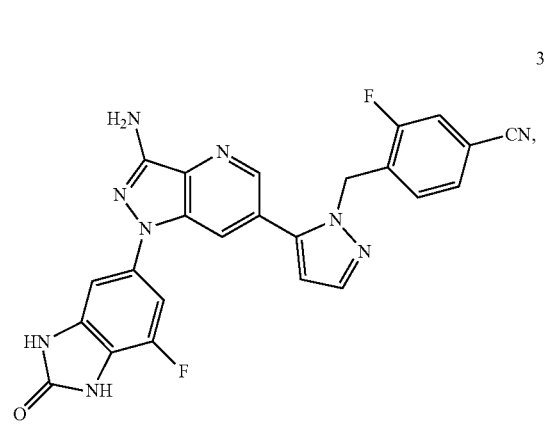
338
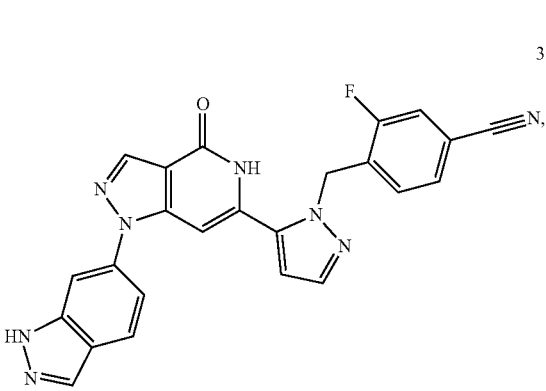
339
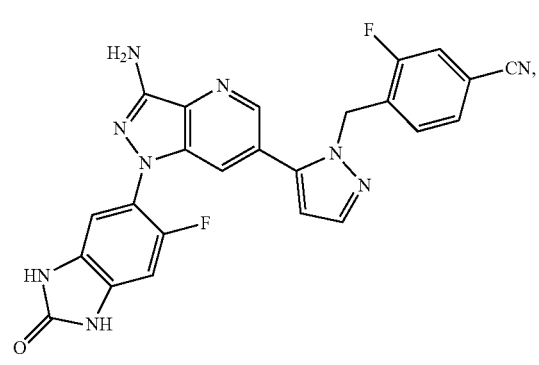
358
-continued
340
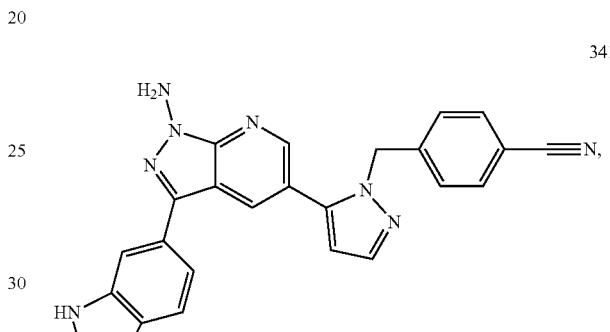
341
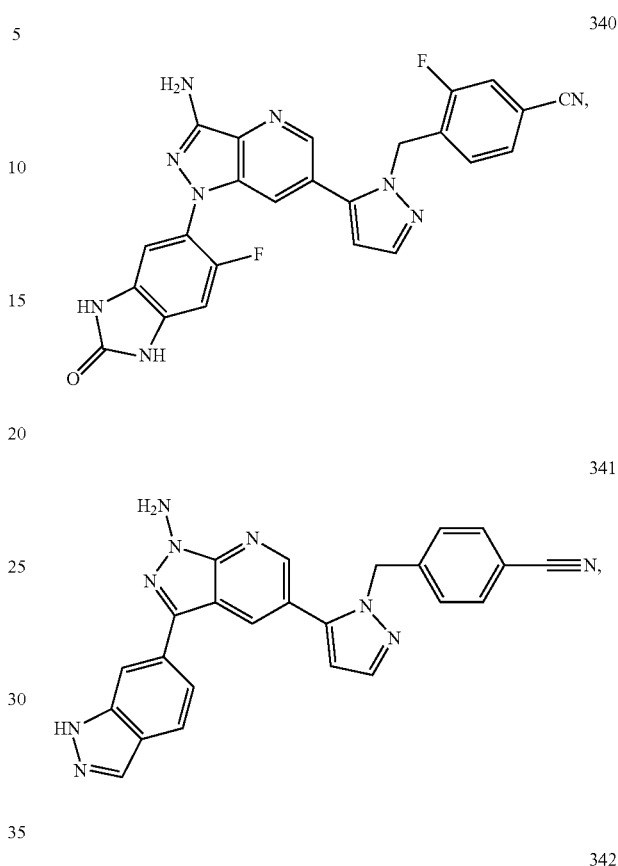
342
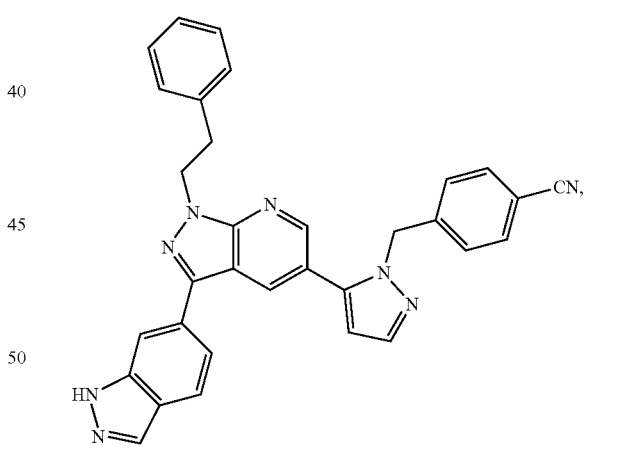
343
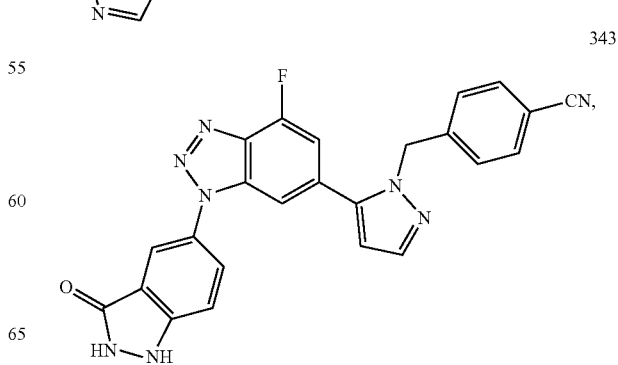

344 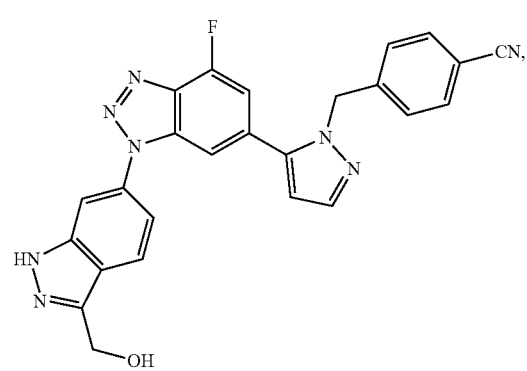
345 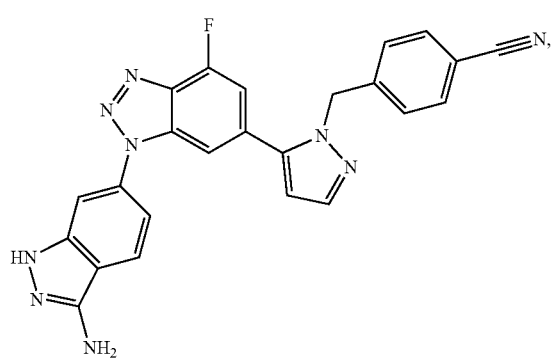
346 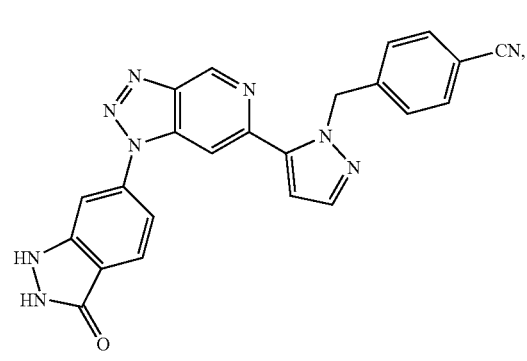
347 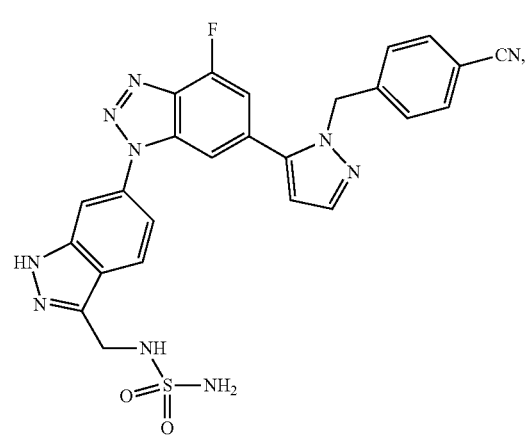
348 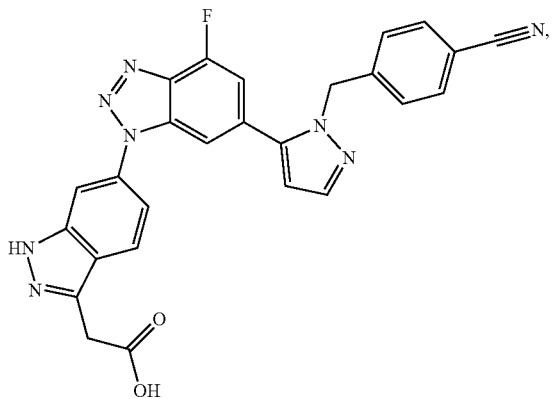
349 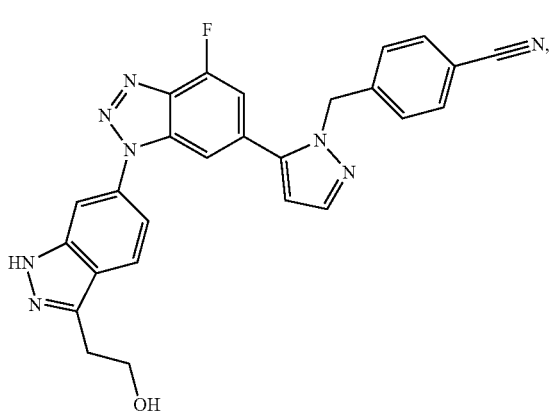
350 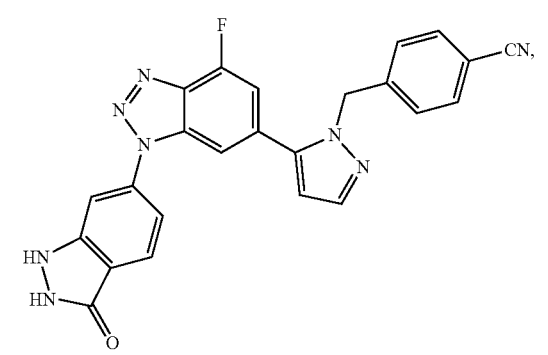
351 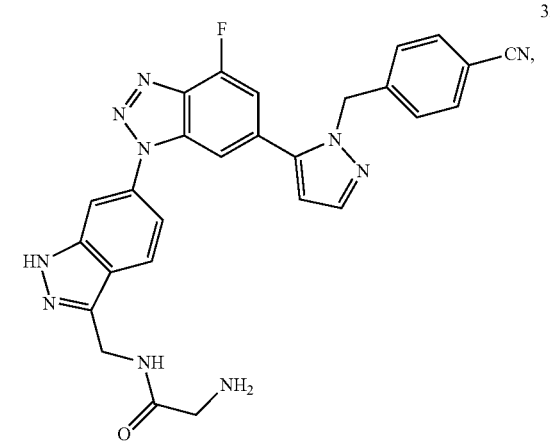

361
-continued
352
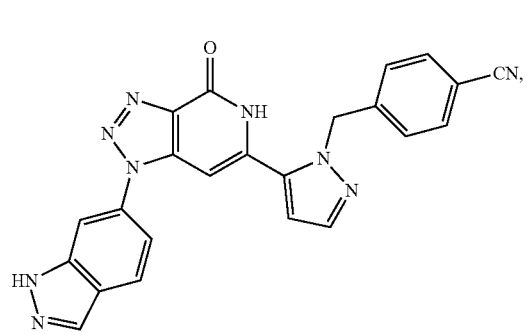
353
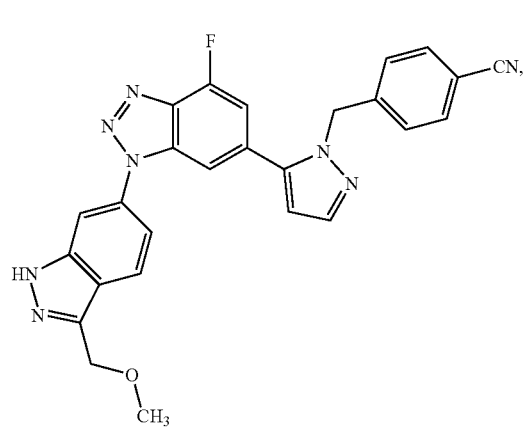
354
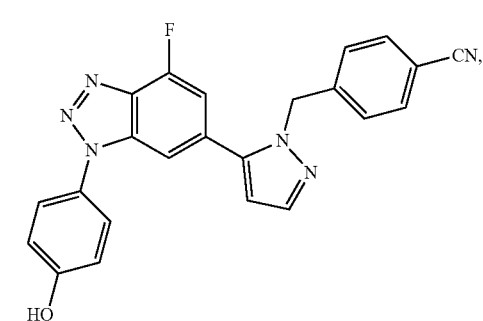
355
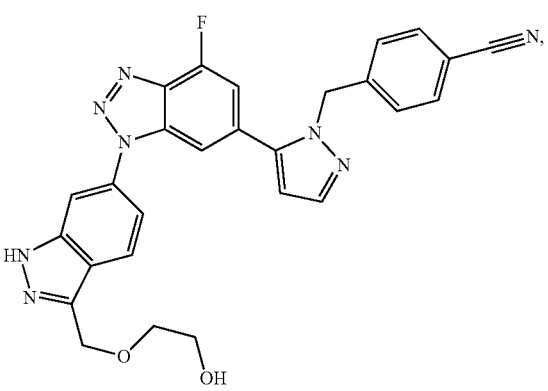
362
-continued
356
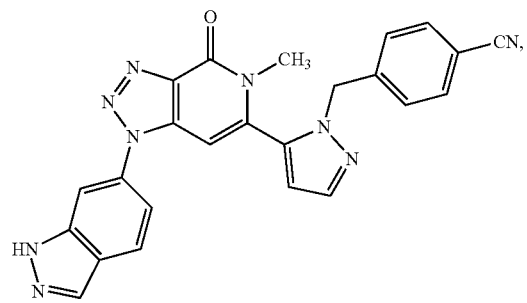
357
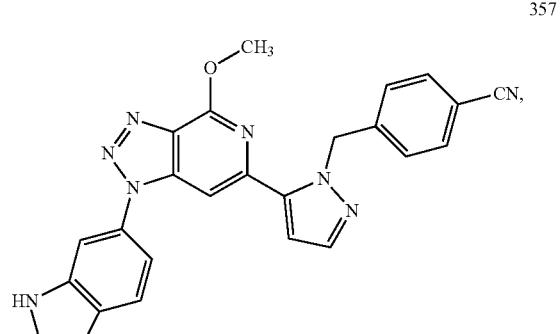
358
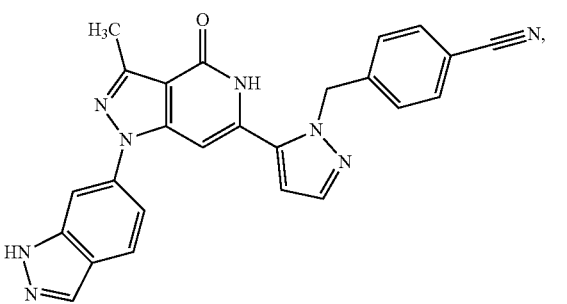
359
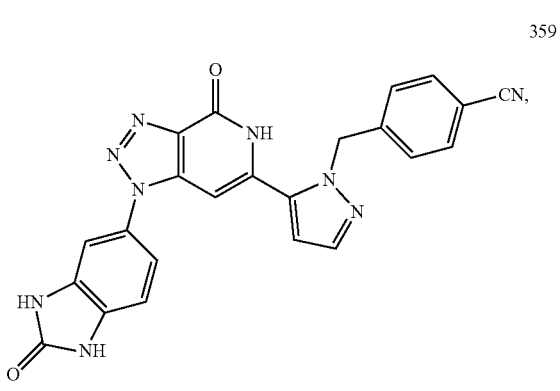

363
-continued
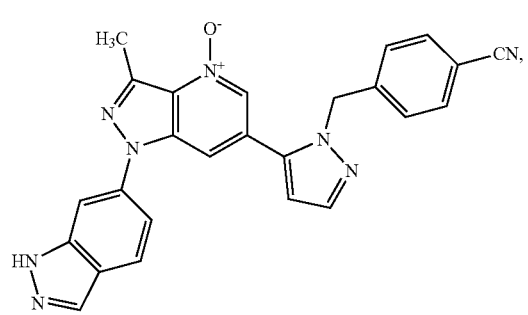
360
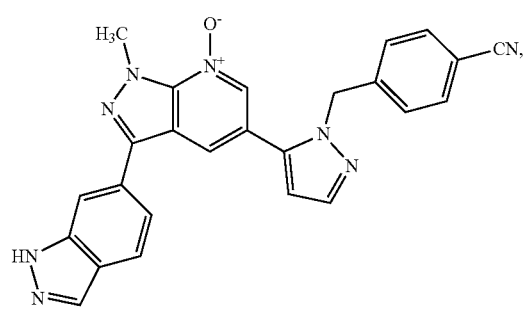
361
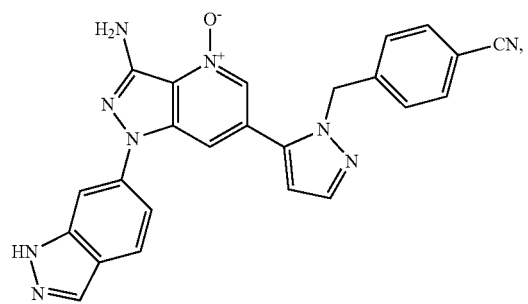
362
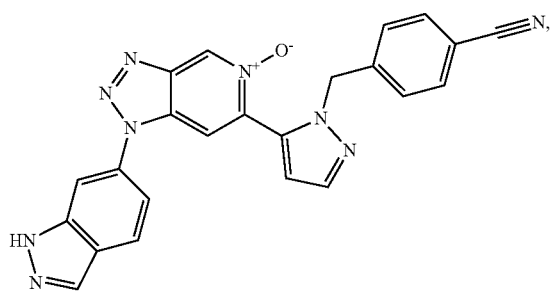
363
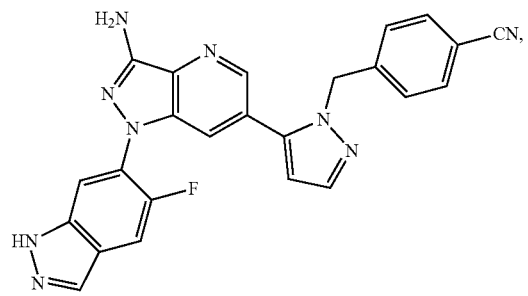
364
364
-continued
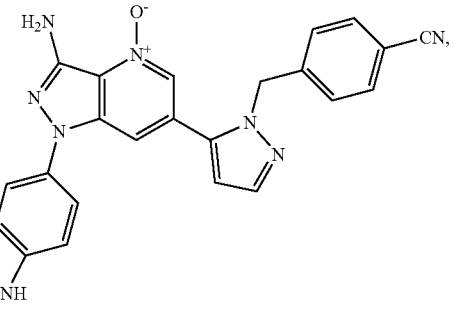
365
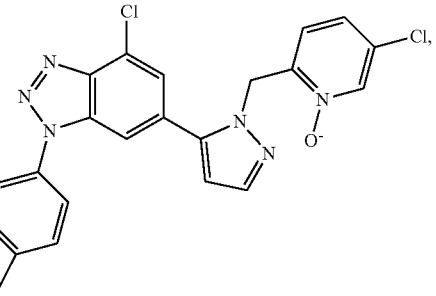
366
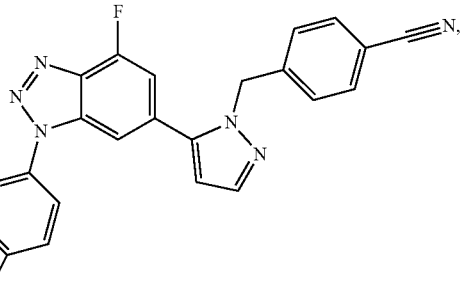
367
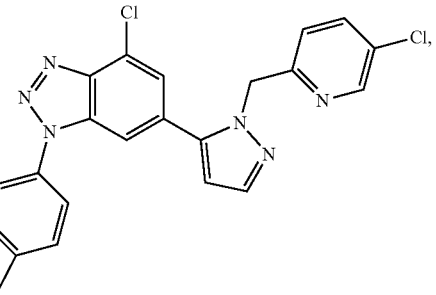
368
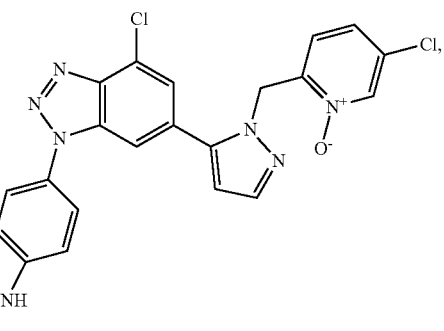
369

370
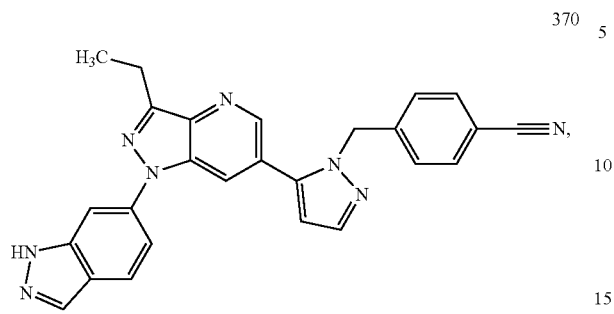
371
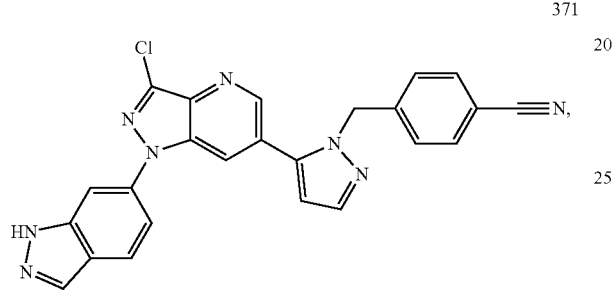
372
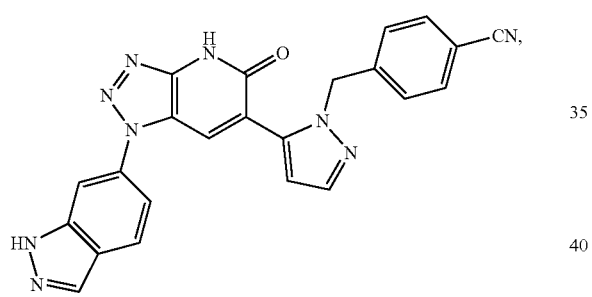
373
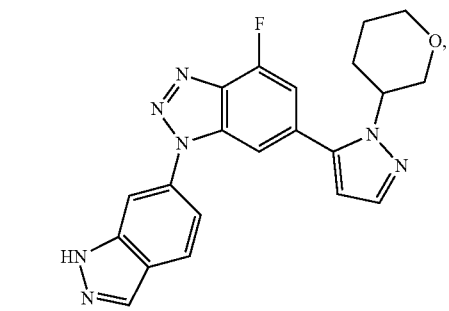
374
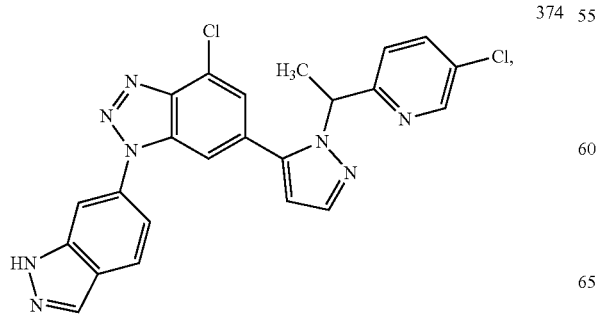
375
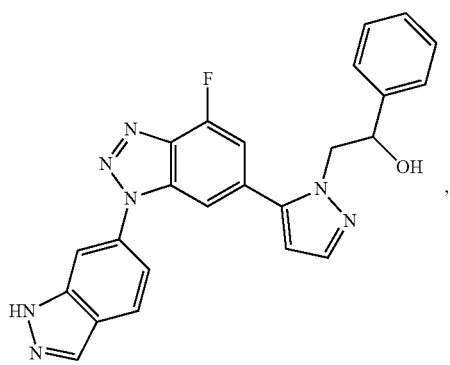
376
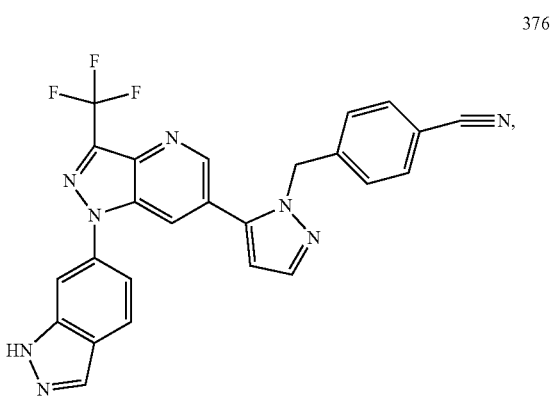
377
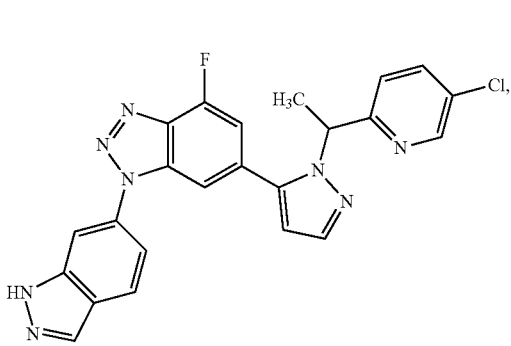
378
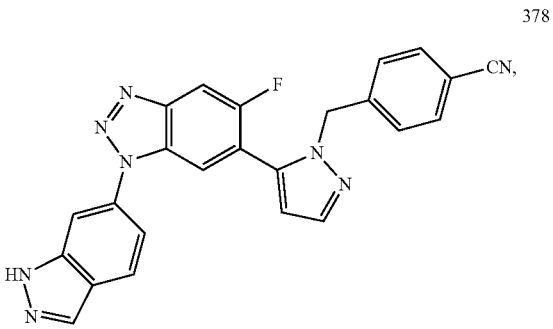

367
-continued
379
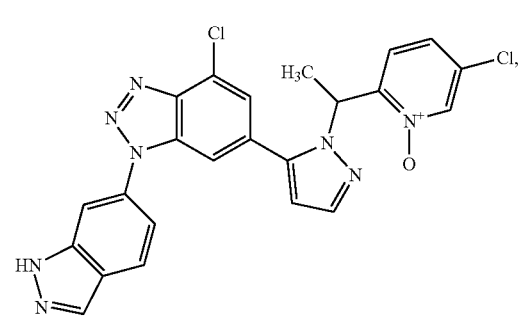
380
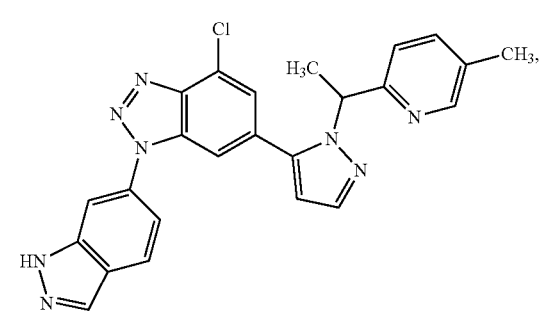
381
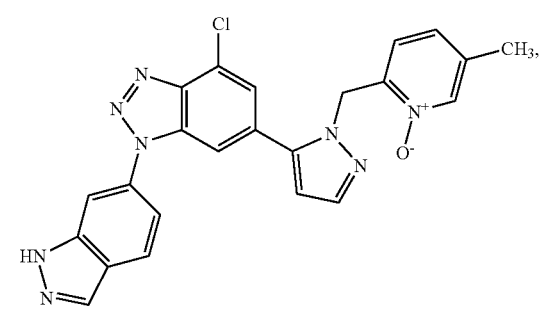
382
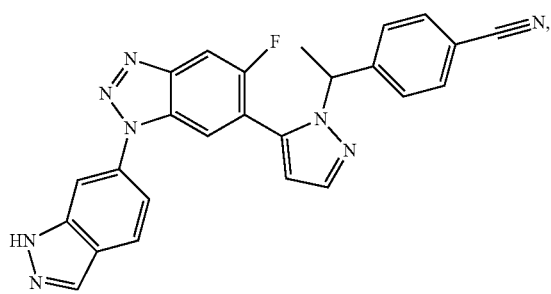
383
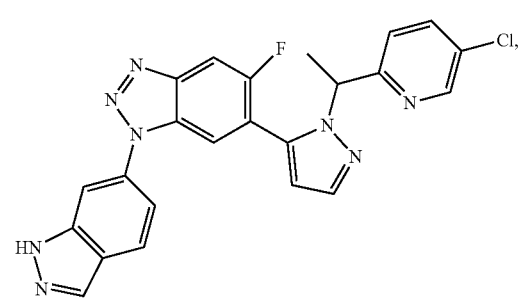
368
-continued
384
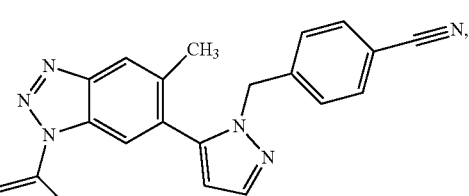
385
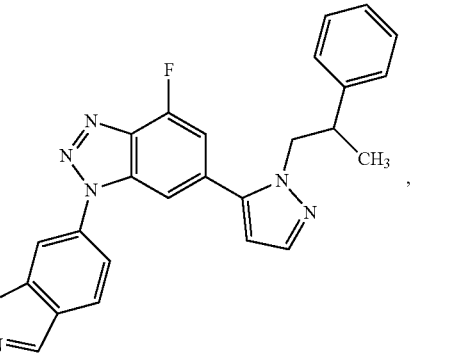
386
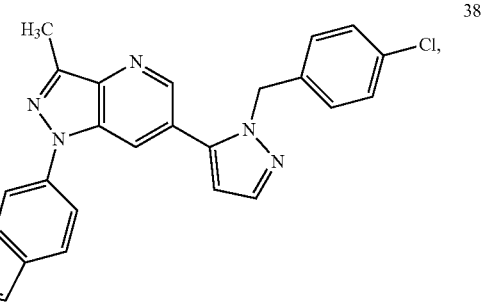
387
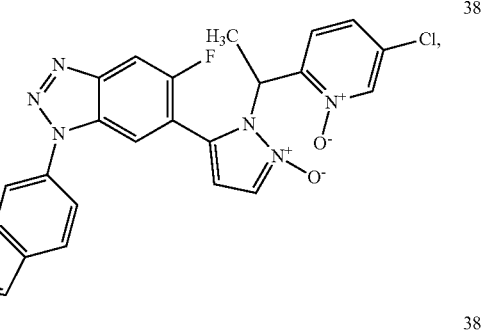
388
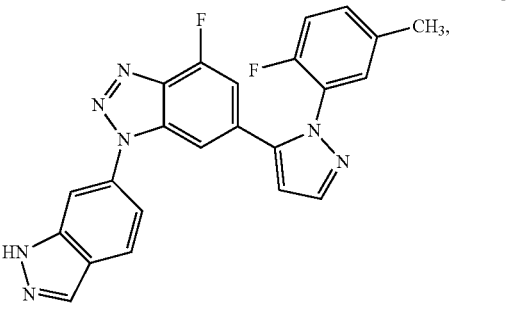

389
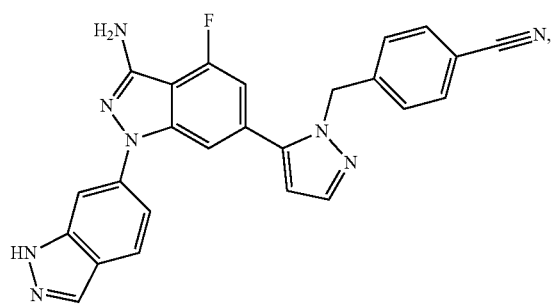
390
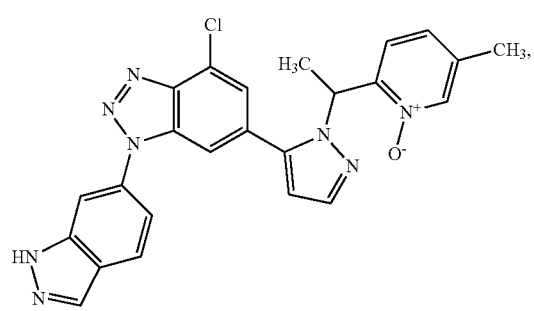
391
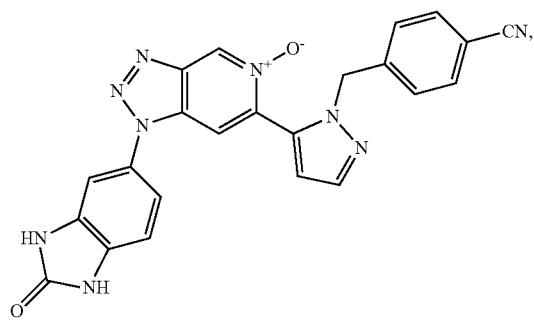
392
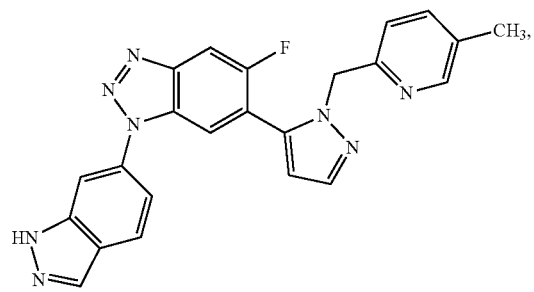
393
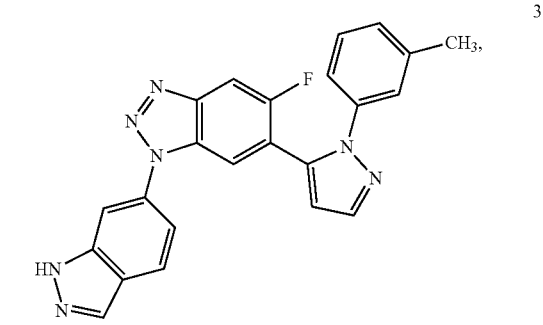
394
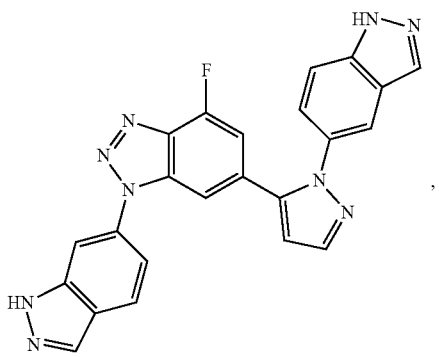
395
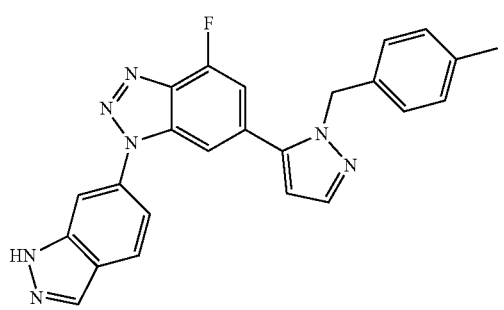
396
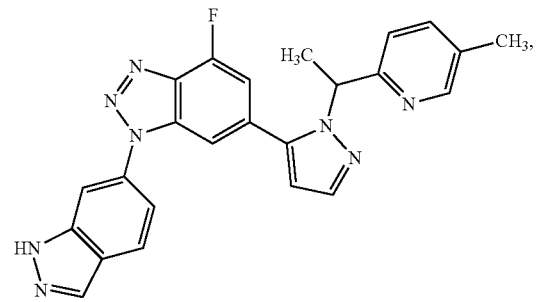
397
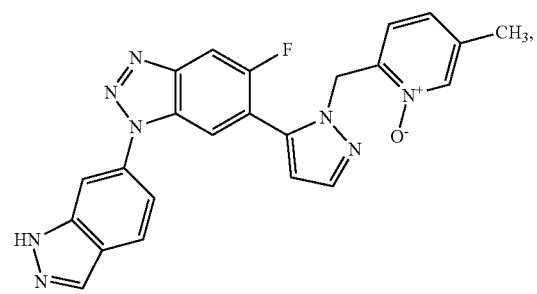
398
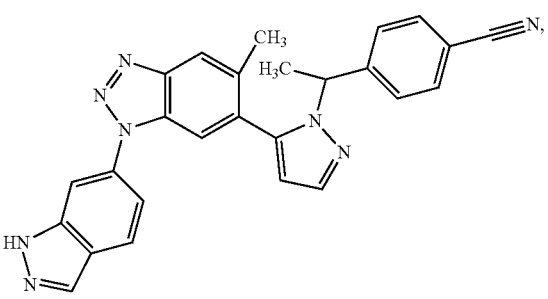

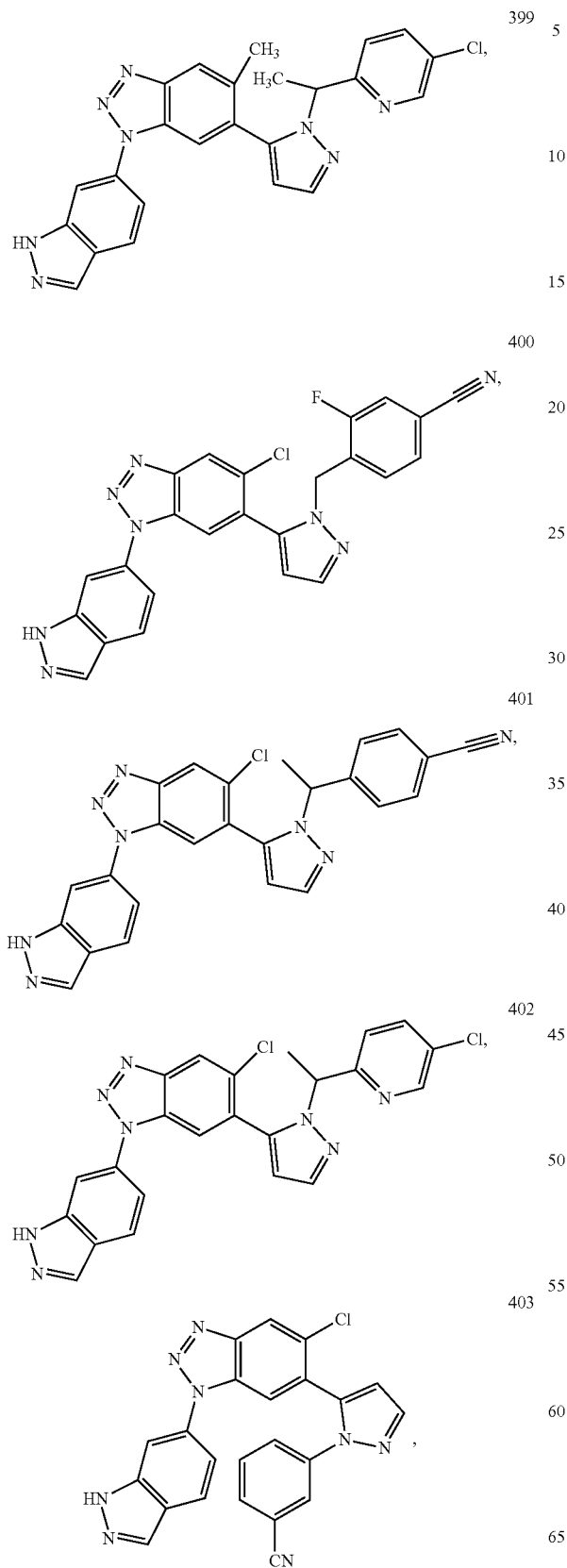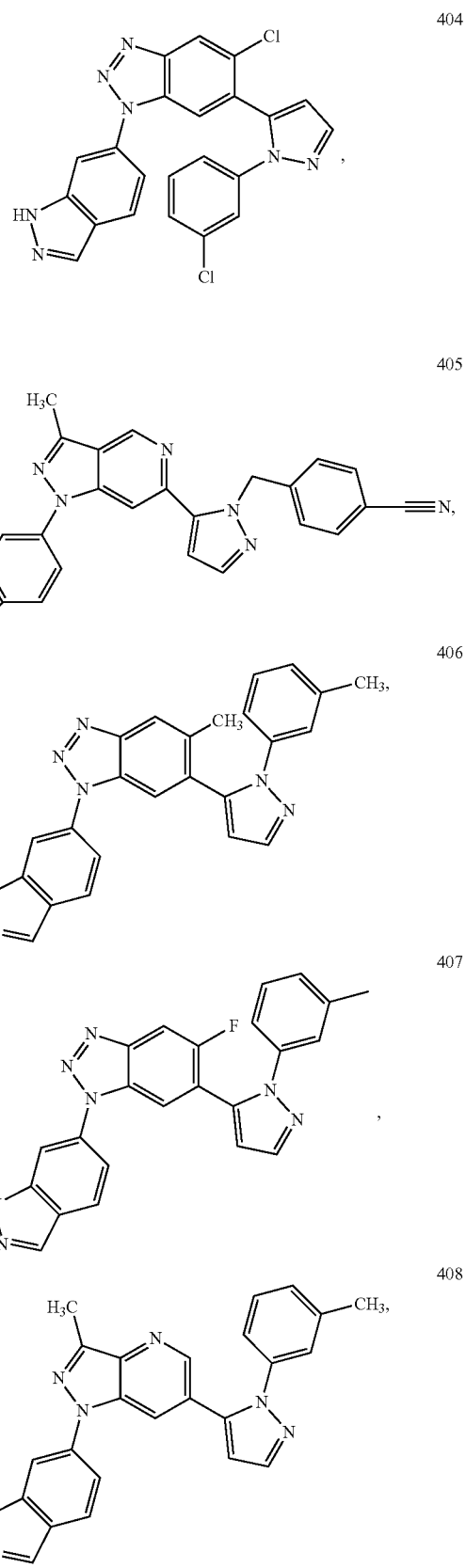

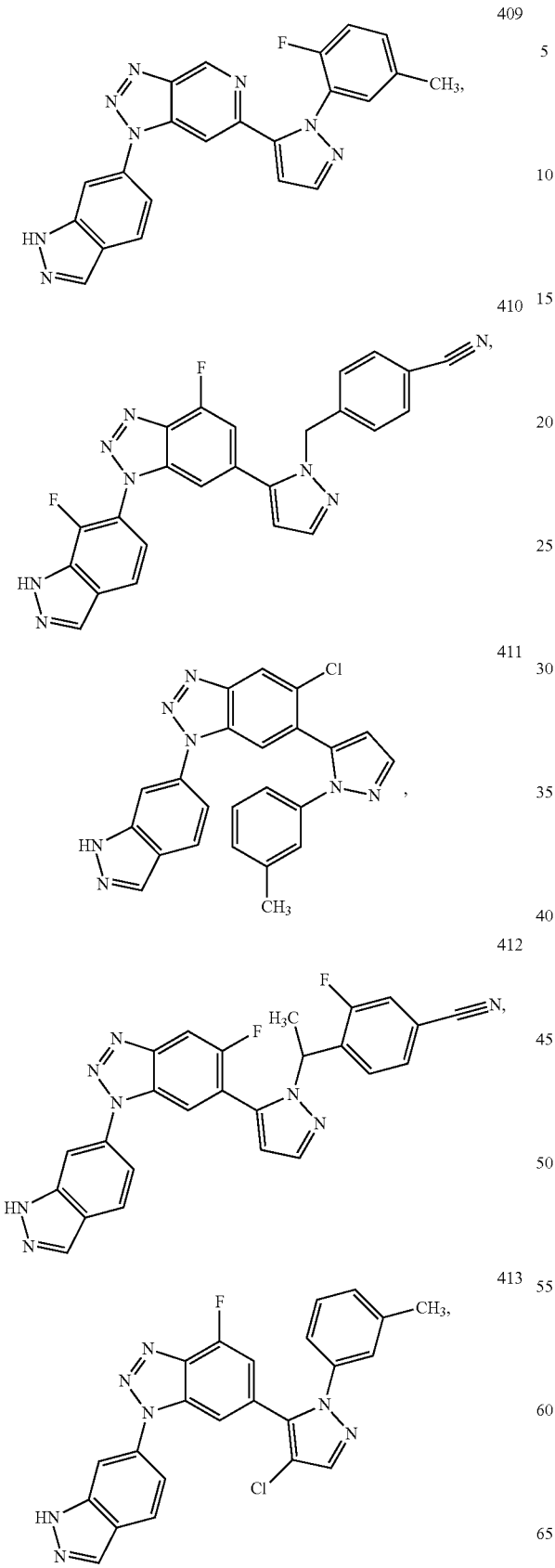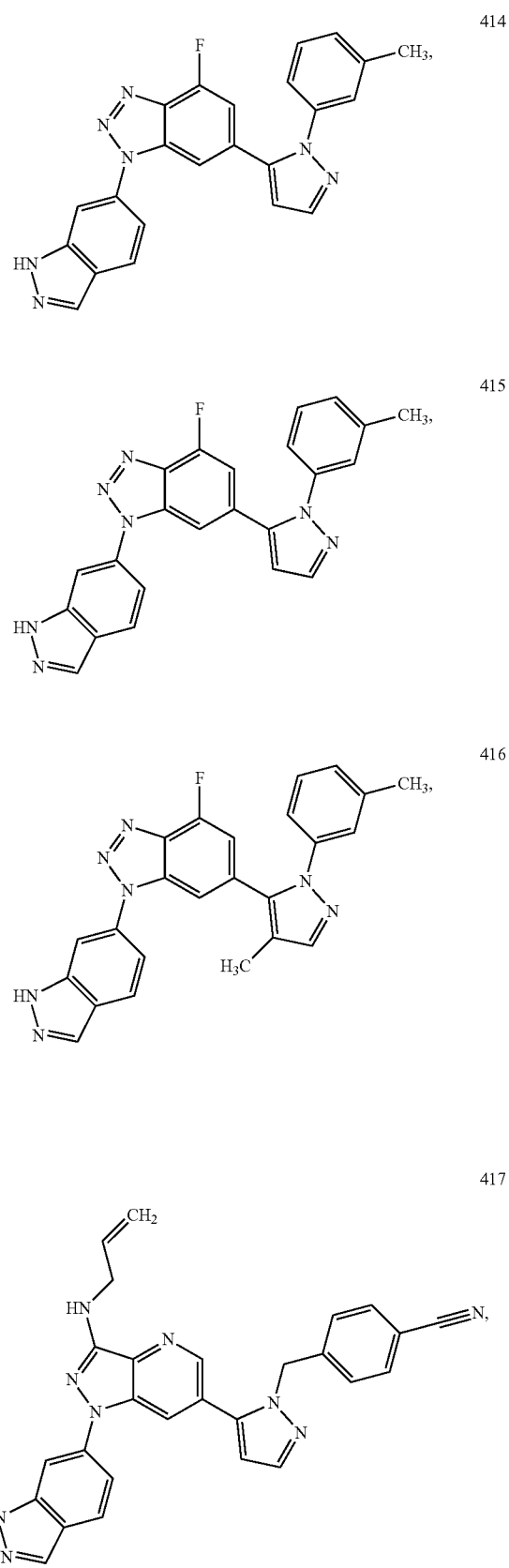

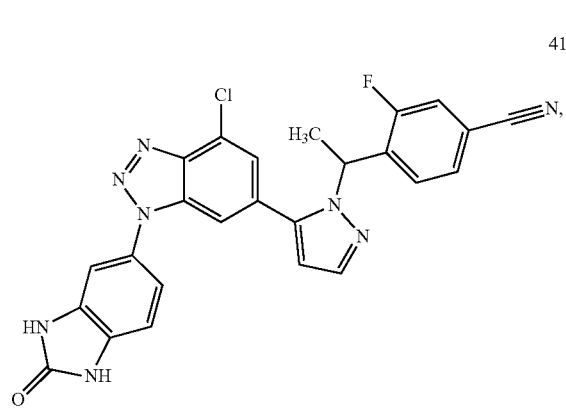
418
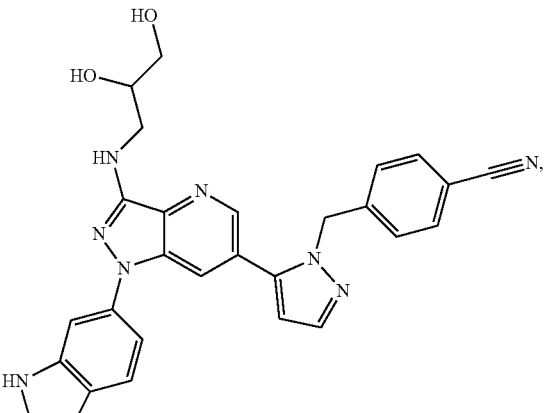
422
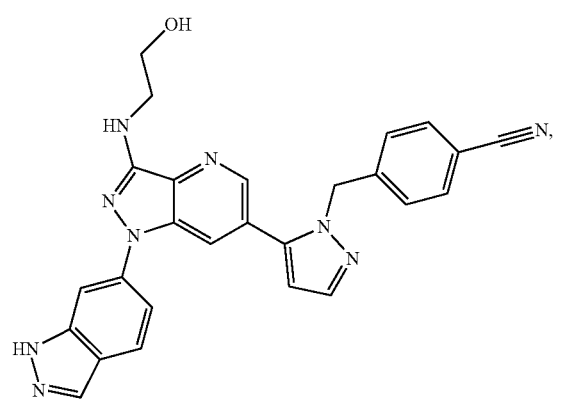
419
423
424
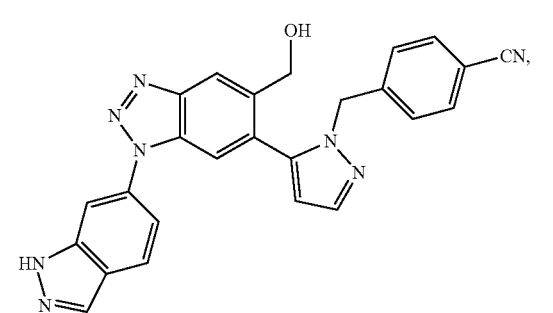
420
421
425
or a pharmaceutically acceptable salt thereof.
11. A pharmaceutical composition comprising a compound of claim 1, and a pharmaceutically acceptable excipient.
* * * * *

UNITED STATES PATENT AND TRADEMARK OFFICE
CERTIFICATE OF CORRECTION

Page 1 of 8

PATENT NO. : 11,931,343 B2
APPLICATION NO. : 17/271795
DATED : March 19, 2024
INVENTOR(S) : Joel Beatty et al.

It is certified that error appears in the above-identified patent and that said Letters Patent is hereby corrected as shown below:

In the Claims

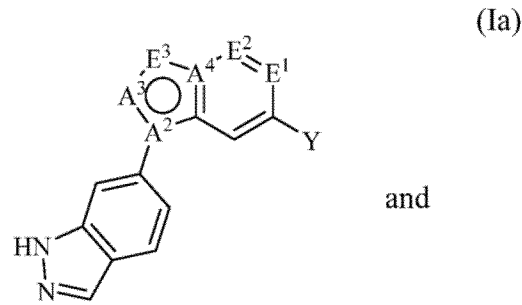

and

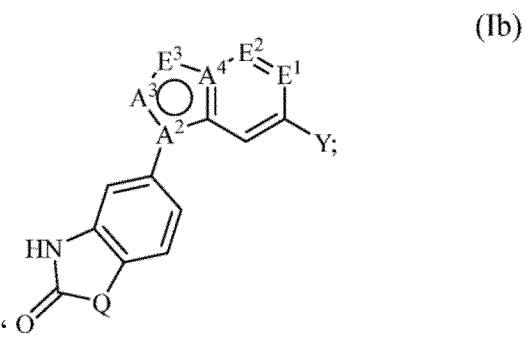

In Claim 1, Column 273, Lines 32 to 55, please replace " " " "

Signed and Sealed this
Eleventh Day of February, 2025

Coke Morgan Stewart
*Acting Director of the United States Patent and Trademark Office* with -- 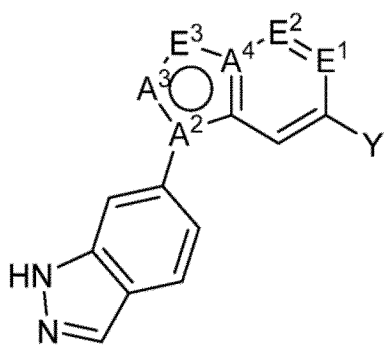 (Ia) 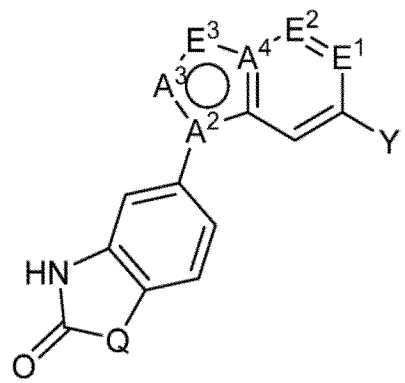 (Ib); --.
In Claim 1, Column 273, Line 64, please replace "N, C(O)" with -- N, NR$^1$, C(O) --.
In Claim 5, Column 276, Lines 15 to 28, please replace
"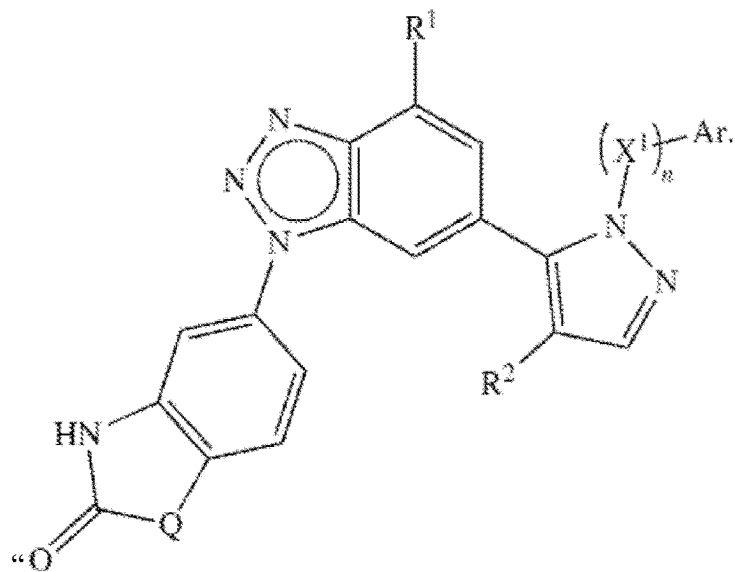 (Ib4)
" with

CERTIFICATE OF CORRECTION (continued)
U.S. Pat. No. 11,931,343 B2

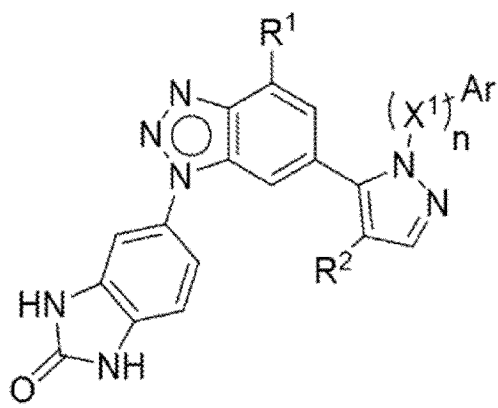

(Ib4).

--        --.

In Claim 10, Column 303, Lines 29 to 41, please replace

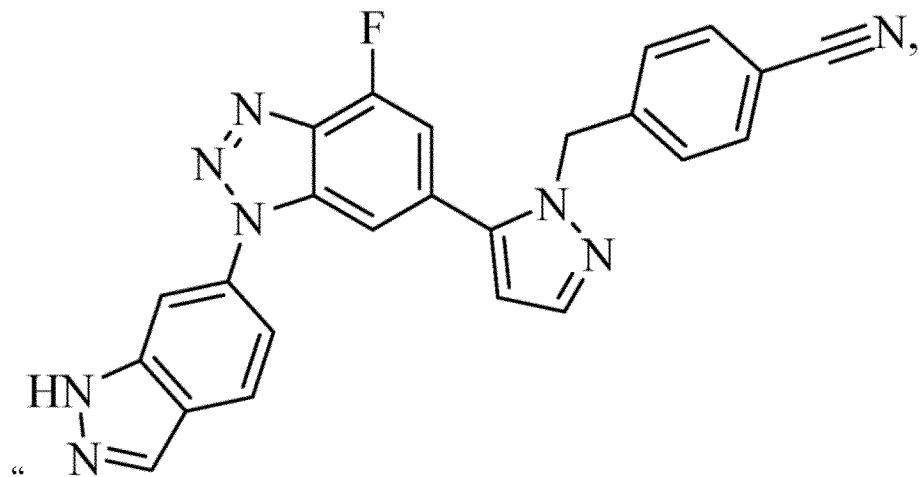

" with

CERTIFICATE OF CORRECTION (continued)
U.S. Pat. No. 11,931,343 B2

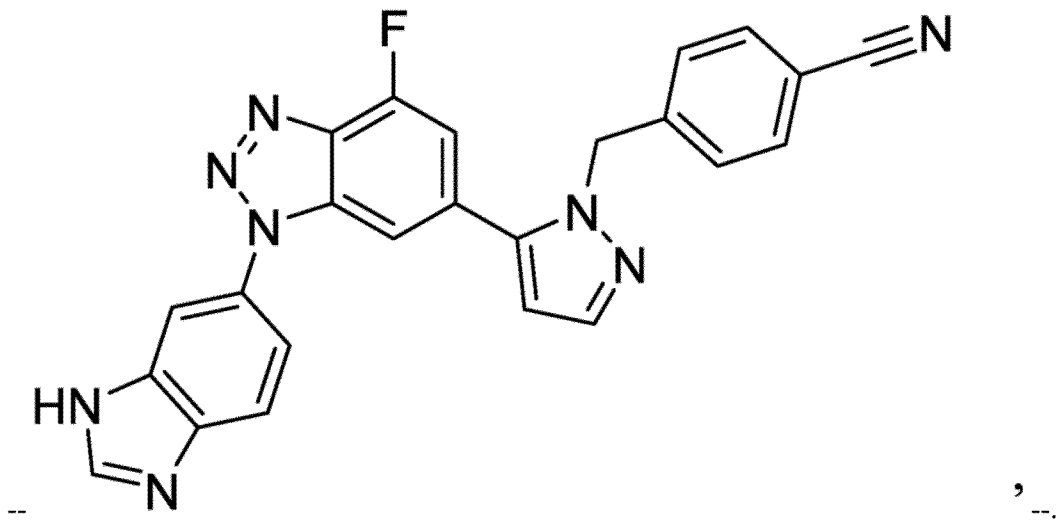

In Claim 10, Column 327, Lines 4 to 19, please replace

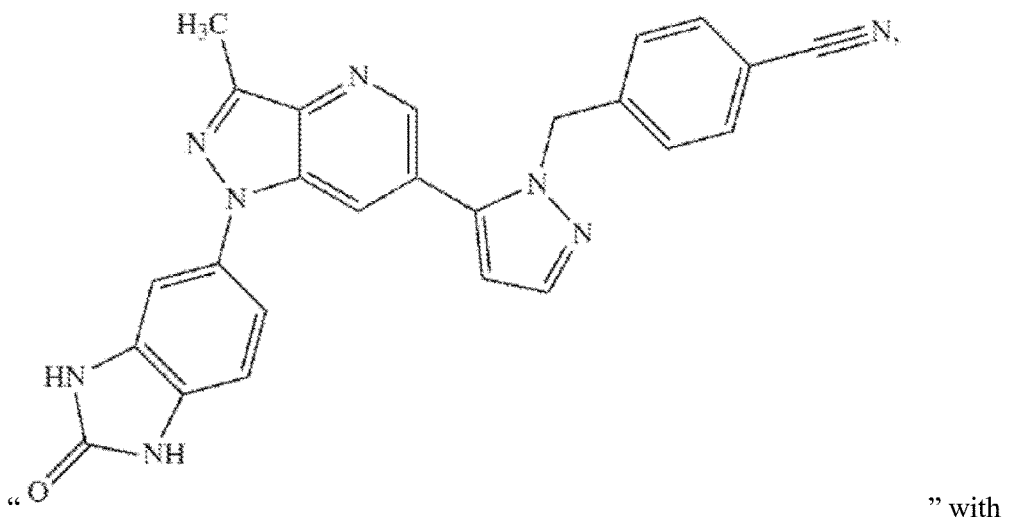

" with

219
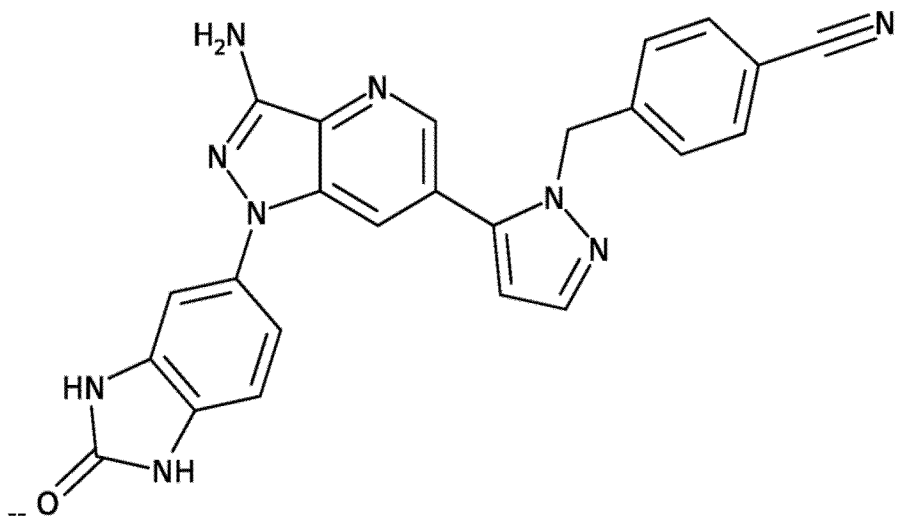
In Claim 10, Column 340, Lines 55 to 68, please replace
274
" 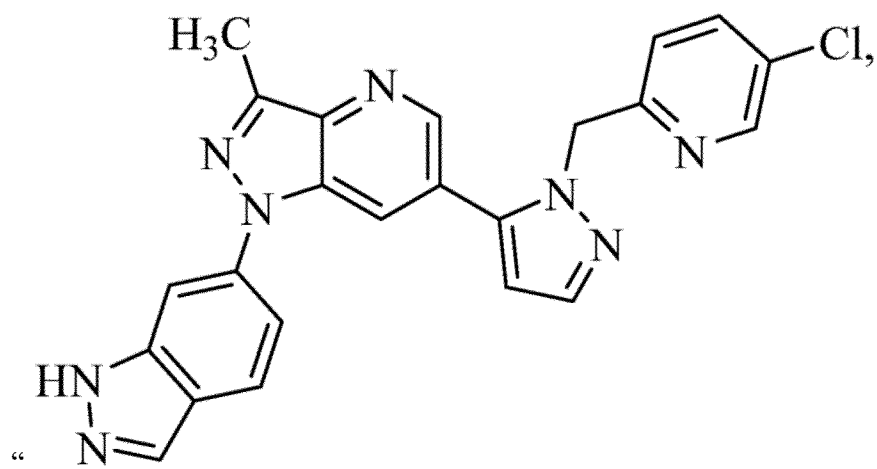 " with

CERTIFICATE OF CORRECTION (continued)
U.S. Pat. No. 11,931,343 B2

274

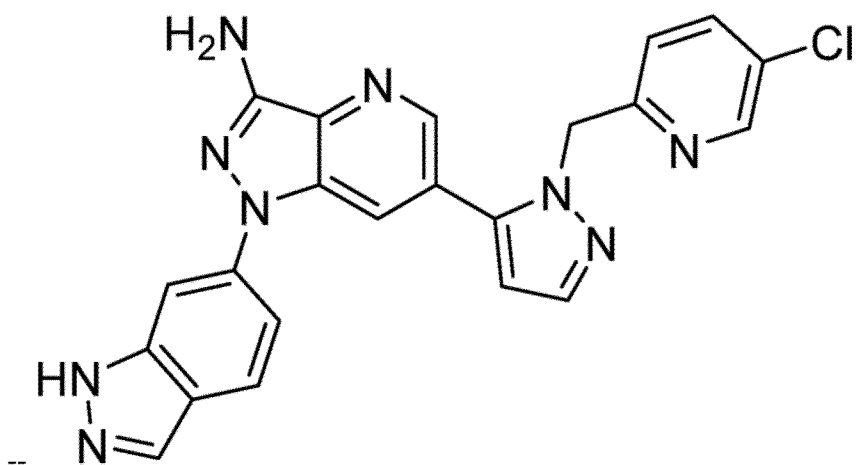

-- --.

In Claim 10, Column 342, Lines 55 to 68, please replace

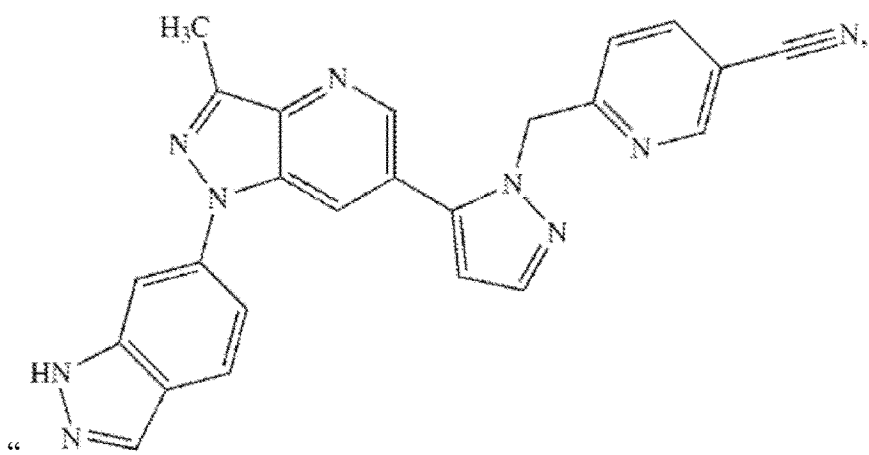

" " with

281
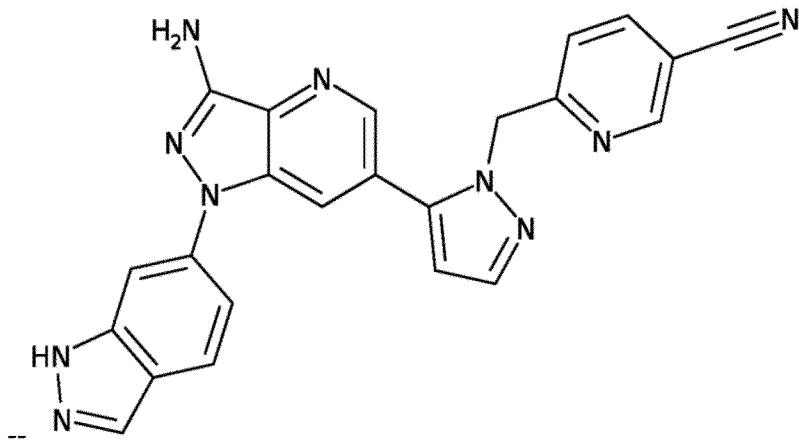
--                                                                  --.
In Claim 10, Column 355, Lines 20 to 35, please replace
" 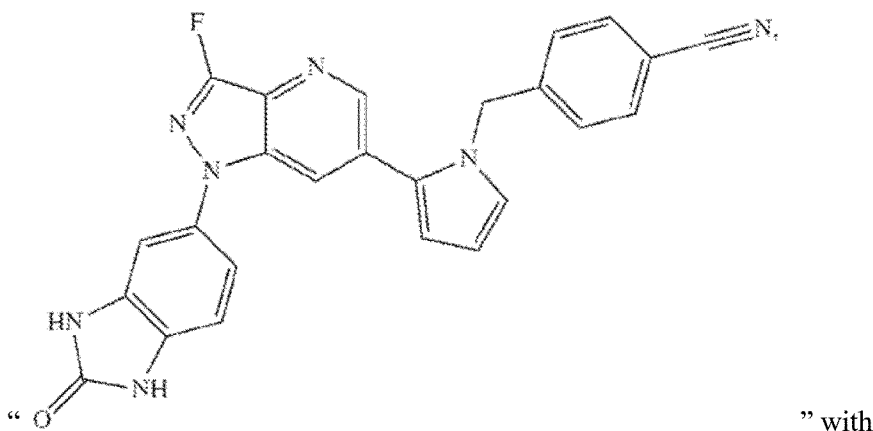 " with
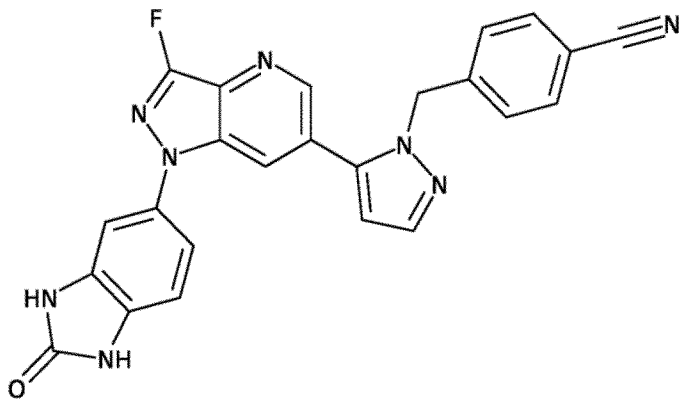
--                                                                  '--.

CERTIFICATE OF CORRECTION (continued)
U.S. Pat. No. 11,931,343 B2

In Claim 10, Column 358, Lines 20 to 35, please replace

"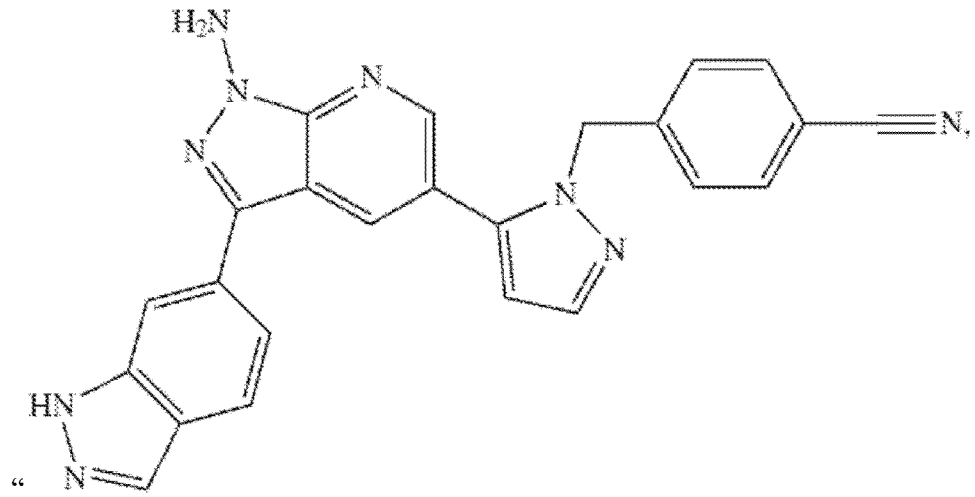" with

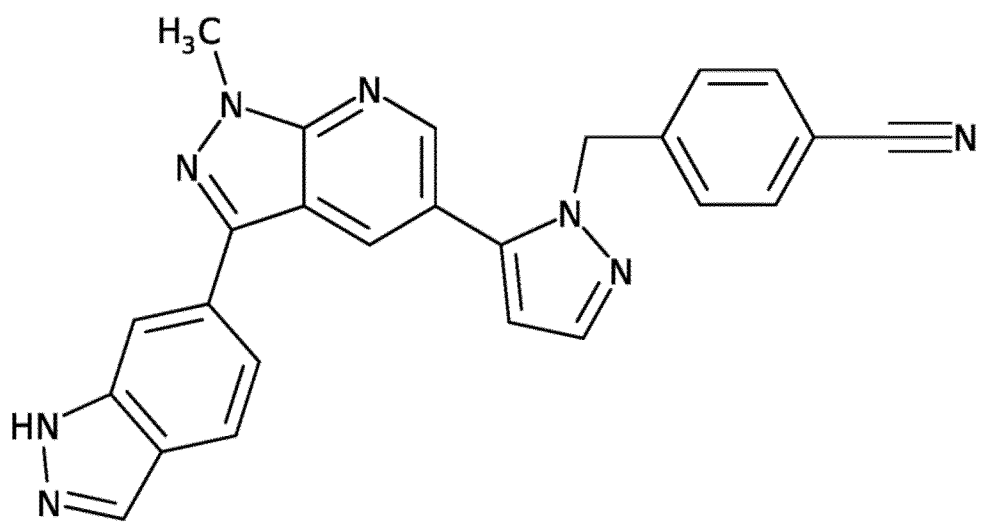',--.